United States Patent
Sorge

(10) Patent No.: US 7,309,573 B2
(45) Date of Patent: *Dec. 18, 2007

(54) METHODS FOR DETECTION OF A NUCLEIC ACID BY SEQUENTIAL AMPLIFICATION

(75) Inventor: Joseph A. Sorge, Del Mar, CA (US)

(73) Assignee: Stratagene California, La Jolla, CA (US)

( * ) Notice: Subject to any disclaimer, the term of this patent is extended or adjusted under 35 U.S.C. 154(b) by 17 days.

This patent is subject to a terminal disclaimer.

(21) Appl. No.: 11/198,762

(22) Filed: Aug. 5, 2005

(65) Prior Publication Data

US 2006/0110748 A1   May 25, 2006

Related U.S. Application Data

(60) Continuation-in-part of application No. 10/981,942, filed on Nov. 5, 2004, which is a division of application No. 09/717,602, filed on Nov. 21, 2000, now Pat. No. 6,893,819.

(51) Int. Cl.
  *C12Q 1/68* (2006.01)
  *C12P 19/34* (2006.01)
  *C07H 21/04* (2006.01)

(52) U.S. Cl. .............. 435/6; 435/91.1; 435/91.2; 536/24.3

(58) Field of Classification Search .......... 435/6, 435/91.1, 91.2; 536/24.3
See application file for complete search history.

(56) References Cited

U.S. PATENT DOCUMENTS

| | | | |
|---|---|---|---|
| 4,683,195 A | 7/1987 | Mullis et al. | 435/6 |
| 4,683,202 A | 7/1987 | Mullis | 435/91 |
| 4,800,159 A | 1/1989 | Mullis et al. | 435/172.3 |
| 5,210,015 A | 5/1993 | Gelfand et al. | 435/6 |
| 5,487,972 A | 1/1996 | Gelfand et al. | 435/6 |
| 5,645,987 A | 7/1997 | Richards | 435/6 |
| 5,719,028 A | 2/1998 | Dahlberg et al. | 435/6 |
| 5,733,733 A | 3/1998 | Auerbach | 435/6 |

(Continued)

FOREIGN PATENT DOCUMENTS

WO   WO93/17127   9/1993

OTHER PUBLICATIONS

Hosfield, et al., Cell., 95:135 (1998a).

(Continued)

*Primary Examiner*—Kenneth R. Horlick

(57) ABSTRACT

The invention relates to methods and compositions for detecting a target nucleic acid. The methods include subjecting a target, template, cleavage agent, polymerase and first, second and third oligonucleotide to reaction conditions that permit: (1) formation of a duplex between the target and first oligonucleotide; (2) extension of the first oligonucleotide; (3) cleavage of a first cleavage structure; (4) formation of a second duplex with a released flap; (5) extension of the released flap and (6) cleavage of a second cleavage structure within the third oligonucleotide. A signal generated by the release of the third oligonucleotide produces a signal that is detected and indicative of the presence of the target in the sample.

46 Claims, 31 Drawing Sheets

U.S. PATENT DOCUMENTS

| | | | |
|---|---|---|---|
| 5,837,450 A | 11/1998 | Dahlberg et al. | 435/6 |
| 5,843,669 A | 12/1998 | Kaiser et al. | 435/6 |
| 5,846,717 A | 12/1998 | Brow et al. | 435/6 |
| 5,888,780 A | 3/1999 | Dahlberg et al. | 435/91.53 |
| 5,985,557 A | 11/1999 | Prudent et al. | 435/6 |
| 5,994,069 A | 11/1999 | Hall et al. | 435/6 |
| 6,001,567 A | 12/1999 | Brow et al. | 435/6 |
| 6,090,543 A | 7/2000 | Prudent et al. | 435/6 |
| 6,090,606 A | 7/2000 | Kaiser et al. | 435/199 |
| 6,335,184 B1 | 1/2002 | Reyes et al. | 435/91.2 |
| 6,423,495 B1 | 7/2002 | Oultram et al. | 435/6 |
| 7,118,860 B2* | 10/2006 | Sorge et al. | 435/6 |
| 2006/0110748 A1* | 5/2006 | Sorge | 435/6 |
| 2006/0246469 A1* | 11/2006 | Sorge | 435/6 |

OTHER PUBLICATIONS

Lyamichev et al., Nat. Biotechnol., 17:292 (1999).
Saiki, et al., Science, 230: 1350 (1985).
Yutaka Takarada, "Highly Sensitive and Specific Amplication by Primer Digestion", Nucleic Acid Research, 1994, V. 22, No. 11 pp. 2170-2172.
The International Search Report (PCT/US01/47360) (2001).

* cited by examiner

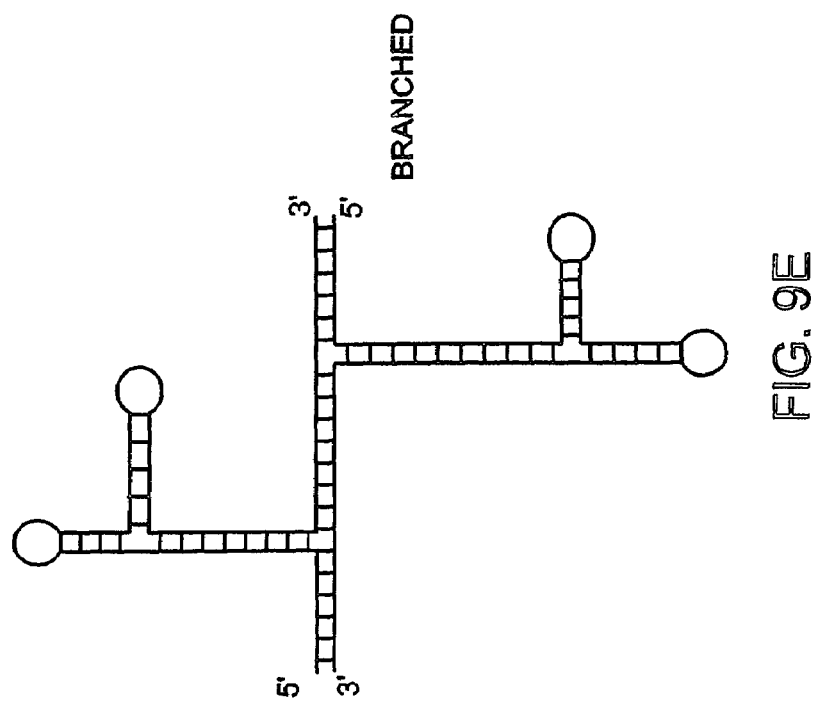
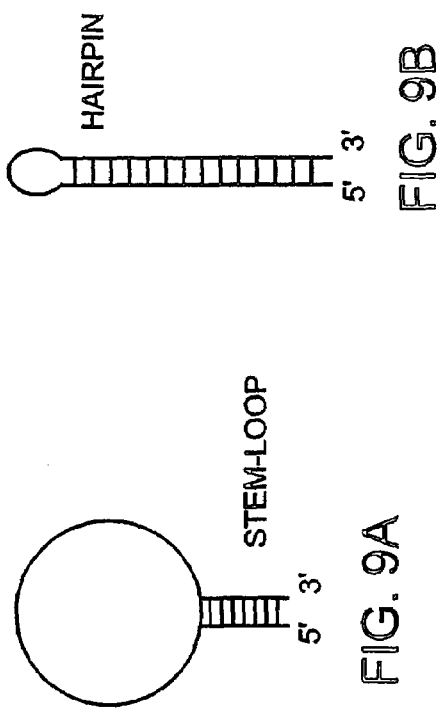
FIG. 9A STEM-LOOP
FIG. 9B HAIRPIN
FIG. 9C INTERNAL LOOP
FIG. 9D BULGE
FIG. 9E BRANCHED

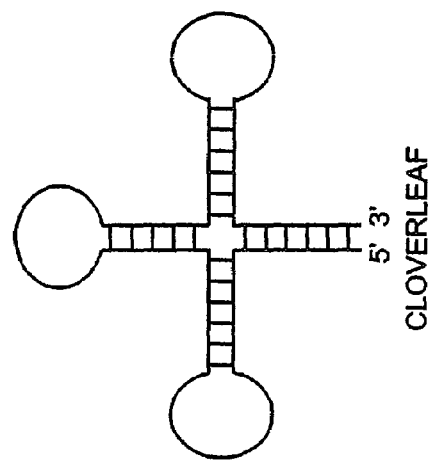
FIG. 9G
CLOVERLEAF
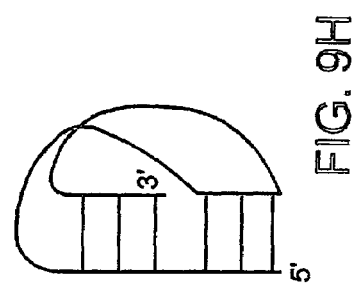
FIG. 9H
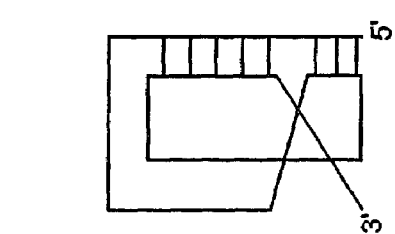
FIG. 9F
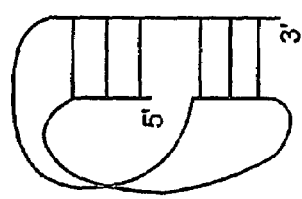
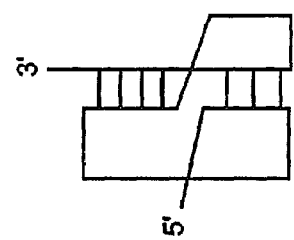
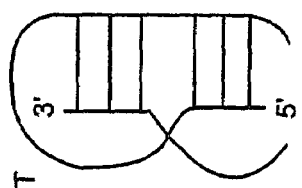
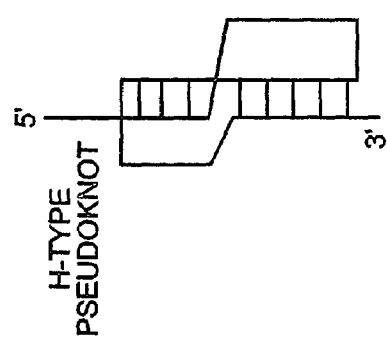
H-TYPE PSEUDOKNOT
PSEUDOKNOT

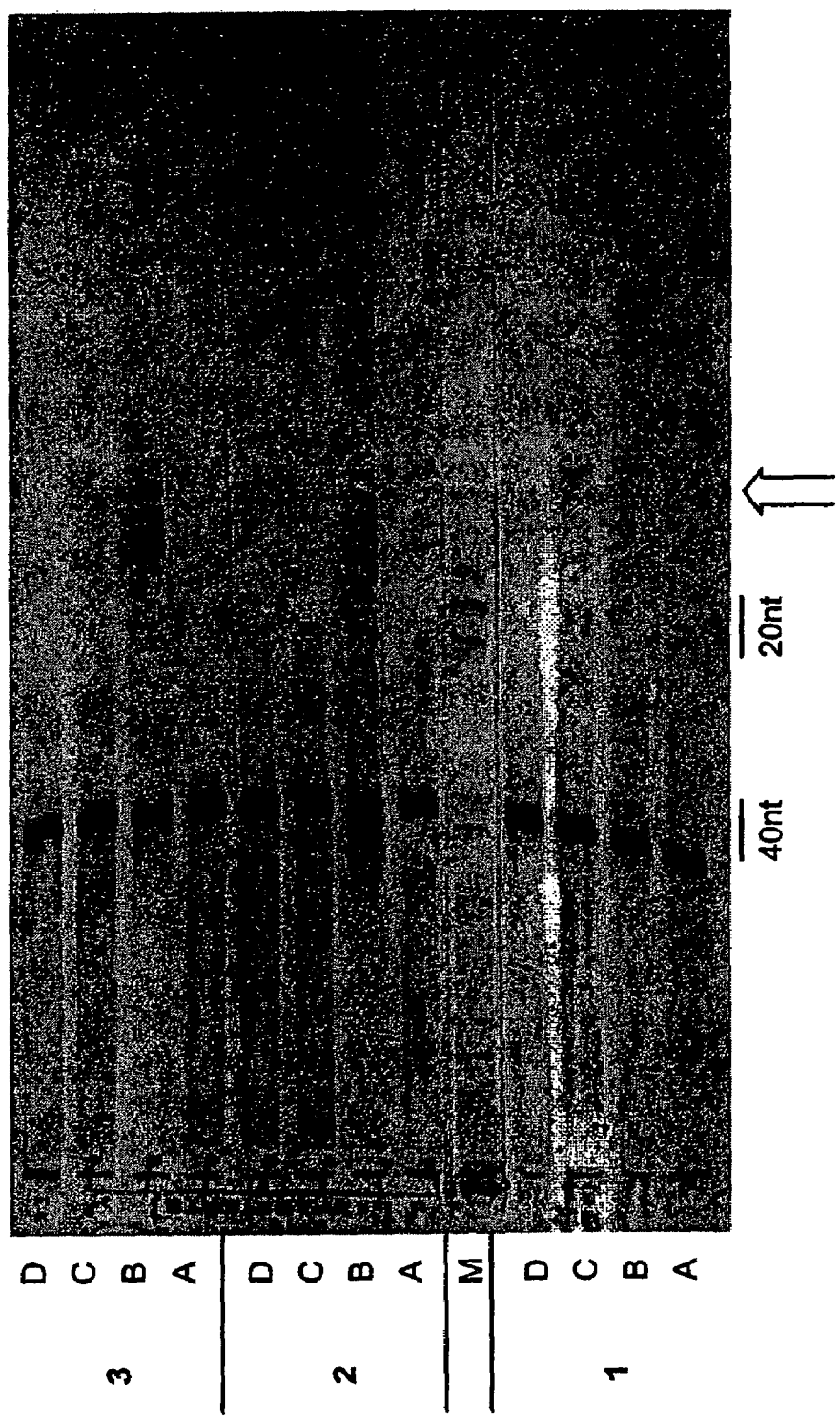

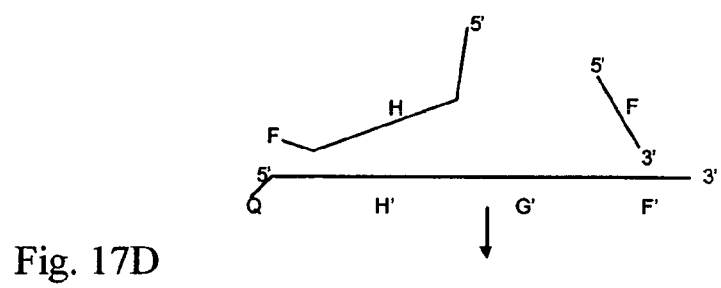
Fig. 17D
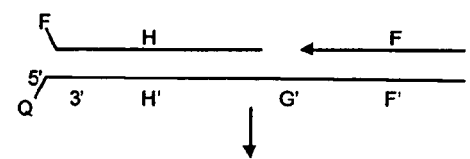
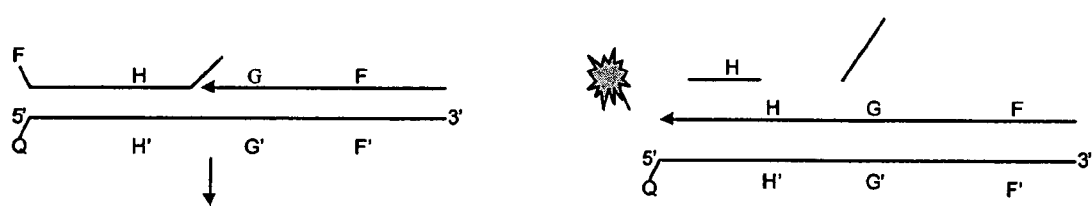
Fig. 17E
Fig. 17F

SEQUENCE LISTING

```
<160> NUMBER OF SEQ ID NOS: 7

<210> SEQ ID NO 1
<211> LENGTH: 43
<212> TYPE: DNA
<213> ORGANISM: Artificial
<220> FEATURE:
<221> NAME/KEY: misc_feature
<222> LOCATION: (1)..(43)
<223> OTHER INFORMATION: synthetic sequence template for evaluation of
      FEN nuclease activity

<400> SEQUENCE: 1
aaaataaata aaaaaaatac tgttgggaag ggcgatcggt gcg                    43

<210> SEQ ID NO 2
<211> LENGTH: 18
<212> TYPE: DNA
<213> ORGANISM: Artificial
<220> FEATURE:
<221> NAME/KEY: misc_feature
```

```
<222> LOCATION: (1)..(18)
<223> OTHER INFORMATION: Cleavage product of FEN cleavage of SEQ ID NO:
      1 template

<400> SEQUENCE: 2
aaaataaata aaaaaaat                                                    18

<210> SEQ ID NO 3
<211> LENGTH: 23
<212> TYPE: DNA
<213> ORGANISM: Artificial
<220> FEATURE:
<221> NAME/KEY: misc_feature
<222> LOCATION: (1)..(23)
<223> OTHER INFORMATION: Synthetic primer that binds to M13
      bacteriophage sequence.

<400> SEQUENCE: 3
ccattcgcca ttcaggctgc gca                                              23

<210> SEQ ID NO 4
<211> LENGTH: 49
<212> TYPE: DNA
<213> ORGANISM: Artificial
<220> FEATURE:
<221> NAME/KEY: misc_feature
<222> LOCATION: (1)..(49)
<223> OTHER INFORMATION: Synthetic oligonucleotide for amplification of
      P. furiosus FEN nuclease; includes sequences added to permit
      directional cloning.

<400> SEQUENCE: 4
gacgacgaca agatgggtgt cccaattggt gagattatac caagaaaag                  49

<210> SEQ ID NO 5
<211> LENGTH: 56
<212> TYPE: DNA
<213> ORGANISM: Artificial
<220> FEATURE:
<221> NAME/KEY: misc_feature
<222> LOCATION: (1)..(56)
<223> OTHER INFORMATION: Synthetic oligonucleotide for amplification of
      P. furiosus FEN nuclease; includes sequences added to permit
      directional cloning.

<400> SEQUENCE: 5
ggaacaagac ccgtttatct cttgaaccaa ctttcaaggg ttgattgttt tccact          56

<210> SEQ ID NO 6
<211> LENGTH: 44
<212> TYPE: DNA
<213> ORGANISM: Mus musculus
<220> FEATURE:
<221> NAME/KEY: misc_feature
<222> LOCATION: (29)..(32)
<223> OTHER INFORMATION: N at positions 29-32 can be any nucleotide, g,
      a, t or c.

<400> SEQUENCE: 6
cagccgtcga tccgcaggtc gacactgcnn nncgtcgacg gctg                       44

<210> SEQ ID NO 7
<211> LENGTH: 19
<212> TYPE: DNA
<213> ORGANISM: Artificial
<220> FEATURE:
<221> NAME/KEY: misc_feature
<222> LOCATION: (1)..(19)
<223> OTHER INFORMATION: Synthetic oligonucleotide; example of safety
```

```
            pin probe.

<400> SEQUENCE: 7
tcgcagtgtc gacctgcga                                                     19
```

METHODS FOR DETECTION OF A NUCLEIC ACID BY SEQUENTIAL AMPLIFICATION

RELATED APPLICATIONS

This application is a continuation-in-part of application Ser. No. 10/981,942, filed Nov. 5, 2004, which is a divisional of application Ser. No. 09/717,602, now U.S. Pat. No. 6,893,819, filed Nov. 21, 2000. The entire teachings of the above applications are incorporated herein by reference.

BACKGROUND OF THE INVENTION

The fidelity of DNA replication, recombination, and repair is essential for maintaining genome stability, and all of these processes depend on 5' 3' exonuclease enzymes which are present in all organisms. For DNA repair, these enzymes are required for damaged fragment excision and recombinational mismatch correction. For replication, these nucleases are critical for the efficient processing of Okazaki fragments during lagging strand DNA synthesis. In *Escherichia coli*, this latter activity is provided by DNA polymerase I (PolI); *E. Coli* strains with inactivating mutations in the PolI 5' 3' exonuclease domain are not viable due to an inability to process Okazaki fragments. Eukaryotic DNA polymerases, however, lack an intrinsic 5'→3' exonuclease domain, and this critical activity is provided by the multi-functional, structure-specific metallonuclease FEN-1 (five' exonuclease-1 or flap endonuclease-1), which also acts as an endonuclease for 5' DNA flaps (Reviewed in Hosfield et al., 1998a, *Cell*, 95:135).

Methods of detecting and/or measuring a nucleic acid wherein an enzyme produces a labeled nucleic acid fragment are known in the art.

U.S. Pat. Nos. 5,843,669, 5,719,028, 5,837,450, 5,846,717 and 5,888,780 disclose a method of cleaving a target DNA molecule by incubating a 5' labeled target DNA with a DNA polymerase isolated from *Thermus aquaticus* (Taq polymerase) and a partially complementary oligonucleotide capable of hybridizing to sequences at the desired point of cleavage. The partially complementary oligonucleotide directs the Taq polymerase to the target DNA through formation of a substrate structure containing a duplex with a 3' extension opposite the desired site of cleavage wherein the non-complementary region of the oligonucleotide provides a 3' arm and the unannealed 5' region of the substrate molecule provides a 5' arm. The partially complementary oligonucleotide includes a 3' nucleotide extension capable of forming a short hairpin either when unhybridized or when hybridized to a target sequence at the desired point of cleavage. The release of labeled fragment is detected following cleavage by Taq polymerase.

U.S. Pat. Nos. 5,843,669, 5,719,028, 5,837,450, 5,846,717 and 5,888,780 disclose the generation of mutant, thermostable DNA polymerases that have very little or no detectable synthetic activity, and wild type thermostable nuclease activity. The mutant polymerases are said to be useful because they lack 5' to 3' synthetic activity; thus synthetic activity is an undesirable side reaction in combination with a DNA cleavage step in a detection assay.

U.S. Pat. Nos. 5,843,669, 5,719,028, 5,837,450, 5,846,717 and 5,888,780 disclose that wild type Taq polymerase or mutant Taq polymerases that lack synthetic activity can release a labeled fragment by cleaving a 5' end labeled hairpin structure formed by heat denaturation followed by cooling, in the presence of a primer that binds to the 3' arm of the hairpin structure. Further, U.S. Pat. Nos. 5,843,669, 5,719,028, 5,837,450, 5,846,717 and 5,888,780 teach that the mutant Taq polymerases lacking synthetic activity can also cleave this hairpin structure in the absence of a primer that binds to the 3' arm of the hairpin structure.

U.S. Pat. Nos. 5,843,669, 5,719,028, 5,837,450, 5,846,717 and 5,888,780 also disclose that cleavage of this hairpin structure in the presence of a primer that binds to the 3' arm of the hairpin structure by mutant Taq polymerases lacking synthetic activity yields a single species of labeled cleaved product, while wild type Taq polymerase produces multiple cleavage products and converts the hairpin structure to a double stranded form in the presence of dNTPs, due to the high level of synthetic activity of the wild type Taq enzyme.

U.S. Pat. Nos. 5,843,669, 5,719,028, 5,837,450, 5,846,717 and 5,888,780 also disclose that mutant Taq polymerases exhibiting reduced synthetic activity, but not wild type Taq polymerase, can release a single labeled fragment by cleaving a linear nucleic acid substrate comprising a 5' end labeled target nucleic acid and a complementary oligonucleotide wherein the complementary oligonucleotide hybridizes to a portion of the target nucleic acid such that 5' and 3' regions of the target nucleic acid are not annealed to the oligonucleotide and remain single stranded.

U.S. Pat. Nos. 5,846,717, 6,090,543, 6,001,567, 6,090,606, 5,985,557 and 5,994,069 relate to methods for forming a nucleic acid cleavage structure on a target sequence and cleaving the nucleic acid cleavage structure in a site specific manner. These patents also relate to using the 5' nuclease activity of a variety of enzymes to cleave the target-dependent cleavage structure, thereby indicating the presence of a specific nucleic acid sequence or variations thereof.

Methods of detecting and/or measuring a nucleic acid wherein a FEN-1 enzyme is used to generate a labeled nucleic acid fragment are known in the art.

U.S. Pat. No. 5,843,669 discloses a method of detecting polymorphisms by cleavase fragment length polymorphism analysis using a thermostable FEN-1 nuclease in the presence or absence of a mutant Taq polymerase exhibiting reduced synthetic activity. According to this method, double stranded Hepatitis C virus (HCV) DNA fragments are labeled by using 5' end labeled primers (labeled with TMR fluorescent dye) in a PCR reaction. The TMR labeled PCR products are denatured by heating to 95° C. and cooled to 55° C. to generate a cleavage structure. U.S. Pat. No. 5,843,669 discloses that a cleavage structure comprises a region of a single stranded nucleic acid substrate containing secondary structure. Cleavage is carried out in the presence of CleavaseBN nuclease, FEN-1 nuclease derived from the archaebacteria *Methanococcus jannaschii* or both enzymes. Labeled reaction products are visualized by gel electrophoresis followed by fluoroimaging. U.S. Pat. No. 5,843,669 discloses that CleavaseBN nuclease and *Methanococcus jannaschii* FEN-1 nuclease produce cleavage patterns that are easily distinguished from each other, and that the cleavage patterns from a reaction containing both enzymes include elements of the patterns produced by cleavage with each individual enzyme but are not merely a composite of the cleavage patterns produced by each individual enzyme. This indicates that some of the fragments that are not cleaved by one enzyme (and which appear as a band in that enzyme's pattern) can be cleaved by a second enzyme in the same reaction mixture.

Lyamichev et al. disclose a method for detecting DNAs wherein overlapping pairs of oligonucleotide probes that are partially complementary to a region of target DNA are mixed with the target DNA to form a 5' flap region, and wherein cleavage of the labeled downstream probe by a thermostable FEN-1 nuclease produces a labeled cleavage product. Lyamichev et al. also disclose reaction conditions wherein multiple copies of the downstream oligonucleotide probe can be cleaved for a single target sequence in the absence of temperature cycling, so as to amplify the cleavage signal and allow quantitative detection of target DNA at sub-attomole levels (Lyamichev et al., 1999, *Nat. Biotechnol.*, 17:292).

The polymerase chain reaction (PCR) technique, is disclosed in U.S. Pat. Nos. 4,683,202, 4,683,195 and 4,800,159. In its simplest form, PCR is an in vitro method for the enzymatic synthesis of specific DNA sequences, using two oligonucleotide primers that hybridize to opposite strands and flank the region of interest in the target DNA. A repetitive series of reaction steps involving template denaturation, primer annealing and the extension of the annealed primers by DNA polymerase results in the exponential accumulation of a specific fragment whose termini are defined by the 5' ends of the primers. PCR is reported to be capable of producing a selective enrichment of a specific DNA sequence by a factor of $10^9$. The PCR method is also described in Saiki et al., 1985, *Science*, 230:1350.

While the PCR technique is an extremely powerful method for amplifying nucleic acid sequences, the detection of the amplified material requires additional manipulation and subsequent handling of the PCR products to determine whether the target DNA is present. It is desirable to decrease the number of subsequent handling steps currently required for the detection of amplified material. An assay system, wherein a signal is generated while the target sequence is amplified, requires fewer handling steps for the detection of amplified material, as compared to a PCR method that does not generate a signal during the amplification step.

U.S. Pat. Nos. 5,210,015 and 5,487,972 disclose a PCR based assay for releasing labeled probe comprising generating a signal during the amplification step of a PCR reaction in the presence of a nucleic acid to be amplified, Taq polymerase that has 5' to 3' exonuclease activity and a 5', 3' or 5' and 3' end-labeled probe comprising a region complementary to the amplified region and an additional non-complementary 5' tail region. U.S. Pat. Nos. 5,210,015 and 5,487,972 disclose further that this PCR based assay can liberate the 5' labeled end of a hybridized probe when the Taq polymerase is positioned near the labeled probe by an upstream probe in a polymerization independent manner, e.g. in the absence of dNTPs.

There is a need in the art for a method of generating a signal that can be easily distinguished from oligonucleotide fragments that may arise from nuclease contaminants, using a nucleic acid cleavage reaction.

There is also a need in the art for a method of generating a signal wherein a target is amplified in either a linear or an exponential manner.

There is a need in the art for a method of generating a signal wherein a target is amplified in either a linear or an exponential manner in an isothermal reaction that utilizes a probe comprising secondary structure wherein some or all of the self-complementary regions of the probe that anneal to form the secondary structure are melted when the probe hybridizes with a target nucleic acid, thereby reducing non-specific binding of the probe to the target, and increasing the specificity of the assay.

U.S. Pat. Nos. 5,843,669, 5,719,028, 5,837,450, 5,846,717 and 5,888,780 also disclose a method of cleaving a labeled nucleic acid substrate at naturally occurring areas of secondary structure. According to this method, biotin labeled DNA substrates are prepared by PCR, mixed with wild type Taq polymerase or CleavaseBN (a mutant Taq polymerase with reduced synthetic activity and wild type 5' to 3' nuclease activity), incubated at 95° C. for 5 seconds to denature the substrate and then quickly cooled to 65° C. to allow the DNA to assume its unique secondary structure by allowing the formation of intra-strand hydrogen bonds between the complementary bases. The reaction mixture is incubated at 65° C. to allow cleavage to occur and biotinylated cleavage products are detected.

There is a need in the art for a method of generating a signal using a nucleic acid cleavage reaction wherein the cleavage structure is not required to contain areas of secondary structure and wherein a target is amplified in either a linear or an exponential manner.

SUMMARY OF THE INVENTION

The invention relates to nucleic acid, flap-mediated, sequential amplification methods which permit detection of a nucleic acid target in a nucleic acid sample. The invention provides for nucleic acid synthesis dependent, flap-mediated amplification methods for sequentially producing detectable, released flaps to detect a target nucleic acid. The invention provides for both linear, and exponential nucleic acid synthesis dependent, flap-mediated, sequential amplification methods. The methods of the invention provide for either duplex structures comprising a preformed flap or duplex structures wherein a flap is formed by the activity of a polymerization means with strand displacement activity. Nucleic acid synthesis dependent, flap-mediated sequential amplification methods according to the invention comprise a template nucleic acid, a downstream oligonucleotide and an upstream primer. The invention may be performed isothermally or under nucleic acid amplifying conditions. The invention may be used in real-time PCR detection.

In one embodiment, detectable released flaps are produced by a nucleic acid synthesis dependent, flap-mediated, sequential amplification method which includes the step of providing one or more template nucleic acids (e.g., A'B'C', FIG. 1, step 1), which comprise in 3' to 5' order a first region, an extension region, and a second region, an upstream primer (e.g., A, FIG. 1, step 1) that is at least partially complementary to the first region of the template nucleic acid, and one or more copies of a downstream oligonucleotide (e.g., AC, FIG. 1, step 1) comprising a 5' region and a 3' region, wherein the 3' region is at least partially complementary to the second region of the template nucleic acid and wherein the 5' region is at least partially complementary to a region that may be upstream of, downstream of, or comprise the first region of the template nucleic acid. One or more template nucleic acids refers to identical or non-identical template nucleic acids. Non-identical means a least one nucleotide (1, 2, 5, 10, 20 or more) is different.

This method also includes the step of forming a first duplex (FIG. 1, step 1) by mixing at least the template nucleic acid and the upstream primer and downstream oligonucleotide under conditions which permit formation of a duplex between the template nucleic acid and each of the upstream primer and the 3' region of the downstream oligonucleotide, wherein the 5' region of the downstream oligonucleotide is a flap. A first cleavage structure is then formed (FIG. 1, step 2) by subjecting the duplex to a nucleic acid polymerization activity under conditions which permit extension of the upstream primer by polymerization of a nucleic acid strand complementary to a length of the extension region sufficient to form a first cleavage structure. The first cleavage structure is cleaved (FIG. 1, step 2) by providing a cleavage means under conditions such that cleavage of the first cleavage structure occurs at a site located within the downstream oligonucleotide in a manner dependent upon the formation of the first cleavage structure, thereby permitting cleavage and release of the flap of the downstream oligonucleotide (e.g., A, FIG. 1, step 3).

The released flap of the downstream oligonucleotide associates with either i) another copy of the template nucleic acid or ii) a denatured version of the template nucleic acid used to form the first duplex, and an uncleaved downstream oligonucleotide to form a second duplex (FIG. 1, step 4a or 4b) comprising the template nucleic acid and each of the released flap of the downstream oligonucleotide and an uncleaved downstream oligonucleotide, wherein the 5' region of the uncleaved downstream oligonucleotide is a second flap. At this step, the released flap of the downstream oligonucleotide can associate with a template nucleic acid that is identical (FIG. 1, step 4a) or non-identical (FIG. 1, step 4b) to the template nucleic acid used to form the first duplex.

A second cleavage structure is formed (FIG. 1, step 5a or 5b) by subjecting the second duplex to a nucleic acid polymerization activity under conditions which permit extension of the released flap by polymerization of a nucleic acid strand complementary to a length of the extension region sufficient to form a second cleavage structure. A second cleavage structure is cleaved (FIG. 1, step 5a or 5b) by providing a cleavage means under conditions such that cleavage of the second cleavage structure occurs at a site located within the uncleaved downstream oligonucleotide in a manner dependent upon the formation of the second cleavage structure, thereby permitting cleavage and release of the second flap (e.g., A, FIG. 1, step 6a, or A, FIG. 1, step 6b). Released first and/or second flaps are detected. These steps can be repeated, for example 1-2 million times and preferably 1-10,000 times, to produce a detectable level of first and/or second flaps.

The invention also provides for linear synthesis dependent, flap-mediated, sequential amplification methods for target nucleic acid detection.

In one embodiment, duplex structures comprise a preformed flap. This embodiment of the invention comprises the step of providing the following: a target nucleic acid (e.g., A'B'C', FIG. 2, step 1), which comprises in 3' to 5' order a first region, an extension region, and a second region; one or more template nucleic acids (e.g., F'G'H', FIG. 2, step 4), which comprise in 3' to 5' order a first region, an extension region, and a second region; a first oligonucleotide (e.g., A, FIG. 1, step 1) that is at least partially complementary to the first region of the target nucleic acid; a second oligonucleotide (e.g., FC, FIG. 2, step 1) comprising a 5' region and a 3' region, wherein the 3' region is at least partially complementary to the second region of the target nucleic acid and wherein the 5' region is not complementary to the extension region of the target nucleic acid but is at least partially complementary to the first region of the template nucleic acid; and one or more third oligonucleotides comprising a 5' region and a 3' region, wherein the 3' region is at least partially complementary to the second region of the template nucleic acid and the 5' region is not complementary to the template nucleic acid.

According to this embodiment, a first duplex is formed (FIG. 2, step 1) by mixing at least the target nucleic acid and the first and second oligonucleotides under conditions which permit formation of a duplex between the target nucleic acid and each of the first oligonucleotide and the 3' region of the second oligonucleotide, wherein the 5' region of the second oligonucleotide is a flap. A first cleavage structure is formed (FIG. 2, step 2) by subjecting the duplex to a nucleic acid polymerization activity under conditions which permit extension of the first oligonucleotide by polymerization of a nucleic acid strand complementary to a length of the extension region sufficient to form a first cleavage structure. A first cleavage structure is cleaved (FIG. 2, step 2) by providing a cleavage means under conditions such that cleavage of the first cleavage structure occurs at a site located within the second oligonucleotide in a manner dependent upon the formation of the first cleavage structure, thereby permitting cleavage and release of the flap (e.g., F, FIG. 2, step 3) of the second oligonucleotide. The released flap of the second oligonucleotide, the template nucleic acid, and the third oligonucleotide form a second duplex (FIG. 2, step 4) between the template nucleic acid and each of the released flap of the second oligonucleotide and the third oligonucleotide, wherein the 5' region of the third oligonucleotide is a second flap. A second cleavage structure is formed (FIG. 2, step 5) by subjecting the second duplex to a nucleic acid polymerization activity under conditions which permit extension of the released flap by polymerization of a nucleic acid strand complementary to a length of the extension region sufficient to form a second cleavage structure. A second cleavage structure is cleaved (FIG. 2, step 5) by providing a cleavage means under conditions such that cleavage of the second cleavage structure occurs at a site located within the third oligonucleotide in a manner dependent upon the formation of the second cleavage structure, thereby permitting cleavage and release of the second flap of the third oligonucleotide (e.g., F, FIG. 2, step 6). Released first and/or second flaps are detected. These steps can be repeated, for example 1-2 million times, preferably 1-10,000 times, to produce a detectable level of first and second flaps.

In a related embodiment, a linear nucleic acid synthesis dependent, flap-mediated, sequential amplification method for detecting a target nucleic acid comprises cleavage structures wherein the flap of at least one of the cleavage structures is formed by the activity of a polymerization means with strand displacement activity (see FIG. 3). According to this embodiment, at least 6 nucleotides are displaced by the strand displacement activity of the polymerization means (FIG. 3, step 2). A second oligonucleotide according to this embodiment, further comprises a 5' region that is at least partially complementary to a region that may be upstream of, downstream of, or comprising the first region of the target nucleic acid (e.g., FC, FIG. 3, step 1). A third oligonucleotide according to this embodiment of the invention further comprises a 5' region that is at least partially complementary to a region that may be upstream of, downstream of, or comprising the first region of the template nucleic acid (e.g., FH, FIG. 3, step 4).

The invention provides for compositions for linear nucleic acid synthesis dependent, flap-mediated amplification methods for sequentially producing detectable, released flaps to detect a target nucleic acid.

The invention provides for a composition comprising one or more template nucleic acids, each of which comprises in 3' to 5' order a first region, an extension region, and a second region; a first oligonucleotide that is at least partially complementary to the first region of the template nucleic acid, and one or more second oligonucleotides each comprising a 5' region and a 3' region, wherein the 3' region of each second oligonucleotide is at least partially complementary to the second region of the template nucleic acid and wherein the 5' region is at least partially complementary to a corresponding region that may be upstream of, downstream of, or comprise the first region of the template nucleic acid.

A composition comprising: a target nucleic acid, which comprises in 3' to 5' order a first region, an extension region, and a second region, a template nucleic acid, which comprises in 3' to 5' order a first region, an extension region, and a second region, a first oligonucleotide that is at least partially complementary to the first region of the target nucleic acid, and a second oligonucleotide comprising a 5' region and a 3' region, wherein the 3' region is at least partially complementary to the second region of the target nucleic acid and wherein the 5' region is not complementary to the extension region of the target nucleic acid but is at least partially complementary to the first region of the template nucleic acid; and a third oligonucleotide comprising a 5' region and a 3' region, wherein the 3' region is at least partially complementary to the second region of the template nucleic acid and the 5' region is not complementary to the first region of the template nucleic acid.

A composition comprising: a target nucleic acid, which comprises in 3' to 5' order a first region, an extension region, and a second region, a template nucleic acid, which comprises in 3' to 5' order a first region, an extension region, and a second region, a first oligonucleotide that is at least partially complementary to the first region of the target nucleic acid, and a second oligonucleotide comprising a 5' region and a 3' region, wherein the 3' region is at least partially complementary to the second region of the target nucleic acid and wherein the 5' region is at least partially complementary to a region that may be upstream of, downstream of, or comprising the first region of the target nucleic acid and is at least partially complementary to the first region of the template nucleic acid; and a third oligonucleotide comprising a 5' region and a 3' region, wherein the 3' region is at least partially complementary to the second region of the template nucleic acid and the 5' region is at least partially complementary to a region that may be upstream of, downstream of, or comprise the first region of the template nucleic acid.

Preferably, in any one of the compositions, the composition may further include either or both of a cleavage means which permits cleavage of a flap from a nucleic acid duplex structure, and a nucleic acid polymerizing activity.

A kit comprising any one of the compositions including a target nucleic acid as described hereinabove, and packaging materials therefore.

Preferably, the kit may further include either or both of a cleavage means which permits cleavage of a flap from a nucleic acid duplex structure, and a nucleic acid polymerizing activity.

The invention contemplates both linear and exponential amplification methods. The invention provides for exponential, synthesis dependent, flap-mediated, amplification methods for sequentially producing released flaps for detecting a target nucleic acid.

In one embodiment, detectable released flaps are produced by a nucleic acid synthesis dependent, flap-mediated, sequential amplification method which includes the step of providing: one or more template nucleic acids (e.g., F'G1'H1'G2'H2', FIG. 4A, step 1), which comprise in 3' to 5' order a first region, a first extension region, a second region, a second extension region, and a third region, an upstream primer (e.g., F, FIG. 4a, step 1) that is at least partially complementary to the first region of the template nucleic acid, and one or more copies of a first downstream oligonucleotide (e.g., FH1, FIG. 4a, step 1) comprising a 5' region and a 3' region, wherein the 3' region is at least partially complementary to the second region of the template nucleic acid and wherein the 5' region is at least partially complementary to a region that may be upstream of, downstream of, or comprise the first region of the template nucleic acid; and a second downstream oligonucleotide (e.g., FH2, FIG. 4a, step 1) which is downstream of the first downstream oligonucleotide and which comprises a 5' region and a 3' region, wherein the 3' region is at least partially complementary to the third region of the template nucleic acid and wherein the 3' region of the first downstream oligonucleotide may or may not be identical in sequence to the 3' region of the second downstream oligonucleotide, and wherein the 5' region of the second downstream oligonucleotide is at least partially complementary to a region that may be upstream of, downstream of, or comprise the first region of the template nucleic acid. One or more template nucleic acids refers to identical or non-identical template nucleic acids.

This method also includes the step of forming a first duplex (FIG. 4a, step 1) by mixing at least the template nucleic acid and the upstream primer and the first and second downstream oligonucleotides under conditions which permit formation of a duplex between the template nucleic acid and each of the upstream primer and the 3' regions of the first and second downstream oligonucleotides, wherein the 5' regions of the first and second downstream oligonucleotides are flaps.

A first cleavage structure is then formed (FIG. 4a, step 2) by subjecting the duplex to a nucleic acid polymerization activity under conditions which permit extension of the upstream primer by polymerization of a nucleic acid strand complementary to a length of the first extension region sufficient to form a first cleavage structure. The first cleavage structure is cleaved (FIG. 4a, step 2) by providing a cleavage means under conditions such that cleavage of the first cleavage structure occurs at a site located within the first downstream oligonucleotide in a manner dependent upon the formation of the first cleavage structure, thereby permitting cleavage and release of the flap of the first downstream oligonucleotide (e.g., F, FIG. 4a, step 3).

A second cleavage structure is then formed (FIG. 4a, steps 3 and 4) by subjecting the duplex to a nucleic acid polymerization activity under conditions which permit extension of the upstream primer by polymerization of a nucleic acid strand complementary to a length of the second extension region sufficient to form a second cleavage structure. According to this embodiment, the polymerization activity causes displacement of the uncleaved portion of the first downstream oligonucleotide (e.g., H1, FIG. 4a, step 3).

The second cleavage structure is cleaved (FIG. 4a, step 4) by providing a cleavage means under conditions such that cleavage of the second cleavage structure occurs at a site located within the second downstream oligonucleotide in a manner dependent upon the formation of the second cleavage structure, thereby permitting cleavage and release of the flap of the second downstream oligonucleotide (e.g., F, FIG. 4a, step 5). The released flap of the first or second downstream oligonucleotide associates with either i) another copy of the template nucleic acid or ii) a denatured version of the template nucleic acid used to form the first duplex, and uncleaved first and second downstream oligonucleotides to form a second duplex (FIG. 4a, step 1 or FIG. 4b, step 6) comprising the template nucleic acid and either of the released flap of the first or second downstream oligonucleotide, uncleaved first downstream oligonucleotide, and uncleaved second downstream oligonucleotide, wherein the 5' region of each uncleaved downstream oligonucleotide, independently, is a flap. At this step, the released flap of the first or second downstream oligonucleotide can associate with a template nucleic acid that is identical (e.g., F'G1'H1'G2'H2', FIG. 4a, step 1) or non-identical (e.g., F'I1'H1'I2'H2', FIG. 4b, step 6) to the template nucleic acid used to form the first duplex.

A third cleavage structure is formed (FIG. 4a, step 2 or FIG. 4b, step 7) by subjecting the second duplex to a nucleic acid polymerization activity under conditions which permit extension of the released flap by polymerization of a nucleic acid strand complementary to a length of the first extension region sufficient to form a third cleavage structure. A third cleavage structure is cleaved (FIG. 4a, step 2 or FIG. 4b, step 7) by providing a cleavage means under conditions such that cleavage of the third cleavage structure occurs at a site located within the uncleaved first downstream oligonucleotide in a manner dependent upon the formation of the third cleavage structure, thereby permitting cleavage and release of the third flap (e.g., F, FIG. 4a, step 3 or F, FIG. 4b, step 8).

A fourth cleavage structure is then formed (FIG. 4a, steps 3 and 4 or FIG. 4b, steps 8 and 9) by subjecting the duplex to a nucleic acid polymerization activity under conditions which permit extension of the upstream primer by polymerization of a nucleic acid strand complementary to a length of the second extension region sufficient to form a fourth cleavage structure. According to this embodiment, the polymerization activity causes displacement of the uncleaved portion of the first downstream oligonucleotide.

The fourth cleavage structure is cleaved (FIG. 4a, step 4 or FIG. 4b, step 9) by providing a cleavage means under conditions such that cleavage of the fourth cleavage structure occurs at a site located within the second downstream oligonucleotide in a manner dependent upon the formation of the fourth cleavage structure, thereby permitting cleavage and release of the flap of the second downstream oligonucleotide (e.g., F, FIG. 4a, step 5 or F, FIG. 4b, step 10). Released first and/or second and/or third and/or fourth flaps are detected. These steps can be repeated, for example 1-100 times and preferably 1-50 times, to produce a detectable level of first and/or second flaps.

In one embodiment, duplex structures comprise a preformed flap. This embodiment of the invention comprises the step of providing: a target nucleic acid (e.g., A'B'C', FIG. 2, step 1) suspected of containing the nucleic acid of interest, which comprises in 3' to 5' order a first region, an extension region, and a second region; a template nucleic acid (e.g., F'G1'H1'G2'H2', FIG. 5, step 1), which comprises in 3' to 5' order a first region, a first extension region, a second region, a second extension region and a third region; a first oligonucleotide (e.g., A, FIG. 2, step 1) that is at least partially complementary to the first region of the target nucleic acid; a second oligonucleotide (e.g., FC, FIG. 2, step 1) comprising a 5' region and a 3' region, wherein the 3' region is at least partially complementary to the second region of the target nucleic acid and wherein the 5' region is not complementary to the extension region of the target nucleic acid but is at least partially complementary to the first region of the template nucleic acid; a third oligonucleotide (e.g., FH1, FIG. 5, step 1) comprising a 5' region and a 3' region, wherein the 3' region is at least partially complementary to the second region of the template nucleic acid, and wherein the 5' region is not complementary to the first extension region of the template nucleic acid, and a fourth oligonucleotide (e.g., FH2, step 1) comprising a 5' region and a 3' region, wherein the 3' region is at least partially complementary to the third region of the template nucleic acid, and wherein the 3' region of the third oligonucleotide may or may not be identical in sequence to the 3' region of the fourth oligonucleotide, and wherein the 5' region of the fourth oligonucleotide is not complementary to the second extension region of the template nucleic acid.

This method also includes the step of forming a first duplex (FIG. 2, step 1) by mixing at least the target nucleic acid and the first and second oligonucleotides under conditions which permit formation of a duplex between the target nucleic acid and each of the first oligonucleotide and the 3' region of the second oligonucleotide, wherein the 5' region of the second oligonucleotide is a first flap. A first cleavage structure is formed (FIG. 2, step 2) by subjecting the duplex to a nucleic acid polymerization activity under conditions which permit extension of the first oligonucleotide by polymerization of a nucleic acid strand complementary to a length of the extension region sufficient to form a first cleavage structure. A first cleavage structure is cleaved (FIG. 2, step 2) by providing a cleavage means under conditions such that cleavage of the first cleavage structure occurs in the second oligonucleotide in a manner dependent upon the formation of the first cleavage structure, thereby permitting cleavage and release of the first flap of the second oligonucleotide (e.g., F, FIG. 2, step 3). The released first flap of the second oligonucleotide (e.g., F, FIG. 2, step 3), the template nucleic acid, the third oligonucleotide, and the fourth oligonucleotide associate to form a second duplex (FIG. 4, step 1), wherein the 5' region of the third oligonucleotide is a second flap, and the 5' region of the fourth oligonucleotide is a third flap.

A second cleavage structure is formed (FIG. 5, step 1) by subjecting the second duplex to a nucleic acid polymerization activity under conditions which permit extension of the released first flap of the second duplex by polymerization of a nucleic acid strand complementary to a length of the first extension region of the second duplex sufficient to form a second cleavage structure.

A second cleavage structure is cleaved (FIG. 5, step 2) by providing a cleavage means under conditions such that cleavage of the second cleavage structure occurs in the third oligonucleotide in a manner dependent upon the formation of the second cleavage structure, thereby permitting cleavage and release of the second flap of the third oligonucleotide (e.g., F, FIG. 5, step 3) and cleavage of the second cleavage structure.

A third cleavage structure is formed (FIG. 5, steps 3 and 4) by subjecting the second duplex to a nucleic acid polymerization activity under conditions which permit extension of the released first flap by polymerization of a nucleic acid strand complementary to a length of the second extension region of the cleaved second cleavage structure sufficient to form a third cleavage structure. According to this embodiment, the polymerization activity causes displacement of the uncleaved portion of the third oligonucleotide (e.g., H1, FIG. 5, step 3). A third cleavage structure is cleaved (FIG. 5, step 4) by providing a cleavage means under conditions such that cleavage of the third cleavage structure occurs in the fourth oligonucleotide in a manner dependent upon the formation of the third cleavage structure, thereby permitting cleavage and release of the third flap of the fourth oligonucleotide (e.g., F, FIG. 5, step 5). At least one of the first, second or third released flaps are detected.

In a related embodiment, an exponential, synthesis dependent, flap-mediated, sequential amplification method for detecting a target nucleic acid comprises first, second and third cleavage structures wherein the flap of at least one of the first, second and third cleavage structures is formed by the activity of a polymerization means with strand displacement activity (see FIG. 6). According to this embodiment, a polymerization means displaces at least 6 nucleotides. Duplex structures according to this embodiment, do not comprise a preformed flap.

A second oligonucleotide according to this embodiment further comprises a 5' region that is at least partially complementary to a region that may be upstream of, downstream of, or comprising the first region of the target nucleic acid. A third oligonucleotide according to this embodiment, further comprises a 5' region that is at least partially complementary to a region that may be upstream of, downstream of or comprising the first region of the template nucleic acid. A fourth oligonucleotide according to this embodiment, further comprises a 5' region that is at least partially complementary to a region that may be upstream of, downstream of, or comprising the second region of the template nucleic acid.

The invention provides for compositions for exponential nucleic acid synthesis dependent, flap-mediated amplification methods for sequentially producing detectable, released flaps to detect a target nucleic acid.

The invention provides for a composition comprising one or more template nucleic acids, which comprise in 3' to 5' order a first region, a first extension region, a second region, a second extension region, and a third region, an upstream primer that is at least partially complementary to the first region of the template nucleic acid; one or more copies of a first downstream oligonucleotide comprising a 5' region and a 3' region, wherein the 3' region is at least partially complementary to the second region of the template nucleic acid and wherein the 5' region is at least partially complementary to a region that may be upstream of, downstream of, or comprise the first region of the template nucleic acid; one or more copies of a second downstream oligonucleotide comprising a 5' region and a 3' region, wherein the 3' region is at least partially complementary to the third region of the template nucleic acid and wherein the 5' region is at least partially complementary to a region that may be upstream of, downstream of, or comprise the second region of the template nucleic acid.

A composition comprising: a target nucleic acid suspected of containing the nucleic acid of interest, which comprises in 3' to 5' order a first region, an extension region, and a second region, a template nucleic acid, which comprises in 3' to 5' order a first region, a first extension region, a second region, a second extension region and a third region, a first oligonucleotide that is at least partially complementary to the first region of the target nucleic acid, and a second oligonucleotide comprising a 5' region and a 3' region, wherein the 3' region is at least partially complementary to the second region of the target nucleic acid and wherein the 5' region is not complementary to the extension region of the target nucleic acid but is at least partially complementary to the first region of the template nucleic acid; and a third oligonucleotide comprising a 5' region and a 3' region, wherein the 3' region is at least partially complementary to the second region of the template nucleic acid, and wherein the 5' region is not complementary to the first extension region of the template nucleic acid, and a fourth oligonucleotide comprising a 5' region and a 3' region, wherein the 3' region is at least partially complementary to the third region of the template nucleic acid, and wherein the 3' region of the third oligonucleotide is not identical in sequence to the 3' region of the fourth oligonucleotide, and wherein the 5' region of the fourth oligonucleotide is not complementary to the second extension region of the template nucleic acid.

A composition comprising: a target nucleic acid suspected of containing the nucleic acid of interest, which comprises in 3' to 5' order a first region, an extension region, and a second region, a template nucleic acid, which comprises in 3' to 5' order a first region, a first extension region, a second region, a second extension region and a third region, a first oligonucleotide that is at least partially complementary to the first region of the target nucleic acid, and a second oligonucleotide comprising a 5' region and a 3' region, wherein the 3' region is at least partially complementary to the second region of the target nucleic acid and wherein the 5' region is at least partially complementary to a region that may be upstream of, downstream of, or comprising the first region of the target nucleic acid and is at least partially complementary to the first region of the template nucleic acid; and a third oligonucleotide comprising a 5' region and a 3' region, wherein the 3' region is at least partially complementary to the second region of the template nucleic acid, and wherein the 5' region is at least partially complementary to a region that may be upstream of, downstream of, or comprising the first region of the template nucleic acid, and a fourth oligonucleotide comprising a 5' region and a 3' region, wherein the 3' region is at least partially complementary to the third region of the template nucleic acid, and wherein the 3' region of the third oligonucleotide is not identical in sequence to the 3' region of the fourth oligonucleotide, and wherein the 5' region of the fourth oligonucleotide is at least partially complementary to a region that may be upstream of, downstream of, or comprising the second region of the template nucleic acid.

Preferably, in any one of the compositions, the composition may further include either or both of a cleavage means which permits cleavage of a flap from a nucleic acid duplex structure, and a nucleic acid polymerizing activity.

A kit comprising any one of the compositions including a target nucleic acid as described hereinabove, and packaging materials therefore.

Preferably, the kit may further include either or both of a cleavage means which permits cleavage of a flap from a nucleic acid duplex structure, and a nucleic acid polymerizing activity.

In another aspect, the invention provides for a method of detecting a target nucleic acid by: providing a set of reagents, mixing the set of reagents, and detecting a signal (See FIG. 17). The method of the invention includes providing a target nucleic acid (FIG. 17; A'B'C'), a template nucleic acid (FIG. 17; H'G'F'), a first oligonucleotide (FIG. 17; A), a second oligonucleotide (FIG. 17; FC), a third oligonucleotide (FIG. 17; H), a cleavage means and a polymerization activity. The target and template nucleic acids have, in 3' to 5' order, a first region, an extension region, and a second region. The first oligonucleotide is at least partially complementary to the first region of the target nucleic acid. The second oligonucleotide's 3' region is at least partially complementary to the second region of the target nucleic acid and its 5' region is not complementary to the target nucleic acid but is at least partially complementary to the first region of the template nucleic acid. The third oligonucleotide's 3' region is at least partially complementary to the second region of the template nucleic acid and its 5' region is not complementary to the template nucleic acid.

The reagents are mixed under a series of reaction conditions that permit: formation of a duplex between the target and the first and second oligonucleotides, extension of the first oligonucleotide, cleavage of a first cleavage structure, formation of a second duplex, extension of a released flap, and formation of a second cleavage structure. The target nucleic acid, template nucleic acid, first oligonucleotide, second oligonucleotide, third oligonucleotide, cleavage means and polymerization activity are mixed under the series of reaction conditions. The reaction conditions permit formation of a duplex between the target nucleic acid and each of the first oligonucleotide and the 3' region of the second oligonucleotide (FIG. 17A). The 5' region of the second oligonucleotide forms a flap. The first oligonucleotide is extended by polymerization of a nucleic acid strand complementary to a length of the extension region of the target nucleic acid sufficient to form a first cleavage structure (FIG. 17B). The first cleavage structure is then cleaved within the second oligonucleotide by the cleavage means, thereby permitting release of the flap of the second oligonucleotide (FIG. 17C). A second duplex is formed with the released flap of the second oligonucleotide, the template nucleic acid, and the third oligonucleotide (FIG. 17D). The 5' region of the third oligonucleotide forms a second flap. The released flap is then extended by polymerization of a nucleic acid strand complementary to a length of the extension region of the template nucleic acid sufficient to form a second cleavage structure (FIG. 17E). The second cleavage structure is then cleaved within the third oligonucleotide by the cleavage means, thereby permitting release of the third oligonucleotide (FIG. 17F). The signal generated by the release of the third oligonucleotide from the template nucleic acid is detected.

In yet another aspect, the invention provides for a method of detecting a target nucleic acid by: providing a set of reagents, mixing the set of reagents, and detecting a signal. The method includes providing a target nucleic acid, a template nucleic acid, a first oligonucleotide, a second oligonucleotide, a third oligonucleotide, a cleavage means, and a polymerization activity. The target and template nucleic acids have, in 3' to 5' order, a first region, an extension region, and a second region. The first oligonucleotide is at least partially complementary to the first region of the target nucleic acid. The second oligonucleotide has a 3' region that is at least partially complementary to the second region of the target nucleic acid and a 5' region that is not complementary to the target nucleic acid but is at least partially complementary to the first region of the template nucleic acid. The third oligonucleotide includes a 3' region that is at least partially complementary to the second region of the template nucleic acid and a 5' region that is at least partially complementary to a region that is 3' of the second region.

The reagents are mixed under a series of reaction conditions that permit formation of a duplex between the target and the first and second oligonucleotides, extension of the first oligonucleotide, cleavage of a first cleavage structure, formation of a second duplex, extension of a released flap, and formation of a second cleavage structure. The target nucleic acid, template nucleic acid, first oligonucleotide, second oligonucleotide, third oligonucleotide, cleavage means and polymerization activity are mixed under the series of reaction conditions. The reaction conditions permit formation of a duplex between the target nucleic acid and each of the first oligonucleotide and the 3' region of the second oligonucleotide. The 5' region of the second oligonucleotide forms a flap. The first oligonucleotide is extended by polymerization of a nucleic acid strand complementary to a length of the extension region of the target nucleic acid sufficient to form a first cleavage structure. The first cleavage structure, within the second oligonucleotide, is cleaved by the cleavage means, thereby permitting release of the flap of the second oligonucleotide. A second duplex is formed with the released flap of the second oligonucleotide, the template nucleic acid, and the third oligonucleotide. The released flap is extended by polymerization of a nucleic acid strand complementary to a length of the extension region of the template nucleic acid sufficient to form a second cleavage structure. The second cleavage structure, within the third oligonucleotide, is then cleaved by the cleavage means, thereby permitting release of the third oligonucleotide. A signal generated by the release of the third oligonucleotide from the template nucleic acid is detected.

In either of the last two aspects of the invention, the polymerization activity and cleavage means may be present in a single enzyme. Such enzymes providing both activities include *E. coli* DNA polymerase I, T7 DNA polymerase, Tth DNA polymerase, or Taq DNA polymerase. In an alternative embodiment, the polymerization activity and cleavage means are each provided by a separate enzyme, e.g., a Pfu DNA polymerase and a FEN-1 nuclease. The polymerase activity is provided by a polymerase that may be a DNA polymerase and/or thermostable. The polymerase may lack a 5' to 3' exonuclease activity. The cleavage means can include a 5' nuclease activity. Such 5' nuclease activity is present in a FEN-1 nuclease. The FEN-1 nuclease may be a flap specific nuclease. In one embodiment, the FEN-1 nuclease is thermostable.

In yet another embodiment of either of the last two aspects of the invention, the series of reaction conditions are nucleic acid polymerization reaction conditions. In a further embodiment, the nucleic acid polymerization reaction conditions are polymerase chain reaction conditions.

In some embodiment, the cleavage structures are formed when the polymerized complementary nucleic acid is adjacent at its 3' end to the downstream oligonucleotide in the duplex. In another embodiment, the cleavage structures are formed when the extension regions are fully duplexed. In yet another embodiment, the cleavage structures are formed when the template strand of the extension region has a two, four, six, eight or ten nucleotide gap between the 3' end of the complementary polymerized nucleic acid and the downstream oligonucleotide.

In some embodiments of either of the last two aspects of the invention, the template nucleic acid is operably coupled to a first member of a pair of interactive labels and the third oligonucleotide is operably coupled to a second member of the pair of interactive labels. The first member may be operatively coupled to the 5' nucleotide of the template nucleic acid and the second member may be operatively coupled to the 3' nucleotide of the third oligonucleotide. In one embodiment, the pair of interactive levels is a fluorophore and a quencher. In the method of the invention, the signal may be detected by determining a change in fluorescence between the first and second members of the pair of interactive labels upon release of the third oligonucleotide.

In some embodiments of the invention, the second oligonucleotide is not detectably labeled. In yet another embodiment of the invention, the 5' portion of the second oligonucleotide is at least partially complementary to the 3' portion of the second oligonucleotide. In yet a further embodiment, the 3' portion and the 5' portion of the second oligonucleotide form a stem structure when the second oligonucleotide is not hybridize to the target nucleic acid. The second oligonucleotide may include a linker sequence between the 5' portion and the 3' portion of the second oligonucleotide. The linker portion may not be complementary to the target nucleic acid but can be complementary to the first portion of the template nucleic acid. The 3' nucleotide of the second oligonucleotide and/or the template nucleic acid may be blocked.

In yet another aspect of the invention, the invention is directed to a composition including a target nucleic acid, a template nucleic acid, a first oligonucleotide, a second oligonucleotide and a third oligonucleotide. The target and template nucleic acids have, in 3' to 5' order, a first region, an extension region, and a second region. The template nucleic acid has a first member of a pair of interactive labels. The first oligonucleotide is at least partially complementary to the first region of the target nucleic acid. The second oligonucleotide's 3' region is at least partially complementary to the second region of the target nucleic acid and its 5' region is not complementary to the target nucleic acid but is at least partially complementary to the first region of the template nucleic acid. The third oligonucleotide's 3' region is at least partially complementary to the second region of the template nucleic acid, while its 5' region is not complementary to the template nucleic acid. The third oligonucleotide is operatively coupled to a second member of the pair of interactive labels.

In yet another aspect, the invention is directed to a composition having a target nucleic acid, template nucleic acid, first oligonucleotide, second oligonucleotide and a third oligonucleotide. The target and template nucleic acids include, in 3' to 5' order, a first region, an extension region, and a second region. The template nucleic acid is operable coupled to a first member of a pair of interactive labels. The first oligonucleotide is at least partially complementary to the first region of the target nucleic acid. The second oligonucleotide's 3' region is at least partially complementary to the second region of the target nucleic acid and its 5' region is not complementary to the target nucleic acid but is at least partially complementary to the first region of the template nucleic acid. The third oligonucleotide's 3' region is at least partially complementary to the second region of the template nucleic acid and its 5' region is at least partially complementary to a region that is 3' of the second region of the template nucleic acid. The third oligonucleotide is operatively coupled to a second member of the pair of interactive labels.

In one embodiment of either of the last two aspects, the compositions further include a cleavage means. In yet a further embodiment, the compositions also include a polymerase. The polymerase and cleavage means may be present in a single enzyme. Such enzymes providing both activities include E. coli DNA polymerase I, T7 DNA polymerase, Tth DNA polymerase, or Taq DNA polymerase. In an alternative embodiment, the polymerization activity and cleavage means are each provided by a separate enzyme, e.g., a Pfu DNA polymerase and a FEN-1 nuclease. The polymerase activity is provided by a polymerase that may be a DNA polymerase and/or thermostable. The polymerase may lack a 5' to 3' exonuclease activity. The cleavage means can include a 5' nuclease activity. Such 5' nuclease activity is present in a FEN-1 nuclease. The FEN-1 nuclease may be a flap specific nuclease. The cleavage means may be a FEN-1 nuclease and the polymerase may be a Pfu DNA Polymerase.

In another embodiment of the compositions, the 3' nucleotide of the second oligonucleotide is blocked and/or the 3' nucleotide of the template nucleic acid is blocked. In some embodiments, the second oligonucleotide may not have a detectable label.

In some embodiments of either of the last two aspects of the invention, the pair of interactive labels includes a fluorophore and a quencher. In yet another embodiment, the second member of the pair of interactive labels is operatively coupled to the 3' nucleotide of the third oligonucleotide and/or the first member of the pair of interactive labels is operatively coupled to the 5' nucleotide of the template nucleic acid.

In yet another embodiment, the 5' portion of the second oligonucleotide is at least partially complementary to the 3' portion of the second oligonucleotide. In a further embodiment, the 3' portion and the 5' portion of the second oligonucleotide form a stem structure when the second oligonucleotide is not hybridize to the target nucleic acid. The second oligonucleotide may include a linker sequence between the 5' portion and the 3' portion of the second oligonucleotide. In some embodiments, the linker sequence is not complementary to the target nucleic acid but is complementary to the first portion of the template nucleic acid.

A kit comprising any one of the compositions as described hereinabove, and packaging materials therefore.

As used herein, a "target nucleic acid" refers to a polynucleotide which comprises in 3' to 5' order a first region that is complementary to at least a portion of a first oligonucleotide, an extension region and a second region that complementary to at least a portion of a second oligonucleotide. The target nucleic acid may comprise single or double-stranded DNA or RNA.

As used herein, a "first region" as it refers to a target nucleic acid, means a length of nucleotides sufficient to permit hybridization and extension of a first oligonucleotide wherein the "first region" is complementary to at least a portion of a first oligonucleotide, defined herein. A "first region" is in the range of about 6 nucleotides to about 1000 nucleotides in length, with a preferred range of about 8 to 30 nucleotides, and optimally, a range of 10 to 25 nucleotides.

As used herein, a "first region" as it refers to a template nucleic acid, described herein below, means a length of nucleotides sufficient to permit hybridization and extension of a released flap of a second oligonucleotide wherein the "first region" is complementary to at least a portion of a released flap of the second oligonucleotide, defined herein. A "first region" is in the range of about 6 nucleotides to about 1000 nucleotides in length, with a preferred range of about 8 to 30 nucleotides, and optimally, a range of 10 to 25 nucleotides.

As used herein, "extension region" refers to a length of nucleotides sufficient to permit extension of an oligonucleotide (e.g., a first oligonucleotide or the released flap of a second oligonucleotide) via a nucleic acid polymerization activity. An "extension region" of about 1 nucleotide to about 1000 nucleotides in length, with a preferred range of about 1-100 nucleotides, a more preferred range of 3 to 50, and optimally, a range of 3-10 nucleotides in length. An "extension region" is of a length that is sufficient such that a cleavage means according to the invention will not cleave a downstream oligonucleotide (e.g., a second oligonucleotide or third oligonucleotide) unless the upstream primer (e.g., a first oligonucleotide or the released flap of a second oligonucleotide, as defined herein) has been extended via polymerization of a nucleic acid complementary to the extension region such that the 3' end of the primer is close enough to the downstream oligonucleotide (i.e., that hybridizes to the second region) to permit cleavage of the flap (which is the 5' portion of the downstream oligonucleotide) by the cleavage means.

As used herein, a "second region" as it refers to a target nucleic acid, means a length of nucleotides that is sufficient to permit hybridization of a second oligonucleotide, wherein the "second region" is complementary to at least a portion of a second oligonucleotide, defined herein. A "second region" is in the range of about 6 nucleotides to about 1000 nucleotides in length, with a preferred range of about 8 to 30 nucleotides, and optimally, a range of 10 to 25 nucleotides.

As used herein, a "second region" as it refers to a template nucleic acid, described herein below, means a length of nucleotides that is sufficient to permit hybridization of a third oligonucleotide, wherein the "second region" is complementary to at least a portion of a third oligonucleotide, defined herein. A "second region" is in the range of about 6 nucleotides to about 1000 nucleotides in length, with a preferred range of about 8 to 30 nucleotides, and optimally, a range of 10 to 25 nucleotides.

As used herein, "at least a portion of", as it refers to a first, second, third or fourth oligonucleotide, means less than 100%, (e.g., 99%, 90%, 75%, 50%, 25% etc . . . ) of the nucleotides of the first, second, third or fourth oligonucleotide.

As used herein, a "template nucleic acid" refers to a polynucleotide which comprises in 3' to 5' order a first region that is complementary to at least a portion of the released flap of the second oligonucleotide, an extension region and a second region that is complementary to at least a portion of a third oligonucleotide. A "template nucleic acid" also refers to a polynucleotide which comprises in 3' to 5' order a first region that is complementary to at least a portion of the released flap of the second oligonucleotide, defined herein below, a first extension region, a second region that is complementary to at least a portion of a third oligonucleotide, a second extension region, and a third region that is complementary to at least a portion of a fourth oligonucleotide. The template nucleic acid may comprise single or double-stranded DNA or RNA or chemical modifications or unnatural variants of such.

As used herein, "oligonucleotide" refers to a nucleic acid comprising a region that is complementary to a target nucleic acid sequence and/or a template nucleic acid sequence.

As used herein, the term "oligonucleotide" also refers to primers, probes, and oligomer fragments to be detected, and shall be generic to polydeoxyribonucleotides (containing 2-deoxy-D-ribose), to polyribonucleotides (containing D-ribose), and to any other type of polynucleotide which is an N-glycoside of a purine or pyrimidine base, or modified purine or pyrimidine bases (including abasic sites). The term "oligonucleotide" includes double- and single-strand DNA, as well as double- and single-strand RNA. The term "oligonucleotide" intends a polynucleotide of genomic DNA or RNA, cDNA, semisynthetic, or synthetic origin which, by virtue of its synthetic origin or manipulation: (1) is not associated with all or a portion of the polynucleotide with which it is associated in nature; and/or (2) is linked to a polynucleotide other than that to which it is linked in nature. Where the oligonucleotide is used as a primer for the polymerizing activity to polymerize nucleotides from its 3' end complementary to the extension region, the oligonucleotide also may be referred to as a primer. An "oligonucleotide" according to the invention also refers to peptide nucleic acids (PNA) or hybrids of nucleic acids and peptide nucleic acids.

Oligonucleotides useful in the invention are generally in the range of about 8 nucleotides to about 200 nucleotides in length.

A "first oligonucleotide" according to the invention is preferably 6 to 100, more preferably 8 to 30 and most preferably 20 nucleotides in length. A "first" oligonucleotide is at least partially complementary to the target nucleic acid, and must be complementary to the target nucleic acid at a length of its 3' terminus sufficient to permit its use as a primer for nucleic acid synthesis using the target nucleic acid as a template.

A "second oligonucleotide" according to the invention is preferably 20-120, more preferably 25-45 and most preferably 35 nucleotides in length. A "second oligonucleotide" comprises a 3' and a 5' region. The 3' region of a "second oligonucleotide" is at least partially complementary to the target nucleic acid and is preferably 8-80 and most preferably 10-20 nucleotides. A 5' region of a "second oligonucleotide" is preferably 0 to 80 and most preferably 10 to 20 nucleotides in length for embodiments wherein a duplex structure comprises a preformed flap, or most preferably 0 to 20 nucleotides in length for embodiments wherein a flap is formed by the activity of a polymerization means that displaces at least 6 nucleotides. In one embodiment of the invention, a 5' region of a "second oligonucleotide" is at least partially complementary to a region of a target nucleic acid. In another embodiment of the invention, the 5' region of the second oligonucleotide according to the invention is not complementary to a target nucleic acid.

A "third oligonucleotide" and "fourth oligonucleotide" according to the invention are preferably 20-120, more preferably 25-45 and most preferably 35 nucleotides in length. A "third oligonucleotide" and "fourth oligonucleotide" comprise a 3' and a 5' region. Third and fourth oligonucleotides according to the invention comprise a 3' region that is at least partially complementary to a region of a template nucleic acid and is preferably 8 to 80 and most preferably 10-20 nucleotides. A 5' region of a "third oligonucleotide" or "fourth oligonucleotide" is preferably 0 to 80, most preferably 10 to 20 nucleotides in length for embodiments wherein a duplex structure comprises a preformed flap, or most preferably 0 to 20 nucleotides in length for embodiments wherein a flap is formed by the activity of a polymerization means that displaces at least 6 nucleotides. In an embodiment of the invention, a 5' region of a "third oligonucleotide" or "fourth oligonucleotide" is at least partially complementary to a region of a template nucleic acid. In another embodiment of the invention, the 5' region of the "third oligonucleotide" or "fourth oligonucleotide" according to the invention is not complementary to a template nucleic acid.

As used herein, an "upstream primer" according to the invention is preferably 6 to 100, more preferably 8 to 30 and most preferably 20 nucleotides in length. An "upstream primer" is at least partially complementary to the target nucleic acid and/or the template nucleic acid at a length of its 3' terminus sufficient to permit its use as a primer for nucleic acid synthesis using the target nucleic acid or the template nucleic acid as a template. An "upstream primer" according to the invention includes a "first oligonucleotide", as defined herein and a "released flap", as defined herein.

As used herein, a "downstream oligonucleotide" according to the invention is preferably 20-120, more preferably 25-45 and most preferably 35 nucleotides in length. A "downstream oligonucleotide" comprises a 3' and a 5' region. The 3' region of a downstream oligonucleotide is at least partially complementary to a target nucleic acid and/or a template nucleic acid. A 5' region of a "downstream oligonucleotide" is preferably 0 to 80 nucleotides in length, most preferably 10 to 20 nucleotides in length for embodiments wherein a duplex structure comprises a preformed flap, and most preferably 0 to 20 nucleotides in length for embodiments wherein a flap is formed by the strand displacement activity (of at least 6 nucleotides) of a polymerization means. In one embodiment, the 5' region of a "downstream oligonucleotide" is at least partially complementary to a region that may be upstream of, downstream of, or comprise any of the first or second region of a target nucleic acid, or any of the first, second or third region of a template nucleic acid. In one embodiment the 5' region of a "downstream oligonucleotide" is not complementary to a target nucleic acid or a template nucleic acid. A "downstream oligonucleotide" according to the invention includes a "first" and a "second" downstream oligonucleotide wherein a "second downstream oligonucleotide" is downstream of a "first downstream oligonucleotide". A "downstream oligonucleotide" according to the invention also includes a second, third or fourth oligonucleotide, as defined herein.

As used herein, "fully complementary" means that 100% of the nucleotides of an oligonucleotide can hydrogen bond to the corresponding complementary nucleotides of the target of template nucleic acid.

As used herein, "at least partially complementary" as it refers to an oligonucleotide, means that less than 100%, (e.g., 99%, 90%, 75%, 50%, 25% etc . . . ) of the nucleotides of the oligonucleotide can hybridize (that is form hydrogen bonds) with nucleotides of the target or template nucleic acid under standard stringent conditions. Where an oligonucleotide is "partially complementary", the region of complementary nucleotides may or may not be contiguous nucleotides.

For a "first oligonucleotide", as defined herein, (which also serves as a primer for nucleic acid synthesis), the 5' region of the oligonucleotide may contain non-complementary nucleotides (with respect to the target nucleic acid), and the 3' region of the oligonucleotide must comprise a region of complementarity with the target that is sufficient to permit formation of a hybrid with the target nucleic acid and nucleic acid synthesis from the 3' terminus of the first oligonucleotide using the target as the complementary strand. Nucleic acid synthesis refers to the addition of at least one nucleotide (for example a radiolabeled nucleotide (e.g., $^{35}$S or $^{32}$P labeled deoxyribonucleoside triphosphates (dNTPs)), preferably 1-10, and most preferably 1-250 nucleotides, to the 3' end of a nucleic acid molecule (for example as determined by a dideoxy sequencing reaction (according to methods well-known in the art) or in a labeling/termination sequencing reaction using modified T7 DNA polymerase (Sequenase™) (according to methods well known in the art). Alternatively, DNA synthesis is determined in a 3' end labeling reaction in the presence of a radiolabeled dNTP and a polymerase (e.g., the Klenow fragment of E. coli DNA polymerase I) (according to methods well known in the art). The amount of synthesis can be determined by measuring the size of the radiolabeled fragment by gel electrophoresis. In one embodiment, the 3' region of a first oligonucleotide comprises a region of complementarity with the target nucleic acid that includes a length of 10 nucleotides or greater (20, 30, 40, 50, etc.), over contiguous nucleotides (with respect to the target). In another embodiment, the 3' region of a first oligonucleotide comprises a region of complementarity with the target nucleic acid that includes a sufficient number of non-contiguous nucleotides, that are complementary with the target nucleic acid, to permit formation of a hybrid with the target nucleic acid and nucleic acid synthesis from the 3' terminus of the first oligonucleotide using the target as the complementary strand.

For a "second oligonucleotide", as defined herein, which does not serve as a primer for nucleic acid synthesis, but rather provides a flap at its 5' region, "partial complementarity" refers to a region of nucleotides of non-complementarity with respect to the target nucleic acid, followed by a region of sufficient complementarity to permit hydrogen bonding to the target nucleic acid under standard stringent conditions, wherein the second oligonucleotide is capable of forming a duplex and/or cleavage structure according to the invention. In one embodiment, the region of sufficient complementarity may be 10 contiguous nucleotides or longer (e.g., 20, 30, 40, 50, 100, etc.). In another embodiment, the region of sufficient complementarity includes a sufficient number of non-contiguous nucleotides, that are complementary with the target nucleic acid, to permit formation of a hybrid with the target nucleic acid. The 3' terminus of the "second oligonucleotide" can be but is not required to be complementary to the target nucleic acid. Where the 3' terminus is not complementary to the target nucleic acid (for example, in such instances where the 3' terminus is labeled and/or serves a function in detection of the hybridized or non/hybridized oligonucleotide), the region of non-complementary may or may not be contiguous. In one embodiment, the region of non-complementarity may be contiguous for 1 nucleotide, 2 nucleotides, 3, 4, 5 nucleotides, etc., or over a longer stretch of 10 or greater contiguous nucleotides (20, 30, 40, 50, etc.). In another embodiment, the region of non-complementarity includes a sufficient number of non-contiguous nucleotides that are non-complementary with the target nucleic acid.

A "first flap", "second flap", "third flap" or "fourth flap", or a "first released flap", "second released flap", "third released flap" or "fourth released flap", according to the invention, is preferably 6 to 80 and most preferably 10-25 nucleotides in length.

For a "released flap", as defined herein, which may serve as a primer for nucleic acid synthesis when hybridized to the template nucleic acid, the 5' region of the flap may contain non-complementary nucleotides (with respect to the template), however, the 3' terminus of the flap may or may not be complementary with the template. In one embodiment, the 3' terminus of the flap is complementary with the template for a length of 10 nucleotides or greater (20, 30, 40, 50, etc.), over contiguous nucleotides. In another embodiment, the 3' terminus of the flap comprises a region of complementarity with the template nucleic acid that includes a sufficient number of non-contiguous nucleotides that are complementary to the template nucleic acid. The region of complementarity must include a sufficient number of contiguous nucleotides to permit formation of a hybrid with the template nucleic acid and nucleic acid synthesis from the 3' terminus of the flap using the template as the complementary strand.

For a "third oligonucleotide", as defined herein, which does not serve as a primer for nucleic acid synthesis, but rather provides a flap at its 5' region, "partial complementarity" refers to a region of at least 10 contiguous nucleotides (20, 30, 40, 50 nucleotides, etc.) of non-complementarity with respect to the template nucleic acid, followed by a region of sufficient complementarity to permit hydrogen bonding to the template nucleic acid under standard stringent conditions. This region of sufficient complementarity may be 10 contiguous nucleotides or longer (e.g., 20, 30, 40, 50, 100, etc.). The 3' terminus of the "third oligonucleotide" can be but is not required to be complementary to the template nucleic acid. Where the 3' terminus is not complementary to the template nucleic acid (for example, in such instances where the 3' terminus is labeled and/or serves a function in detection of the hybridized or non/hybridized oligonucleotide), it may be non-complementary for 1 nucleotide, 2 nucleotides, 3, 4, 5 nucleotides, etc., or over a longer stretch of 10 or greater contiguous nucleotides (20, 30, 40, 50, etc.) so long as the complementarity of the third oligonucleotide with the template nucleic acid is not disrupted.

A "third oligonucleotide", as defined herein, may provide a 5' flap which may be cleaved and released from a cleavage structure, and also may serve as a primer for nucleic acid synthesis. Where the third oligonucleotides serves as a primer for nucleic acid synthesis, the 5' region of the oligonucleotide may contain non-complementary nucleotides (with respect to the template nucleic acid), but the 3' terminus of the oligonucleotide must be complementary, for a length of 10 nucleotides or greater (20, 30, 40, 50, etc.), over contiguous nucleotides (with respect to the template). The region of complementarity with the template must include a sufficient number of contiguous nucleotides to permit formation of a hybrid with the template nucleic acid and nucleic acid synthesis from the 3' terminus of the third oligonucleotide using the template as the complementary strand.

For a "fourth oligonucleotide", as defined herein, which does not serve as a primer for nucleic acid synthesis, but rather provides a flap at its 5' region, "partial complementarity" refers to a region of at least 10 contiguous nucleotides (20, 30, 40, 50 nucleotides, etc.) of non-complementarity with respect to the template nucleic acid, followed by a region of sufficient complementarity to permit hydrogen bonding to the template nucleic acid under standard stringent conditions. This region of sufficient complementarity may be 10 contiguous nucleotides or longer (e.g., 20, 30, 40, 50, 100, etc.). The 3' terminus of the "fourth oligonucleotide" can be but is not required to be complementary to the template nucleic acid. Where the 3' terminus is not complementary to the template nucleic acid (for example, in such instances where the 3' terminus is labeled and/or serves a function in detection of the hybridized or non/hybridized oligonucleotide), it may be non-complementary for 1 nucleotide, 2 nucleotides, 3, 4, 5 nucleotides, etc., or over a longer stretch of 10 or greater contiguous nucleotides (20, 30, 40, 50, etc.) so long as the complementarity of the fourth oligonucleotide with the template nucleic acid is not disrupted.

As used herein, "mixing" means combining, in any order.

As used herein, "conditions which permit formation of a duplex" refer to a buffer (i.e., of a specified salt and organic solvent concentration), a temperature, an incubation time, and the concentrations of the components of the duplex (for example a target nucleic acid, a first oligonucleotide and a second oligonucleotide) that are possible and preferably optimal for the formation of a duplex of the invention. For example, in one embodiment of the invention, under "conditions which permit formation of a duplex", a target nucleic acid, a first oligonucleotide and a second oligonucleotide will hybridize such that the 5' region of the second oligonucleotide is a flap and the extension region of the target nucleic acid is not hybridized to a first, second, third or fourth oligonucleotide (FIG. 2).

As used herein, "duplex" refers to a complex comprising a target or template nucleic acid, a first oligonucleotide or an upstream primer and at least a 3' region of a second oligonucleotide or a downstream oligonucleotide, wherein the complementary nucleotide bases of the target or template nucleic acid and each of the first oligonucleotide or upstream primer and, at least a 3' region of a second oligonucleotide or a downstream oligonucleotide are hybridized due to the formation of hydrogen bonds and where the "at least a portion of the extension region" is not hydrogen bonded to a first, second, third, fourth or downstream oligonucleotide, as defined herein.

As used herein, "first duplex" refers to a complex comprising a target or template nucleic acid, a first oligonucleotide and at least a 3' region of a second oligonucleotide, wherein the complementary nucleotide bases of the target or template nucleic acid and each of the first oligonucleotide and, at least a 3' region of a second oligonucleotide are hybridized due to the formation of hydrogen bonds, and wherein the 5' region of a second oligonucleotide and the extension region of the target nucleic acid are not complementary and thus do not form a hybrid in the duplex. The extension region may thus be single-stranded.

As used herein, "first duplex" also refers to a complex comprising a template nucleic acid, an upstream primer and at least a 3' region of a downstream oligonucleotide, wherein the complementary nucleotide bases of the template nucleic acid and each of the upstream primer and at least a 3' region of the downstream oligonucleotide are hybridized due to the formation of hydrogen bonds, wherein the 5' region of the downstream oligonucleotide is a flap.

As used herein, "first duplex" also refers to a complex comprising a template nucleic acid, an upstream primer, at least a 3' region of a first downstream oligonucleotide and at least a 3' region of a second downstream oligonucleotide, wherein the complementary nucleotide bases of the template nucleic acid and each of the upstream primer, the at least a 3' region of the first downstream oligonucleotide, and the at least a 3' region of the second downstream oligonucleotide are hybridized due to the formation of hydrogen bonds, wherein the 5' regions of each of the first and second downstream oligonucleotides are, independently, flaps.

As used herein, "second duplex" refers to a complex comprising a template nucleic acid, the released flap of the second oligonucleotide, and at least a 3' region of a third oligonucleotide, wherein the complementary nucleotide bases of the template nucleic acid and each of the released flap of the second oligonucleotide, and the at least a 3' region of a third oligonucleotide are hybridized due to the formation of hydrogen bonds with the template nucleic acid.

As used herein, "second duplex" refers to a complex comprising a template nucleic acid, the released flap of the second oligonucleotide, and at least a 3' region of a third oligonucleotide, wherein the complementary nucleotide bases of the target nucleic acid and each of the released flap of the second oligonucleotide, and the at least a 3' region of a third oligonucleotide are hybridized to the template due to the formation of hydrogen bonds, and wherein the 5' region of the third oligonucleotide and the extension region of the template nucleic acid are not complementary and thus do not form a hybrid in the duplex. The extension region thus may be single-stranded.

As used herein, "second duplex" also refers to a complex comprising a template nucleic acid, an upstream primer and at least a 3' region of a downstream oligonucleotide, wherein the complementary nucleotide bases of the template nucleic acid and each of the upstream primer and at least a 3' region of the downstream oligonucleotide are hybridized due to the formation of hydrogen bonds, wherein the 5' region of the downstream oligonucleotide is a flap.

As used herein, "second duplex" also refers to a complex comprising a template nucleic acid, the released flap of the second oligonucleotide, at least a 3' region of a third oligonucleotide, and at least a 3' region of a fourth oligonucleotide wherein the complementary nucleotide bases of the template nucleic acid and each of the released flap of the second oligonucleotide, the at least a 3' region of a third oligonucleotide, and the at least a 3' region of a fourth oligonucleotide are hybridized to the template due to the formation of hydrogen bonds.

As used herein, "second duplex" also refers to a complex comprising a template nucleic acid, the released flap of the second oligonucleotide, at least a 3' region of a third oligonucleotide, and at least a 3' region of a fourth oligonucleotide wherein the complementary nucleotide bases of the template nucleic acid and each of the released flap of the second oligonucleotide, the at least a 3' region of a third oligonucleotide, and the at least a 3' region of a fourth oligonucleotide are hybridized to the template due to the formation of hydrogen bonds, and wherein the 5' region of the third oligonucleotide and the 5' region of the fourth oligonucleotide are not hybridized to, respectively, the first and second extension regions of the template nucleic acid. Thus, the 3' region of the third oligonucleotide, the 3' region of the fourth oligonucleotide, and the first and second extension regions may be single-stranded in the duplex.

As used herein, "second duplex" also refers to a complex comprising a template nucleic acid, an upstream primer, at least a 3' region of a first downstream oligonucleotide and at least a 3' region of a second downstream oligonucleotide, wherein the complementary nucleotide bases of the template nucleic acid and each of the upstream primer, the at least a 3' region of the first downstream oligonucleotide, and the at least a 3' region of the second downstream oligonucleotide are hybridized due to the formation of hydrogen bonds, wherein the 5' regions of each of the first and second downstream oligonucleotides are, independently, flaps.

A "flap" or a "arm" of a branched DNA or DNA/RNA hybrid, refers to a 5' polynucleotide that is not hydrogen-bonded to the branched DNA or hybrid DNA/RNA, but is phosphate-bonded to a hydrogen-bonded member of the branched DNA or DNA/RNA hybrid. A flap thus is a nucleic acid strand which hangs off of (i.e., is the branch off of) a double stranded portion of the structure. A "flap" of a cleavage structure according to the invention is preferably about 1-80 nucleotides, more preferably about 5-25 nucleotides and most preferably about 10-20 nucleotides, and is preferably cleaved at a position located at the phosphate positioned at the "elbow" of the branched structure or at any of one to ten phosphates located proximal and/or distal to the elbow of the flap strand. The cleavage position depends on whether the polymerization means possesses or lacks endonucleolytic activity. As used herein, "elbow" refers to the phosphate bond between the first single stranded nucleotide of the 5' flap and the first double stranded (e.g., hybridized to the target or template nucleic acid) nucleotide. A "flap", according to the invention can be labeled with a detectable label. A "flap" or "arm" according to the invention is cleaved by a cleavage means when it is part of a "cleavage structure", as defined herein, and is released to form a "released arm" which may be single-stranded (i.e., have no double-stranded structure), or may simple be a single strand nucleic acid which contains internal complementarity or is duplexed with another nucleic acid strand that is not phosphate bonded to the branched DNA or DNA/RNA hybrid. In those instances wherein the "released flap" serves as a primer for nucleic acid synthesis, the "released flap" is preferably 6 to 80 and most preferably 10-25 nucleotides in length. In those embodiments wherein the flap is strand displaced (i.e., is not a preformed flap), there may be less than a substantial overlap between the upstream primer and the downstream oligonucleotides. As used herein, "less than a substantial overlap" means an overlap length that permits formation of a "released flap" that is at least 6 nucleotides in length and can serve as a primer for nucleic acid synthesis.

The term "single strand", with respect to a nucleic acid, refers to one polynucleotide strand which may not be hydrogen-bonded to any other nucleic acid, or it may be hydrogen-bonded internally to itself (to form a secondary or tertiary structure) or to another nucleic acid molecule.

The term "single-stranded", with respect to a nucleic acid, refers to a polynucleotide strand which is not hydrogen-bonded to another nucleic acid, and which preferably contains no or little (less than 10%, for example 9%, 5%, 4%, etc. . . .) internal complementarity.

As used herein, "extension" refers to the addition of nucleoside triphosphates to the 3' end of a first oligonucleotide or the released single-stranded arm of the second oligonucleotide in a conventional DNA polymerization reaction. Thus, the 3' end of the first oligonucleotide and the 3' end of the released single-stranded arm of the second oligonucleotide are not blocked, and are also referred to herein as primers.

Generally the 3' terminus of the template, and the second, third and fourth oligonucleotides will be "blocked" to prohibit creation of an extension product. "Blocking" can be achieved by using non-complementary bases or by adding a chemical moiety such as biotin or a phosphate group to the 3' hydroxyl of the last nucleotide. Blocking can also be achieved by removing the 3'-OH or by using a nucleotide that lacks a 3'-OH such as dideoxynucleotide, or by other methods known to one skilled in the art.

As used herein, "nucleic acid polymerization activity" refers to an enzyme that catalyzes the polymerization of nucleoside triphosphates. Generally, the enzyme will initiate synthesis at the 3'-end of the primer annealed to the target sequence, and will proceed in the 5'-direction along the template, and if possessing a 5' to 3' nuclease activity, hydrolyze intervening, annealed probe to release both labeled and unlabeled probe fragments, until synthesis terminates. Known DNA polymerases include, for example, *E. coli* DNA polymerase I, T7 DNA polymerase, *Thermus thermophilus* (Tth) DNA polymerase, *Bacillus stearothermophilus* DNA polymerase, *Thermococcus litoralis* DNA polymerase, *Thermus aquaticus* (Taq) DNA polymerase and *Pyrococcus furiosus* (Pfu) DNA polymerase. If the nucleic acid template is RNA, then "nucleic acid polymerization activity" refers to an RNA-dependent polymerization activity, such as reverse transcriptase.

As used herein, "5' to 3' exonuclease activity" or "5'→3' exonuclease activity" refers to that activity of a template-specific nucleic acid polymerase e.g. a 5'→3' exonuclease activity traditionally associated with some DNA polymerases whereby mononucleotides or oligonucleotides are removed from the 5' end of a polynucleotide in a sequential manner, (i.e., *E. coli* DNA polymerase I has this activity whereas the Klenow (Klenow et al., 1970, Proc. Natl. Acad. Sci., USA, 65:168) fragment does not, (Klenow et al., 1971, Eur. J. Biochem., 22:371)), or polynucleotides are removed from the 5' end by an endonucleolytic activity that may be inherently present in a 5' to 3' exonuclease activity.

As used herein, the phrase "substantially lacks 5' to 3'exonuclease activity" or "substantially lacks 5'→3' exonuclease activity" means having less than 10%, 5%, 1%, 0.5%, or 0.1% of the activity of a wild type enzyme. The phrase "lacking 5' to 3' exonuclease activity" or "lacking 5'→3' exonuclease activity" means having undetectable 5' to 3' exonuclease activity or having less than about 1%, 0.5%, or 0.1% of the 5' to 3' exonuclease activity of a wild type enzyme. 5' to 3' exonuclease activity may be measured by an exonuclease assay which includes the steps of cleaving a nicked substrate in the presence of an appropriate buffer, for example 10 mM Tris-HCl (pH 8.0), 10 mM $MgCl_2$ and 50 µg/ml bovine serum albumin) for 30 minutes at 60° C., terminating the cleavage reaction by the addition of 95% formamide containing 10 mM EDTA and 1 mg/ml bromophenol blue, and detecting nicked or un-nicked product.

According to methods of the invention that include two polymerization steps, each of the polymerization steps can be performed by the same nucleic acid polymerization activity or by different nucleic acid polymerization activities.

As used herein, "polymerization", "polymerization activity" or "polymerase acitivity" refers to the addition of nucleoside triphosphates to the 3' end of an oligonucleotide wherein the 3' end of the oligonucleotide is not blocked.

As used herein, "nucleoside" refers to any purine or pyrimidine base, or modified purine or pyrimidine base, linked to a sugar (e.g. 2-deoxyribose in DNA or ribose in RNA).

As used herein, "nucleotide" refers to any purine or pyrimidine base, or modified purine or pyrimidine base, linked to a sugar, wherein the sugar is linked to a phosphate group.

As used herein, "polymerase chain reaction" or "PCR" refers to an in vitro method for amplifying a specific polynucleotide template sequence. The PCR reaction involves a repetitive series of temperature cycles and is typically performed in a volume of 50-100 µl. The reaction mix comprises dNTPs (each of the four deoxyribonucleotides dATP, dCTP, dGTP, and dTTP), primers, buffers, DNA polymerase, and polynucleotide template. One PCR reaction may consist of 5 to 100 "cycles" of denaturation and synthesis of a polynucleotide molecule. The PCR process is described in U.S. Pat. Nos. 4,683,195 and 4,683,202, the disclosures of which are incorporated herein by reference.

As used herein, "polymerase chain reaction conditions" or "PCR conditions" refer to a buffer, a set of temperature incubation steps and times that are possible and preferably optimal for conducting PCR. The set of temperature incubation steps and times preferably allow for denaturation, annealing, and extension of the nucleic acids of the invention. PCR reaction conditions are known in the art and described herein.

A "nucleic acid amplification reaction" means an increase in number of a particular nucleic acid sequence and may be accomplished, without limitation, by the in vitro methods of polymerase chain reaction or ligase chain reaction.

As used herein, "nucleic acid amplification reaction conditions" refer to a buffer, a set of temperature incubation steps and times that are possible and preferably optimal for conducting amplification of a nucleic acid. Amplification means an increase in the number of a particular nucleic acid sequence and may be accomplished, without limitation, by the in vitro methods of polymerase chain reaction or ligase chain reaction. Such reaction conditions are known in the art and are described herein. Nucleic acid reaction conditions encompass PCR conditions.

A "nucleic acid amplification reaction mixture" refers to a mixture comprising the components necessary for nucleic acid amplification, such as buffer, dNTPs, water, a target nucleic acid, and a polymerase. Depending on methods for nucleic acid amplification, the necessary components may differ. For example, ligase chain reactions require the presence of a ligase, which may not be needed in certain polymerase chain reactions.

As used herein, a "cleavage structure" refers to a polynucleotide structure comprising at least a duplex nucleic acid having a flap. A "cleavage structure" according to the invention preferably comprises a target nucleic acid sequence or a template nucleic acid sequence, and also includes an upstream oligonucleotide that is at least partially and may be fully complementary to the target sequence (for example, A in FIG. 2 or F in FIG. 5), and a downstream oligonucleotide that is complementary to the target sequence and comprises a flap (for example FC or FH in FIG. 2 or FH1 or FH2 in FIG. 5). In one embodiment, a "first cleavage structure" is formed by polymerization from the 3' end of the upstream oligonucleotide (primer) through the extension region to the duplex formed by hydrogen bonding of the downstream oligonucleotide and the target or template nucleic acid (i.e., at the junction of the duplex and the flap). In another embodiment, a "second cleavage structure" is formed by polymerization from the 3' end of the upstream oligonucleotide (primer) (i.e., the released arm of the second oligonucleotide) through the extension region to the duplex formed by hydrogen bonding of the downstream third oligonucleotide (or first downstream oligonucleotide) and the template nucleic acid (i.e., at the junction of the duplex and the flap). A "second cleavage structure" also refers to a cleavage structure wherein polymerization has occurred from the 3' end of the second oligonucleotide to the duplex formed by hydrogen bonding of the downstream fourth oligonucleotide (or second downstream oligonucleotide) and the template nucleic acid (i.e., at the junction of the duplex and the flap). Preferably, the 3' terminus of the upstream oligonucleotide is blocked; blocking the terminus prevents extension of the 3' end of the upstream oligonucleotide.

In a "cleavage structure" according to the invention, polymerization (i.e., from the 3' end of a primer through an extension region to the duplex formed by hydrogen bonding of the downstream oligonucleotide to the target or template nucleic acid) may continue either partially or completely through the extension region.

Alternatively, in some reactions the polymerization may continue either partially or completely through regions 5' to the extension region (e.g., second region of a template nucleic acid or target nucleic acid). In such reactions the downstream probe (e.g., second or third oligonucleotide) may be cleaved such that the downstream probe no longer stable hybridizes with the template or target nucleic acid.

In those reactions where polymerization continues partially through the extension region, the newly polymerized nucleic acid must reach "close enough" to the duplex formed by the hydrogen bonding of the downstream oligonucleotide and target or template nucleic acid (i.e., the three-way flap junction region) so as to form a "cleavage structure") so as to permit cleavage and release of the flap from the cleavage structure. That is, the length of extension region which is rendered double-stranded via polymerization from the 3' end of the upstream primer must be "sufficient" to form a "cleavage structure" and to permit cleavage of the flap by the cleavage means.

Thus, the term "close enough" for the newly polymerized nucleic acid's proximity to the three-way junction formed by the flap, the downstream oligonucleotide to which the flap is phosphate bonded, and the target or template nucleic acid to which the oligonucleotide is hydrogen bonded, as well as the term "length of extension region" "sufficient to permit cleavage", refers to a nucleotide distance (between the 3' end of the newly-synthesized strand and the first nucleotide that is duplexed in the three-way junction) of no greater than 50 nucleotides and preferably 10 nucleotides or less, such as 6 nucleotides, 4 nucleotides, 2 nucleotides, 1 nucleotide, or no nucleotides. However, should a flap cleavage enzyme be discovered or developed which cleaves in the presence of a gap of greater than 50 nucleotides, (e.g., 100 nucleotides or more) the invention contemplates encompassing such a gap length.

As used herein, the alternative term "adjacent to" also may be used.

In those reactions where polymerization of a newly synthesized nucleic acid continues completely through the extension region, the distance referred to above would of course be no nucleotides. Alternatively, in some reactions where the cleavage structure contains a template nucleic acid comprising first and second extension regions, a primer (cleaved and released flap), and third and fourth oligonucleotides, where the third oligonucleotide forms a hybrid with the region of the template strand that is between the first and second extension regions and the fourth oligonucleotide forms a hybrid with the template region downstream of the second extension region, the polymerase activity may continue through the first extension region and displace the third oligonucleotide as it continues through the template second region, fully displacing the third oligonucleotide, and continuing synthesis partially or completely through the second extension region until the 3' end of the newly synthesized nucleic acid comes "close enough" to the three-way junction of the 5' flap of the fourth oligonucleotide, the 3' portion of the fourth oligonucleotide which is hydrogen bonded to the template nucleic acid to permit cleavage and release of the flap from the fourth oligonucleotide.

Thus, a "cleavage structure" according to the invention may be an upstream primer which is hybridized to a template nucleic acid, and a downstream oligonucleotide which includes a flap which is the 5' portion of the downstream oligonucleotide. In this embodiment of the invention, the upstream and downstream oligonucleotides (e.g., A and FC of FIG. 2) may be non-overlapping. In those embodiments wherein the flap is strand displaced (i.e., is not a preformed flap), there may be less than a substantial overlap between the upstream and downstream oligonucleotides. The invention also provides for upstream and downstream oligonucleotides wherein one or both of the oligonucleotides is completely complementary to an extension region.

In forming a "cleavage structure" according to the invention, transitional structures may be formed, such as a polynucleotide structure comprising a loop, a pseudo-Y structure, a single-stranded bubble, a D-loop, a nick or a gap.

A "cleavage structure", as used herein, includes a 5' flap and would not encompass a structure which does not include a 5' flap, for example, a double stranded nucleic acid which contains only a 3' flap. As used herein, a "cleavage structure" comprises ribonucleotides or deoxyribonucleotides and thus can be RNA or DNA.

As used herein a "cleavage means" refers to an agent, preferably an enzyme, that is specific for, that is, cleaves a cleavage structure according to the invention.

In one embodiment of the invention wherein the cleavage means is used in combination with a nucleic acid polymerization activity that has strand displacement activity, or is itself a nucleic acid polymerization activity that has strand displacement activity, the cleavage means will not cleave a cleavage structure unless the cleavage product, that is, the released flap, is of a length that is sufficient to permit hybridization of the released flap to a template nucleic acid and extension of the released flap by polymerization.

The term "cleavage means" includes an enzyme that possesses 5' endonucleolytic activity for example a DNA polymerase, e.g. DNA polymerase I from *E. coli*, and DNA polymerase from *Thermus aquaticus* (Taq), *Thermus thermophilus* (Tth), and *Thermus flavus* (Tfl). The term "cleavage means" includes agents that cleave a cleavage structure according to the invention comprising an extension region single stranded gap (that is a portion of the extension region that is unhybrized to an upstream primer and/or a downstream probe) of 0-2 nucleotides, 2-20 nucleotides, 20-50 nucleotides or more than 50 nucleotides. The term "cleavage means" also embodies FEN nucleases. The term "FEN nuclease" encompasses an enzyme that possesses 5' exonuclease and/or an endonuclease activity. The term "FEN nuclease" also embodies a 5' flap-specific nuclease. The term "cleavage means" includes a FEN nuclease that cleaves a cleavage structure according to the invention comprising an extension region single stranded gap (that is a portion of the extension region that is unhybrized to an upstream primer and/or a downstream probe) of 0-2 nucleotides, 2-20 nucleotides, 20-50 nucleotides or more than 50 nucleotides.

A "cleavage means" according to the invention includes but is not limited to a FEN nuclease enzyme derived from *Archaeglobus fulgidus, Methanococcus jannaschii, Pyrococcus furiosus*, human, mouse or *Xenopus laevis*. A nuclease according to the invention also includes *Saccharomyces cerevisiae* RAD27, and *Schizosaccharomyces pombe* RAD2, Pol I DNA polymerase associated 5' to 3' exonuclease domain, (e.g. *E. coli, Thermus aquaticus* (Taq), *Thermus flavus* (Tfl), *Bacillus caldotenax* (Bca), *Streptococcus pneumoniae*) and phage functional homologs of FEN including but not limited to T5 5' to 3' exonuclease, T7 gene 6 exonuclease and T3 gene 6 exonuclease. Preferably, only the 5' to 3' exonuclease domains of Taq, Tfl and Bca FEN nuclease are used. A "cleavage means" according to the invention also includes an agent, preferably an enzyme, that cleaves a cleavage structure according to the invention comprising an RNA/DNA complex wherein the RNA is the template or target nucleic acid. The term "cleavage means" does not include RNAse H.

"Cleavage means" also includes enzymes that can cleave a cleavage structure comprising an upstream oligonucleotide (for example A, FIG. 2) and one or more downstream oligonucleotides (for example (FC, FIG. 2) wherein polymerization has occurred from the 3' end of the upstream oligonucleotide such that the extended 3' end of the upstream oligonucleotide is adjacent to the flap of the downstream oligonucleotide (for example F, FIG. 2).

As used herein, "adjacent" refers to separated by less than 20 nucleotides, e.g., 15 nucleotides, 10 nucleotides, 5 nucleotides, or 0 nucleotides.

"Cleavage means" also includes enzymes that can cleave a cleavage structure comprising an upstream oligonucleotide (for example A, FIG. 2) and one or more downstream oligonucleotides (for example (FC, FIG. 2) wherein polymerization has occurred from the 3' end of the upstream oligonucleotide such that the extended 3' end of the upstream oligonucleotide is less than 50 nucleotides from the flap of the downstream oligonucleotide (for example F, FIG. 2). According to this embodiment of the invention, the distance between the 3' end of the upstream oligonucleotide across the extension region and sufficiently close to the junction of the flap of the downstream oligonucleotide is of a length that permits a sufficient amount of polymerization to occur from the 3' end of the upstream oligonucleotide to form a cleavage structure according to the invention.

According to methods of the invention that include two cleavage steps, each of the cleavage steps can be performed by the same cleavage means or by a different cleavage means.

A "cleavage means" according to the invention can be a single enzyme that possesses both polymerase and nuclease activity or an enzyme that possesses nuclease activity but lacks polymerase activity.

As used herein, "permitting" means allowing a reaction to proceed such that a duplex or a second duplex, as defined herein, is formed if all of the components required for duplex formation (e.g., the first and second oligonucleotide and the target nucleic acid, or the released flap of the second oligonucleotide, the template nucleic acid and the third oligonucleotide) are present. "Permitting" also means adding any required components (e.g., the released flap of the second oligonucleotide) to a mixture comprising the template and the third oligonucleotide, and allowing the reaction to proceed such that a "second duplex", as defined herein, is formed. "Permitting" also means adding any required components (e.g., the released flap of the second oligonucleotide) to a mixture comprising the template the third oligonucleotide, and the fourth oligonucleotide, and allowing the reaction to proceed such that a "second duplex", as defined herein, is formed. "Permitting" also means adding any required components (e.g., template and third oligonucleotide) to the released flap of the second oligonucleotide and allowing the reaction to proceed such that a duplex or a second duplex, as defined herein, is formed.

As used herein, "detecting a target nucleic acid sequence" or "measuring a target nucleic acid sequence" refers to determining the presence of a particular target nucleic acid sequence in a sample or determining the amount of a particular target nucleic acid sequence in a sample as an indication of the presence of a target nucleic acid sequence in a sample. The amount of a target nucleic acid sequence that can be measured or detected is preferably about 1 molecule to $10^{20}$ molecules, more preferably about 100 molecules to $10^{17}$ molecules and most preferably about 1000 molecules to $10^{14}$ molecules. According to one embodiment of the invention, the detected nucleic acid is derived from the labeled 5' end of at least one of a first, second or third flaps, defined herein (for example F in FIGS. 2 and 5). According to the present invention, a label is attached to the 5' end of at least one of a second, third or fourth oligonucleotide, defined herein (for example FC, FH1 or FH2 in FIGS. 2 and 5). Alternatively, a label is attached to the 3' end at least one of a second, third or fourth oligonucleotide, defined herein (for example FC, FH1 or FH2 in FIGS. 2 and 5) and a quencher is attached to the 5' end at least one of a second, third or fourth oligonucleotide. According to the invention, a label may be attached to the 3' end at least one of a second, third or fourth oligonucleotide comprising a cleavage structure according to the invention. In another embodiment, the detected nucleic acid is derived from the unlabeled released flap and the released flap is detected by gel electrophoresis or by hybridization according to methods well know in the art.

In another embodiment, the detected nucleic acid is derived from a fragment of the third oligonucleotide, defined herein (for example H in FIG. 17). According to this embodiment, a label is operably coupled to the 3' end, 5' end or an internal region of a third oligonucleotide and a quencher is operably coupled to a template nucleic acid.

In yet another embodiment, the detected nucleic acid is derived from a fragment of a template nucleic acid. According to the present invention, a label is operably coupled to the 5' end, 3' end or an internal region of the template nucleic acid and a quencher is operably coupled to a third oligonucleotide. A quencher is operably coupled to an oligonucleotide of the invention so as to inhibit the detectable signal when the template nucleic acid and third oligonucleotide are hybridized to each other. In one embodiment, the label is one member or moiety of a pair of interactive labels. In this embodiment, the pair of interactive labels interact when the third oligonucleotide and template nucleic acid hybridize and produce a detectable signal, e.g., increase in fluorescence, when the third oligonucleotide and template nucleic acid are not hybridized, e.g., after the third oligonucleotide is cleaved and disassociates from the template nucleic acid.

According to the invention, an oligonucleotide according to the invention (e.g., a first, second, third fourth oligonucleotide or a template nucleic acid) can be labelled by attaching a label to the 5' end, the 3' end or by labelling the oligonucleotide internally.

In another embodiment, the probe is labeled with a pair of interactive labels (e.g., a FRET or non-FRET pair) positioned to permit the separation of the labels during oligonucleotide probe unfolding (e.g., for example due to hybridization to a target or template nucleic acid, or due to a change in the secondary structure of the probe, as defined hereinbelow, or hydrolysis.

In another embodiment, the probe and template nucleic acid are each labeled with one member of a pair of interactive labels (e.g., a FRET or non-FRET pair). The members of the interactive pair of labels interact when the probe (e.g., third oligonucleotide) and the template nucleic acid hybridize. Separation of the probe and template nucleic acid (e.g., cleavage of the probe) generates a detectable signal (e.g. fluorescence). The pair of interactive labels may be placed anywhere along the third oligonucleotide and template nucleic acid so long as the pair of interactive labels interact when hybridized and produce a detectable signal when they are not hybridized As used herein "detection of a signal generated by the release of a third oligonucleotide" refers to determining the presence of a cleaved labeled third oligonucleotide in a sample or determining the amount of the cleaved labeled third oligonucleotide. Methods well known in the art and described herein can be used to detect or measure the release of the labelled third oligonucleotide. The presence or amount of a cleaved labelled third oligonucleotide may be determined by detecting a change in fluorescence. For example, upon cleavage of the third oligonucleotide and separation of the pair of interactive labels present on the third oligonucleotide and a template nucleic acid. The detection methods described herein are operative for detecting a released third oligonucleotide wherein any amount of a released third oligonucleotide is detected whether that be a small or large proportion of the released third oligonucleotides generated in the reaction. A method of detecting or measuring release of the third oligonucleotide will be appropriate for measuring or detecting the labelled moiety that is present on the released third oligonucleotide or on the template nucleic acid.

As used in at least one embodiment, "detecting at least one of the released first and second flaps" or "detecting release of at least one of the first, second and third flaps" refers to determining the presence of a labelled or unlabeled flap in a sample or determining the amount of a labelled or unlabeled flap in a sample. Methods well known in the art and described herein can be used to detect or measure release of labelled or unlabeled flaps. The detection methods described herein are operative for detecting a flap wherein any amount of a flap is detected whether that be a small or large proportion of the flaps generated in the reaction. A method of detecting or measuring release of labelled flaps will be appropriate for measuring or detecting the labelled moiety that is present on the labelled flap. Methods of detecting or measuring release of unlabeled flaps include, for example, gel electrophoresis or by hybridization, according to methods well known in the art. The detection methods described herein are operative when as little as 1 or 2 molecules (and up to 1 or 2 million, for example 10, 100, 1000, 10,000, 1 million) of released flap are detected.

As used herein, "labelled flaps" refers to cleaved mononucleotides or small oligonucleotides or oligonucleotides derived from the labelled cleavage structure according to the invention wherein the cleaved oligonucleotides are preferably between about 6-80 nucleotides, and more preferably between 10-25 nucleotides, which are cleaved from a cleavage structure by a nuclease and can be detected by methods well known in the art and described herein.

In a preferred embodiment, the first and second flaps comprise an identical sequence.

In another preferred embodiment, the first and second flaps comprise non-identical sequences.

In another preferred embodiment, the first oligonucleotide and the second oligonucleotide hybridize to non-overlapping regions of the target nucleic acid, and the released flap of the second oligonucleotide and the third oligonucleotide hybridize to non-overlapping regions of the template nucleic acid.

In a preferred embodiment, the first, second and third flaps comprise an identical sequence.

In another preferred embodiment, the first and second flaps comprise an identical sequence.

In another preferred embodiment, the first and third flaps comprise an identical sequence.

In another preferred embodiment, the first flap comprises a sequence that is not identical to either of the second or third flaps.

In another preferred embodiment, the first and second oligonucleotides hybridize to non-overlapping regions of the target nucleic acid, and each of the released first flap of the second oligonucleotide, the third oligonucleotide and the fourth oligonucleotide hybridize to non-overlapping regions of the template nucleic acid.

As used herein, "non-overlapping" means that if two oligonucleotides are hybridized to the target (or template) nucleic acid, then the two oligonucleotides will not compete with each other with respect to hybridization with the target (or template) nucleic acid. Thus, the two respective hybridization regions of the target (or template) nucleic acid do not involve one or more nucleotides in common.

In another preferred embodiment, the cleavage means comprises a 5' nuclease activity for which cleavage of a flap from a cleavage structure is dependent upon the formation of duplex DNA the site of cleavage.

In another preferred embodiment, the cleavage means comprises a FEN-1 nuclease.

In another preferred embodiment, the polymerization activity comprises strand displacement activity.

Nucleic acid polymerases exhibiting strand displacement activity and useful according to the invention include but are not limited to archaeal DNA polymerases with "temperature activated" strand displacement activity (exo plus and exo minus versions of Vent, Deep Vent, Pfu, JDF-3, KOD (LTI's tradename Pfx), Pwo, 9 degrees North, *Thermococcus aggregans, Thermococcus gorgonarius*), and eubacterial DNA polymerases with strand displacement activity (exo minus Bst, exo minus Bca, Genta, Klenow fragment, exo minus Klenow fragment exo minus T7 DNA polymerase (Sequenase).

In another preferred embodiment, the method is carried out isothermally.

As used herein, "isothermally" refers to a temperature that supports, and is preferably optimal, for the activity of a cleavage means and a polymerization means according to the invention.

In another preferred embodiment, the method is carried out under a series of reaction conditions.

As used herein, "a series of reaction conditions" refers to two or more temperature incubations that are optimal for the steps of duplex formation, polymerization and cleavage according to the invention. For example, a series of reaction conditions include PCR reaction and nucleic acid reaction conditions.

In another preferred embodiment, a single enzyme comprises a polymerization activity and a cleavage means.

In another preferred embodiment, a single enzyme comprising a polymerization activity and a cleavage means is selected from the group consisting of *E. coli* DNA polymerase I, T7 DNA polymerase, Tth DNA polymerase, or Taq DNA polymerase.

In another preferred embodiment, a first enzyme comprises a polymerization activity and a second enzyme comprises a cleavage means.

In another preferred embodiment, the first enzyme comprises *Thermus thermophilus* DNA pol or Reverse transcriptase and the second enzyme comprises a FEN-1 nuclease.

Further features and advantages of the invention will become more fully apparent in the following description of the embodiments and drawings thereof, and from the claims.

BRIEF DESCRIPTION OF DRAWINGS

FIG. 9 demonstrates secondary structures.

FIG. 16 is an autoradiograph of a FEN-1 nuclease assay.

FIG. 17A-E illustrates one embodiment of the invention utilizing a labeled third oligonucleotide and template nucleic acid FIG. 17A illustrates the formation of a first duplex.

FIG. 17B illustrates the polymerization or extension step of the first duplex.

FIG. 17C illustrates the cleavage of the first duplex.

FIG. 17D illustrates the formation of the second duplex.

FIG. 17E illustrates the polymerization or extension step of the second duplex.

FIG. 17F illustrates the cleavage and detection steps of the second duplex.

DESCRIPTION

Figure 1:
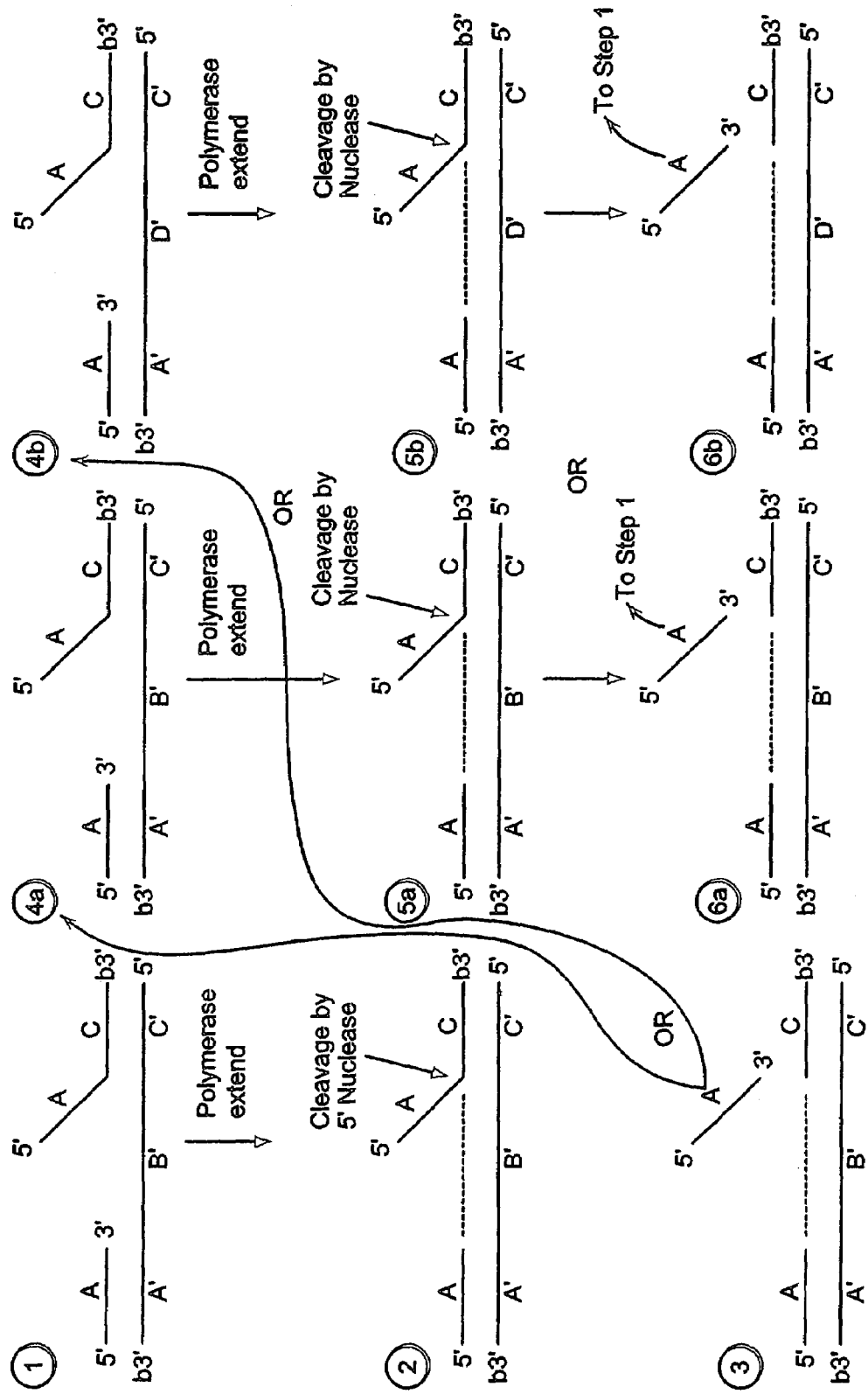
FIG. 1 is a representation of linear amplification of a template nucleic acid sequence.

The invention provides a method wherein, a target nucleic acid is detected by sequentially forming and cleaving a first cleavage structure comprising a target nucleic acid, and a first and second oligonucleotide. The first cleavage structure is formed when the first and second oligonucleotides hybridize to the target nucleic acid and the first oligonucleotide is extended by a polymerase. A 5' flap of the second oligonucleotide is cleaved and released, serving as a primer in a second cleavage structure. The second cleavage structure comprises a template nucleic acid, the released flap of the second oligonucleotide and a third oligonucleotide. The second cleavage structure is formed when the released flap and third oligonucleotide hybridize to the template nucleic acid and the released flap is extended by a polymerase. The third oligonucleotide is cleaved which causes the disassociation of the third oligonucleotide from the template nucleic acid. The presence and/or amount of the target nucleic acid is determined by detecting the cleavage and subsequent release of the third oligonucleotide from the template nucleic acid.

The invention also provides a method wherein a target nucleic acid is detected by linear amplification by sequentially forming and cleaving a first cleavage structure comprising a target nucleic acid, and a first and second oligonucleotide, wherein the cleavage reaction releases the flap of the second oligonucleotide; and forming and cleaving a second cleavage structure comprising a template nucleic acid, the released flap of the second oligonucleotide and a third oligonucleotide, wherein the cleavage reaction releases the flap of the third oligonucleotide. The presence and/or amount of a target nucleic acid is determined by detecting the released first and/or second flaps, wherein there is a 1:1 ratio of released first flap to released second flap.

The invention also provides for an exponential amplification method for detection of a target nucleic acid. A target nucleic acid is detected by exponential amplification by sequentially forming and cleaving a first cleavage structure comprising a target nucleic acid, and a first and second oligonucleotide, wherein the cleavage reaction releases the flap of the second oligonucleotide; and forming and cleaving a second cleavage structure comprising a template nucleic acid, the released flap of the second oligonucleotide, a third oligonucleotide, and a fourth oligonucleotide, wherein the cleavage reaction releases the flaps of the third and fourth oligonucleotide. The presence and/or amount a target nucleic acid is determined by detecting the released first and/or second flaps, wherein there is a 1:2 ratio of released first flap to the combination of released second flap and released third.

These methods of the invention are performed isothermally or under thermal cycling conditions.

The practice of the present invention will employ, unless otherwise indicated, conventional techniques of molecular biology, microbiology and recombinant DNA techniques, which are within the skill of the art. Such techniques are explained fully in the literature. See, e.g., Sambrook, Fritsch & Maniatis, 1989, *Molecular Cloning: A Laboratory Manual*, Second Edition; *Oligonucleotide Synthesis* (M. J. Gait, ed., 1984); *Nucleic Acid Hybridization* (B. D. Harnes & S. J. Higgins, eds., 1984); *A Practical Guide to Molecular Cloning* (B. Perbal, 1984); and a series, *Methods in Enzymology* (Academic Press, Inc.); *Short Protocols In Molecular Biology*, (Ausubel et al., ed., 1995). All patents, patent applications, and publications mentioned herein, both supra and infra, are hereby incorporated by reference.

I. Nucleic Acids

A. Nucleic Acid Sequences Useful in the Invention

The invention provides for methods of detecting or measuring a target nucleic acid sequence; and also utilizes oligonucleotides, primers and probes for forming a cleavage structure according to the invention and primers for amplifying a template nucleic acid sequence. As used herein, the terms "nucleic acid", "polynucleotide" and "oligonucleotide" refer to primers, probes, and oligomer fragments to be detected, and shall be generic to polydeoxyribonucleotides (containing 2-deoxy-D-ribose), to polyribonucleotides (containing D-ribose), and to any other type of polynucleotide which is an N-glycoside of a purine or pyrimidine base, or modified purine or pyrimidine bases (including abasic sites) or analogs such as protein nucleic acid (PNA). There is no intended distinction in length between the term "nucleic acid", "polynucleotide" and "oligonucleotide", and these terms will be used interchangeably. These terms refer only to the primary structure of the molecule. Thus, these terms include double- and single-stranded DNA, as well as double- and single-stranded RNA.

The complement of a nucleic acid sequence as used herein refers to an oligonucleotide which, when aligned with the nucleic acid sequence such that the 5' end of one sequence is paired with the 3' end of the other, is in "antiparallel association."

The oligonucleotide is not necessarily physically derived from any existing or natural sequence but may be generated in any manner, including chemical synthesis, DNA replication, reverse transcription or a combination thereof. The terms "oligonucleotide" or "nucleic acid" intend a polynucleotide of genomic DNA or RNA, cDNA, semisynthetic, or synthetic origin which, by virtue of its synthetic origin or manipulation: (1) is not associated with all or a portion of the polynucleotide with which it is associated in nature; and/or (2) is linked to a polynucleotide other than that to which it is linked in nature.

Because mononucleotides are reacted to make oligonucleotides in a manner such that the 5' phosphate of one mononucleotide pentose ring is attached to the 3' oxygen of its neighbor in one direction via a phosphodiester linkage, an "end" or "terminus" of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence which is internal within a larger oligonucleotide, may be said to be a 5' or a 3' region, depending upon whether it is located closer to the 5' or 3' terminus of the molecule.

When two different, non-overlapping oligonucleotides anneal to different regions of the same linear complementary nucleic acid sequence, and the 3' end of one oligonucleotide points toward the 5' end of the other, the former may be called the "upstream" oligonucleotide and the latter the "downstream" oligonucleotide.

Certain bases not commonly found in natural nucleic acids may be included in the nucleic acids of the present invention and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength, and incidence of mismatched base pairs.

Stability of a nucleic acid duplex is measured by the melting temperature, or "$T_m$". The $T_m$ of a particular nucleic acid duplex under specified conditions is the temperature at which half of the base pairs have disassociated.

B. Oligonucleotides Useful According to the Invention

The invention provides for oligonucleotide primers, oligonucleotide probes, and template nucleic acids useful for detecting or measuring a nucleic acid, for amplifying a template nucleic acid sequence, and for forming a cleavage structure according to the invention.

As used herein, "amplifying" refers to producing additional copies of a nucleic acid sequence by isothermal methods or by methods that require thermal cycling, including the method of the polymerase chain reaction.

1. Primers

The invention provides for a first oligonucleotide (defined herein) and a released flap of a second oligonucleotide (defined herein) that are extendible by polymerization.

The term "primer" may refer to more than one primer and refers to an oligonucleotide, whether occurring naturally, as in a purified restriction digest, or produced synthetically, which is capable of acting as a point of initiation of synthesis along a complementary strand when placed under conditions in which synthesis of a primer extension product which is complementary to a nucleic acid strand is catalyzed. Thus, a "primer" can include a first oligonucleotide (defined herein) and a released flap of a second oligonucleotide (defined herein). Conditions suitable for synthesis of a primer extension product (e.g., from a first oligonucleotide or from the released flap of a second oligonucleotide, as defined herein) include the presence of four different deoxyribonucleoside triphosphates and a polymerization-inducing agent such as DNA polymerase or reverse transcriptase, in a suitable buffer ("buffer" includes substituents which are cofactors, or which affect pH, ionic strength, etc.), and at a suitable temperature. The primer is preferably single-stranded for maximum efficiency in amplification.

Oligonucleotide primers useful according to the invention are single-stranded DNA or RNA molecules that are hybridizable to a template nucleic acid sequence and prime enzymatic synthesis of a second nucleic acid strand. The primer is complementary to a portion of a target molecule present in a pool of nucleic acid molecules. It is contemplated that oligonucleotide primers according to the invention are prepared by synthetic methods, either chemical or enzymatic. Alternatively, such a molecule or a fragment thereof is naturally-occurring, and is isolated from its natural source or purchased from a commercial supplier.

A "first oligonucleotide" according to the invention is preferably 6 to 100, more preferably 8 to 30 and most preferably 20 nucleotides in length. A "first" oligonucleotide is a least partially complementary to the target nucleic acid.

A "released flap of a second oligonucleotide" according to the invention is preferably 6-80 nucleotides, and most preferably about 10-25 nucleotides. A "released flap of a second oligonucleotide" and a first oligonucleotide are of a length that is sufficient to permit hybridization to a target or template nucleic acid and extension by polymerization.

Primers useful according to the invention are also designed to have a particular melting temperature (Tm) by the method of melting temperature estimation. Commercial programs, including Oligo™, Primer Design and programs available on the internet, including Primer3 and Oligo Calculator can be used to calculate a Tm of a nucleic acid sequence useful according to the invention. Preferably, the Tm of an amplification primer useful according to the invention, as calculated for example by Oligo Calculator, is preferably between about 15 and 80° C. and more preferably between about 50 and 60° C. Oligonucleotide primers can be designed with these considerations in mind and synthesized according to the following methods.

a. Oligonucleotide Primer Design Strategy

The design of a particular oligonucleotide primer according to the invention, involves selecting a sequence that is capable of recognizing the target sequence, but has a minimal predicted secondary structure. Furthermore, the Tm of the oligonucleotide is optimized by analysis of the length and GC content of the oligonucleotide. Furthermore, when designing a PCR primer useful for the amplification of genomic DNA, the selected primer sequence does not demonstrate significant matches to sequences in the GenBank database (or other available databases).

The design of a primer is facilitated by the use of readily available computer programs, developed to assist in the evaluation of the several parameters described above and the optimization of primer sequences. Examples of such programs are "PrimerSelect" of the DNAStar™ software package (DNAStar, Inc.; Madison, Wis.), OLIGO 4.0 (National Biosciences, Inc.), PRIMER, Oligonucleotide Selection Program, PGEN and AMPLIFY (described in Ausubel et al., 1995, Short Protocols in Molecular Biology, 3rd Edition, John Wiley & Sons). In one embodiment, primers are designed with sequences that serve as targets for other primers to produce a PCR product that has known sequences on the ends which serve as targets for further amplification (e.g. to sequence the PCR product). If many different target nucleic acid sequences are amplified with specific primers that share a common 'tail' sequence', the PCR products from these distinct genes can subsequently be sequenced with a single set of primers. Alternatively, in order to facilitate subsequent cloning of amplified sequences, primers are designed with restriction enzyme site sequences appended to their 5' ends. Thus, all nucleotides of the primers are derived from a target nucleic acid sequence or sequences adjacent to a target nucleic acid sequence, except for the few nucleotides necessary to form a restriction enzyme site. Such enzymes and sites are well known in the art. If the genomic sequence of a target nucleic acid sequence and the sequence of the open reading frame of a target nucleic acid sequence are known, design of particular primers is well within the skill of the art.

b. Synthesis

The primers themselves are synthesized using techniques that are also well known in the art. Methods for preparing oligonucleotides of specific sequence are known in the art, and include, for example, cloning and restriction digest analysis of appropriate sequences and direct chemical synthesis. Once designed, oligonucleotides are prepared by a suitable chemical synthesis method, including, for example, the phosphotriester method described by Narang et al., 1979, Methods in Enzymology, 68:90, the phosphodiester method disclosed by Brown et al., 1979, Methods in Enzymology, 68:109, the diethylphosphoramidate method disclosed in Beaucage et al., 1981, Tetrahedron Letters, 22:1859, and the solid support method disclosed in U.S. Pat. No. 4,458,066, or by other chemical methods using either a commercial automated oligonucleotide synthesizer (which is commercially available) or VLSIPS™ technology.

c. Labels

A primer according to the invention can be labeled (e.g., by the attachment of a radiolabel, a fluorescent label a quencher or any of the labels recited in the section entitled "Cleavage Structure". A labeled oligonucleotide primer is prepared according to methods well known in the art (see Sambrook et al., supra; Ausubel et al., supra).

C. Probes

The invention provides for oligonucleotides probes useful for forming a cleavage structure or a labeled cleavage structure as defined herein. Methods of preparing a labeled cleavage structure according to the invention are provided in the section entitled "Cleavage Structure" below. The invention provides for second, third and fourth oligonucleotides (all defined hereinabove) that are components of one or more of a first or second duplex, according to the invention, or a first or second cleavage structure, according to the invention. As used herein, "probe" refers to any one of a second, third or fourth oligonucleotide according to the invention.

A "second oligonucleotide" according to the invention is preferably 20-120, more preferably 25-45 and most preferably 35 nucleotides in length. A "second oligonucleotide" comprises a 3' and a 5' region. The 3' region of a "second oligonucleotide" is at least partially complementary to the target nucleic acid. A 5' region of a "second oligonucleotide" is preferably 8 to 80 and most preferably 10 to 20 nucleotides in length. In one embodiment of the invention, a 5' region of a "second oligonucleotide" is at least partially complementary to a region of a target nucleic acid. In another embodiment of the invention, the 5' region of the second oligonucleotide according to the invention is not complementary to a target nucleic acid.

A "third oligonucleotide" and "fourth oligonucleotide" according to the invention are preferably 20-120, more preferably 25-45 and most preferably 35 nucleotides in length. A "third oligonucleotide" and "fourth oligonucleotide" comprise a 3' and a 5' region. Third and fourth oligonucleotides according to the invention comprise a 3' region that is at least partially complementary to a region of a template nucleic acid and is preferably 8 to 80 and most preferably 10-20 nucleotides. A 5' region of a "third oligonucleotide" or "fourth oligonucleotide" is preferably 8 to 80 and most preferably 10 to 20 nucleotides in length. In an embodiment of the invention, a 5' region of a "third oligonucleotide" or "fourth oligonucleotide" is at least partially complementary to a region of a template nucleic acid. In another embodiment of the invention, the 5' region of the "third oligonucleotide" or "fourth oligonucleotide" according to the invention is not complementary to a template nucleic acid.

The probe, preferably, does not contain a sequence complementary to sequence(s) used in the primer extension(s). Generally the 3' terminus of the probe will be "blocked" to prohibit incorporation of the probe into a primer extension product.

1. Labels

A probe according to the invention can be labeled (e.g., by the attachment of a radiolabel, a fluorescent label a quencher or any of the labels recited in the section entitled "Cleavage Structure"). A labeled oligonucleotide probe is prepared according to methods well known in the art (see Sambrook et al., supra; Ausubel et al., supra).

2. Probes Comprising a Secondary Structure

Figure 7:
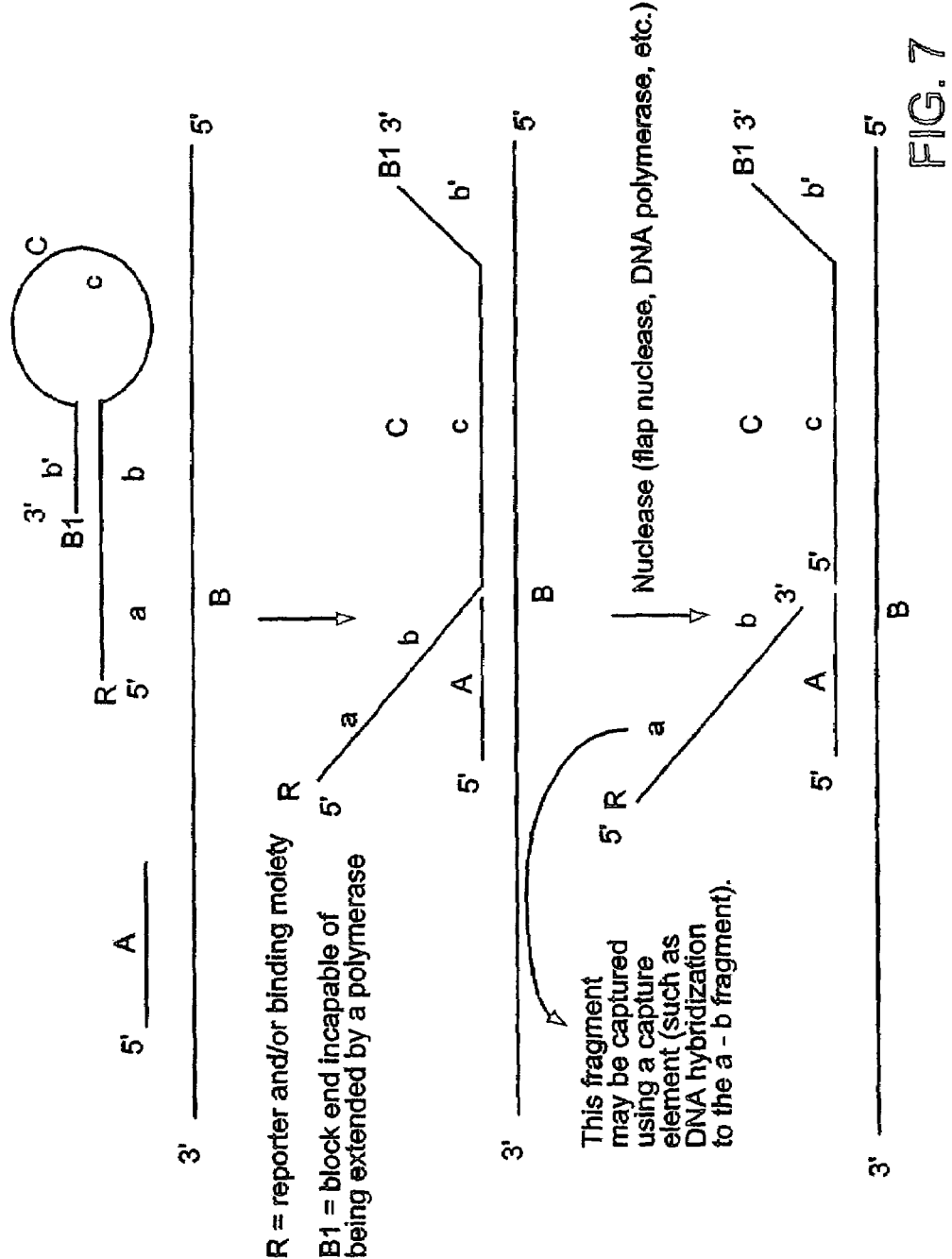
FIG. 7 is a diagram illustrating a probe comprises secondary structure that changes upon binding to a target or template nucleic acid sequence, wherein the probe further comprises a binding moiety and/or a tag.

A "probe" according to one embodiment of the invention can be a single stranded nucleic acid comprising a region or regions that are complementary to a target or a template nucleic acid sequence (e.g., target or template nucleic acid binding sequences) (for example c in FIG. 7). A "probe" according to this embodiment of the invention has a secondary structure that changes upon binding of the probe to the target or template nucleic acid sequence and can further comprise a binding moiety. A "probe" according to this embodiment of the invention binds to a target or template nucleic acid sequence to form a cleavage structure that can be cleaved by a cleavage means, wherein cleaving is performed at a cleaving temperature, and wherein the secondary structure of the probe when not bound to the target or template nucleic acid sequence is preferably stable at or below the cleaving temperature. A probe according to the invention cannot be cleaved to generate a signal by a "cleavage means", as defined herein, prior to binding to a target or template nucleic acid. In one embodiment of the invention, a probe may comprise a region that cannot bind or is not complementary to a target or template nucleic acid sequence. In another embodiment of the invention, a probe does not have a secondary structure when bound to a target or template nucleic acid.

Figure 8:
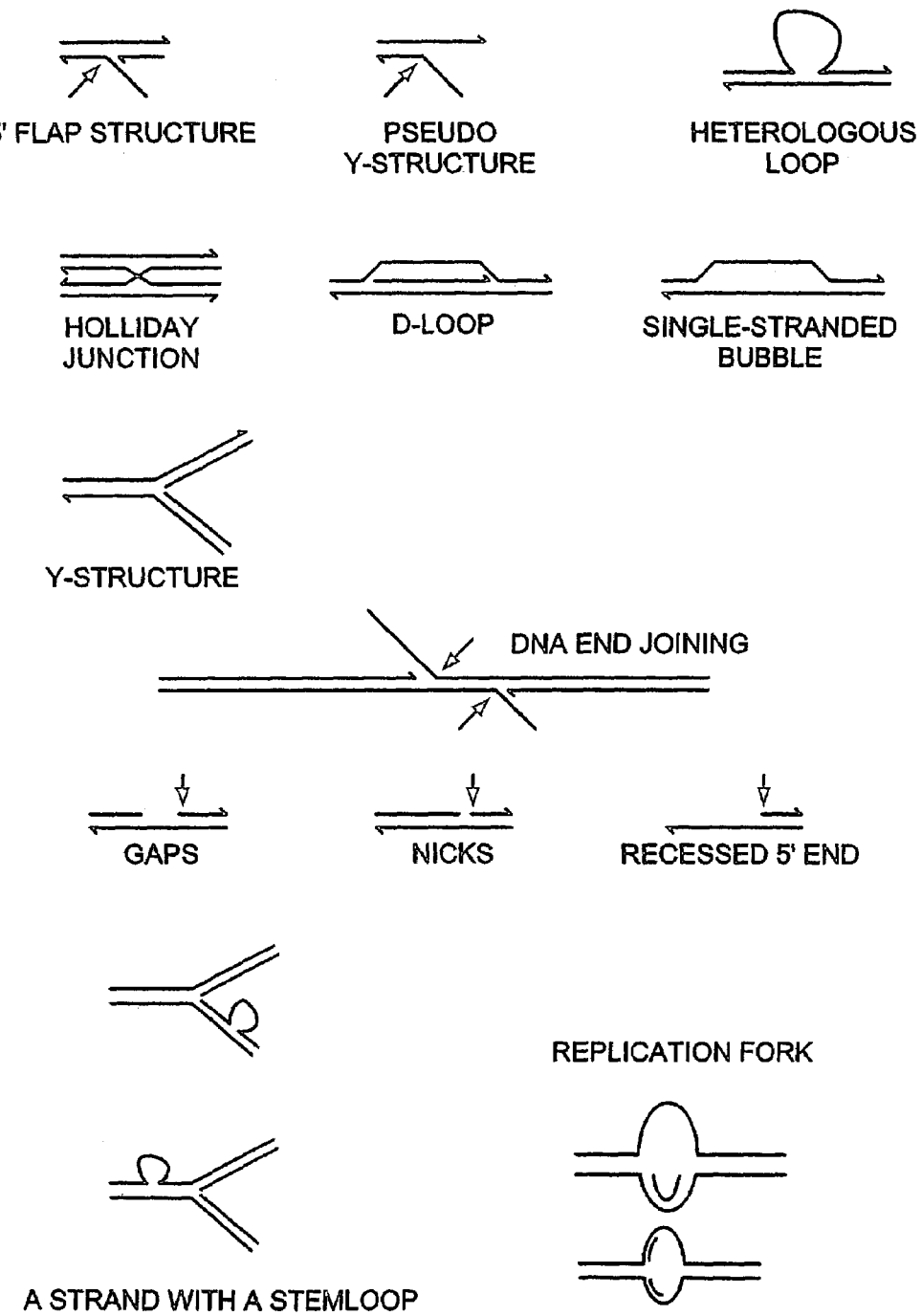
FIG. 8 demonstrates FEN nuclease cleavage structures.
Figure 11:
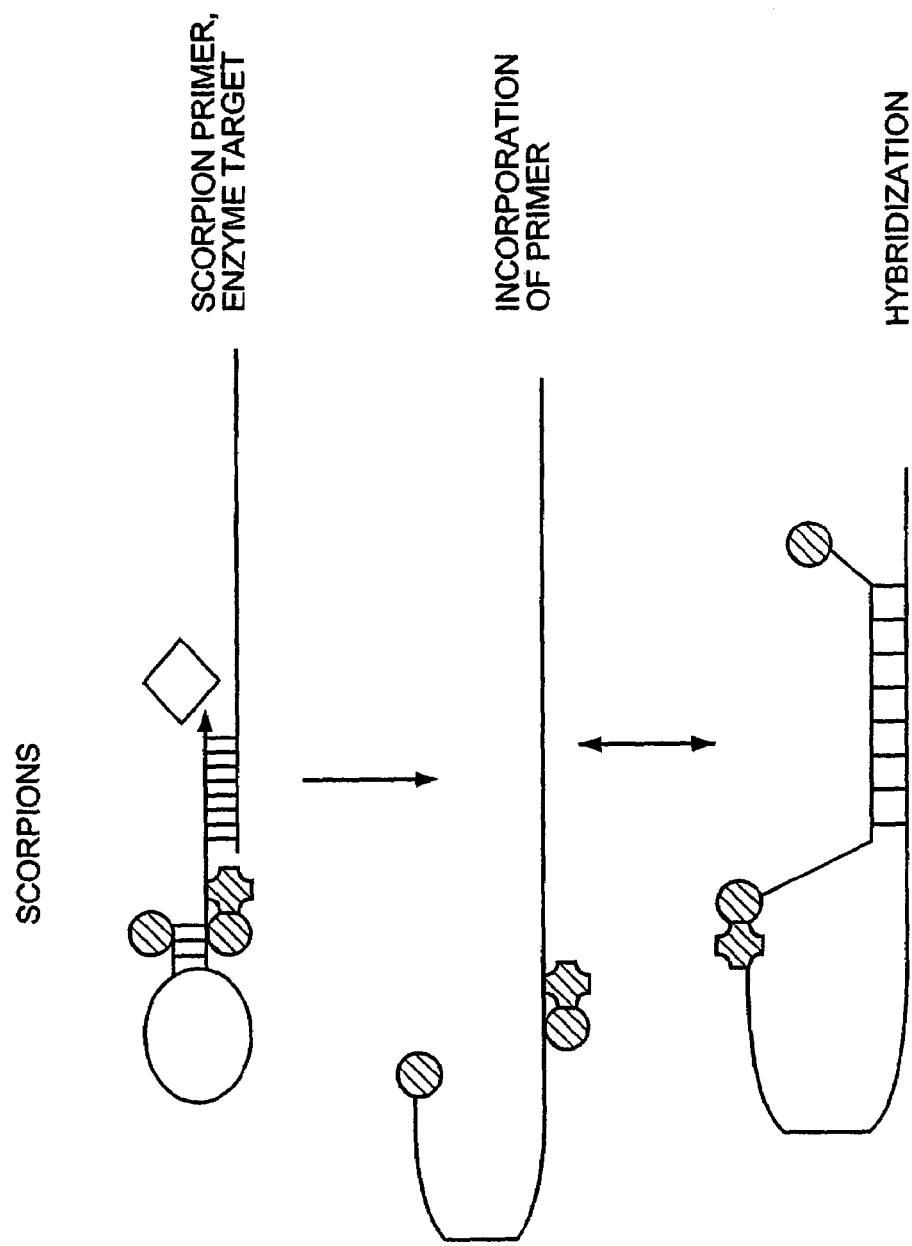
FIG. 11 is a representation of a scorpion probe.
Figure 12:
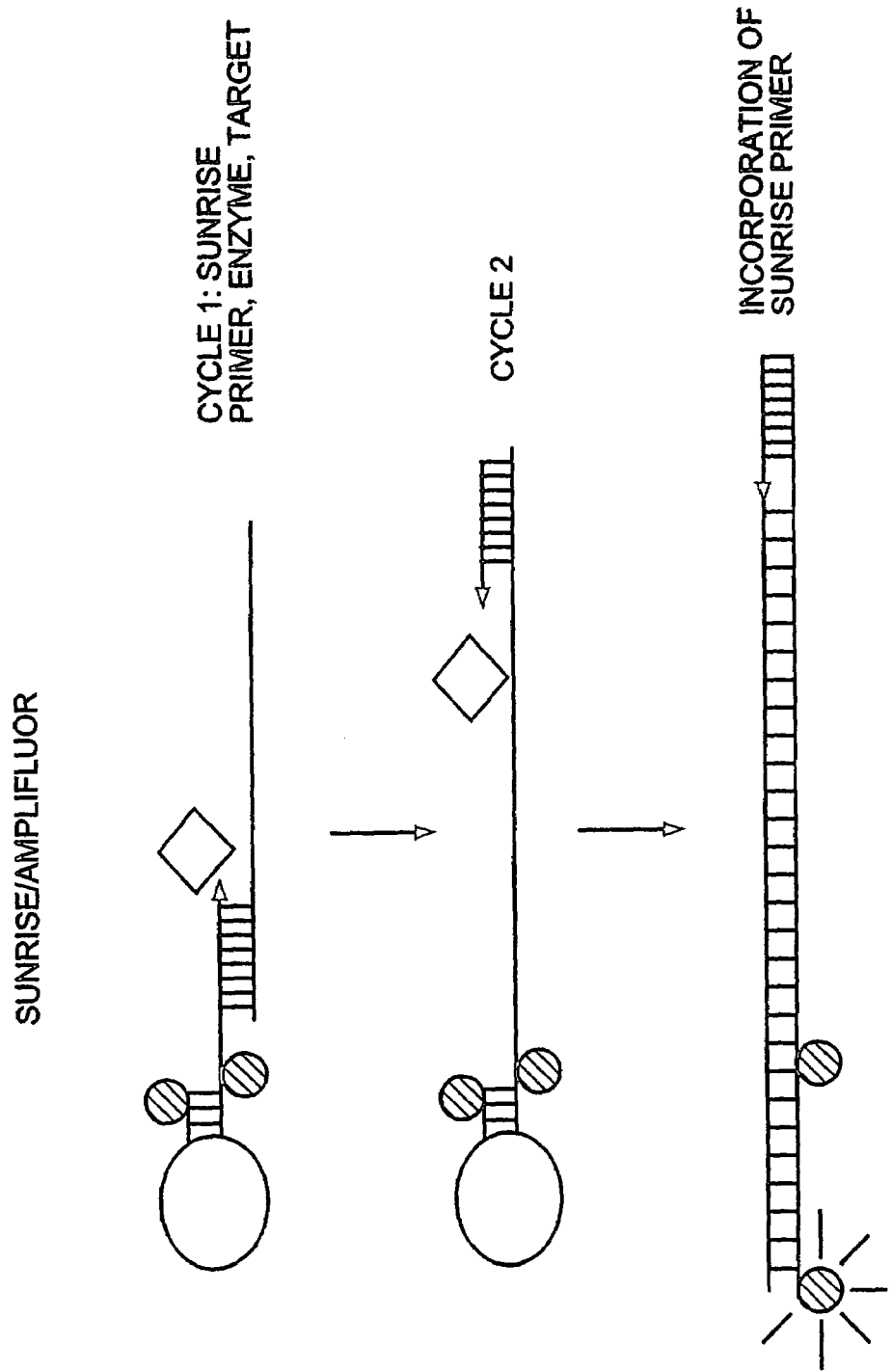
FIG. 12 is a representation of a sunrise/amplifluor probe.
Figure 21:
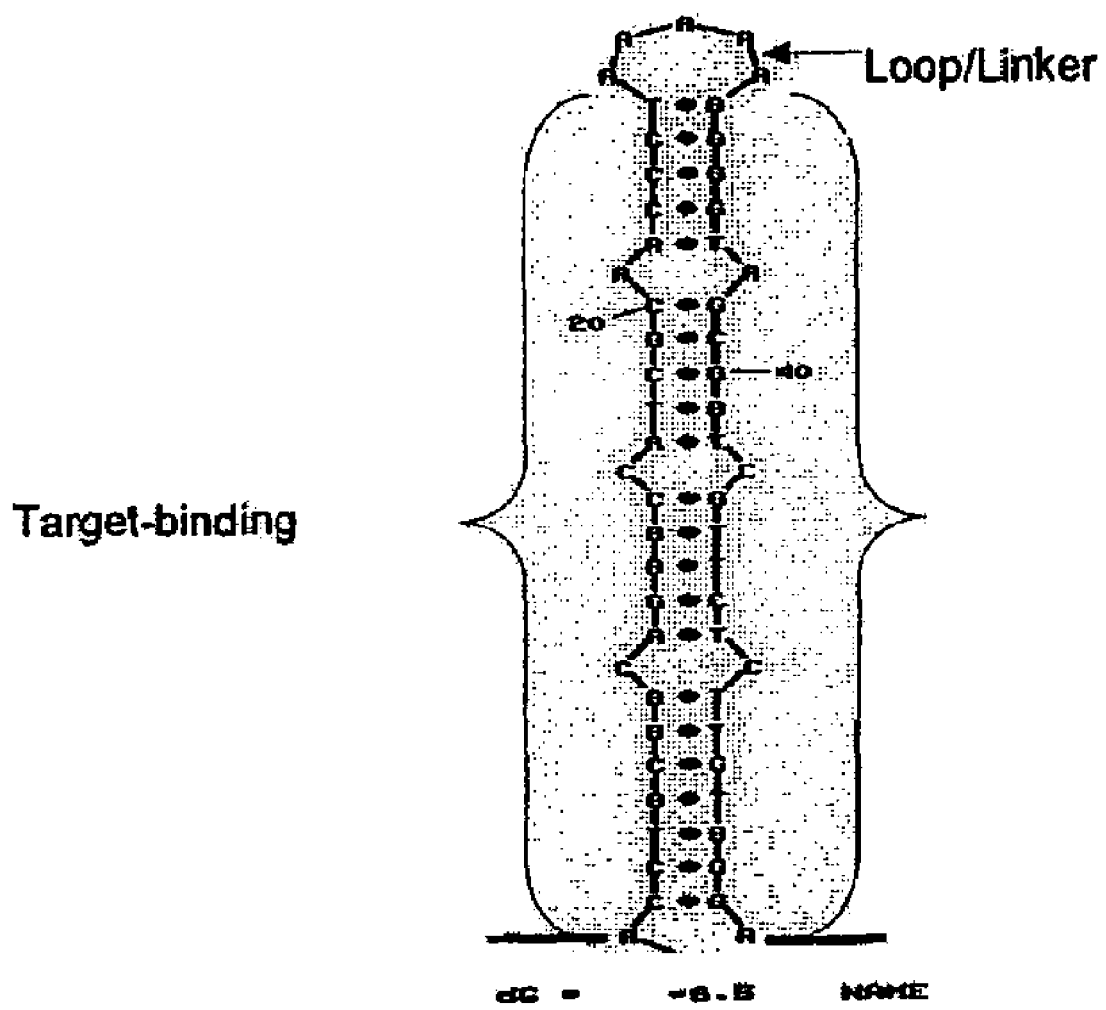
FIG. 21 is a representation of a key probe.

As used herein, "secondary structure" refers to a three-dimensional conformation (for example a hairpin, a stem-loop structure, an internal loop, a bulge loop, a branched structure or a pseudoknot, FIGS. 8, 9 and 21; multiple stem loop structures, cloverleaf type structures or any three dimensional structure. As used herein, "secondary structure" includes tertiary, quaternary etc. . . . structure. A probe comprising such a three-dimensional structure binds to a target or template nucleic acid sequence to form a cleavage structure that can be cleaved by a cleavage means at a cleaving temperature. The three dimensional structure of the probe when not bound to the target or template nucleic acid sequence is preferably stable at or below the cleaving temperature. "Secondary structure" as used herein, means a sequence comprising a first single-stranded sequence of bases (referred to herein as a "complementary nucleic acid sequence" (for example b' in FIG. 7)) followed by a second complementary sequence either in the same molecule (for example b' in FIG. 7), or in a second molecule comprising the probe, folds back on itself to generate an antiparallel duplex structure, wherein the single-stranded sequence and the complementary sequence (that is, the complementary nucleic acid sequences) anneal by the formation of hydrogen bonds. Oligonucleotide probes, as used in the present invention include oligonucleotides comprising secondary structure, including, but not limited to molecular beacons, safety pins (FIG. 10), scorpions (FIG. 11), sunrise/amplifluor probes (FIG. 12), and key probes (FIG. 21) the details and structures of which are described below and in the corresponding figures.

As used herein, first and second "complementary" nucleic acid sequences are complementary to each other and can anneal by the formation of hydrogen bonds between the complementary bases.

A secondary structure also refers to the conformation of a nucleic acid molecule comprising an affinity pair, defined herein, wherein the affinity pair reversibly associates as a result of attractive forces that exist between the pair of moieties comprising the affinity pair. As used herein, if a probe according to this embodiment further comprises a binding moiety, secondary structure prevents the binding moiety on the probe from binding to a capture element, and a change in secondary structure upon binding of the probe to the target nucleic acid and subsequent cleavage of the bound probe permits the binding moiety to be captured by the capture element.

A "probe" according to this embodiment of the invention can be unimolecular. As used herein, a "unimolecular" probe comprises a single molecule that binds to a target or template nucleic acid sequence to form a cleavage structure that can be cleaved by a cleavage means, wherein cleaving is performed at a cleaving temperature, and wherein the secondary structure of the "unimolecular" probe when not bound to the target or template nucleic acid sequence is preferably stable at or below the cleaving temperature. Unimolecular probes useful according to the invention include but are not limited to beacon probes, probes comprising a hairpin, stem-loop, internal loop, bulge loop or pseudoknot structure, scorpion probes and sunrise/amplifluor probes.

A "probe" according to this embodiment of the invention can be more than one molecule (e.g., bi-molecular or multi-molecular). At least one of the molecules comprising a bi-molecular or multi-molecular probe binds to a target or template nucleic acid sequence to form a cleavage structure that can be cleaved by a cleavage means, wherein cleaving is performed at a cleaving temperature, and wherein the secondary structure of the molecule of the probe when not bound to the target or template nucleic acid sequence is preferably stable at or below the cleaving temperature. The molecules comprising the multimolecular probe associate with each other via intermolecular bonds (e.g., hydrogen bonds or covalent bonds). For example, a heterologous loop (see FIG. 8, FIG. 21), or a cloverleaf structure wherein one or more loops of the cloverleaf structure (see FIG. 9) comprises a distinct molecule, and wherein the molecules that associate to form the cloverleaf structure associate via intermolecular bonding (e.g., hydrogen bonding or covalent bonding), are examples of multimolecular probes useful according to the invention.

As used herein, a "molecule" refers to a polynucleotide, and includes a polynucleotide further comprising an attached member or members of an affinity pair.

A "probe" or a "molecule" comprising a probe, according to this embodiment of the invention, is 5-10,000 nucleotides in length, ideally from 17-40 nucleotides in length, although probes or a molecule comprising a probe of different lengths are useful.

A "probe" according to this embodiment of the invention has a target or template nucleic acid binding sequence that is from about 5 to about 10,000 nucleotides, and preferably from 10 to about 140 nucleotides. In one embodiment of the invention, a "probe" according to the invention comprises at least first and second complementary nucleic acid sequences or regions that are 3-250, preferably 4-15, and more preferably 5-11 nucleotides long. The first and second complementary nucleic acid sequences may or may not have the same length. The invention provides for a probe wherein the first and second complementary nucleic acid sequences are both located upstream (5') of the target or template nucleic acid binding site. Alternatively, the first and second complementary nucleic acid sequences can both be located downstream (3') of the target or template nucleic acid binding site. In another embodiment, the invention provides for a probe wherein the first complementary nucleic acid sequence is upstream (5') of the target or template nucleic acid binding site and the second complementary nucleic acid sequence is downstream (3') of the target or template nucleic acid binding site. In another embodiment, the invention provides for a probe wherein the second complementary nucleic acid sequence is upstream (5') of the target or template nucleic acid binding site and the first complementary nucleic acid sequence is downstream (3') of the target or template nucleic acid binding site. The actual length will be chosen with reference to the target or template nucleic acid binding sequence such that the secondary structure of the probe is stable when the probe is not bound to the target or template nucleic acid at the temperature at which cleavage of a cleavage structure comprising the probe bound to a target or template nucleic acid is performed. As the target or template nucleic acid binding sequence increases in size up to 500 nucleotides, the length of the complementary nucleic acid sequences may increase up to 15-125 nucleotides. For a target or template nucleic acid binding sequence greater than 100 nucleotides, the length of the complementary nucleic acid sequences are not increased further. If the probe is also an allele-discriminating probe, the lengths of the complementary nucleic acid sequences are more restricted, as is discussed below.

As used herein, the "target nucleic acid binding sequence" refers to the region of the probe that binds specifically to the target nucleic acid.

As used herein, the "template nucleic acid binding sequence" refers to the region of the probe that binds specifically to the template nucleic acid.

A probe according to the invention is capable of forming a secondary structure, as defined herein, (including a stem loop, a hairpin, an internal loop, a bulge loop, a branched structure and a pseudoknot) or multiple secondary structures or any three-dimensional structure as defined herein.

For example, according to one embodiment of the present invention, a probe can be an oligonucleotide with secondary structure such as a hairpin or a stem-loop, and includes, but is not limited to molecular beacons, safety pins, scorpions, sunrise/amplifluor probes, and key probes.

Molecular beacon probes comprise a hairpin, or stem-loop structure which possesses a pair of interactive signal generating labeled moieties (e.g., a fluorophore and a quencher) effectively positioned to quench the generation of a detectable signal when the beacon probe is not hybridized to the target nucleic acid sequence. The loop comprises a region that is complementary to a target nucleic acid. The loop is flanked by 5' and 3' regions ("arms") that reversibly interact with one another by means of complementary nucleic acid sequences when the region of the probe that is complementary to a nucleic acid target sequence is not bound to the target nucleic acid. Alternatively, the loop is flanked by 5' and 3' regions ("arms") that reversibly interact with one another by means of attached members of an affinity pair to form a secondary structure when the region of the probe that is complementary to a nucleic acid target sequence is not bound to the target nucleic acid. As used herein, "arms" refers to regions of a molecular beacon probe that a) reversibly interact with one another by means of complementary nucleic acid sequences when the region of the probe that is complementary to a nucleic acid target sequence is not bound to the target nucleic acid or b) regions of a probe that reversibly interact with one another by means of attached members of an affinity pair to form a secondary structure when the region of the probe that is complementary to a nucleic acid target sequence is not bound to the target nucleic acid. When a molecular beacon probe is not hybridized to target, the arms hybridize with one another to form a stem hybrid, which is sometimes referred to as the "stem duplex". This is the closed conformation. When a molecular beacon probe hybridizes to its target the "arms" of the probe are separated. This is the open conformation. In the open conformation an arm may also hybridize to the target. Such probes may be free in solution, or they may be tethered to a solid surface. When the arms are hybridized (e.g., form a stem) the quencher is very close to the fluorophore and effectively quenches or suppresses its fluorescence, rendering the probe dark. Such probes are described in U.S. Pat. No. 5,925,517 and U.S. Pat. No. 6,037,130.

As used herein, a molecular beacon probe can also be an "allele-discriminating" probe as described herein.

Molecular beacon probes have a fluorophore attached to one arm and a quencher attached to the other arm. The fluorophore and quencher, for example, tetramethylrhodamine and DABCYL, need not be a FRET pair.

For stem loop probes useful in this invention, the length of the probe sequence that is complementary to the target, the length of the regions of a probe (e.g., stem hybrid) that reversibly interact with one another by means of complementary nucleic acid sequences, when the region complementary to a nucleic acid target sequence is not bound to the target nucleic acid, and the relation of the two, is designed according to the assay conditions for which the probe is to be utilized. The lengths of the target-complementary sequences and the stem hybrid sequences for particular assay conditions can be estimated according to what is known in the art. The regions of a probe that reversibly interact with one another by means of complementary nucleic acid sequences when the region of the probe that is complementary to a nucleic acid target sequence is not bound to the target nucleic acid are in the range of 6 to 100, preferably 8 to 50 nucleotides and most preferably 8 to 25 nucleotides each. The length of the probe sequence that is complementary to the target is preferably 17-40 nucleotides, more preferably 17-30 nucleotides and most preferably 17-25 nucleotides long.

The oligonucleotide sequences of molecular beacon probes modified according to this invention may be DNA, RNA, cDNA or combinations thereof. Modified nucleotides may be included, for example nitropyrole-based nucleotides or 2'-O-methylribonucleotides. Modified linkages also may be included, for example phosphorothioates. Modified nucleotides and modified linkages may also be incorporated in wavelength-shifting primers according to this invention.

Figure 10:
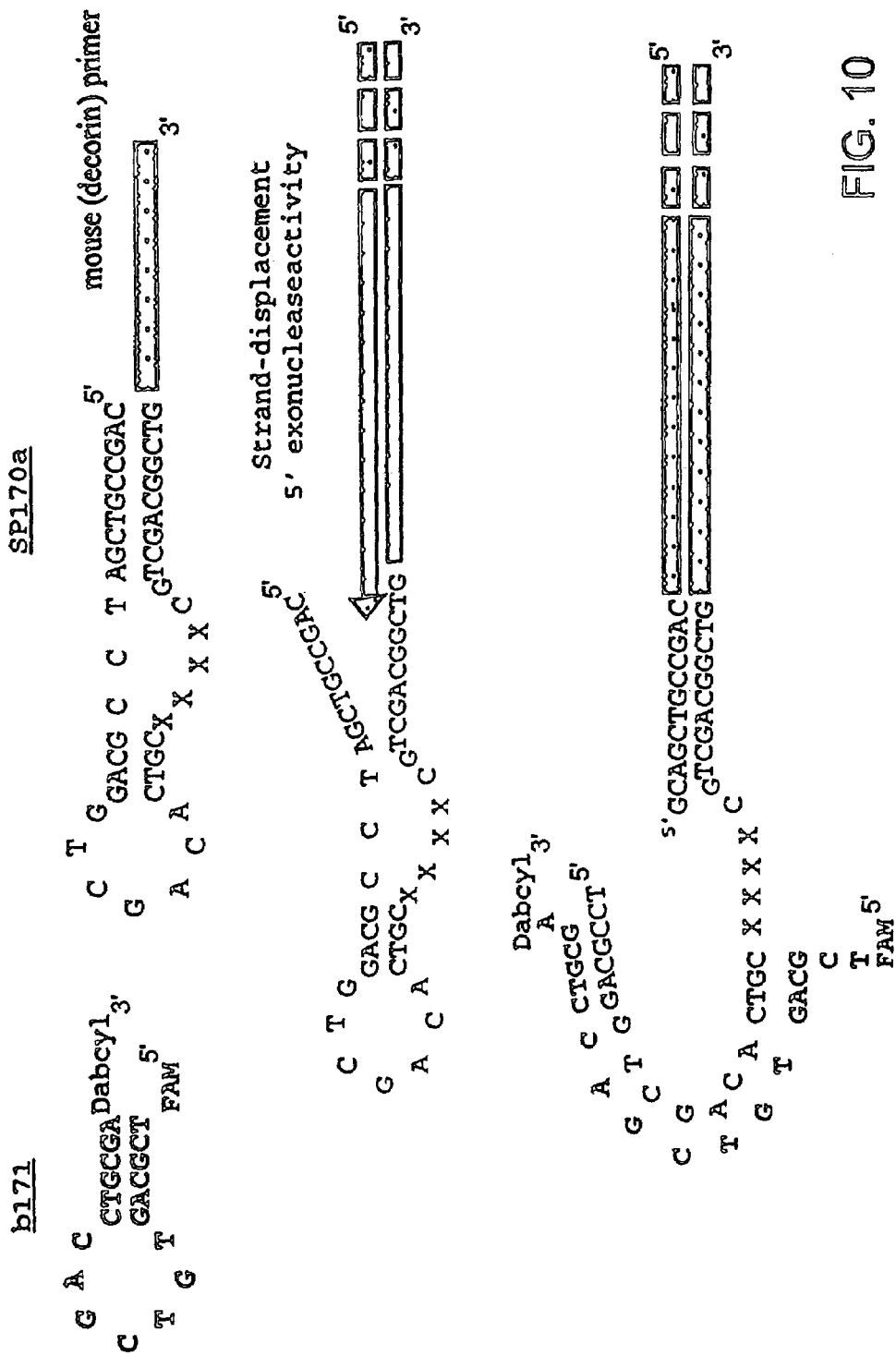
FIG. 10 is a representation of a safety pin probe.

A safety pin probe, as utilized in the present invention, requires a "universal" hairpin probe 1 (FIG. 10, b171), comprising a hairpin structure, with a fluorophore (FAM) on the 5' arm of the hairpin and a quencher (Dabcyl) on the 3' arm, and a probe 2 (FIG. 10, SP170a) comprising a stem-loop comprising two domains: the 5' two thirds of probe 2 have a (universal) sequence complementary to the hairpin probe 1, and nucleotides that will stop the DNA polymerase, and the 3' one third of probe 2, which serves as the target specific primer. As the polymerase, primed from the reverse primer (that is, the 3' one third of probe 2) synthesizes the top strand, the 5' end of probe 2 will be displaced and degraded by the 5' exonucleolytic activity until the "stop nucleotides" are reached. At this time the remainder of probe 2 opens up or unfolds and serves as a target for hairpin probe 1, thereby separating the fluorophore from the quencher (FIG. 10).

Scorpion probes, as used in the present invention comprise a 3' primer with a 5' extended probe tail comprising a hairpin structure which possesses a fluorophore/quencher pair. The probe tail is "protected" from replication in the 5'→3' direction by the inclusion of hexethlyene glycol (HEG) which blocks the polymerase from replicating the probe. During the first round of amplification the 3' target-specific primer anneals to the target and is extended such that the scorpion is now incorporated into the newly synthesized strand, which possesses a newly synthesized target region for the 5' probe. During the next round of denaturation and annealing, the probe region of the scorpion hairpin loop will hybridize to the target, thus separating the fluorophore and quencher and creating a measurable signal. Such probes are described in Whitcombe et al., *Nature Biotechnology* 17: 804-807 (1999), and in FIG. 11.

An additional oligonucleotide probe useful in the present invention is the sunrise/amplifluor probe. The sunrise/amplifluor probe is of similar construction as the scorpion probe with the exception that is lacks the HEG monomer to block the 5'→3' replication of the hairpin probe region. Thus, in the first round of amplification, the 3' target specific primer of the sunrise/amplifluor anneals to the target and is extended, thus incorporating the hairpin probe into the newly synthesized strand (sunrise strand). During the second round of amplification a second, non-labeled primer anneals to the 3' end of the sunrise strand (Cycle 2 in FIG. 12).

However, as the polymerase reaches the 5' end of the hairpin, due to the lack of the HEG stop sequence, the polymerase will displace and replicate the hairpin, thus separating the fluorophore and quencher, and incorporating the linearized hairpin probe into the new strand. Probes of this type are described further in Nazarneko et al., *Nucleic Acid Res.* 25: 2516-2521 (1997), and in FIG. 12.

An additional oligonucleotide probe useful in the present invention is the key probe. The key probe is described in U.S. Application No. 60/665,400, which is herein incorporated by reference in its entirety. The key probe can be formed from a target binding oligonucleotide joined to its complementary sequence, optionally through a linker oligonucleotide sequence, to form a hairpin structure comprising stem and, optionally, loop portions (See FIG. 21). The loop portion contains the optional linker sequence, or just a covalent bond joining the ends of the first and second sequences. The linker sequence, which forms the loop structure, may or may not hybridize to the target sequence. No more than 5 contiguous nucleotides of the optional linker sequence are complementary to the target sequence. The stem portion optionally contains one or more mismatches between the first and second sequences; the number of mismatches can be used to adjust the melting temperature of the probe. The stem portion may also contain modified nucleotides, for example minor groove binders or LNA, which can alter the affinity of the probe for the target sequence and also can be used to adjust the melting temperature. The key probe may also contain an interactive pair of labels, for example a fluorophore/quencher pair, attached at or near the ends of the probe such that a detectable signal, e.g., increased fluorescence emission of the fluorophore, is produced when the probe hybridizes to the target sequence.

For safety pin, scorpion, sunrise/amplifluor, and key probes useful in this invention, the length of the probe sequence that is complementary to the target, the length of the regions of a probe (e.g., stem hybrid) that reversibly interact with one another by means of complementary nucleic acid sequences when the region complementary to a nucleic acid target sequence is not bound to the target nucleic acid and the relation of the two is designed according to the assay conditions for which the probe is to be utilized. The lengths of the target-complementary sequences and the stem hybrid sequences for particular assay conditions can be estimated according to what is known in the art. The regions of a probe that reversibly interact with one another by means of complementary nucleic acid sequences when the region complementary to a nucleic acid target sequence is not bound to the target nucleic acid are in the range of 6 to 100, preferably 8 to 50 nucleotides and most preferably 8 to 25 nucleotides each. The length of the probe sequence that is complementary to the target is preferably 17-40 nucleotides, more preferably 17-30 nucleotides and most preferably 17-25 nucleotides long. The stability of the interaction between the regions of a probe that reversibly interact with one another by means of complementary nucleic acid sequences is determined by routine experimentation to achieve proper functioning. In addition to length, the stability of the interaction between the regions of a probe that reversibly interact with one another by means of complementary nucleic acid sequences between the regions of a probe that reversibly interact with one another by means of complementary nucleic acid sequences can be adjusted by altering the G-C content and inserting destabilizing mismatches. One of the regions of a probe that reversibly interact with one another by means of complementary nucleic acid sequences can be designed to be partially or completely complementary to the target. If the 3' arm is complementary to the target the probe can serve as a primer for a DNA polymerase. Also, wavelength-shifting molecular beacon probes can be immobilized to solid surfaces, as by tethering, or be free-floating.

A wide range of fluorophores may be used in probes and primers according to this invention. Available fluorophores include coumarin, fluorescein, tetrachlorofluorescein, hexachlorofluorescein, Lucifer yellow, rhodamine, BODIPY, tetramethylrhodamine, Cy3, Cy5, Cy7, eosine, Texas red and ROX. Combination fluorophores such as fluorescein-rhodamine dimers, described, for example, by Lee et al. (1997), Nucleic Acids Research 25:2816, are also suitable. Fluorophores may be chosen to absorb and emit in the visible spectrum or outside the visible spectrum, such as in the ultraviolet or infrared ranges.

Suitable quenchers described in the art include particularly DABCYL and variants thereof, such as DABSYL, DABMI and Methyl Red. Fluorophores can also be used as quenchers, because they tend to quench fluorescence when touching certain other fluorophores. Preferred quenchers are either chromophores such as DABCYL or malachite green, or fluorophores that do not fluoresce in the detection range when the probe is in the open conformation.

A "hairpin structure" or a "stem" refers to a double-helical region formed by base pairing between adjacent, inverted, complementary sequences in a single strand of RNA or DNA.

A "stem-loop" structure refers to a hairpin structure, further comprising a loop of unpaired bases at one end.

As used herein, a probe with "stable" secondary structure when not bound to a target or template nucleic acid sequence, refers to a secondary structure wherein 50% or more (e.g., 50%, 55%, 75% or 100%) of the base pairs that constitute the probe are not dissociated under conditions which permit hybridization of the probe to the target or template nucleic acid, but in the absence of the target or template nucleic acid.

"Stability" of a nucleic acid duplex is determined by the melting temperature, or "$T_m$". The $T_m$ of a particular nucleic acid duplex under specified conditions (e.g., salt concentration and/or the presence or absence of organic solvents) is the temperature at which half (50%) of the base pairs of the duplex molecule have disassociated (that is, are not hybridized to each other in a base-pair).

The "stability" of the secondary structure of a probe when not bound to the target or template nucleic acid is defined in a melting temperature assay, in a fluorescence resonance energy transfer (FRET) assay or in a fluorescence quenching assay, (the details or which are described in a section entitled, "Determining the Stability or the Secondary Structure of a Probe").

A probe useful according to this embodiment of the invention must have secondary structure that is "stable" at or below the temperature of the cleavage reaction. Thus, the temperature at which cleavage of a cleavage structure by a cleavage means is performed according to the invention, must be lower than the Tm of the secondary structure of the probe. The secondary structure of the probe is "stable" in a melting temperature assay at a temperature that is at or below the temperature of the cleavage reaction (i.e., at which cleavage is performed) if the level of light absorbance at the temperature at or below the temperature of the cleavage reaction is less than (i.e., at least 5% less than, preferably 20% less than and most preferably 25% less than etc. . . .) than the level of light absorbance at a temperature that is equal to the Tm of the probe.

According to the method of the invention, the stability of a secondary structure is measured by a FRET assay or a fluorescence quenching assay (described in the section entitled, "Determining the Stability of the Secondary Structure of a Probe"). As used herein, a fluorescence quenching assay can include a FRET assay. A probe according to the invention is labeled with an appropriate pair of interactive labels (e.g., a FRET pair (for example as described in the section entitled, "Determining the Stability of the Secondary Structure of the Probe", below) that can interact over a distance of, for example 2 nucleotides, or a non-FRET-pair, (e.g., tetramethylrhodamine and DABCYL) that can interact over a distance of, for example, 20 nucleotides. For example, a probe according to this embodiment of the invention may be labeled with a fluorophore and a quencher and fluorescence is then measured, in the absence of a target nucleic acid, at different temperatures. The Tm is the temperature at which the level of fluorescence is 50% of the maximal level of fluorescence observed for a particular probe, see FIG. 13e. The Tm for a particular probe wherein the nucleic acid sequence of the probe is known, can be predicted according to methods known in the art. Thus, fluorescence is measured over a range of temperatures, e.g., wherein the lower temperature limit of the range is at least 50° below, and the upper temperature limit of the range is at least 50° above the Tm or predicted Tm, for a probe according to the invention.

Figure 13A:
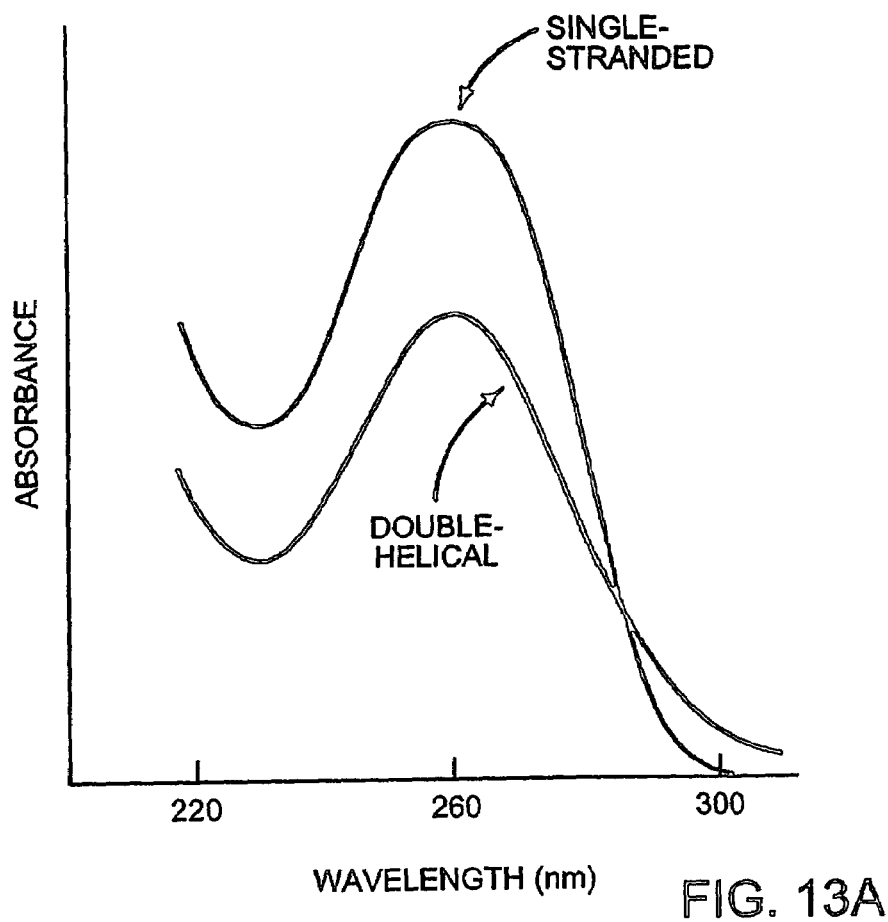
FIG. 13a is a graph demonstrating the difference in light absorbance of double-stranded versus single-stranded DNA.
Figure 13B:
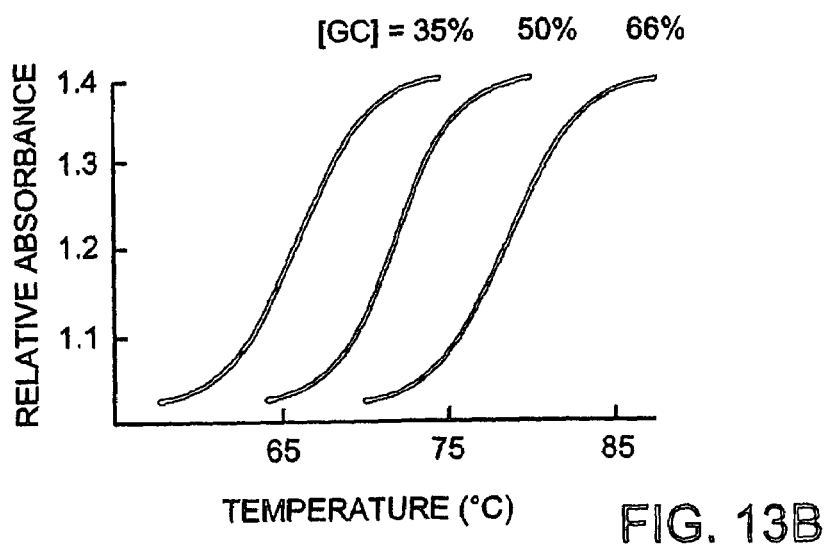
FIG. 13b is a graph demonstrating DNA melting curves.
Figure 13C:
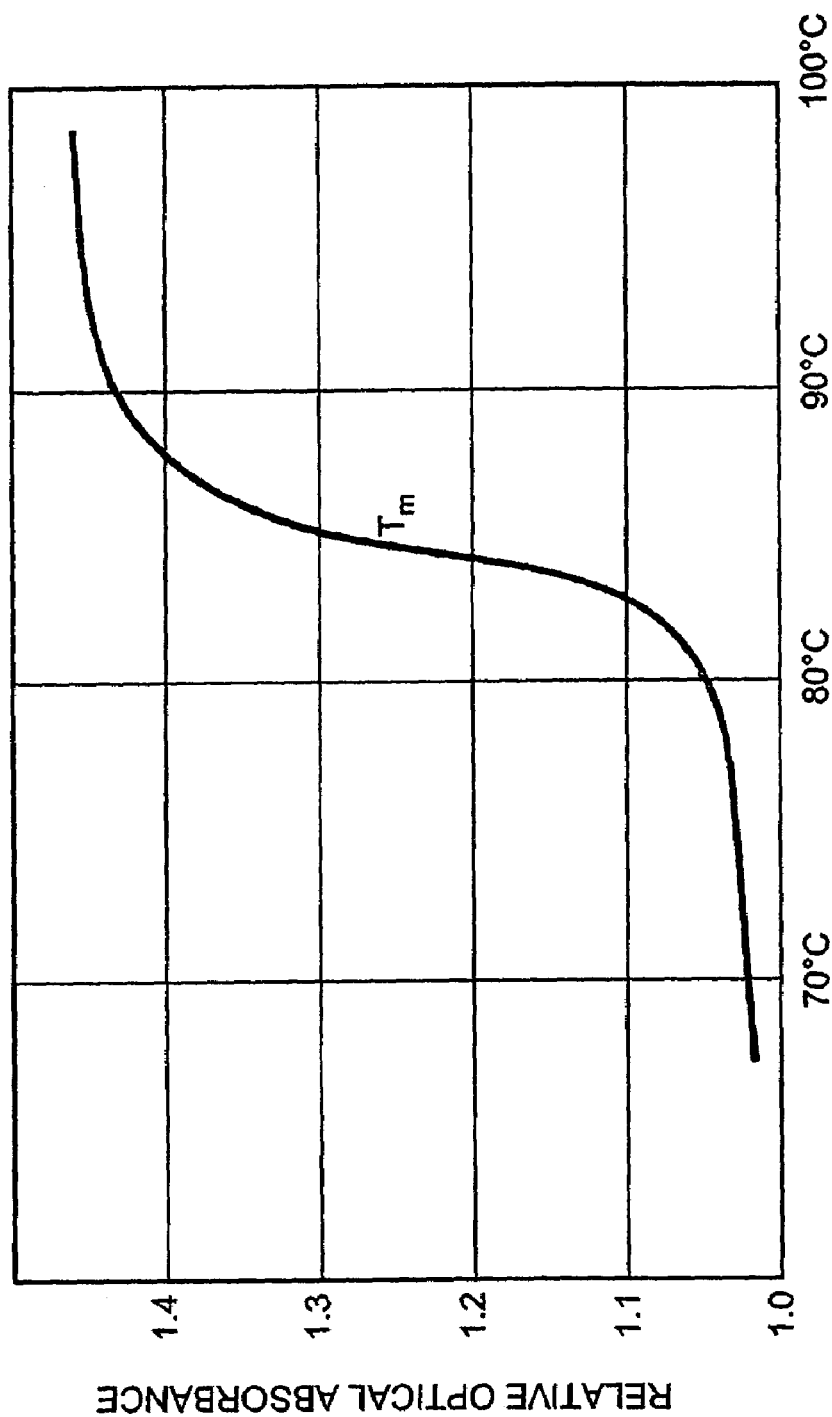
FIG. 13c is a graph demonstrating the effects of temperature on the relative light absorbance of DNA.
Figure 13D:
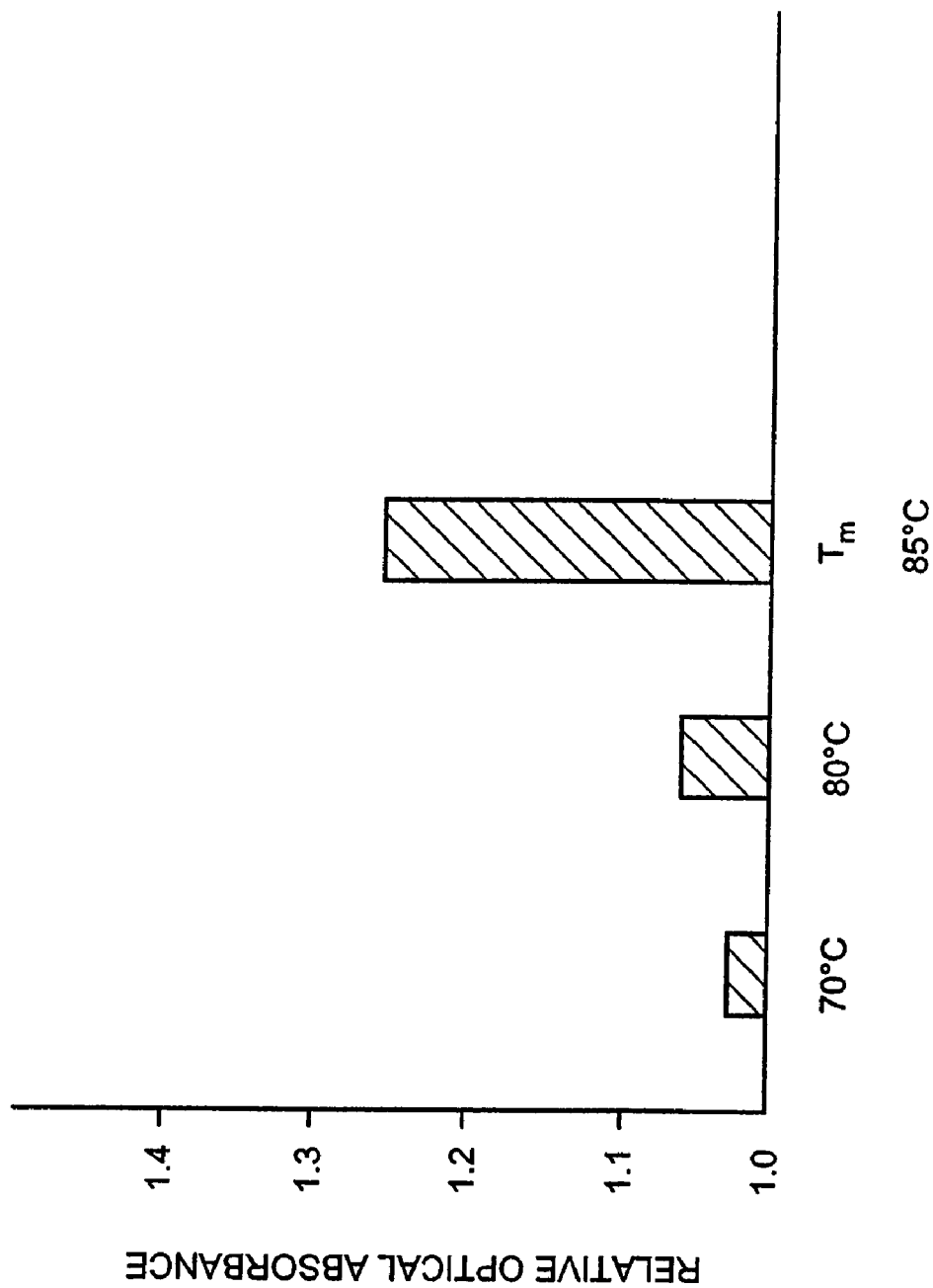
FIG. 13d is a graph demonstrating the effects of temperature on the relative optical absorbance of DNA.
Figure 13E:
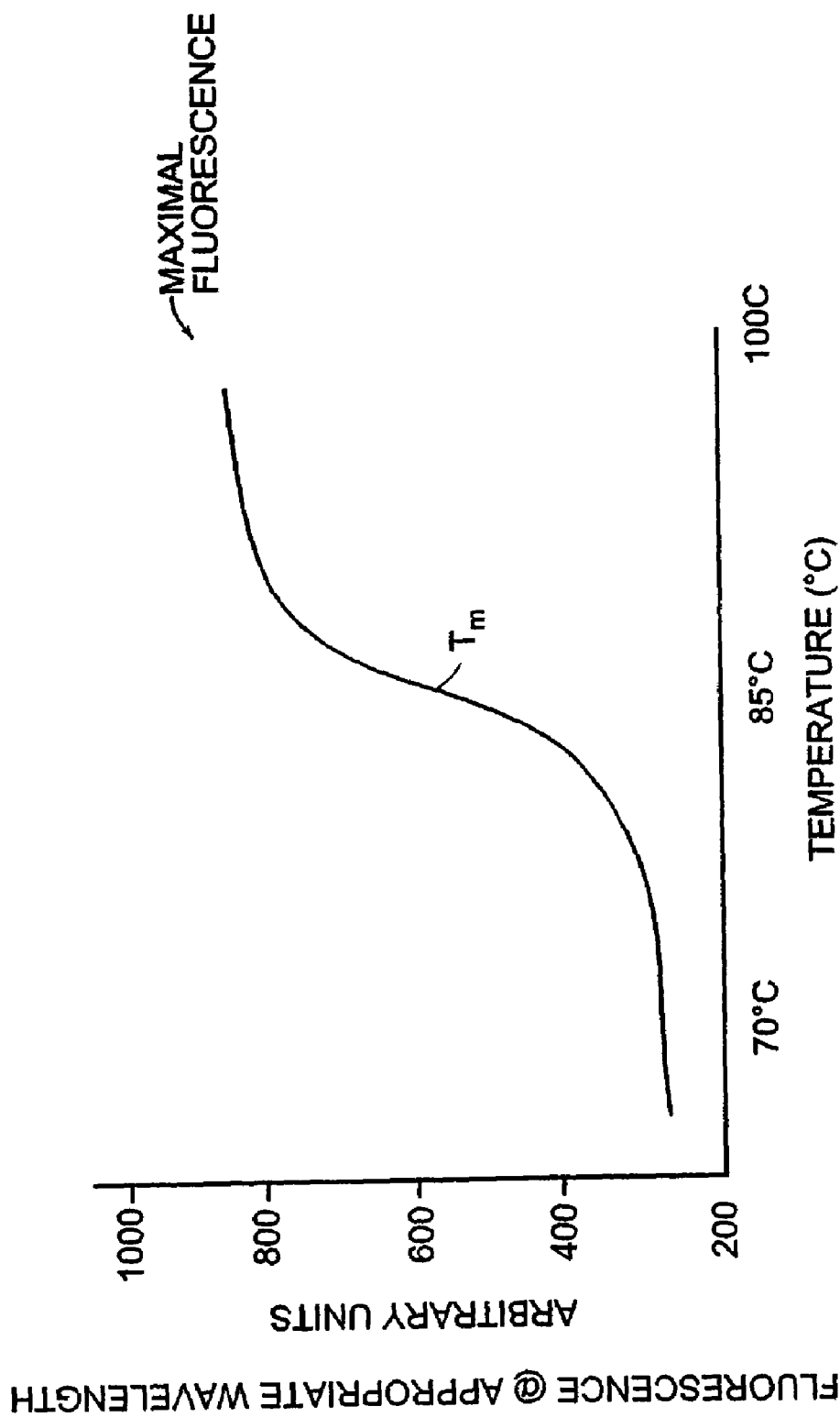
FIG. 13e is a graph demonstrating the effects of temperature on the fluorescence of DNA labeled with a pair of interactive labels.

A secondary structure is herein defined as "stable" in a FRET assay at a temperature that is at or below the cleaving temperature if the level of fluorescence is increased or decreased (e.g., at least 5% less than, preferably 20% less than and more preferably 25 less than, etc. . . .) the level of FRET that is observed at the Tm of the probe (see FIGS. 13e and f). For example, an increase or a decrease in FRET car occur in a FRET assay according to the invention. In another embodiment, a shift in wavelength, which results in an increase in the new, shifted wavelength or, a decrease in the new shifted wavelength, can occur in a FRET assay according to the invention.

A "change" in a secondary structure, according to the invention is measured in a FRET assay wherein a probe according to this embodiment of the invention comprises a fluorophore and a quencher that are positioned such that in the absence of a target or template nucleic acid, and at temperatures below the Tm of the probe there is quenching of the FRET pair (as described above). As used herein, a "change" in secondary structure that occurs when a probe according to the invention binds to a target nucleic acid, refers to an increase in fluorescence in such an assay, such that the level of fluorescence after binding of the probe to the target or template nucleic acid at a temperature below the Tm of the probe, is greater than (e.g., at least 5%, preferably 5-20% and most preferably 25 or more) the level of fluorescence observed in the absence of a target or template nucleic acid sequence (see FIG. 13g).

A secondary structure, according to this embodiment of the invention, is detected by subjecting a probe comprising a fluorophore and a quencher to a FRET assay (as described above). A probe according to this embodiment of the invention that exhibits a change in fluorescence that correlates with a change in temperature (e.g., fluorescence increases as the temperature of the FRET reaction is increased) is capable of forming a secondary structure.

As used herein, a "cleaving temperature" that is useful according to this embodiment of the invention is a temperature that is less than (at least 1° C. and preferably 10° C.) the $T_m$ of a probe having a secondary structure. The "cleaving temperature" is initially selected to be possible and preferably optimal for the particular cleavage means being employed in the cleavage reaction.

Generally the 3' terminus of the probe will be "blocked" to prohibit incorporation of the probe into a primer extension product if an active polymerase is used in the reaction. "Blocking" can be achieved by using non-complementary bases or by adding a chemical moiety such as biotin or a phosphate group to the 3' hydroxyl of the last nucleotide, which may, depending upon the selected moiety, serve a dual purpose by also acting as a label for subsequent detection or capture of the nucleic acid attached to the label. Blocking can also be achieved by removing the 3'-OH or by using a nucleotide that lacks a 3'-OH such as dideoxynucleotide.

The term probe encompasses an allele-discriminating probe. As used herein, an "allele-discriminating" probe preferentially hybridizes to perfectly complementary target nucleic acid sequences and discriminates against sequences that vary by at least one nucleotide. A nucleic acid sequence which differs by at least one nucleotide, as compared to a target nucleic acid sequence, hereafter referred to as a "target-like nucleic acid sequence", is thus not a target nucleic acid sequence for an allele-discriminating probe according to the invention.

Allele-discriminating probes do not hybridize sufficiently to a target-like nucleic acid sequence that contains one or more nucleotide mismatches as compared to the target nucleic acid complementary sequence, at a particular temperature or within a range of temperatures determined by experimental optimization according to methods well known in the art, and thus do not undergo a change in secondary structure upon binding to a target-like nucleic acid sequence in the presence of only a target-like nucleic acid sequence, and under conditions that would support hybridization of the allele discriminating probe to a target nucleic acid sequence.

In one embodiment, an "allele-discriminating probe" according to the invention refers to a probe that hybridizes to a target-like nucleic acid sequence that varies by at least one nucleotide from the target nucleic acid sequence, wherein the variant nucleotide(s) is/are not located in the allele-discriminating site. According to this embodiment of the invention, "an allele-discriminating probe" cannot bind to a target-like nucleic acid sequence that also varies by at least one nucleotide in the allele-discriminating site at a particular temperature or within a range of temperatures determined by experimental optimization according to methods well known in the art. Single nucleotide differences only affect the percentage of a probe that is bound to a target or target-like nucleic acid sequence. For example, the invention provides for a perfectly matched probe, wherein as much as 100% of the target or template is in a probe-target or probe-template complex (e.g., is bound by probe), in the presence of excess probe. The invention also provides for probes comprising at least a single base mismatch wherein at least 1-5% and preferably 5-10% of the target-like or template-like sequence is bound by the probe under the same conditions used to form a complex comprising a target or template sequence and a perfectly matched probe.

As used herein, "allele-discriminating site" refers to a region of a target nucleic acid sequence that is different (i.e., by at least one nucleotide) from the corresponding region in all possible alleles comprising the target nucleic acid sequence.

Allele-discriminating probes useful according to the invention also include probes that bind less effectively to a target-like sequence, as compared to a target sequence. The effectiveness of binding of a probe to a target sequence or a target-like sequence is measured in a FRET assay, performed at a temperature that is below (at least 5° C. and preferably 10° C. or more) the Tm of the secondary structure of probe, in the presence of a target-like sequence or a target sequence. The change in the level of fluorescence in the presence or absence of a target sequence compared to the change in the level of fluorescence in the presence or absence of a target-like sequence, provides an effective measure of the effectiveness of binding of a probe to a target or target-like sequence.

In a method according to the invention, a probe that binds less effectively to a target-like sequence as compared to a target sequence would undergo a smaller (e.g., preferably 25-50%, more preferably 50-75% and most preferably 75-90% of the value of the change in fluorescence upon binding to a target nucleic acid sequence) change in secondary structure, as determined by measuring fluorescence in a FRET assay as described herein, upon hybridization to a target-like sequence as compared to a target nucleic acid sequence. In a method according to the invention, a probe that binds less effectively to a target-like sequence as compared to a target sequence would generate a signal that is indicative of the presence of a target-like nucleic acid sequence in a sample. However, the intensity of the signal would be altered (e.g., preferably 25-50%, more preferably 50-75% and most preferably 75-90% less than or more than the value of the change in fluorescence upon binding to a target nucleic acid sequence) the intensity of a signal generated in the presence of a target sequence, as described hereinabove for a smaller change.

A "signal that is indicative of the presence of a target nucleic acid sequence" or a "target-like nucleic acid sequence" refers to a signal that is equal to a signal generated from 1 molecule to $10^{20}$ molecules, more preferably about 100 molecules to $10^{17}$ molecules and most preferably about 1000 molecules to $10^{14}$ molecules of a target nucleic acid sequence or a target-like nucleic acid sequence.

3. Probes Comprising Secondary Structure and a Binding Moiety

A probe according to one embodiment of the invention can have a secondary structure that changes upon binding of the probe to the target nucleic acid sequence and further comprises a binding moiety.

As used herein, a "binding moiety" refers to a region of a probe (for example ab in FIG. 7) that is released upon cleavage of the probe by a cleavage means and binds specifically to a capture element as a result of attractive forces that exist between the binding moiety and the capture element, and wherein specific binding between the binding moiety and the capture element only occurs when the secondary structure of the probe has "changed", as defined herein. "Binds specifically" means via hydrogen binding with a complementary nucleic acid or via an interaction between for example, the binding moiety and a binding protein capable of binding specifically to the nucleic acid sequence of the binding moiety. A "binding moiety" does not interfere with the ability of a probe to bind to a target or template nucleic acid sequence. A binding moiety is incapable of binding to a capture element when the probe is in its native secondary structural conformation and that, upon binding to a target or template nucleic acid, the secondary structure changes in a way that allows the binding moiety to bind to the capture element, preferably after cleavage by a cleavage agent. In one embodiment, the region of a probe that is cleaved to form a binding moiety cannot hybridize to a target nucleic acid sequence but can bind to a template nucleic acid. The region of a "binding moiety" that is not a "complementary nucleic acid sequence", as defined herein, (e.g., a in FIG. 7), is from 1-60 nucleotides, preferably from 1-25 nucleotides and most preferably from 1-10 nucleotides in length. Methods of detecting specific binding between a binding moiety as defined herein, and a capture element as defined herein, are well known in the art (see for example, Sambrook et al., supra; Ausubel et al., supra).

In one embodiment of the invention, a probe, according to this embodiment of the invention, further comprises a "reporter".

As used herein, a "reporter" refers to a "label", defined hereinbelow and/or a "tag" defined herein.

As used herein, "label" or "labeled moiety capable of providing a signal" refers to any atom or molecule which can be used to provide a detectable (preferably quantifiable) signal, and which can be operatively linked to a nucleic acid. Labels may provide signals detectable by fluorescence, radioactivity, colorimetry, gravimetry, X-ray diffraction or absorption, magnetism, enzymatic activity, mass spectrometry, binding affinity, hybridization radiofrequency, nanocrystals and the like. A labeled probe according to this embodiment of the invention is labeled at the 5' end, the 3' end or internally. The label can be "direct", i.e. a dye, or "indirect". i.e. biotin, digoxin, alkaline phosphatase (AP), horse radish peroxidase (HRP) etc. . . . For detection of "indirect labels" it is necessary to add additional components such as labeled antibodies, or enzyme substrates to visualize the, captured, released, labeled nucleic acid fragment. In one embodiment of the invention, a label cannot provide a detectable signal unless the secondary structure has "changed", as defined herein, (for example, such that the binding moiety is accessible).

As used herein, a "binding moiety" also refers to a tag. As used herein, a "tag" refers to a moiety that is operatively linked to the 5' end of a probe (for example R in FIG. 7) and specifically binds to a capture element as a result of attractive forces that exist between the tag and the capture element, and wherein specific binding between the tag and the capture element only occurs when the secondary structure of the probe has changed (for example, such that the tag is accessible to a capture element). "Specifically binds" as it refers to a "tag" and a capture element means via covalent or hydrogen bonding or electrostatic attraction or via an interaction between, for example a protein and a ligand, an antibody and an antigen, protein subunits, or a nucleic acid binding protein and a nucleic acid binding site. A tag does not interfere with the ability of a probe to anneal to a target or template nucleic acid sequence. Second binding moieties include but are not limited to biotin, streptavidin, a hapten, a protein, or a chemically reactive moiety.

As used herein, a "capture element" refers to a substance that is irreversibly attached to a solid substrate for example by chemical crosslinking or covalent binding, wherein the substance specifically binds to (e.g., via hydrogen bonding or via an interaction between, a nucleic acid binding protein and a nucleic acid binding site or between complementary nucleic acids) a binding moiety as a result of attractive forces that exist between the binding moiety and the capture element, and wherein specific binding between the binding moiety and the capture element only occurs when the secondary structure of the probe comprising the binding moiety has "changed", as defined herein. Capture elements include but are not limited to a nucleic acid binding protein or a nucleotide sequence.

As used herein, a "capture element" also refers to a substance that is irreversibly attached to a solid substrate for example by chemical crosslinking or covalent binding, wherein the substance specifically binds to (e.g. via covalent or hydrogen bonding or electrostatic attraction via an interaction between, for example a protein and a ligand, an antibody and an antigen, protein subunits, a nucleic acid binding protein and a nucleic acid binding site or between complementary nucleic acids) a tag as a result of attractive forces that exist between the tag and the capture element, and wherein specific binding between the tag and the capture element only occurs when the secondary structure of the probe comprising the binding moiety has "changed", as defined herein. Capture elements include but are not limited to biotin, streptavidin, a hapten, a protein, or a chemically reactive moiety.

As used herein, "solid support" means a surface to which a molecule (e.g. a first or capture element) can be irreversibly bound, including but not limited to membranes, sepharose beads, magnetic beads, tissue culture plates, silica based matrices, membrane based matrices, beads comprising surfaces including but not limited to styrene, latex or silica based materials and other polymers for example cellulose acetate, teflon, polyvinylidene difluoride, nylon, nitrocellulose, polyester, carbonate, polysulphone, metals, zeolites, paper, alumina, glass, polypropyle, polyvinyl chloride, polyvinylidene chloride, polytetrafluorethylene, polyethylene, polyamides, plastic, filter paper, dextran, germanium, silicon, (poly)tetrafluorethylene, gallium arsenide, gallium phosphide, silicon oxide, silicon nitrate and combinations thereof. Methods of attaching a capture element as defined herein are well known in the art and are defined hereinbelow. Additional solid supports are also discussed below.

As used herein, "affinity pair" refers to a pair of moieties (for example complementary nucleic acid sequences, protein-ligand, antibody-antigen, protein subunits, and nucleic acid binding proteins-binding sites) that can reversibly associate as a result of attractive forces that exist between the moieties. An "affinity pair" includes the combination of a binding moiety and the corresponding capture element and the combination of a tag and the corresponding capture element.

In embodiments wherein the affinity pair comprises complementary nucleic acid regions that reversibly interact with one another, the lengths of the target nucleic acid binding sequences, and the nucleic acid sequences comprising the affinity pair, are chosen for the proper thermodynamic functioning of the probe under the conditions of the projected hybridization assay. Persons skilled in hybridization assays will understand that pertinent conditions include probe, target and solute concentrations, detection temperature, the presence of denaturants and volume excluders, and other hybridization-influencing factors. The length of a target or template nucleic acid binding sequence can range from 7 to about 10,000 nucleotides, preferably from 10 nucleotides to about 140 nucleotides. If the probe is also an allele-discriminating probe, the length is more restricted, as is discussed below.

In embodiments wherein the affinity pair comprises complementary nucleic acid regions that reversibly interact with one another, and cannot hybridize or are not complementary to a target or template nucleic acid sequence, the complementary nucleic acid region sequences of the affinity pair should be of sufficient length that under the conditions of the assay and at the detection temperature, when the probe is not bound to a target, the structure of the probe is such that the binding moiety of the probe will not bind to the capture element, e.g., the complementary nucleic acid sequences are associated. Depending upon the assay conditions used, complementary nucleic acid sequences of 3-25 nucleotide lengths can perform this function. An intermediate range of 4-15, and more preferably 5-11, nucleotides is often appropriate. The actual length will be chosen with reference to the target nucleic acid binding sequence such that the secondary structure of the probe is stable when not bound to the target or template nucleic acid at the temperature at which cleavage of a cleavage structure comprising the probe bound to a target or template nucleic acid is performed. As the target nucleic acid binding sequence increases in size up to 100 nucleotides, the length of the complementary nucleic acid sequences may increase up to 15-25 nucleotides. For a target or template nucleic acid binding sequence greater than 100 nucleotides, the length of the complementary nucleic acid sequences are not increased further. If the probe is also an allele-discriminating probe, the lengths of the complementary nucleic acid sequences are more restricted, as is discussed below.

According to this embodiment of the invention, allele-discriminating probes that do not hybridize sufficiently to a target-like nucleic acid sequence that contains one or more nucleotide mismatches as compared to the target nucleic acid complementary sequence, must be designed such that, under the assay conditions used, reduction or elimination of secondary structure in the probe and hybridization with a target nucleic acid sequence will occur efficiently only when the target nucleic acid complementary sequence finds a perfectly complementary target sequence under certain reaction conditions (e.g., at a particular temperature or within a range of temperatures determined by experimental optimization according to methods well known in the art to prevent efficient binding of an allele-discriminating probe to a target-like or template-like nucleic acid sequence).

In one embodiment, an "allele-discriminating probe" according to the invention refers to a probe that hybridizes to a target-like nucleic acid sequence that varies by at least one nucleotide from the target nucleic acid sequence, wherein the variant nucleotide(s) is/are not located in the allele-discriminating site. According to this embodiment of the invention, "an allele-discriminating probe" cannot bind efficiently to a target-like nucleic acid sequence that also varies by at least one nucleotide in the allele-discriminating site (e.g., at a particular temperature or within a range of temperatures determined by experimental optimization according to methods well known in the art to prevent efficient binding of an allele-discriminating probe to a target-like or template-like nucleic acid sequence).

In one embodiment of the invention, an allele discriminating probe according to the invention preferably comprises a target nucleic acid binding sequence from 6 to 50 and preferably from 7 to 25 nucleotides, and complementary nucleic acid sequences from 3 to 8 nucleotides. The guanosine-cytidine content of the secondary structure and probe-target hybrids, salt, and assay temperature should all be considered, for example magnesium salts have a strong stabilizing effect that is particularly important to consider when designing short, allele-discriminating probes.

If an allele-discriminating probe is to have a target nucleic acid binding sequence near the upper limits of 50 nucleotides long, the sequence should be designed such that a single nucleotide mismatch to be discriminated against occurs at or near the middle of the target nucleic acid complementary sequence. For example, probes comprising a sequence that is 21 nucleotides long should preferably be designed so that the mismatch occurs opposite one of the 14 most centrally located nucleotides of the target nucleic acid complementary sequence and most preferably opposite one of the 7 most centrally located nucleotides. Designing a probe so that the mismatch to be discriminated against occurs in or near the middle of the target nucleic acid binding sequence/target-like nucleic acid binding sequence is believed to improve the performance of an allele-discriminating probe.

As used herein, "captured" as it refers to capture of a binding moiety by a capture element or capture of a tag by a capture element, means specifically bound by hydrogen bonding, covalent bonding, or via an interaction between, for example a protein and a ligand, an antibody and an antigen, protein subunits, a nucleic acid binding protein and a nucleic acid binding site, or between complementary nucleic acids, wherein one member of the interacting pair is attached to a solid support. Under conditions of stable capture, binding results in the formation of a heterodimer with a dissociation constant ($K_D$) of at least about $1\times10^3$ $M^{-1}$, usually at least $1\times10^4$ $M^{-1}$, typically at least $1\times10^5$ $M^{-1}$, preferably at least $1\times10^6$ $M^{-1}$ to $1\times10^7$ $M^{-1}$ or more, under suitable conditions.

Methods of performing binding reactions between a capture element, as defined herein, and a binding moiety or tag, respectively, as defined herein, are well-known in the art and are described hereinbelow. Methods of attaching a capture element according to the invention to a solid support, as defined herein, are well-known in the art and are defined hereinbelow.

Detection or verification of the labeled fragments or released flaps may be accomplished by a variety of methods well known in the art and may be dependent on the characteristics of the labeled moiety or moieties comprising a labeled cleavage structure. According to the method of the invention wherein a probe comprises a secondary structure that changes upon binding to a target or template nucleic acid and further comprises a binding moiety, the released labeled fragments or released flaps are captured by binding of a binding moiety to a capture element attached to a solid support.

a. Capture Element

A capture element, according to the invention can be any moiety that specifically binds (e.g. via hydrogen bonding or via an interaction between, for example a nucleic acid binding protein and a nucleic acid binding site or between complementary nucleic acids) a binding moiety, as a result of attractive forces that exist between the binding moiety and the capture element. Methods of performing a reaction wherein specific binding occurs between a capture element, as defined herein, and a binding moiety, as defined herein, are well-known in the art (see for example, Sambrook et al., supra; Ausubel et al., supra). A capture element, according to the invention can be any moiety that specifically binds (e.g. via covalent or hydrogen bonding or electrostatic attraction or via an interaction between, for example a protein and a ligand, an antibody and an antigen, protein subunits, a nucleic acid binding protein and a nucleic acid binding site) a binding moiety, as a result of attractive forces that exist between the tag and the capture element. Methods of performing a reaction wherein specific binding occurs between a capture element, as defined herein, and a tag, as defined herein, are well-known in the art, see for example, Sambrook et al., supra, Ausubel et al., supra. Specific binding only occurs when the secondary structure of the probe comprising a binding moiety has "changed", as defined herein. Capture elements useful according to the invention include but are not limited to a nucleic acid binding protein or a nucleotide sequence. Capture elements useful according to the invention include but are not limited to biotin, streptavidin, a hapten, a protein, a nucleotide sequence or a chemically reactive moiety.

In one embodiment of the invention, the reaction products, including the released labeled fragments, are subjected to size analysis. Methods for determining the size of a labeled fragment are known in the art and include, for example, gel electrophoresis, sedimentation in gradients, gel exclusion chromatography, mass spectroscopy, and homochromatography.

b. Solid Substrate

A solid substrate or solid support according to the invention is any surface to which a molecule (e.g., a capture element) can be irreversibly bound, including but not limited to membranes, magnetic beads, tissue culture plates, silica based matrices, membrane based matrices, beads comprising surfaces including but not limited to styrene, latex or silica based materials and other polymers for example cellulose acetate, teflon, polyvinylidene difluoride, nylon, nitrocellulose, polyester, carbonate, polysulphone, metals, zeolites, paper, alumina, glass, polypropyle, polyvinyl chloride, polyvinylidene chloride, polytetrafluorethylene, polyethylene, polyamides, plastic, filter paper, dextran, germanium, silicon, (poly)tetrafluorethylene, gallium arsenide, gallium phosphide, silicon oxide, silicon nitrate and combinations thereof. Useful solid substrates according to the invention are also described in Sambrook et al., supra; Ausubel et al., supra; U.S. Pat. Nos. 5,427,779, 5,512,439, 5,589,586, 5,716,854 and 6,087,102; Southern et al., *Nature Genetics Supplement*, 21:5 and Joos et al., 1997, *Analytical Biochemistry*, 247:96.

Methods of attaching a capture element to a solid support are known in the art and are described in Sambrook et al., supra, Ausubel et al., supra, U.S. Pat. Nos. 5,427,779, 5,512,439, 5,589,586, 5,716,854 and 6,087,102; Southern et al., supra and Joos et al., supra. Methods of immobilizing a nucleic acid sequence on a solid support are also provided by the manufacturers of the solid support, e.g., for membranes: Pall Corporation, Schleicher & Schuell, for magnetic beads; Dyal, for culture plates: Costar, Nalgenenunc, and for other supports useful according to the invention, CPG, Inc.

The amount of released labeled fragment, wherein "fragment" refers to a released flap, as defined herein, and "released labeled fragment" refers to a released labeled flap, that is bound to a capture element attached to a solid support can be measured while the labeled fragment remains bound to the capture element or after release of the labeled fragment from the capture element. Release of a labeled fragment from a capture element is carried out by incubating labeled fragment-capture element complexes in the presence of an excess amount of a competing, unlabeled fragment or by the addition of a buffer that inhibits binding of the labeled fragment to the capture element, for example as a result of salt concentration or pH of the buffer.

During or after amplification, separation of the released labeled fragments from, a reaction mixture can be accomplished by, for example, contacting the reaction mixture with a solid phase extractant (SPE). For example, materials having an ability to bind nucleic acids on the basis of size, charge, or interaction with the nucleic acid bases can be added to the reaction mixture, under conditions where labeled, uncleaved nucleic acids are bound and short, labeled fragments are not. Such SPE materials include ion exchange resins or beads, such as the commercially available binding particles Nensorb (DuPont Chemical Co.), Nucleogen (The Nest Group), PEI, BakerBond™ PEI, Amicon PAE 1,000, Selectacel™ PEI, Boronate SPE with a 3'-ribose probe, SPE containing sequences complementary to the 3'-end of the probe, and hydroxylapatite. In a specific embodiment, if a dual labeled oligonucleotide comprising a biotin label separated from a second label by a nuclease susceptible cleavage site is employed as the signal means, the reaction mixture can be contacted with materials containing a capture element such as avidin or streptavidin, or an antibody or monoclonal antibody to biotin, bound to a solid support, such as beads and particles, including magnetic particles.

Following the step in which a reaction mixture, for example a PCR mixture has been contacted with an SPE, the SPE material can be removed by filtration, sedimentation, or magnetic attraction, leaving the labeled fragments free of uncleaved labeled oligonucleotides and available for detection.

c. Binding Moieties

A binding moiety according to the invention refers to a region of a probe that is released upon cleavage of the probe by a nuclease and binds specifically (via hydrogen binding with a complementary nucleic acid or via an interaction with a binding protein) to a capture element as a result of attractive forces that exist between the binding moiety and the capture element, and wherein specific binding between the binding moiety and the capture element only occurs when the secondary structure of the probe has "changed", as defined herein.

A "tag" refers to a moiety that is operatively linked to the 5' end of a probe (for example R in FIG. 7) and specifically binds to a capture element as a result of attractive forces that exist between the tag and the capture element, and wherein specific binding between the tag and the capture element only occurs when the secondary structure of the probe has changed (for example, such that the tag is accessible to a capture element). "Specifically binds" as it refers to a "tag" and a capture element means via covalent or hydrogen bonding or electrostatic attraction or via an interaction between, for example a protein and a ligand, an antibody and an antigen, protein subunits, or a nucleic acid binding protein and a nucleic acid binding site. Second binding moieties include but are not limited to biotin, streptavidin, a hapten, a protein, or a chemically reactive moiety.

Methods of incorporating a tag, as defined herein, into a nucleic acid (e.g., a probe according to the invention) are well known in the art and are described in Ausubel et al., supra, Sambrook et al., supra, and U.S. Pat. Nos. 5,716,854 and 6,087,102.

d. Target Nucleic Acid

The invention provides for a "target nucleic acid" that is a polynucleotide which comprises in 3' to 5' order a first region that is at least partially complementary to a first oligonucleotide, an extension region and a second region that is at least partially complementary to a second oligonucleotide. The target nucleic acid may comprise single or double-stranded DNA or RNA.

A target nucleic acid according to the invention comprises a "first region" that is a length of nucleotides sufficient to permit hybridization and extension of a primer (e.g., a first oligonucleotide as defined herein) wherein the "first region" is at least partially complementary to a primer (e.g., a first oligonucleotide as defined herein). A "first region" is in the range of about 6 nucleotides to about 1000 nucleotides in length, with a preferred range of about 8-30 nucleotides, and optimally, a range of 10-25 nucleotides.

A target nucleic acid according to the invention also comprises an "extension region" that is a length of nucleotides sufficient to permit extension of an oligonucleotide (e.g., a first or second oligonucleotide) via a nucleic acid polymerization activity. An "extension region" is in the range of about 1 nucleotide to about 1000 nucleotides in length, with a preferred range of about 3-100 nucleotides, and optimally, a range of 3-30 nucleotides in length.

The second region of a target nucleic acid is a length of nucleotides that is at least partially complementary to a probe (e.g., a second oligonucleotide, defined herein). A "second region" is in the range of about 6 nucleotides to about 1000 nucleotides in length, with a preferred range of about 8-30 nucleotides, and optimally, a range of 10-25 nucleotides.

e. Template Nucleic Acid

The invention also provides for a "template nucleic acid" that is a polynucleotide which comprises in 3' to 5' order a first region that is at least partially complementary to a primer (e.g., the released flap of a second oligonucleotide, defined herein), an extension region and a second region that is at least partially complementary to a probe (e.g., a third oligonucleotide, as defined herein).

The invention also provides for a "template nucleic acid" that is a polynucleotide which comprises in 3' to 5' order a first region that is at least partially complementary to a primer (e.g., the released flap of a second oligonucleotide, defined herein below), a first extension region, a second region that is at least partially complementary to a first probe (e.g., a third oligonucleotide, defined herein), a second extension region, and a third region that is at least partially complementary to a second probe (e.g., a third oligonucleotide, defined herein). The template nucleic acid may comprise single or double-stranded DNA or RNA.

A template nucleic acid according to the invention comprises a "first region" that is a length of nucleotides sufficient to permit hybridization and extension of a primer (e.g., the released flap of a second oligonucleotide as defined herein) wherein the "first region" is at least partially complementary to a primer (e.g., the released flap of a second oligonucleotide as defined herein). A "first region" is in the range of about 6 nucleotides to about 1000 nucleotides in length, with a preferred range of about 8-30 nucleotides, and optimally, a range of 10-25 nucleotides.

A template nucleic acid according to the invention also comprises an "extension region" that is a length of nucleotides sufficient to permit extension of an oligonucleotide (e.g., the released flap of a second oligonucleotide as defined herein) via a nucleic acid polymerization activity. An "extension region" is in the range of about 1 nucleotide to about 1000 nucleotides in length, with a preferred range of about 3-100 nucleotides, and optimally, a range of 3-30 nucleotides in length.

The second region of a template nucleic acid is a length of nucleotides that is at least partially complementary to a probe (e.g., a third oligonucleotide, defined herein). A "second region" is in the range of about 6 nucleotides to about 1000 nucleotides in length, with a preferred range of about 8-30 nucleotides, and optimally, a range of 10-25 nucleotides.

1. Labels

A template nucleic acid according to the invention can be labeled e.g., by the attachment of a radiolabel, a fluorescent label a quencher or any of the labels recited in the section IV, B. titled "How to Prepare a Labeled Cleavage Structure." A labeled template nucleic acid is prepared according to methods well known in the art (see Sambrook et al., supra; Ausubel et al., supra) and described herein.

In one embodiment, the template nucleic acid is operable coupled to one member of a pair of interactive labels. In a further embodiment, the interactive label is a quencher or fluorescer. In yet another embodiment the interactive, the label is operable coupled to the 5' nucleotide of the template nucleic acid.

2. Solid Support

In one embodiment, a template nucleic acid is attached to a solid support, e.g., membrane, as taught in the Section entitled "Solid Substrate". The solid support may have multiple different template nucleic acids attached in an array format. In this embodiment, the template nucleic acid can be labeled with a first member of a pair of interactive labels, e.g., reporter or quencher group. A detectable signal is generated by the cleavage and displacement of a third oligonucleotide which is operable coupled to a second member of a pair of interactive labels. In this embodiment, the reporter signal is localized to the region of the solid support to which the specific template nucleic acid is attached. Each different target nucleic acid can produce a detectable signal indicative of the presence or amount of a target nucleic acid.

f. Hybridization

Primers and probes according to the invention (e.g., first, second, third or fourth oligonucleotides or the released flap of a second oligonucleotide) can be labeled and can be used to prepare a labeled cleavage structure. The following combinations of primers and probes can be annealed to sequences within a target nucleic acid sequence: a second oligonucleotide or a second oligonucleotide and first oligonucleotide. The following combinations of primers and probes can be annealed to sequences within a template nucleic acid: a third oligonucleotide, a third oligonucleotide and the released flap of a second oligonucleotide, a fourth oligonucleotide, a third and a fourth oligonucleotide, and a third oligonucleotide, a fourth oligonucleotide and the released flap of a target nucleic acid.

In one embodiment, a hybridized first oligonucleotide is extended by polymerization to form a cleavage structure and the cleavage structure is cleaved by a cleavage means, according to the invention, to release a flap of the second oligonucleotide. In another embodiment, a hybridized released flap of a second oligonucleotide is extended by polymerization to form a cleavage structure and the cleavage structure is cleaved by a cleavage means, according to the invention, to release a flap of a third oligonucleotide, or flaps of a third and a fourth oligonucleotide, or to release a third or a fourth oligonucleotide from a template nucleic acid Typically, selective hybridization occurs when two nucleic acid sequences are substantially complementary (at least about 65% complementary over a stretch of at least 14 to 25 nucleotides, preferably at least about 75%, more preferably at least about 90% complementary). See Kanehisa, M., 1984, Nucleic Acids Res. 12: 203, incorporated herein by reference. As a result, it is expected that a certain degree of mismatch at the priming site of a primer, as defined herein, is tolerated. Such mismatch may be small, such as a mono-, di- or tri-nucleotide. Alternatively, a region of mismatch may encompass loops, which are defined as regions in which there exists a mismatch in an uninterrupted series of four or more nucleotides.

Numerous factors influence the efficiency and selectivity of hybridization of an oligonucleotide probe to a second nucleic acid molecule. These factors, which include oligonucleotide length, nucleotide sequence and/or composition, hybridization temperature, buffer composition and potential for steric hindrance in the region to which the oligonucleotide is required to hybridize, will be considered when designing oligonucleotide primers according to the invention.

A positive correlation exists between oligonucleotide length and both the efficiency and accuracy with which an oligonucleotide will anneal to a target sequence. In particular, longer sequences have a higher melting temperature ($T_M$) than do shorter ones, and are less likely to be repeated within a given target sequence, thereby minimizing promiscuous hybridization. Oligonucleotide sequences with a high G-C content or that comprise palindromic sequences tend to self-hybridize, as do their intended target sites, since unimolecular, rather than bimolecular, hybridization kinetics are generally favored in solution. However, it is also important to design an oligonucleotide that contains sufficient numbers of G-C nucleotide pairings since each G-C pair is bound by three hydrogen bonds, rather than the two that are found when A and T bases pair to bind the target sequence, and therefore forms a tighter, stronger bond. Hybridization temperature varies inversely with oligonucleotide annealing efficiency, as does the concentration of organic solvents, e.g., formamide, that might be included in a priming reaction or hybridization mixture, while increases in salt concentration facilitate binding. Under stringent annealing conditions, longer hybridization probes, or synthesis primers, hybridize more efficiently than do shorter ones, which are sufficient under more permissive conditions. As herein used, the term "standard stringent conditions" means hybridization will occur only if there is at least 95% and preferably at least 97% identity between the sequences. The sequences hybridize under stringent conditions following incubation of the sequences overnight at 42° C., followed by stringent washes (0.2×SSC at 65° C.). Certain embodiments, for example wherein an allele discriminating probe is used to discriminate against sequences that vary, for example by at least one nucleotide, may require higher hybridization temperatures for specific hybridization. As several factors affect the stringency of hybridization, the combination of parameters is more important than the absolute measure of a single factor.

g. Production of a Nucleic Acid

The invention provides nucleic acids to be detected and or measured, for amplification of a target nucleic acid sequence and for formation of a cleavage structure.

The present invention utilizes nucleic acids comprising RNA, cDNA, genomic DNA, synthetic forms, and mixed polymers. The invention includes both sense and antisense strands of a nucleic acid. According to the invention, the nucleic acid may be chemically or biochemically modified or may contain non-natural or derivatized nucleotide bases. Such modifications include, for example, labels, methylation, substitution of one or more of the naturally occurring nucleotides with an analog, internucleotide modifications such as uncharged linkages (e.g. methyl phosphonates, phosphorodithioates, etc.), pendent moieties (e.g., polypeptides), intercalators, (e.g. acridine, psoralen, etc.) chelators, alkylators, and modified linkages (e.g. alpha anomeric nucleic acids, etc.) Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

1. Nucleic Acids Comprising DNA a. Cloning

Nucleic acids comprising DNA can be isolated from cDNA or genomic libraries by cloning methods well known to those skilled in the art (Ausubel et al., supra). Briefly, isolation of a DNA clone comprising a particular nucleic acid sequence involves screening a recombinant DNA or cDNA library and identifying the clone containing the desired sequence. Cloning will involve the following steps. The clones of a particular library are spread onto plates, transferred to an appropriate substrate for screening, denatured, and probed for the presence of a particular nucleic acid. A description of hybridization conditions, and methods for producing labeled probes is included below.

The desired clone is preferably identified by hybridization to a nucleic acid probe or by expression of a protein that can be detected by an antibody. Alternatively, the desired clone is identified by polymerase chain amplification of a sequence defined by a particular set of primers according to the methods described below.

The selection of an appropriate library involves identifying tissues or cell lines that are an abundant source of the desired sequence. Furthermore, if a nucleic acid of interest contains regulatory sequence or intronic sequence a genomic library is screened (Ausubel et al., supra).

b. Genomic DNA

Nucleic acid sequences of the invention are amplified from genomic DNA. Genomic DNA is isolated from tissues or cells according to the following method.

To facilitate detection of a variant form of a gene from a particular tissue, the tissue is isolated free from surrounding normal tissues. To isolate genomic DNA from mammalian tissue, the tissue is minced and frozen in liquid nitrogen. Frozen tissue is ground into a fine powder with a prechilled mortar and pestle, and suspended in digestion buffer (100 mM NaCl, 10 mM Tris-HCl, pH 8.0, 25 mM EDTA, pH 8.0, 0.5% (w/v) SDS, 0.1 mg/ml proteinase K) at 1.2 ml digestion buffer per 100 mg of tissue. To isolate genomic DNA from mammalian tissue culture cells, cells are pelleted by centrifugation for 5 min at 500×g, resuspended in 1-10 ml ice-cold PBS, repelleted for 5 min at 500×g and resuspended in 1 volume of digestion buffer.

Samples in digestion buffer are incubated (with shaking) for 12-18 hours at 50° C., and then extracted with an equal volume of phenol/chloroform/isoamyl alcohol. If the phases are not resolved following a centrifugation step (10 min at 1700×g), another volume of digestion buffer (without proteinase K) is added and the centrifugation step is repeated. If a thick white material is evident at the interface of the two phases, the organic extraction step is repeated. Following extraction the upper, aqueous layer is transferred to a new tube to which will be added ½ volume of 7.5M ammonium acetate and 2 volumes of 100% ethanol. The nucleic acid is pelleted by centrifugation for 2 min at 1700×g, washed with 70% ethanol, air dried and resuspended in TE buffer (10 mM Tris-HCl, pH 8.0, 1 mM EDTA, pH 8.0) at 1 mg/ml. Residual RNA is removed by incubating the sample for 1 hour at 37° C. in the presence of 0.1% SDS and 1 µg/ml DNase-free RNase, and repeating the extraction and ethanol precipitation steps. The yield of genomic DNA, according to this method is expected to be approximately 2 mg DNA/1 g cells or tissue (Ausubel et al., supra). Genomic DNA isolated according to this method can be used for PCR analysis, according to the invention.

c. Restriction Digest (of cDNA or Genomic DNA)

Following the identification of a desired cDNA or genomic clone containing a particular target nucleic acid sequence, nucleic acids of the invention may be isolated from these clones by digestion with restriction enzymes.

The technique of restriction enzyme digestion is well known to those skilled in the art (Ausubel et al., supra). Reagents useful for restriction enzyme digestion are readily available from commercial vendors including Stratagene, as well as other sources.

d. PCR

Nucleic acids of the invention may be amplified from genomic DNA or other natural sources by the polymerase chain reaction (PCR). PCR methods are well-known to those skilled in the art.

PCR provides a method for rapidly amplifying a particular DNA sequence by using multiple cycles of DNA replication catalyzed by a thermostable, DNA-dependent DNA polymerase to amplify the target sequence of interest. PCR requires the presence of a target nucleic acid sequence to be amplified, two single stranded oligonucleotide primers flanking the sequence to be amplified, a DNA polymerase, deoxyribonucleoside triphosphates, a buffer and salts.

PCR, is performed as described in Mullis and Faloona, 1987, Methods Enzymol., 155: 335, herein incorporated by reference.

The polymerase chain reaction (PCR) technique, is disclosed in U.S. Pat. Nos. 4,683,202, 4,683,195 and 4,800,159. In its simplest form, PCR is an in vitro method for the enzymatic synthesis of specific DNA sequences, using two oligonucleotide primers that hybridize to opposite strands and flank the region of interest in the target DNA. A repetitive series of reaction steps involving template denaturation, primer annealing and the extension of the annealed primers by DNA polymerase results in the exponential accumulation of a specific fragment whose termini are defined by the 5' ends of the primers. PCR is reported to be capable of producing a selective enrichment of a specific DNA sequence by a factor of $10^9$. The PCR method is also described in Saiki et al., 1985, Science 230:1350.

PCR is performed using template DNA (at least 1 fg; more usefully, 1-1000 ng) and at least 25 pmol of oligonucleotide primers. A typical reaction mixture includes: 2 µl of DNA, 25 pmol of oligonucleotide primer, 2.5 µl of a suitable buffer, 0.4 µl of 1.25 µM dNTP, 2.5 units of Taq DNA polymerase (Stratagene) and deionized water to a total volume of 25 µl. Mineral oil is overlaid and the PCR is performed using a programmable thermal cycler.

The length and temperature of each step of a PCR cycle, as well as the number of cycles, are adjusted according to the stringency requirements in effect. Annealing temperature and timing are determined both by the efficiency with which a primer is expected to anneal to a template and the degree of mismatch that is to be tolerated. The ability to optimize the stringency of primer annealing conditions is well within the knowledge of one of moderate skill in the art. An annealing temperature of between 30° C. and 72° C. is used. Initial denaturation of the template molecules normally occurs at between 92° C. and 99° C. for 4 minutes, followed by 20-40 cycles consisting of denaturation (94-99° C. for 15 seconds to 1 minute), annealing (temperature determined as discussed above; 1-2 minutes), and extension (72° C. for 1 minute). The final extension step is generally carried out for 4 minutes at 72° C., and may be followed by an indefinite (0-24 hour) step at 4° C.

Detection methods generally employed in standard PCR techniques use a labeled probe with the amplified DNA in a hybridization assay. Preferably, the probe is labeled, e.g., with $^{32}P$, biotin, horseradish peroxidase (HRP), etc., to allow for detection of hybridization.

Other means of detection include the use of fragment length polymorphism (PCR FLP), hybridization to allele-specific oligonucleotide (ASO) probes (Saiki et al., 1986, *Nature* 324:163), or direct sequencing via the dideoxy method (using amplified DNA rather than cloned DNA). The standard PCR technique operates (essentially) by replicating a DNA sequence positioned between two primers, providing as the major product of the reaction a DNA sequence of discrete length terminating with the primer at the 5' end of each strand. Thus, insertions and deletions between the primers result in product sequences of different lengths, which can be detected by sizing the product in PCR-FLP. In an example of ASO hybridization, the amplified DNA is fixed to a nylon filter (by, for example, UV irradiation) in a series of "dot blots", then allowed to hybridize with an oligonucleotide probe labeled with HRP under stringent conditions. After washing, terramethylbenzidine (TMB) and hydrogen peroxide are added: HRP oxidizes the hydrogen peroxide, which in turn oxidizes the TMB to a blue precipitate, indicating a hybridized probe.

2. Nucleic Acids Comprising RNA

The present invention also provides a nucleic acid comprising RNA.

Nucleic acids comprising RNA can be purified according to methods well known in the art (Ausubel et al., supra). Total RNA can be isolated from cells and tissues according to methods well known in the art (Ausubel et al., supra) and described below.

RNA is purified from mammalian tissue according to the following method. Following removal of the tissue of interest, pieces of tissue of ≦2 g are cut and quick frozen in liquid nitrogen, to prevent degradation of RNA. Upon the addition of a suitable volume of guanidinium solution (for example 20 ml guanidinium solution per 2 g of tissue), tissue samples are ground in a tissuemizer with two or three 10-second bursts. To prepare tissue guanidinium solution (1 L) 590.8 g guanidinium isothiocyanate is dissolved in approximately 400 ml DEPC-treated $H_2O$. 25 ml of 2 M Tris-HCl, pH 7.5 (0.05 M final) and 20 ml $Na_2EDTA$ (0.01 M final) is added, the solution is stirred overnight, the volume is adjusted to 950 ml, and 50 ml 2-ME is added.

Homogenized tissue samples are subjected to centrifugation for 10 min at 12,000×g at 12° C. The resulting supernatant is incubated for 2 min at 65° C. in the presence of 0.1 volume of 20% Sarkosyl, layered over 9 ml of a 5.7M CsCl solution (0.1 g CsCl/ml), and separated by centrifugation overnight at 113,000×g at 22° C. After careful removal of the supernatant, the tube is inverted and drained. The bottom of the tube (containing the RNA pellet) is placed in a 50 ml plastic tube and incubated overnight (or longer) at 4° C. in the presence of 3 ml tissue resuspension buffer (5 mM EDTA, 0.5% (v/v) Sarkosyl, 5% (v/v) 2-ME) to allow complete resuspension of the RNA pellet. The resulting RNA solution is extracted sequentially with 25:24:1 phenol/chloroform/isoamyl alcohol, followed by 24:1 chloroform/isoamyl alcohol, precipitated by the addition of 3 M sodium acetate, pH 5.2, and 2.5 volumes of 100% ethanol, and resuspended in DEPC water (Chirgwin et al., 1979, *Biochemistry*, 18: 5294).

Alternatively, RNA is isolated from mammalian tissue according to the following single step protocol. The tissue of interest is prepared by homogenization in a glass teflon homogenizer in 1 ml denaturing solution (4M guanidinium thiosulfate, 25 mM sodium citrate, pH 7.0, 0.1M 2-ME, 0.5% (w/v) N-laurylsarkosine) per 100 mg tissue. Following transfer of the homogenate to a 5-ml polypropylene tube, 0.1 ml of 2 M sodium acetate, pH 4, 1 ml water-saturated phenol, and 0.2 ml of 49:1 chloroform/isoamyl alcohol are added sequentially. The sample is mixed after the addition of each component, and incubated for 15 min at 0-4° C. after all components have been added. The sample is separated by centrifugation for 20 min at 10,000×g, 4° C., precipitated by the addition of 1 ml of 100% isopropanol, incubated for 30 minutes at −20° C. and pelleted by centrifugation for 10 minutes at 10,000×g, 4° C. The resulting RNA pellet is dissolved in 0.3 ml denaturing solution, transferred to a microfuge tube, precipitated by the addition of 0.3 ml of 100% isopropanol for 30 minutes at −20° C., and centrifuged for 10 minutes at 10,000×g at 4° C. The RNA pellet is washed in 70% ethanol, dried, and resuspended in 100-200 μl DEPC-treated water or DEPC-treated 0.5% SDS (Chomczynski and Sacchi, 1987, *Anal. Biochem.*, 162: 156).

Nucleic acids comprising RNA can be produced according to the method of in vitro transcription.

The technique of in vitro transcription is well known to those of skill in the art. Briefly, the gene of interest is inserted into a vector containing an SP6, T3 or T7 promoter. The vector is linearized with an appropriate restriction enzyme that digests the vector at a single site located downstream of the coding sequence. Following a phenol/chloroform extraction, the DNA is ethanol precipitated, washed in 70% ethanol, dried and resuspended in sterile water. The in vitro transcription reaction is performed by incubating the linearized DNA with transcription buffer (200 mM Tris-HCl, pH 8.0, 40 mM $MgCl_2$, 10 mM spermidine, 250 NaCl [T7 or T3] or 200 mM Tris-HCl, pH 7.5, 30 mM $MgCl_2$, 10 mM spermidine [SP6]), dithiothreitol, RNase inhibitors, each of the four ribonucleoside triphosphates, and either SP6, T7 or T3 RNA polymerase for 30 min at 37° C. To prepare a radiolabeled polynucleotide comprising RNA, unlabeled UTP will be omitted and $^{35}$S-UTP will be included in the reaction mixture. The DNA template is then removed by incubation with DNaseI. Following ethanol precipitation, an aliquot of the radiolabeled RNA is counted in a scintillation counter to determine the cpm/μl (Ausubel et al., supra).

Alternatively, nucleic acids comprising RNA are prepared by chemical synthesis techniques such as solid phase phosphoramidite (described above).

3. Nucleic Acids Comprising Oligonucleotides

A nucleic acid comprising oligonucleotides can be made by using oligonucleotide synthesizing machines which are commercially available (described above).

It is well known by those with skill in the art that oligonucleotides can be synthesized with certain chemical and/or capture moieties, (including capture elements as defined herein) such that they can be coupled to solid supports and bind to a binding moiety or a tag. Suitable capture elements include, but are not limited to a nucleic acid binding protein or a nucleotide sequence, biotin, a hapten, a protein, or a chemically reactive moiety. Such oligonucleotides may either be used first in solution, and then captured onto a solid support, or first attached to a solid support and then used in a detection reaction. An example of the latter would be to couple a upstream probe molecule to a solid support, such that the 5' end of the upstream probe molecule comprised a fluorescent quencher. The same upstream probe molecule would also comprise a fluorophore in a location such that a FEN nuclease cleavage would physically separate the quencher from the fluorophore. For example, the target nucleic acid could hybridize with the solid-phase upstream probe oligonucleotide, and a liquid phase upstream primer could also hybridize with the target molecule, such that a FEN cleavage reaction occurs on the solid support and liberates the 5' quencher moiety from the complex. This would cause the solid support-bound fluorophore to be detectable, and thus reveal the presence of a cleavage event upon a suitably labeled or identified solid support. Different upstream probe molecules could be bound to different locations on an array. The location on the array would identify the probe molecule, and indicate the presence of the template to which the probe molecule can hybridize.

II. Duplexes

The invention provides for duplexes that are used to prepare cleavage structures according to the invention.

A duplex, according to the invention, is formed by mixing, in any order, the components of the duplex, under conditions that permit hybridization of the components of the duplex and formation of the duplex. In one embodiment, the duplex is formed by first hybridizing the target nucleic acid or the template nucleic acid with the probe or probes, and then adding the primer. In another embodiment, the duplex is formed by hybridizing the target nucleic acid and/or template nucleic acid simultaneously with one or more probes and primers. In one embodiment, the duplex is formed during an annealing step of a thermal cycling reaction. Hybridization of a target or template nucleic acid with one or more probes is performed under suitable conditions. Suitable conditions include, for example, a temperature that permits denaturation of a probe comprising a secondary structure and the formation of hydrogen bonds between complementary bases of the target or template nucleic acid and the probe or probes. In certain embodiments, a suitable amount of a denaturing agent, such as dimethylsulfoxide (DMSO) or glycerol is added to the hybridization mixture. A suitable amount of a denaturing agent is sufficient to permit hybridization and formation of a first or second duplex, according to the invention, as well as subsequent steps of polymerization and cleavage, described below. A concentration of a denaturing agent that is useful according to the invention will vary depending on the base pair compositions of the components of the duplex. A concentration of a denaturing agent that is useful according to the invention will be determined experimentally by methods known in the art and described herein, to be sufficient to permit hybridization of complementary nucleic acids, polymerization of a primer (e.g., a first oligonucleotide or the released flap of a second oligonucleotide) and cleavage of a cleavage structure to release flaps, according to the invention. In one embodiment, the denaturing agent is DMSO, used at concentration of 0 to 6%, and preferably around 1.5 to 2% for nucleic acids in the range of approximately 0.1 to 1 kb. A concentration of DMSO greater than 2% may be used for nucleic acids greater than 10 kb. Alternatively, glycerol can be used as a denaturing agent at a concentration of from 0 to 10%, and preferably 5 to 8%. Both, or even other denaturing agents, may be used in combination at concentrations that are determined experimentally by methods known in the art.

Methods of determining "conditions that permit hybridization" of components of a duplex are known in the art, and parameters that influence nucleic acid hybridization are discussed in detail in the section entitled "Nucleic Acids".

A. First Duplex

Figure 2:
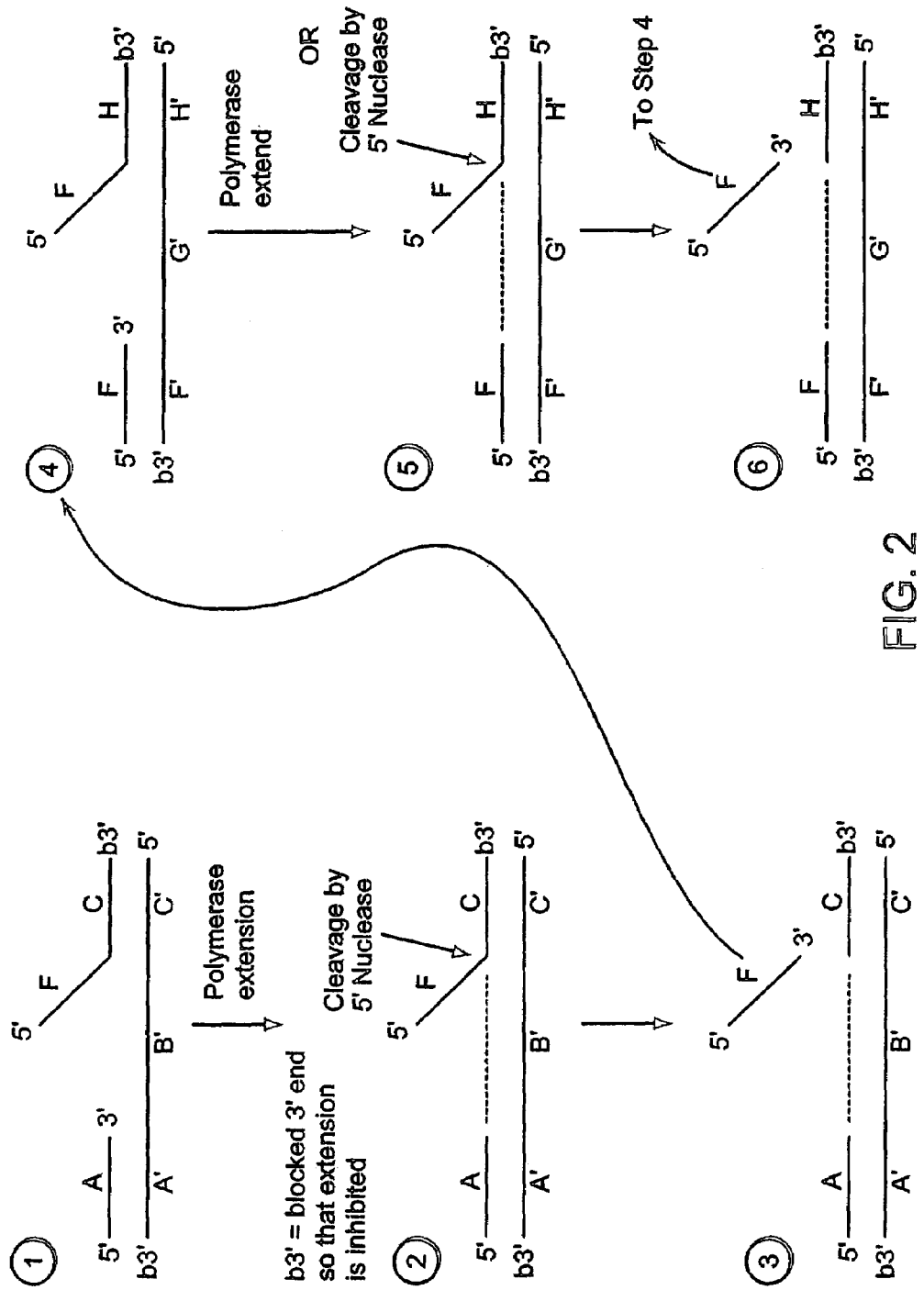
FIG. 2 is a representation of a linear amplification of a target nucleic acid sequence comprising a duplex structure comprising a preformed flap.
Figure 3:
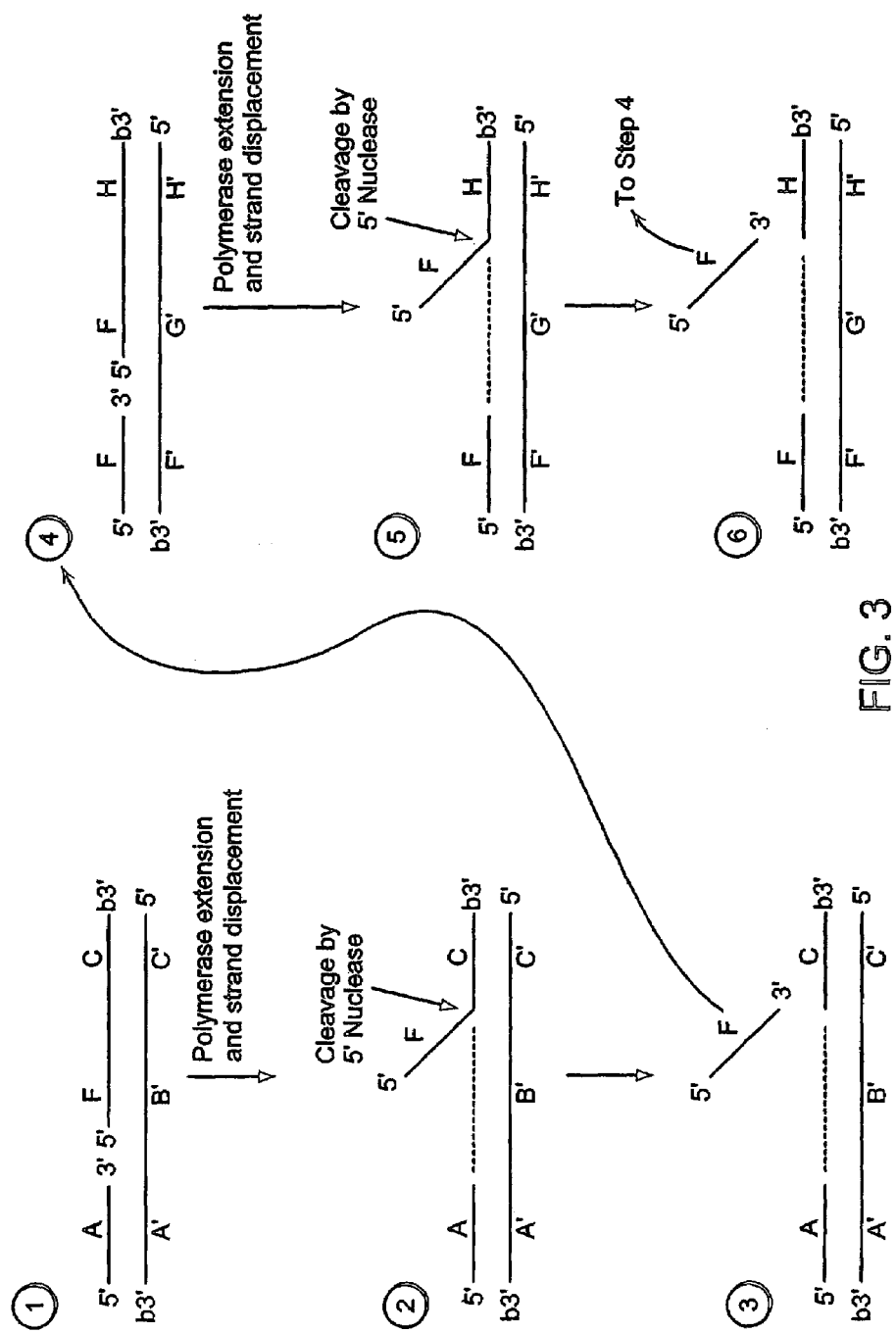
FIG. 3 is a representation of a linear amplification of a target nucleic acid sequence wherein a flap is formed by the activity of a polymerization means with strand displacement activity.
Figure 4A:
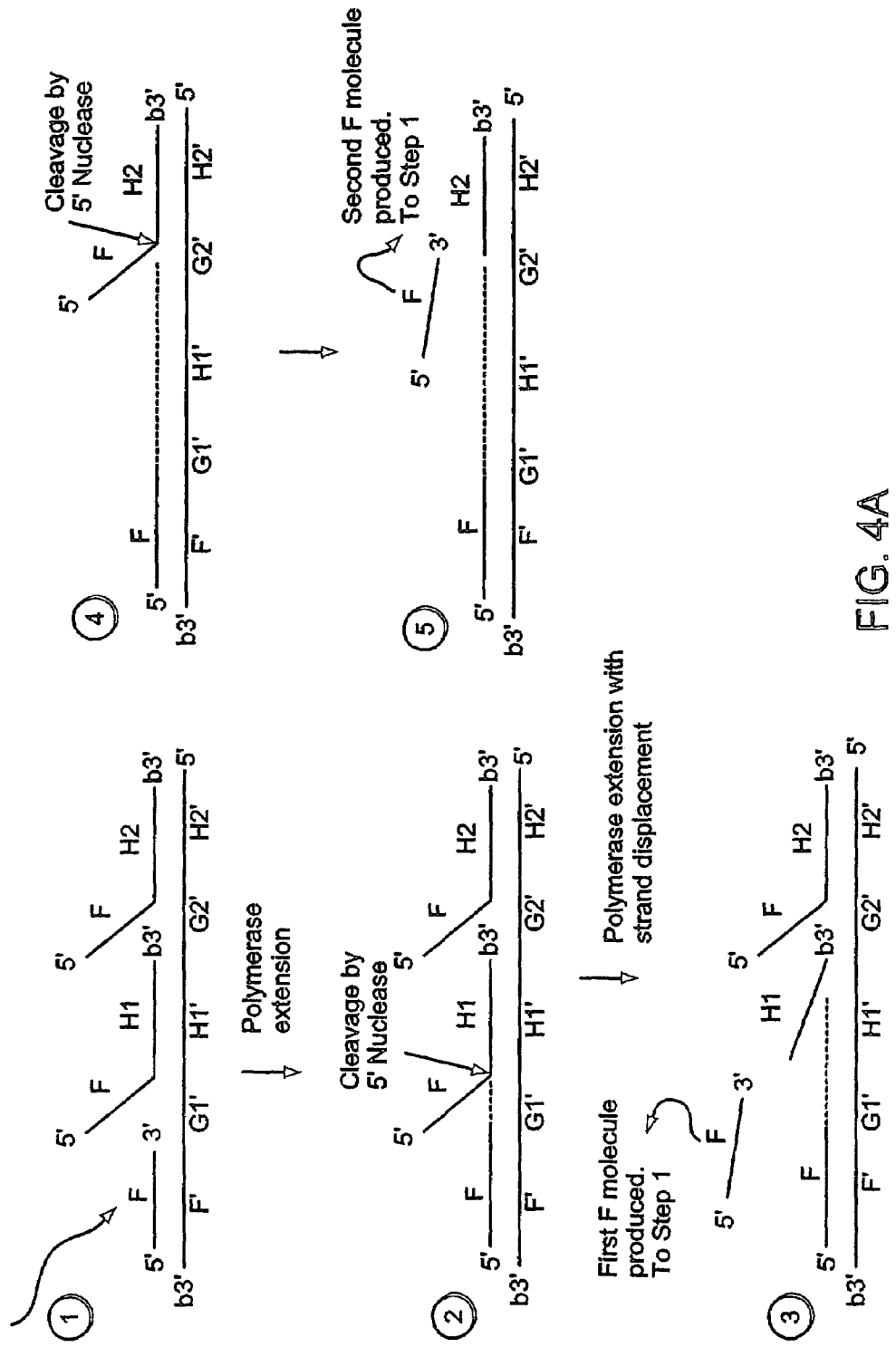
FIGS. 4a and 4b are representations of an exponential amplification of a template nucleic acid sequence.
Figure 4B:
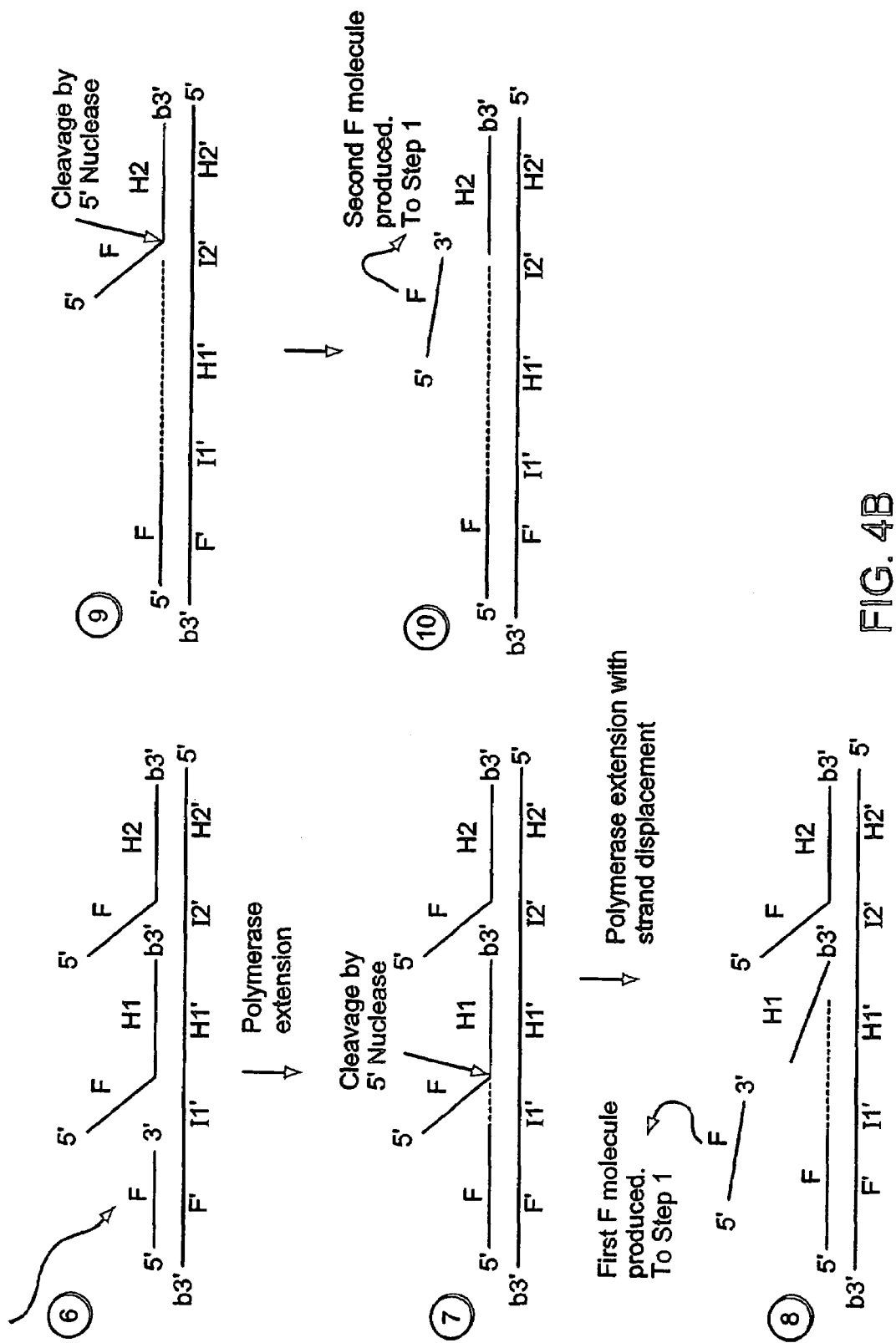

The invention provides for a first duplex comprising a target nucleic acid (e.g., A'B'C', FIG. 2; A'B' C', FIG. 17A), a primer (e.g., a first oligonucleotide, e.g., A, FIG. 2 or FIG. 17A) and a probe (e.g., a second oligonucleotide, e.g., FC, FIG. 2 or FIG. 17A). In one embodiment, the probe (e.g., a second oligonucleotide) comprises a 5' region that is not complementary to the target nucleic acid. According to this embodiment, a duplex is formed such that the 5' region of the probe is a flap and the extension region of the target nucleic acid is single-stranded. In a second embodiment, the primer and the 5' region of the probe hybridize to non-overlapping regions of the target nucleic acid, as defined herein. According to this embodiment, a duplex is formed such that the 5' region of the second oligonucleotide is not a flap, and the extension region of the target nucleic acid is completely single-stranded, is partially single stranded (that is, less than 100% (e.g., 99%, 90%, 75%, 50%, 25%, 5%, etc. . . .) of the extension region is single-stranded), or is completely single stranded. A duplex comprising an extension region that is partially single stranded or completely double-stranded further comprises the following: 1. a primer and probe wherein one or both of the primer and probe is/are partially complementary, defined hereinabove, to the extension region; or 2. a primer and a probe wherein one or both of the primer and probe is/are completely complementary to the extension region. Formation of a cleavage structure from a duplex wherein the 5' region of the probe is hybridized to the target nucleic acid requires a nucleic acid polymerization activity that possesses strand displacement activity.

In one embodiment, a duplex is formed by first hybridizing the target nucleic acid with the probe and then adding the primer.

In another embodiment, a duplex is formed by simultaneously hybridizing the target nucleic acid with the probe and primer.

B. Second Duplex

The invention provides for a second duplex comprising a template nucleic acid (e.g., F'G'H', FIG. 2 or FIG. 17D), a primer (e.g., the released flap of a second oligonucleotide, e.g., F, FIG. 2 or FIG. 17D) and a probe (e.g., a third oligonucleotide, e.g., FH, FIG. 2; H, FIG. 17D). In one embodiment, the third oligonucleotide comprises a 5' region that is not complementary to the template nucleic acid. According to this embodiment, a duplex is formed such that the 5' region of the third oligonucleotide is a flap and the extension region of the template nucleic acid is single-stranded. In a second embodiment, the primer (e.g., the released flap of a second oligonucleotide) and a probe (e.g., a third oligonucleotide) hybridize to non-overlapping regions of the template nucleic acid, defined herein. According to this embodiment, a duplex if formed such that the 5' region of the probe (e.g., the third oligonucleotide) is not a flap, and the extension region of the target nucleic acid is completely single stranded, is partially single stranded (that is, less than 100% (e.g., 99%, 90%, 75%, 50%, 25%, 5%, etc . . . ) of the extension region is single-stranded), or is completely single stranded. A duplex comprising an extension region that is partially single stranded or completely double-stranded further comprises the following: 1. a primer and a probe wherein one or both of the primer and probe is/are partially complementary, defined hereinabove, to the extension region; or 2. a primer and a probe wherein one or both of the primer and probe is/are completely complementary to the extension region.

Figure 5:
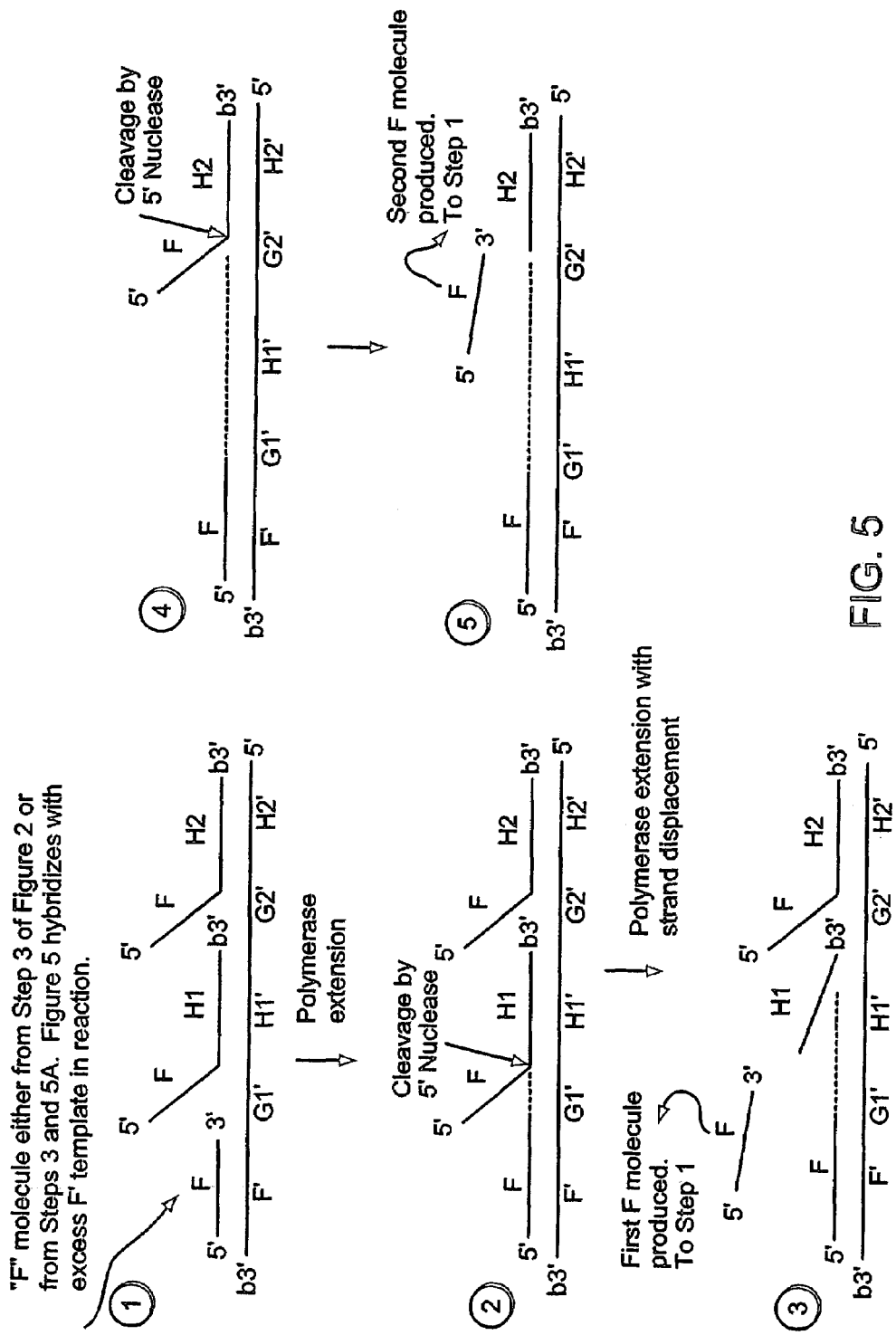
FIG. 5 is a representation of an exponential amplification of a target nucleic acid sequence comprising a duplex structure comprising a preformed flap.
Figure 6:
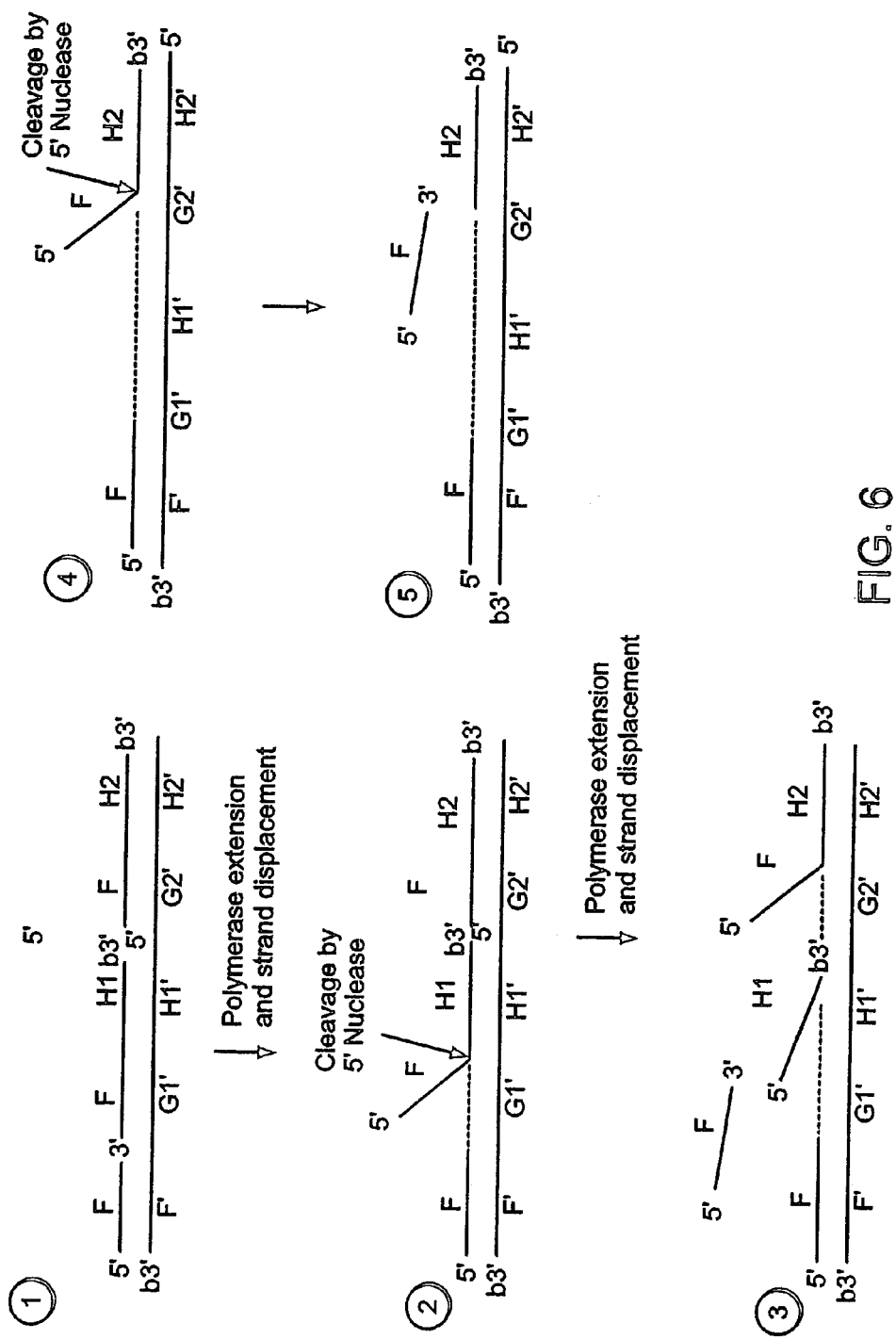
FIG. 6 is a representation of an exponential amplification of a target nucleic acid sequence wherein a flap is formed by the activity of a polymerization means with strand displacement activity.

The invention also provides for a second duplex comprising a template nucleic acid (e.g., F'G1'H1'G2'H2', FIG. 5), a primer (e.g., the released flap of a second oligonucleotide, e.g., F, FIG. 5) a first probe (e.g., a third oligonucleotide, e.g., FH1, FIG. 5) and a fourth probe (e.g., a fourth oligonucleotide, e.g., FH2, FIG. 5). In one embodiment, the first probe comprises a 5' region that is not complementary to the template nucleic acid. In another embodiment, the second probe comprises a 5' region that is not complementary to the template nucleic acid. In another embodiment, both the first and second probes comprise a 5' region that is not complementary to the template nucleic acid. According to these embodiments, a duplex is formed such that the 5' region of the first probe, the second probe, or both the first and second probe, is/are a flap(s) and the extension regions of the template nucleic acid are single-stranded. In a second embodiment, the primer (e.g., the released flap of a second oligonucleotide) and the 5' region of the first probe (e.g., a third oligonucleotide), or the 5' region of the second probe (e.g., a fourth oligonucleotide) or the 5' regions of both the first and second probe hybridize to non-overlapping regions of the template nucleic acid. According to this embodiment, a duplex is formed such that the 5' region of the first probe (e.g., the third oligonucleotide) or the 5' region of the second probe, or the 5' regions of both the first and second probe is/are not a flap, and the extension regions of the target nucleic acid are single stranded, are partially single stranded (that is, less than 100% (e.g., 99%, 90%, 75%, 50%, 25%, 5%, etc. . . .) of the extension regions are single-stranded), or are completely single stranded. A duplex comprising an extension region that is partially single stranded or completely double-stranded further comprises either a primer and two probes wherein at least one of the primer and probes is/are partially complementary, defined hereinabove, to the extension region(s), or a primer and two probes wherein at least one of the primer and probes is/are completely complementary to the extension region(s).

Formation of a cleavage structure from a duplex wherein the 5' region of the first and/or second probe is hybridized to the template nucleic acid requires a nucleic acid polymerization activity that possesses strand displacement activity. In one embodiment, a second duplex is formed by first hybridizing the template nucleic acid with the first probe or with both the first and second probes, prior to the addition of the primer. In an another embodiment, a second duplex is formed by hybridizing the template nucleic acid with both the probes and primers simultaneously.

III. Nucleic Acid Polymerization Activities

The invention provides for nucleic acid polymerization activities (including nucleic acid polymerases) that are useful in an isothermal reaction. A nucleic acid polymerization activity that is useful in an isothermal reaction according to the invention includes, but is not limited to any of the nucleic acid polymerases listed below.

A nucleic acid polymerase according to the invention can be thermostable. As used herein, "thermostable" refers to an enzyme which is stable and active at temperatures as great as preferably between about 90-100° C. and more preferably between about 70-98° C. to heat as compared, for example, to a non-thermostable form of an enzyme with a similar activity. For example, a thermostable nucleic acid polymerase or FEN nuclease derived from thermophilic organisms such as *P. furiosus, M. jannaschii, A. fulgidus* or *P. horikoshii* are more stable and active at elevated temperatures as compared to a nucleic acid polymerase from *E. coli* or a mammalian FEN enzyme. A representative thermostable nucleic acid polymerase isolated from *Thermus aquaticus* (Taq) is described in U.S. Pat. No. 4,889,818 and a method for using it in conventional PCR is described in Saiki et al., 1988, *Science* 239:487. Another representative thermostable nucleic acid polymerase isolated from *P. furiosus* (Pfu) is described in Lundberg et al., 1991, *Gene,* 108:1-6. Additional representative temperature stable polymerases include, e.g., polymerases extracted from the thermophilic bacteria *Thermus flavus, Thermus ruber, Thermus thermophilus, Bacillus stearothermophilus* (which has a somewhat lower temperature optimum than the others listed), *Thermus lacteus, Thermus rubens, Thermotoga maritima,* or from thermophilic archaea *Thermococcus litoralis,* and *Methanothermus fervidus.*

Temperature stable polymerases and FEN nucleases are preferred in a thermocycling process wherein double stranded nucleic acids are denatured by exposure to a high temperature (about 950 C) during the PCR cycle.

Known DNA polymerases useful according to the invention include, for example, *E. coli* DNA polymerase I, *Thermus thermophilus* (Tth) DNA polymerase, *Bacillus stearothermophilus* DNA polymerase, *Thermococcus litoralis* DNA polymerase, *Thermus aquaticus* (Taq) DNA polymerase and *Pyrococcus furiosus* (Pfu) DNA polymerase.

Nucleic acid polymerases substantially lacking 5' to 3' exonuclease activity useful according to the invention include but are not limited to Klenow and Klenow exo-, and T7 DNA polymerase (Sequenase).

Thermostable nucleic acid polymerases substantially lacking 5' to 3' exonuclease activity useful according to the invention include but are not limited to Pfu, exo- Pfu (a mutant form of Pfu that lacks 3' to 5' exonuclease activity), the Stoffel fragment of Taq, N-truncated Bst, N-truncated Bca, Genta, JdF3 exo-, Vent, Vent exo- (a mutant form of Vent that lacks 3' to 5' exonuclease activity), Deep Vent, Deep Vent exo- (a mutant form of Deep Vent that lacks 3' to 5' exonuclease activity), UlTma, and ThermoSequenase.

Nucleic acid polymerases useful in certain embodiments of the invention substantially lack 3' to 5' exonuclease activity and include but are not limited to exo- Pfu DNA polymerase (a mutant form of Pfu DNA polymerase that substantially lacks 3' to 5' exonuclease activity, Cline et al., 1996, Nucleic Acids Research, 24: 3546; U.S. Pat. No. 5,556,772; commercially available from Stratagene, La Jolla, Calif. Catalogue # 600163), exo- Tma DNA polymerase (a mutant form of Tma DNA polymerase that substantially lacks 3' to 5' exonuclease activity), exo-Tli DNA polymerase (a mutant form of Tli DNA polymerase that substantially lacks 3' to 5' exonuclease activity New England Biolabs, (Cat #257)), exo- *E. coli* DNA polymerase (a mutant form of *E. coli* DNA polymerase that substantially lacks 3' to 5' exonuclease activity) exo- Klenow fragment of *E. coli* DNA polymerase I (Stratagene, Cat #600069), exo- T7 DNA polymerase (a mutant form of T7 DNA polymerase that substantially lacks 3' to 5' exonuclease activity), exo- KOD DNA polymerase (a mutant form of KOD DNA polymerase that substantially lacks 3' to 5' exonuclease activity), exo- JDF-3 DNA polymerase (a mutant form of JDF-3 DNA polymerase that substantially lacks 3' to 5' exonuclease activity), exo-PGB-D DNA polymerase (a mutant form of PGB-D DNA polymerase that substantially lacks 3' to 5' exonuclease activity) New England Biolabs, Cat. #259, Tth DNA polymerase, Taq DNA polymerase (e.g., Cat. Nos. 600131, 600132, 600139, Stratagene); UlTma (N-truncated) Thermatoga martima DNA polymerase; Klenow fragment of DNA polymerase I, 9° Nm DNA polymerase (discontinued product from New England Biolabs, Beverly, Mass.), "3'-5' exo reduced" mutant (Southworth et al., 1996, Proc. Natl. Acad. Sci 93:5281) and Sequenase (USB, Cleveland, Ohio). The polymerase activity of any of the above enzyme can be defined by means well known in the art. One unit of DNA polymerase activity, according to the subject invention, is defined as the amount of enzyme which catalyzes the incorporation of 10 nmoles of total dNTPs into polymeric form in 30 minutes at optimal temperature.

Nucleic acid polymerases useful according to the invention include both native polymerases as well as polymerase mutants, which lack 5' to 3' exonuclease activity. Nucleic acid polymerases useful according to the invention can possess different degrees of thermostability. Preferably, a nucleic acid polymerase according to the invention exhibits strand displacement activity at the temperature at which it can extend a nucleic acid primer. In a preferred embodiment of the invention, a nucleic acid polymerase lacks both 5' to 3' and 3' to 5' exonuclease activity.

Additional nucleic acid polymerases substantially lacking 5' to 3' exonuclease activity with different degrees of thermostability useful according to the invention are listed below.

A. Bacteriophage DNA Polymerases (Useful for 37° C. Assays):

Bacteriophage DNA polymerases are devoid of 5' to 3' exonuclease activity, as this activity is encoded by a separate polypeptide. Examples of suitable DNA polymerases are T4, T7, and φ29 DNA polymerase. The enzymes available commercially are: T4 (available from many sources e.g., Epicentre) and T7 (available from many sources, e.g. Epicentre for unmodified and USB for 3' to 5' exo⁻ T7 "Sequenase" DNA polymerase).

B. Archaeal DNA Polymerases:

There are 2 different classes of DNA polymerases which have been identified in archaea: 1. Family B/pol α type (homologs of Pfu from *Pyrococcus furiosus*) and 2. pol II type (homologs of *P. furiosus* DP1/DP2 2-subunit polymerase). DNA polymerases from both classes have been shown to naturally lack an associated 5' to 3' exonuclease activity and to possess 3' to 5' exonuclease (proofreading) activity. Suitable DNA polymerases (pol α or pol II) can be derived from archaea with optimal growth temperatures that are similar to the desired assay temperatures. Examples of suitable archaea include, but are not limited to:

1. Thermolabile (useful for 37° C. assays)—e.g., *Methanococcus voltae*

2. Thermostable (useful for non-PCR assays)—e.g., *Sulfolobus solfataricus, Sulfolobus acidocaldarium, Methanococcus jannaschi, Thermoplasma acidophilum*. It is estimated that suitable archaea exhibit maximal growth temperatures of ≦80-85° C. or optimal growth temperatures of ≦70-80° C.

3. Thermostable (useful for PCR assays)—e.g., *Pyrococcus* species (*furiosus*, species GB-D, species strain KOD1, *woesii, abysii, horikoshii*), *Thermococcus* species (*litoralis*, species 9° North-7, species JDF-3, *gorgonarius*), *Pyrodictium occultum*, and *Archaeoglobus fulgidus*. It is estimated that suitable archaea would exhibit maximal growth temperatures of ≧80-85° C. or optimal growth temperatures of ≧70-80° C. Appropriate PCR enzymes from the archaeal pol α DNA polymerase group are commercially available, including KOD (Toyobo), Pfx (Life Technologies, Inc.), Vent (New England BioLabs), Deep Vent (New England BioLabs), and Pwo (Boehringer-Mannheim).

Additional archaea related to those listed above are described in the following references: *Archaea: A Laboratory Manual* (Robb, F. T. and Place, A. R., eds.), Cold Spring Harbor Laboratory Press, Cold Spring Harbor, N.Y., 1995 and *Thermophilic Bacteria* (Kristjansson, J. K., ed.) CRC Press, Inc., Boca Raton, Fla., 1992.

C. Eubacterial DNA Polymerases:

There are 3 classes of eubacterial DNA polymerases, pol I, II, and III. Enzymes in the Pol I DNA polymerase family possess 5' to 3' exonuclease activity, and certain members also exhibit 3' to 5' exonuclease activity. Pol II DNA polymerases naturally lack 5' to 3' exonuclease activity, but do exhibit 3' to 5' exonuclease activity. Pol III DNA polymerases represent the major replicative DNA polymerase of the cell and are composed of multiple subunits. The pol III catalytic subunit lacks 5' to 3' exonuclease activity, but in some cases 3' to 5' exonuclease activity is located in the same polypeptide.

There are no commercial sources of eubacterial pol II and pol III DNA polymerases.

There are a variety of commercially available Pol I DNA polymerases, some of which have been modified to reduce or abolish 5' to 3' exonuclease activity. Methods used to eliminate 5' to 3' exonuclease activity of pol I DNA polymerases include:

mutagenesis (as described in Xu et al., 1997, *J. Mol. Biol.*, 268:284 and Kim et al., 1997, *Mol. Cells*, 7:468).

N-truncation by proteolytic digestion (as described in Klenow et al., 1971, *Eur. J. Biochem.*, 22: 371), or N-truncation by cloning and expressing as C-terminal fragments (as described in Lawyer et al., 1993, *PCR Methods Appl.*, 2:275).

As for archaeal sources, the assay-temperature requirements determine which eubacteria should be used as a source of a DNA polymerase useful according to the invention (e.g., mesophiles, thermophiles, hyperthermophiles).

1. Mesophilic/Thermolabile (Useful for 37° C. Assays)

i. DNA polymerases naturally substantially lacking 5' to 3' exonuclease activity: pol II or the pol III catalytic subunit from mesophilic eubacteria, such as *Escherichia coli, Streptococcus pneumoniae, Haemophilus influenza, Mycobacterium* species (*tuberculosis, leprae* ii. DNA polymerase mutants substantially lacking 5' to 3' exonuclease activity: Pol I DNA polymerases for N-truncation or mutagenesis can be isolated from the mesophilic eubacteria listed above (Ci). A commercially-available eubacterial DNA polymerase pol I fragment is the Klenow fragment (N-truncated *E. coli* pol I; Stratagene).

2. Thermostable (Useful for Non PCR Assays)

i. DNA polymerases naturally substantially lacking 5' to 3' exonuclease activity: Pol II or the pol III catalytic subunit from thermophilic eubacteria, such as *Bacillus* species (e.g., *stearothermophilus, caldotenax, caldovelox*)

ii. DNA polymerase mutants substantially lacking 5' to 3' exonuclease activity: Suitable pol I DNA polymerases for N-truncation or mutagenesis can be isolated from thermophilic eubacteria such as the *Bacillus* species listed above. Thermostable N-truncated fragments of *B. stearothermophilus* DNA polymerase pol I are commercially available and sold under the trade names Bst DNA polymerase I large fragment (Bio-Rad and Isotherm DNA polymerase (Epicentre)). A C-terminal fragment of *Bacillus caldotenax* pol I is available from Panvera (sold under the tradename Ladderman).

3. Thermostable (Useful for PCR Assays)

i. DNA polymerases naturally substantially lacking 5' to 3' exonuclease activity: Pol II or pol III catalytic subunit from *Thermus* species (aquaticus, thermophilus, flavus, ruber, caldophilus, filiformis, brokianus) or from *Thermotoga maritima*. The catalytic pol III subunits from *Thermus thermophilus* and *Thermus aquaticus* are described in Yi-Ping et al., 1999, *J. Mol. Evol.*, 48:756 and McHenry et al., 1997, *J. Mol. Biol.*, 272:178.

ii. DNA polymerase mutants substantially lacking 5' to 3' exonuclease activity: Suitable pol I DNA polymerases for N-truncation or mutagenesis can be isolated from a variety of thermophilic eubacteria, including *Thermus* species and *Thermotoga maritima* (see above). Thermostable fragments of *Thermus aquaticus* DNA polymerase pol I (Taq) are commercially available and sold under the trade names KlenTaq1 (Ab Peptides), Stoffel fragment (Perkin-Elmer), and *ThermoSequenase* (Amersham). In addition to C-terminal fragments, 5' to 3' exonuclease$^-$ Taq mutants are also commercially available, such as TaqFS (Hoffman-LaRoche). In addition to 5'-3' exonuclease$^-$ versions of Taq, an N-truncated version of *Thermotoga maritima* DNA polymerase I is also commercially available (tradename UlTma, Perkin-Elmer).

Additional eubacteria related to those listed above are described in *Thermophilic Bacteria* (Kristjansson, J. K., ed.) CRC Press, Inc., Boca Raton, Fla., 1992.

D. Eukaryotic 5' to 3' Exonuclease$^-$ DNA Polymerases (Useful for 37° C. Assays)

There are several DNA polymerases that have been identified in eukaryotes, including DNA pol α (replication/repair), δ (replication), ε (replication), β (repair) and γ (mitochondrial replication). Eukaryotic DNA polymerases are devoid of 5' to 3' exonuclease activity, as this activity is encoded by a separate polypeptide (e.g., mammalian FEN-1 or yeast RAD2). Suitable thermolabile DNA polymerases may be isolated from a variety of eukaryotes (including but not limited to yeast, mammalian cells, insect cells, *Drosophila*) and eukaryotic viruses (e.g., EBV, adenovirus).

It is possible that DNA polymerase mutants lacking 3'-5' exonuclease (proofreading) activity, in addition to lacking 5' to 3' exonuclease activity, could exhibit improved performance in FEN-based detection strategies. For example, reducing or abolishing inherent 3' to 5' exonuclease activity may lower background signals by diminishing non-specific exonucleolytic degradation of labeled probes. Three 3' to 5' exonuclease motifs have been identified, and mutations in these regions have been shown to abolish 3' to 5' exonuclease activity in Klenow, φ29, T4, T7, and Vent DNA polymerases, yeast Pol α, Pol β, and Pol γ, and *Bacillus subtilis* Pol III (reviewed in Derbeyshire et al., 1995, Methods. Enzymol. 262:363). Methods for preparing additional DNA polymerase mutants, with reduced or abolished 3' to 5' exonuclease activity, are well known in the art.

Commercially-available enzymes that lack both 5' to 3' and 3' to 5' exonuclease activities include Sequenase (exo$^-$ T7; USB), Pfu exo$^-$ (Stratagene), exo$^-$ Vent (New England BioLabs), exo$^-$ DeepVent (New England BioLabs), exo$^-$ Klenow fragment (Stratagene), Bst (Bio-Rad), Isotherm (Epicentre), Ladderman (Panvera), KlenTaq1 (Ab Peptides), Stoffel fragment (Perkin-Elmer), ThermoSequenase (USB), and TaqFS (Hoffman-LaRoche).

Nucleic acid polymerases with strand displacement activity are also useful according to the invention.

If polymerases other than Pfu are used, buffers and extension temperatures are selected to allow for optimal activity by the particular polymerase useful according to the invention. Buffers and extension temperatures useful for polymerases according to the invention are know in the art and can also be determined from the Vendor's specifications.

Additional nucleases useful according to the invention include a mutant form of Taq polymerase that lacks a 5' to 3' exonuclease activity but that possesses a 3' to 5' DNA synthetic activity comprises the following mutation: D144S/F667Y Taq wherein D144S eliminates 5' to 3' exonuclease activity and F667Y improves ddNTP incorporation.

Exo- mutants of PolI polymerase can be prepared according to the method of Xu et al., 1997, *J. Mol. Biol.*, 268: 284.

IV. Cleavage Structure

The invention provides for a cleavage structure that can be cleaved by a nuclease (e.g., a FEN nuclease) and therefore teaches methods of preparing a cleavage structure.

A. Preparation of a Cleavage Structure

1. In one embodiment of the invention, a first cleavage structure is formed by incubating a target nucleic acid (A'B'C', FIG. 2 or FIG. 17A), a downstream probe (e.g., a second oligonucleotide, e.g., FC, FIG. 2 or FIG. 17A) comprising a 5' region that is not complementary to the target nucleic acid, and an upstream primer (e.g., a first oligonucleotide, e.g., A, FIG. 2 or FIG. 17A) located not more than 1000 nucleotides from the probe, with a suitable buffer (for example Sentinel Molecular Beacon PCR core buffer (Catalog #600500), 10×Pfu buffer available from Stratagene (Catalog #200536), or 1× FullVelocity QPCR master mix available from Stratagene (Catalog#600561), under conditions that allow the target nucleic acid sequence to hybridize to the oligonucleotides (for example 95° C. for 10 sec-5 minutes followed by cooling to between approximately 50-60° C.) to form a duplex according to the invention. The 5' region of the probe is a flap and the extension region of the target nucleic acid is single-stranded. The optimal temperature will vary depending on the specific probe(s), primers and polymerases. In one embodiment, the 3' end of the upstream primer is extended by a nucleic acid polymerization activity according to the invention such that the newly synthesized 3' end of the upstream oligonucleotide primer is adjacent to, as defined herein, the flap of the downstream probe. Extension can be carried out in the presence of 1× Sentinel Molecular core buffer, 1×Pfu buffer, or 1× FullVelocity QPCR master mix for 15 seconds at 72° C. The extension reaction can also be carried out for 30 seconds at 60° C. utilizing the FullVelocity Q-PCR kit.

Figure 17A:
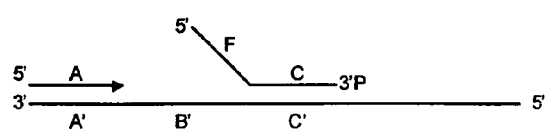

2. In another embodiment of the invention, a first cleavage structure is formed by incubating a target nucleic acid (A'B'C', FIG. 2 or FIG. 17A), a downstream probe (e.g., a second oligonucleotide, e.g., FC, FIG. 2 or FIG. 17A) comprising a 5' region that is complementary to the target nucleic acid, and a upstream primer (e.g., a first oligonucleotide, e.g., A, FIG. 2; FIG. 17A) located not more than 1000 nucleotides from the probe, with a suitable buffer (for example Sentinel Molecular Beacon PCR core buffer (Catalog #600500), 10×Pfu buffer available from Stratagene (Catalog #200536) or 1× FullVelocity QPCR master mix available from Stratagene (Catalog#600561), under conditions that allow the target nucleic acid sequence to hybridize to the oligonucleotides (for example 95° C. for 10 sec.-5 minutes followed by cooling to between approximately 50-60° C.) to form a duplex according to the invention, wherein the 5' region of the probe is hybridized to the target nucleic acid and the extension region of the target nucleic acid is single-stranded. The optimal temperature will vary depending on the specific probe(s), primers and polymerases. The 3' end of the upstream primer is extended by a nucleic acid polymerization activity with strand displacement activity, according to the invention, such that the newly synthesized 3' end of the upstream oligonucleotide primer partially displaces the 5' end of the downstream oligonucleotide probe. Extension can be carried out in the presence of 1× Sentinel Molecular core buffer, 1×Pfu buffer or 1× FullVelocity QPCR master mix for 15 seconds at 72° C. The extension reaction can also be carried out for 30 seconds at 60° C. utilizing the FullVelocity Q-PCR kit.

In one embodiment, a duplex is formed by first hybridizing the target nucleic acid with the probe, and then adding the primer.

3. In one embodiment of the invention, a second cleavage structure is formed by incubating a template nucleic acid (F'G'H', FIG. 2 or FIG. 17D), a downstream probe (e.g., a third oligonucleotide, e.g., FH, FIG. 2 or FIG. 17D) comprising a 5' region that is not complementary to the template nucleic acid, and an upstream primer (e.g., the released flap of a second oligonucleotide, e.g., F, FIG. 2 or FIG. 17D) located not more than 1000 nucleotides from the probe, with a suitable buffer (for example Sentinel Molecular Beacon PCR core buffer (Catalog #600500), 10×Pfu buffer available from Stratagene (Catalog #200536), or 1× FullVelocity QPCR master mix available from Stratagene (Catalog#600561) under conditions that allow the template nucleic acid sequence to hybridize to the oligonucleotides (for example 95° C. for 10 sec.-5 minutes followed by cooling to between approximately 50-60° C.) to form a second duplex according to the invention, wherein the 5' region of the probe is a flap and the extension region of the target nucleic acid is not hybridized to the flap. The optimal temperature will vary depending on the specific probe(s), primers and polymerases. In one embodiment, the 3' end of the upstream primer is extended by a nucleic acid polymerization activity according to the invention such that the newly synthesized 3' end of the upstream oligonucleotide primer is adjacent to, as defined herein, the flap of the downstream probe. Extension is preferably carried out in the presence of 1× Sentinel Molecular core buffer, 1×Pfu buffer or 1× FullVelocity QPCR master mix for 15 seconds at 72° C. The extension reaction can be carried out for 30 seconds at 60° C. utilizing the FullVelocity Q-PCR kit.

4. In another embodiment of the invention, a second cleavage structure is formed by incubating a target nucleic acid (F'G'H', FIG. 2; FIG. 17D), a downstream probe (e.g., a third oligonucleotide, e.g., FH, FIG. 2 or H, FIG. 17D) comprising a 5' region that is complementary to the target nucleic acid, and a upstream primer (e.g., the released flap of a second oligonucleotide, e.g., F, FIG. 2 or FIG. 17D) located not more than 1000 nucleotides from the probe, with a suitable buffer (for example Sentinel Molecular Beacon PCR core buffer (Catalog #600500), 10×Pfu buffer available from Stratagene (Catalog #200536), or 1× FullVelocity QPCR master mix available from Stratagene (Catalog#600561), under conditions that allow the target nucleic acid sequence to hybridize to the oligonucleotides (for example 95° C. for 10 sec-5 minutes followed by cooling to between approximately 50-60° C.) to form a duplex according to the invention, wherein the 5' region of the probe is hybridized to the target nucleic acid and the extension region of the target nucleic acid is single-stranded. The optimal temperature will vary depending on the specific probe(s), primers and polymerases. The 3' end of the upstream primer is extended by a nucleic acid polymerization activity with strand displacement activity, according to the invention, such that the newly synthesized 3' end of the upstream oligonucleotide primer partially displaces the downstream oligonucleotide probe. Extension is preferably carried out in the presence of 1× Sentinel Molecular core buffer, 1×Pfu buffer or 1× FullVelocity QPCR master mix available from Stratagene Calif. (Catalog#600561) for 15 seconds at 72° C. The extension reaction can also be carried out for 30 seconds at 60° C. utilizing the FullVelocity Q-PCR kit.

In one embodiment, a duplex is formed by first hybridizing the template nucleic acid with the probe, and then adding the primer.

In another embodiment, a duplex is formed by hybridizing the template nucleic acid with the probe and primer simultaneously.

5. In another embodiment of the invention, a second cleavage structure is formed by incubating a template nucleic acid (e.g., F'G1'H1'G2'H2', FIG. 5) comprising first and second extension regions, a downstream first probe (e.g., a third oligonucleotide, e.g., FH1, FIG. 5) comprising a 5' region that is not complementary to the template nucleic acid, a downstream second probe (e.g., a fourth oligonucleotide, e.g., FH2, FIG. 5), also comprising a 5' region that is not complementary to the template nucleic acid and an upstream primer (e.g., the released flap of a second oligonucleotide, e.g., F, FIG. 5) located not more than 1000 nucleotides from the downstream first probe, with a suitable buffer (for example Sentinel Molecular Beacon PCR core buffer (Catalog #600500) or 10×Pfu buffer available from Stratagene (Catalog #200536), under conditions that allow the template nucleic acid sequence to hybridize to the oligonucleotides (for example 95° C. for 2-5 minutes followed by cooling to between approximately 50-60° C.) to form a second duplex according to the invention, wherein the 5' regions of the third and fourth probes are flaps and the extension regions of the template nucleic acid do not form hybrids with the respective flaps. The optimal temperature will vary depending on the specific probe(s), primers and polymerases. The 3' end of the upstream primer is extended by a nucleic acid polymerization activity according to the invention such that the newly synthesized 3' end of the upstream oligonucleotide primer is adjacent to, as defined herein, the flap of the first downstream probe. Extension is preferably carried out in the presence of 1× Sentinel Molecular core buffer or 1×Pfu buffer for 15 seconds at 72° C.

The second cleavage structure is cleaved to release the flap of the first downstream probe (for example F, FIG. 5, step 2).

A third cleavage structure is prepared by extending the 3' end of the upstream primer by a nucleic acid polymerization activity such that the newly synthesized end of the upstream oligonucleotide primer is adjacent to, as defined herein, the flap of the second downstream probe. Extension is preferably carried out in the presence of 1× Sentinel Molecular core buffer or 1×Pfu buffer for 15 seconds at 72° C.

6. In another embodiment of the invention, a second cleavage structure is formed by incubating a template nucleic acid comprising first and second extension regions (e.g., F'G1'H1'G2'H2', FIG. 5), a downstream first probe (e.g., a third oligonucleotide, e.g., FH1, FIG. 5) comprising a 5' region that is complementary to the template nucleic acid, a downstream second probe (e.g., a fourth oligonucleotide, e.g. FH2, FIG. 5), also comprising a 5' region that is complementary to the template nucleic acid and an upstream primer (e.g., the released flap of a second oligonucleotide, e.g., F, FIG. 5) located not more than 1000 nucleotides from the upstream first probe, with a suitable buffer (for example Sentinel Molecular Beacon PCR core buffer (Catalog #600500) or 10×Pfu buffer available from Stratagene (Catalog #200536), under conditions that allow the template nucleic acid sequence to hybridize to the oligonucleotides (for example 95° C. for 2-5 minutes followed by cooling to between approximately 50-60° C.) to form a duplex according to the invention, wherein the 5' regions of the third and fourth probes are hybridized to the template nucleic acid and the extension regions of the template nucleic acid do not form hybrids with the respective flaps. The optimal temperature will vary depending on the specific probe(s), primers and polymerases. The 3' end of the upstream primer is extended by a nucleic acid polymerization activity possessing strand displacement activity according to the invention such that the newly synthesized 3' end of the upstream oligonucleotide primer partially displaces the 5' end of the first probe. Extension is preferably carried out in the presence of 1× Sentinel Molecular core buffer or 1×Pfu buffer for 15 seconds at 72° C. The first probe is cleaved by a cleavage means, as described herein, and is released from the template nucleic acid. The newly synthesized 3' end of the upstream oligonucleotide is further extended by a nucleic acid polymerization activity possessing strand displacement activity and partially displaces the 5' end of the second probe to form a third cleavage structure.

In one embodiment, a duplex is formed by first hybridizing the template nucleic acid with the first probe, the second probe or both the first and second probes, prior to the addition of the primer.

In another embodiment, a duplex is formed by hybridizing the template nucleic acid with the probe and primer simultaneously.

A cleavage structure as described in any one of parts 1-6, above can also be prepared as follows. The components of a cleavage structure are hybridized at a temperature (for example 50° C., 69° C., or 72° C., that is optimal for hybridization, and subsequent steps of polymerization and cleavage, and for a time sufficient to permit hybridization and formation of a first duplex, or a second duplex, as defined herein, for example, 15 min-1 hour.

In certain embodiments of the invention, a first or second duplex is formed by incubating the components of a first or second duplex in the presence of a denaturing agent (e.g., DMSO or glycerol) at a concentration that is sufficient to permit hybridization and formation of a first or second duplex, according to the invention, as well as subsequent steps of polymerization and cleavage, described below. A concentration of a denaturing agent that is useful according to the invention will vary depending on the base pair compositions of the components of the duplex. A concentration of a denaturing agent that is useful according to the invention will be determined experimentally by methods known in the art and described herein, to be sufficient to permit hybridization of complementary nucleic acids, polymerization of a primer (e.g., a first oligonucleotide or the released flap of a second oligonucleotide) and cleavage of a cleavage structure to release flaps, according to the invention. In one embodiment, the denaturing agent is DMSO, used at concentration of 0 to 6%, and preferably around 1.5 to 2% for nucleic acids in the range of approximately 0.1 to 1 kb. A concentration of DMSO greater than 2% may be used for nucleic acids greater than 10 kb. Alternatively, glycerol can be used as a denaturing agent at a concentration of from 0 to 10%, and preferably 5 to 8%. Both, or even other denaturing agents, may be used in combination at concentrations that are determined experimentally by methods known in the art.

For an isothermal reaction according to the invention, all of the steps of the reaction that occur after the formation of a first duplex, as defined herein, are performed at the same temperature.

A probe having a secondary structure that changes upon binding of the probe to the target nucleic acid sequence is used to prepare a cleavage structure according to the invention. A probe according to the invention has a secondary structure as defined herein, (including a stem loop, a hairpin, an internal loop, a bulge loop, a branched structure and a pseudoknot) or multiple secondary structures, cloverleaf type structures or any three-dimensional structure, as defined hereinabove. Probes useful for forming a cleavage structure according to the invention may also comprise covalently bound or non-covalently bound subunits (e.g., a bi-molecular or multi-molecular probe as defined herein).

B. How to Prepare a Labeled Cleavage Structure

The invention provides for labeled cleavage structures. A labeled cleavage structure is formed as described in section A1-A6 of the section entitled "Cleavage Structure", above, wherein one or both of the upstream probes is labeled (either at the 5' end or internally at a site that is located in the flap, as defined herein) such that cleavage of the cleavage structure releases a labeled flap or fragment. Methods of labeling a nucleic acid probe or oligonucleotide are well known in the art (See, Sambrook et al., supra; Ausubel et al., supra).

Subsequently, any of several strategies may be employed to distinguish the uncleaved labeled nucleic acid from the cleaved fragments thereof. According to one embodiment, the invention provides for methods for detecting the amount of cleaved, released, nucleic acid fragment that is captured by binding of a binding moiety or a tag to a capture element, respectively, on a solid support. In this manner, the present invention permits identification of those samples that contain a target nucleic acid sequence.

The oligonucleotide probe may be labeled, as described below, by incorporating moieties detectable by spectroscopic, photochemical, biochemical, immunochemical, enzymatic or chemical means. The method of linking or conjugating the label to the oligonucleotide probe depends, of course, on the type of label(s) used and the position of the label on the probe. Preferably a probe is labeled at the 5' end although probes labeled at the 3' end or labeled throughout the length of the probe are also useful in particular embodiments of the invention.

A variety of labels that would be appropriate for use in the invention, as well as methods for their inclusion in the probe, are known in the art and include, but are not limited to, enzymes (e.g., alkaline phosphatase and horseradish peroxidase) and enzyme substrates, radioactive atoms, fluorescent dyes, chromophores, chemiluminescent labels, electrochemiluminescent labels, such as Origen™ (Igen), that may interact with each other to enhance, alter, or diminish a signal. Of course, if a labeled molecule is used in a PCR based assay carried out using a thermal cycler instrument, the label must be able to survive the temperature cycling required in this automated process.

1. Radioactive Labels

Among radioactive atoms, $^{33}$P or, $^{32}$P is preferred. Methods for introducing $^{33}$P or, $^{32}$P into nucleic acids are known in the art, and include, for example, 5' labeling with a kinase, or random insertion by nick translation. "Specific binding partner" refers to a protein capable of binding a ligand molecule with high specificity, as for example in the case of an antigen and a monoclonal antibody specific therefor. Other specific binding partners include biotin and avidin or streptavidin, IgG and protein A, and the numerous receptor-ligand couples known in the art. The above description is not meant to categorize the various labels into distinct classes, as the same label may serve in several different modes. For example, $^{125}$I, may serve as a radioactive label or as an electron-dense reagent. HRP may serve as an enzyme or as antigen for a monoclonal antibody. Further, one may combine various labels for desired effect. For example, one might label a probe with biotin, and detect the presence of the probe with avidin labeled with $^{125}$I, or with an anti-biotin monoclonal antibody labeled with HRP. Other permutations and possibilities will be readily apparent to those of ordinary skill in the art and are considered as equivalents within the scope of the instant invention.

2. Fluorophores

Fluorophores for use as labels in constructing labeled probes of the invention include rhodamine and derivatives (such as Texas Red), fluorescein and derivatives (such as 5-bromomethyl fluorescein), Lucifer Yellow, IAEDANS, 7-Me$_2$N-coumarin-4-acetate, 7-OH-4-CH$_3$-coumarin-3-acetate, 7-NH$_2$-4-CH$_3$-coumarin-3-acetate (AMCA), monobromobimane, pyrene trisulfonates, such as Cascade Blue, and monobromorimethyl-ammoniobimane. In general, fluorophores with wide Stokes shifts are preferred, to allow using fluorimeters with filters rather than a monochromometer and to increase the efficiency of detection.

Probes labeled with fluorophores can readily be used in nuclease (e.g. FEN-nuclease) mediated cleavage of a cleavage structure comprising a labeled probe according to the invention. If the label is on the 5'-end of the probe, the nuclease (e.g. FEN-nuclease) generated labeled fragment is separated from the intact, hybridized probe by procedures well known in the art. In another embodiment of the invention, detection of the hydrolyzed, labeled probe can be accomplished using, for example, fluorescence polarization, a technique to differentiate between large and small molecules based on molecular tumbling. Large molecules (i.e., intact labeled probe) tumble in solution much more slowly than small molecules. Upon linkage of a fluorescent moiety to an appropriate site on the molecule of interest (e.g., the 5' end of a labeled probe), this fluorescent moiety can be measured (and differentiated) based on molecular tumbling, thus differentiating between intact and digested probe.

3. FRET

As used herein, the phrase "interactive pair of labels" as well as the phrase "pair of interactive labels" as well as the phrase "first and second moieties" refer to a pair of molecules which interact physically, optically, or otherwise in such a manner as to permit detection of their proximity by means of a detectable signal. Examples of a "pair of interactive labels" include, but are not limited to, labels suitable for use in fluorescence resonance energy transfer (FRET) (Stryer, L. Ann. Rev. Biochem. 47, 819-846, 1978), scintillation proximity assays (SPA) (Hart and Greenwald, Molecular Immunology 16:265-267, 1979; U.S. Pat. No. 4,658,649), luminescence resonance energy transfer (LRET) (Mathis, G. Clin. Chem. 41, 1391-1397, 1995), direct quenching (Tyagi et al., Nature Biotechnology 16, 49-53, 1998), chemiluminescence energy transfer (CRET) (Campbell, A. K., and Patel, A. Biochem. J. 216, 185-194, 1983), bioluminescence resonance energy transfer (BRET) (Xu, Y., Piston D. W., Johnson, Proc. Natl. Acad. Sc., 96, 151-156, 1999), or excimer formation (Lakowicz, J. R. Principles of Fluorescence Spectroscopy, Kluwer Academic/Plenum Press, New York, 1999).

The first and second moieties are "operatively coupled" to the oligonucleotides of the invention. This means that each moiety is coupled to its respective sequence in any manner consistent with its operation, i.e., in any manner consistent with providing a detectable signal upon cleavage of the probe. For example, the pair of moieties can be either covalently or non-covalently attached to the oligonucleotides of the invention. Examples of non-covalent attachment, any of which can be employed to operatively couple the first or second moiety to the oligonucleotides of the invention, include attachment via hybridization, hydrogen bonds, ionic bonds, hydrophobic interactions, van der Waals interactions, and protein-nucleic acid interactions. Preferred are moieties which are covalently attached at or near the 5' and 3' ends of the oligonucleotides.

As used herein, references to "fluorescence" or "fluorescent groups" or "fluorophores" include luminescence and luminescent groups, respectively.

An "increase in fluorescence", as used herein, refers to an increase in detectable fluorescence emitted by a fluorophore. An increase in fluorescence may result, for example, when the distance between a fluorophore and a quencher is increased, for example due to a cleavage reaction by a cleavage means, such that the quenching is reduced. There is an "increase in fluorescence" when the fluorescence emitted by the fluorophore is increased by at least 2 fold, for example 2, 2.5, 3, 4, 5, 6, 7, 8, 10 fold or more.

a. FRET Compatible Fluorophores

A pair of interactive labels useful for the invention can comprise a pair of FRET-compatible dyes, or a quencher-dye pair. In one embodiment, the pair comprises a fluorophore-quencher pair.

Oligonucleotides of the present invention permit detection/measurement of a target nucleic acid by fluorescence. They can be labeled with a fluorophore and quencher in such a manner that the fluorescence emitted by the fluorophore in intact oligonucleotides is substantially quenched, whereas the fluorescence in cleaved or in some embodiments target hybridized oligonucleotides are not quenched, resulting in an increase in overall fluorescence upon probe cleavage or in some embodiments target hybridization. Furthermore, the generation of a fluorescent signal during real-time detection of an amplification reaction product allows accurate quantitation of the initial number of target sequences in a sample.

A wide variety of fluorophores can be used, including but not limited to: 5-FAM (also called 5-carboxyfluorescein; also called Spiro(isobenzofuran-1(3H), 9'-(9H)xanthene)-5-carboxylic acid, 3',6'-dihydroxy-3-oxo-6-carboxyfluorescein); 5-Hexachloro-Fluorescein ([4,7,2',4',5',7'-hexachloro-(3',6'-dipivaloyl-fluoresceinyl)-6-carboxylic acid]); 6-Hexachloro-Fluorescein ([4,7,2',4',5',7'-hexachloro-(3',6'-dipivaloylfluoresceinyl)-5-carboxylic acid]); 5-Tetrachloro-Fluorescein ([4,7,2',7'-tetra-chloro-(3',6'-dipivaloylfluoresceinyl)-5-carboxylic acid]); 6-Tetrachloro-Fluorescein ([4,7,2',7'-tetrachloro-(3',6'-dipivaloylfluoresceinyl)-6-carboxylic acid]); 5-TAMRA (5-carboxytetramethylrhodamine; Xanthylium, 9-(2,4-dicarboxyphenyl)-3,6-bis(dimethyl-amino); 6-TAMRA (6-carboxytetramethylrhodamine; Xanthylium, 9-(2,5-dicarboxyphenyl)-3,6-bis(dimethylamino); EDANS (5-((2-aminoethyl)amino)naphthalene-1-sulfonic acid); 1,5-IAEDANS (5-((((2-iodoacetyl)amino)ethyl)amino)naphthalene-1-sulfonic acid); DABCYL (4-((4-(dimethylamino)phenyl) azo)benzoic acid) Cy5 (Indodicarbocyanine-5) Cy3 (Indo-dicarbocyanine-3); and BODIPY FL (2,6-dibromo-4,4-difluoro-5,7-dimethyl-4-bora-3a,4a-diaza-s-indacene-3-proprionic acid), Quasar-670 (Bioreseach Technologies), CalOrange (Bioresearch Technologies), Rox, as well as suitable derivatives thereof.

b. FRET Compatible Quenchers

As used herein, the term "quencher" refers to a chromophoric molecule or part of a compound, which is capable of reducing the emission from a fluorescent donor when attached to or in proximity to the donor. Quenching may occur by any of several mechanisms including fluorescence resonance energy transfer, photoinduced electron transfer, paramagnetic enhancement of intersystem crossing, Dexter exchange coupling, and exciton coupling such as the formation of dark complexes. Fluorescence is "quenched" when the fluorescence emitted by the fluorophore is reduced as compared with the fluorescence in the absence of the quencher by at least 10%, for example, 15%, 20%, 30%, 40%, 50%, 60%, 70%, 80%, 90%, 95%, 98%, 99%, 99.9% or more.

The quencher can be any material that can quench at least one fluorescence emission from an excited fluorophore being used in the assay. There is a great deal of practical guidance available in the literature for selecting appropriate reporter-quencher pairs for particular probes, as exemplified by the following references: Clegg (1993, Proc. Natl. Acad. Sci., 90:2994-2998); Wu et al. (1994, Anal. Biochem., 218:1-13); Pesce et al., editors, Fluorescence Spectroscopy (1971, Marcel Dekker, New York); White et al., Fluorescence Analysis: A Practical Approach (1970, Marcel Dekker, New York); and the like. The literature also includes references providing exhaustive lists of fluorescent and chromogenic molecules and their relevant optical properties for choosing reporter-quencher pairs, e.g., Berlman, Handbook of Fluorescence Spectra of Aromatic Molecules, 2nd Edition (1971, Academic Press, New York); Griffiths, Colour and Constitution of Organic Molecules (1976, Academic Press, New York); Bishop, editor, Indicators (1972, Pergamon Press, Oxford); Haugland, Handbook of Fluorescent Probes and Research Chemicals (1992 Molecular Probes, Eugene) Pringsheim, Fluorescence and Phosphorescence (1949, Interscience Publishers, New York), all of which incorporated hereby by reference. Further, there is extensive guidance in the literature for derivatizing reporter and quencher molecules for covalent attachment via common reactive groups that can be added to an oligonucleotide, as exemplified by the following references, see, for example, Haugland (cited above); Ullman et al., U.S. Pat. No. 3,996,345; Khanna et al., U.S. Pat. No. 4,351,760, all of which hereby incorporated by reference.

A number of commercially available quenchers are known in the art, and include but are not limited to DABCYL, BHQ-1, BHQ-2, and BHQ-3. The BHQ ("Black Hole Quenchers") quenchers are a new class of dark quenchers that prevent fluorescence until a hybridization event occurs. In addition, these new quenchers have no native fluorescence, virtually eliminating background problems seen with other quenchers. BHQ quenchers can be used to quench almost all reporter dyes and are commercially available, for example, from Biosearch Technologies, Inc (Novato, Calif.).

c. Attachment of Fluorophore and Quencher

In one embodiment of the invention, the fluorophore or quencher is attached to the 3' nucleotide of an oligonucleotide of the invention. In another embodiment of the invention, the fluorophore or quencher is attached to the 5' nucleotide. In yet another embodiment, the fluorophore or quencher is internally attached to an oligonucleotide of the invention. In some embodiments, either the fluorophore or quencher is attached to the 5' nucleotide of the probe and the other of said fluorophore or quencher is attached to the 3' nucleotide of the probe. In other embodiments, either the fluorophore or quencher is attached to a probe of the invention and the other of said fluorophore or quencher is attached to a template nucleic acid of the invention. Attachment can be made via direct coupling, or alternatively using a spacer molecule of, for example, from about 1 to about 5 atoms in length.

For the internal attachment of the fluorophore or quencher, linkage can be made using any of the means known in the art. Appropriate linking methodologies for attachment of many dyes to oligonucleotides are described in many references, e.g., Marshall, Histochemical J., 7: 299-303 (1975); Menchen et al., U.S. Pat. No. 5,188,934; Menchen et al., European Patent Application 87310256.0; and Bergot et al., International Application PCT/US90/05565. All are hereby incorporated by reference.

Each member of the fluorophore/quencher pair can be attached anywhere within the oligonucleotide, preferably at a distance from the other of the pair such that sufficient amount of quenching occurs when the oligonucleotides are not cleaved or is hybridized to the template nucleic acid.

In one embodiment, one can use two interactive labels (e.g., FRET or non-FRET pairs) on a single oligonucleotide probe with due consideration given for maintaining an appropriate spacing of the labels on the oligonucleotide to permit the separation of the labels during oligonucleotide probe unfolding (e.g., for example due to a change in the secondary structure of the probe) or hydrolysis. In another embodiment, one can use two olgionucltoitides of the invention, e.g., template nucleic acid and third oligonucleotide, each with one member of a pair of interactive labels.

In certain embodiments, the fluorescence of the released label is then compared to the label remaining bound to the target. It is not necessary to separate the nuclease (e.g. FEN-nuclease) generated fragment and the probe that remains bound to the target after cleavage in the presence of nuclease (e.g. FEN-nuclease) if the probe is synthesized with a fluorophore and a quencher that are separated by about 20 nucleotides. Alternatively, the quencher is positioned such that the probe will not fluoresce when not hybridized to the target nucleic acid sequence. Such a dual labeled probe will not fluoresce when intact or when not hybridized to the target nucleic acid sequence (or in the case of bi- or multimolecular probes, when the probe is not dissociated) because the light emitted from the dye is quenched by the quencher. Thus, any fluorescence emitted by an intact probe is considered to be background fluorescence. In one embodiment, when a labeled probe is cleaved by a FEN nuclease, dye and quencher are separated and the released fragment will fluoresce. Alternatively, when a labeled probe is hybridized to a target nucleic acid, the distance between the dye and the quencher is increased and the level of fluorescence increases. In an embodiment wherein the probe is a bi- or multi-molecular probe, dissociation of the molecules comprising the probe results in an increase in fluorescence. The amount of fluorescence is proportional to the amount of nucleic acid target sequence present in a sample.

In yet another embodiment, two labeled nucleic acids are used, each complementary to separate regions of separate strands of a double-stranded target sequence, but not to each other, so that a labeled nucleic acid anneals downstream of each primer. For example, the presence of two probes can potentially double the intensity of the signal generated from a single label and may further serve to reduce product strand reannealing, as often occurs during PCR amplification. The probes are selected so that the probes bind at positions adjacent (downstream) to the positions at which primers bind.

In still another embodiment, two labeled nucleic acids are used, each complementary to at least a portion of each other, e.g., template nucleic acid and third oligonucleotide. For example, the template nucleic acid may be labeled with a quencher and the third oligonucleotide may be labeled with a fluorescer. When hybridized to each other the fluorescer is substantially quenched. However, upon cleavage of the third oligonucleotide the labels are separated and fluorescence substantially increases.

One can also use multiple probes in the present invention to achieve other benefits. For instance, one could test for any number of pathogens in a sample simply by putting as many probes as desired into the reaction mixture; the probes could each comprise a different label to facilitate detection. For example, multiple sets of different second oligonucleotides, template nucleic acids and third oligonucleotides can be added to a reaction mixture. Each of the second oligonucleotides would be complementary to a region of a nucleic acid sequence from a different pathogen. If the pathogen is present in the reaction mixture the corresponding second oligonucleotide would hybridize to the pathogens nucleic acid sequence. Upon polymerization of the first oligonucleotide the second oligonucleotide would be cleaved. The cleaved flap would then hybridize to a template nucleic acid specific for this flap. The flap would be extended by a nucleic acid polymerase forming a second cleavage structure with the third oligonucleotide, which is cleaved. Cleavage of the third oligonucleotide would produce a signal indicative of the particular pathogen. Multiple different signals, e.g., fluorescent signals, could be generated for each pathogen of interest. Such reactions can be conducted in the Mx3000P Real Time PCR system (Stratagene, Calif.).

One can also achieve allele-specific or species-specific discrimination using multiple probes in the present invention, for instance, by using probes that have different $T_m$s and conducting the annealing/cleavage reaction at a temperature specific for only one probe/allele duplex. One can also achieve allele specific discrimination by using only a single probe and examining the types of cleavage products generated. In one embodiment of the invention, the probe is designed to be exactly complementary, at least in the 5' terminal region, to one allele but not to the other allele(s). With respect to the other allele(s), the probe will be mismatched in the 5' terminal region of the probe so that a different cleavage product will be generated as compared to the cleavage product generated when the probe is hybridized to the exactly complementary allele.

Although probe sequence can be selected to achieve important benefits, one can also realize important advantages by selection of probe labels(s). The labels may be attached to the oligonucleotide directly or indirectly by a variety of techniques. Depending on the precise type of label used, the label can be located at the 5' or 3' end of the probe, located internally in the probe, or attached to spacer arms of various sizes and compositions to facilitate signal interactions. Using commercially available phosphoramidite reagents, one can produce oligomers containing functional groups (e.g., thiols or primary amines) at either the 5' or the 3' terminus via an appropriately protected phosphoramidite, and can label them using protocols described in, for example, PCR Protocols: A Guide to Methods and Applications, Innis et al., eds. Academic Press, Ind., 1990.

Methods for introducing oligonucleotide functionalizing reagents to introduce one or more sulfhydryl, amino or hydroxyl moieties into the oligonucleotide probe sequence, typically at the 5' terminus, are described in U.S. Pat. No. 4,914,210. A 5' phosphate group can be introduced as a radioisotope by using polynucleotide kinase and gamma-$^{32}$P-ATP or gamma-$^{33}$P-ATP to provide a reporter group. Biotin can be added to the 5' end by reacting an aminothymidine residue, or a 6-amino hexyl residue, introduced during synthesis, with an N-hydroxysuccinimide ester of biotin. Labels at the 3' terminus may employ polynucleotide terminal transferase to add the desired moiety, such as for example, cordycepin $^{35}$S-dATP, and biotinylated dUTP.

Oligonucleotide derivatives are also available labels. For example, etheno-dA and etheno-A are known fluorescent adenine nucleotides that can be incorporated into a nucleic acid probe. Similarly, etheno-dC or 2-amino purine deoxyriboside is another analog that could be used in probe synthesis. The probes containing such nucleotide derivatives may be hydrolyzed to release much more strongly fluorescent mononucleotides by flap-specific nuclease activity.

A labeled probe having a secondary structure that changes upon binding of the probe to the target nucleic acid sequence is used to prepare a labeled cleavage structure according to the invention. A labeled probe according to the invention has a secondary structure as defined herein, (including a stem loop, a hairpin, an internal loop, a bulge loop, a branched structure and a pseudoknot) or multiple secondary structures, cloverleaf type structures or any three-dimensional structure, as defined hereinabove. Labeled probes useful for forming a labeled cleavage structure according to the invention may also comprise covalently bound or non-covalently bound subunits (e.g., a bi-molecular or multi-molecular probe as defined herein).

C. Cleaving a Cleavage Structure and Generating a Signal

A cleavage structure according to the invention can be cleaved by the methods described in the section above, entitled "Nucleases".

D. Detection of Released Labeled Fragments

Detection or verification of the labeled fragments may be accomplished by a variety of methods well known in the art and may be dependent on the characteristics of the labeled moiety or moieties comprising a labeled cleavage structure.

V. Cleavage Means

Nucleases useful according to the invention include any enzyme that possesses 5' endonucleolytic activity for example a DNA polymerase, e.g. DNA polymerase I from *E. coli*, and DNA polymerase from *Thermus aquaticus* (Taq), *Thermus thermophilus* (Tth), and *Thermus flavus* (Tfl). Nucleases useful according to the invention also include DNA polymerases with 5'-3' exonuclease activity, including but not limited to eubacterial DNA polymerase I, including enzymes derived from *Thermus* species (Taq, Tfl, Tth, Tca (caldophilus) Tbr (brockianus), enzymes derived from *Bacillus* species (Bst, Bca, Magenta (full length polymerases, NOT N-truncated versions)), enzymes derived from *Thermotoga* species (Tma (maritima, Tne (neopolitana) and *E. coli* DNA polymerase I. The term nuclease also embodies FEN nucleases.

FEN-1 is an ~40 kDa divalent metal ion-dependent exo- and endonuclease that specifically recognizes the backbone of a 5' single-stranded flap strand and tracks down this arm to the cleavage site, which is located at the junction wherein the two strands of duplex DNA adjoin the flap. Both the endo- and exonucleolytic activities show little sensitivity to the base at the most 5' position at the flap or nick. Both FEN-1 endo- and exonucleolytic substrate binding and cutting are stimulated by an upstream oligonucleotide (flap adjacent strand or primer). This is also the case for *E. coli* pol I. The endonuclease activity of the enzyme is independent of the 5' flap length, cleaving a 5' flap as small as one nucleotide. The endonuclease and exonuclease activities are insensitive to the chemical nature of the substrate, cleaving both DNA and RNA.

Both the endo- and exonucleolytic activities are inhibited by concentrations of salts in the physiological range. The exonuclease activity is inhibited 50-fold at 50 mM NaCl as compared to 0 mM NaCl. The endonuclease activity is inhibited only sevenfold at 50 mM NaCl (Reviewed in Lieber 1997, supra).

Although a 5'-OH terminus is a good substrate for FEN-1 loading onto a 5' flap substrate, it serves as a very poor substrate when part of a nick in an otherwise double stranded DNA structure. The electrostatic repulsion by the terminal phosphate is likely to favor breathing of the substrate into a pseudo-flap configuration, providing the active form of the substrate for FEN-1. Such an explanation would indicate a single active site and a single mechanism of loading of FEN-1 onto the 5' ssDNA terminus of the flap or pseudo-flap configuration of the nick. Consistent with this model are observations that optimal activity at a nick requires very low $Mg^{2+}$ and monovalent salt concentrations, which destabilize base-pairing and would favor breathing of a nick to a flap. Higher $Mg^{2+}$ and monovalent salt concentrations would disfavor breathing and inhibit cutting of nicked or gapped structures that do require breathing to convert to a flap. Cleavage of stable flap structures is optimal at moderate $Mg^{2+}$ levels and does not decrease with increasing $Mg^{2+}$ concentration. This is because a flap substrate does not have to melt out base pairs to achieve its structure; hence, it is entirely insensitive to $Mg^{2+}$. Though the endonucleolytic activity decreases with monovalent salt, the decline is not nearly as sharp as that seen for the exonucleolytic activity. Furthermore, it has previously been shown that one-nucleotide flaps are efficient substrates. All of these observations are consistent with the fact that when FEN-1 has been interpreted to be functioning as an exonuclease, the size of the degradation products vary from one to several nucleotides in length. Breathing of nicks into flaps of varying length would be expected to vary with local sequence, depending on the G/C content. In summary, a nick breathing to form a transient flap means that the exonucleolytic activity of FEN-1 is the same as the endonucleolytic activity (Reviewed in Lieber, 1997, supra).

The endonuclease and exonuclease activities of FEN-1 cleave both DNA and RNA without requiring accessory proteins. At the replication fork, however, FEN-1 does interact with other proteins, including a DNA helicase and the proliferating cell nuclear antigen (PCNA), the processivity factor for DNA polymerases δ and ε. PCNA significantly stimulates FEN-1 endo- and exonucleolytic activity.

The FEN-1 enzymes are functionally related to several smaller bacteriophage 5'→3' exonucleases such as T5 5' exonuclease and T4 RNase H as well as to the larger eukaryotic nucleotide excision repair enzymes such as XPG, which also acts in the transcription-coupled repair of oxidative base damage. In eubacteria such as *Escherichia coli* and *Thermus aquaticus*, Okazaki processing is provided by the PolI 5'→3' exonuclease domain. These bacterial and phage enzymes share two areas of limited sequence homology with FEN-1, which are termed the N(N-terminal) and I (intermediate) regions, with the residue similarities concentrated around seven conserved acidic residues. Based on crystal structures of T4 RNase H and T5 exonuclease as well as mutagenesis data, it has been proposed that these residues bind to two $Mg^{2+}$ ions that are required for affecting DNA hydrolysis; however, the role each metal plays in the catalytic cycle, which is subtly different for each enzyme, is not well understood (Reviewed in Hosfield et al., 1998b, supra).

FEN-1 genes encoding FEN-1 enzymes useful in the invention include murine fen-1, human fen-1, rat fen-1, Xenopus laevis fen-1, and fen-1 genes derived from four archaebacteria *Archaeglobus fulgidus, Methanococcus jannaschii, Pyrococcus furiosus* and *Pyrococcus horikoshii*. cDNA clones encoding FEN-1 enzymes have been isolated from human (GenBank Accession Nos.: NM_004111 and L37374), mouse (GenBank Accession No.: L26320), rat (GenBank Accession No.: AA819793), *Xenopus laevis* (GenBank Accession Nos.: U68141 and U64563), and *P. furiosus* (GenBank Accession No.: APF03497). The complete nucleotide sequence for *P. horikoshii* flap endonuclease has also been determined (GenBank Accession No.: AB005215). The FEN-1 family also includes the *Saccharomyces cerevisiae* RAD27 gene (GenBank Accession No.: Z28113 Y13137) and the *Saccharomyces pombe* RAD2 gene (GenBank Accession No.: X77041). The archaeal genome of *Methanobacterium thermautotrophiculum* has also been sequenced. Although the sequence similarity between FEN-1 and prokaryotic and viral 5'→3' exonucleases is low, FEN-1s within the eukaryotic kingdom are highly conserved at the amino acid level, with the human and *S. cerevisiae* proteins being 60% identical and 78% similar. The three archaebacterial FEN-1 proteins are also, highly homologous to the eukaryotic FEN-1 enzymes (Reviewed in Matsui et al., 1999., *J. Biol. Chem.*, 274:18297, Hosfield et al., 1998b, *J. Biol. Chem.*, 273:27154 and Lieber, 1997, *BioEssays*, 19:233).

The sequence similarities in the two conserved nuclease domains (N-terminal or N and intermediate or I domains) between human and other FEN-1 family members are 92% (murine), 79% (*S. cerevisiae*), 77% (*S. pombe*), 72% (*A. fulgidus*), 76% (*M. jannaschii*), and 74% (*P. furiosus*).

FEN-1 specifically recognizes the backbone of a 5' single-stranded flap strand and migrates down this flap arm to the cleavage site located at the junction between the two strands of duplex DNA and the flap. If the strand upstream of the flap (sometimes called the flap adjacent strand or primer strand) is removed, the resulting structure is termed a pseudo-Y (see FIG. 8). This structure is cleaved by FEN-1, but at 20- to 100-fold lower efficiency. FEN-1 does not cleave 3' single-stranded flaps. However, FEN-1 acting as an exonuclease will hydrolyze dsDNA substrates containing a gap or nick (Reviewed in Hosfield et al., 1998a, supra, Hosfield et al., 1999b, supra, and Lieber 1997, supra). Exonucleolytically, FEN-1 acts at a nick and, with lower efficiency, at a gap or a recessed 5' end on dsDNA. At gapped structures, the efficiency of FEN-1 binding and cutting decreases with increasing gap size up to approximately five nucleotides and then stabilizes at a level of cleavage that is equivalent to activity on a recessed 5' end within dsDNA. Blunt dsDNA, recessed 3' ends and ssDNA are not cleaved (Reviewed in Lieber 1997, supra).

FEN nucleases that are useful according to the invention have been isolated from a variety of organisms including human (GenBank Accession Nos.: NM_004111 and L37374), mouse (GenBank Accession No.: L26320), rat (GenBank Accession No.: AA819793), yeast (GenBank Accession No.: Z28113 Y13137 and GenBank Accession No.: X77041) and xenopus laevis (GenBank Accession Nos.: U68141 and U64563). Such enzymes can be cloned and overexpressed using conventional techniques well known in the art.

A FEN nuclease according to the invention is preferably thermostable. Thermostable FEN nucleases have been isolated and characterized from a variety of thermostable organisms including four archaebacteria. The cDNA sequence (GenBank Accession No.: AF013497) and the amino acid sequence (Hosfield et al., 1998a, supra and Hosfield et al., 1998b) for *P. furiosus* flap endonuclease have been determined. The complete nucleotide sequence (GenBank Accession No.: AB005215) and the amino acid sequence (Matsui et al., supra) for *P. horikoshii* flap endonuclease have also been determined. The amino acid sequence for *M jannaschii* (Hosfield et al., 1998b and Matsui et al., 1999 supra) and *A. fulgidus* (Hosfield et al., 1998b) flap endonuclease have also been determined.

Thermostable FEN1 enzymes can be cloned and overexpressed using techniques well known in the art and described in Hosfield et al., 1998a, supra, Hosfield et al., 1998b, Kaiser et al., 1999, J. Biol. Chem., 274: 21387 and Matusi et al., supra and herein in Example 5 entitled "Cloning Pfu FEN-1".

The endonuclease activity of a FEN enzyme can be measured by a variety of methods including the following.

A. FEN EENDONUCLEASE ACTIVITY ASSAY

Figure 14:
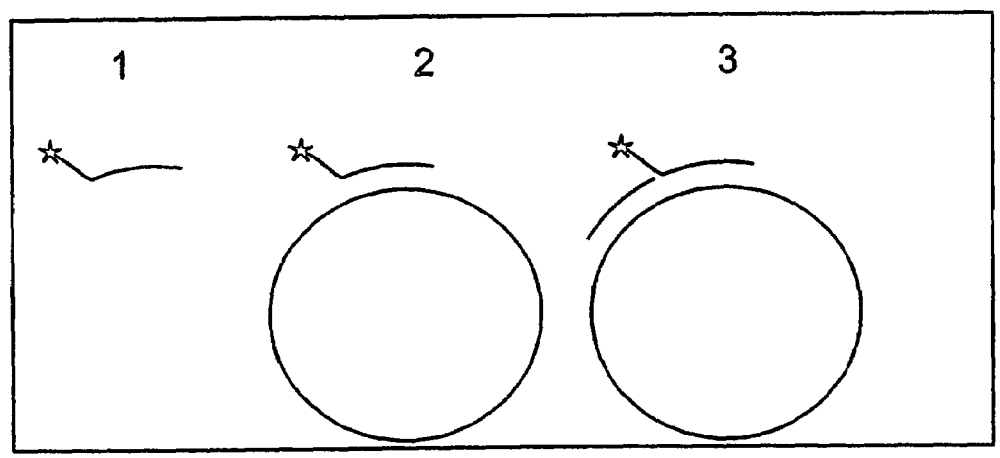
FIG. 14 demonstrates three templates (labeled 1, 2, and 3) that may be used to detect FEN nuclease activity.

1. Templates (for example as shown in FIG. 14) are used to evaluate the activity of a FEN nuclease according to the invention.

Template 1 is a 5'$^{33}$P labeled oligonucleotide (Heltest4) with the following sequence: 5'AAAATAAATAAAAAAAATACTGTTGG-GAAGGGCGATCGGTGCG3'. The underlined section of Heltest4 represents the region complementary to M13mp18+. The cleavage product is an 18 nucleotide fragment with the sequence AAAATAAATAAAAAAAAT.

Heltest4 binds to M13 to produce a complementary double stranded domain as well as a non-complementary 5' overhang. This duplex forms template 2 (FIG. 14) which is also used for helicase assays. Template 3 (FIG. 14) has an additional primer (FENAS) bound to M13 and is directly adjacent to Heltest 4. The sequence of FENAS is: 5'CCAT-TCGCCATTCAGGCTGCGCA3'. In the presence of template 3, FEN binds the free 5' terminus of Heltest4, migrates to the junction and cleaves Heltest4 to produce an 18 nucleotide fragment. Templates 1 and 2 serve as controls, although template 2 can also serve as a template.

Templates are prepared as described below:

|  | Template 1 | Template 2 | Template 3 |
| --- | --- | --- | --- |
| Heltest4 | 14 μl | 14 μl | 14 μl |
| M13 | ** | 14 μl | 14 μl |
| FENAS | ** | ** | 14 μl |
| H$_2$O | 28 μl | 14 μl | ** |
| 10x Pfu Buff. | 4.6 μl | 4.6 μl | 4.6 μl |

10×Pfu buffer is available from Stratagene (Catalog # 200536). According to the method of the invention, 10×Pfu buffer is diluted such that a reaction is carried out in the presence of 1× buffer.

M13 is M13mp18+strand and is at a concentration of 200 ng/μL, $^{33}$P labeled Heltest4 is at an approximate concentration of 0.7 ng/μl, and FENAS is at a concentration of 4.3 ng/μl. Based on these concentrations, the Heltest4 and M13 are at approximately equal molar amounts ($5 \times 10^{-14}$) and FENAS is present in an approximately 10× molar excess ($6 \times 10^{-13}$).

The template mixture is heated at 95° C. for five minutes, cooled to room temperature for 45 minutes and stored at 4° C. overnight.

2 μl of FEN-1 or, as a control, H$_2$O are mixed with the three templates as follows:

| | |
| --- | --- |
| 3 μl | template |
| 0.7 μl | 10x cloned Pfu buffer |
| 0.56 μl | 100 mM MgCl$_2$ |
| 2.00 μl | enzyme or H$_2$O |
| 0.74 μl | H$_2$0 |
| 7.00 μl | total volume |

The reactions are allowed to proceed for 30 minutes at 50° C. and stopped by the addition of 2 μl formamide "Sequencing Stop" solution to each sample. Samples are heated at 95° C. for five minutes and loaded on a 6% acrylamide, 7M urea CastAway (Stratagene) gel.

Alternatively, FEN activity can be analyzed in the following buffer wherein a one hour incubation time is utilized.

10×FEN Buffer 500 mM Tris-HCl pH 8.0

100 mM MgCl$_2$

The reaction mixture below is mixed with 2 μl of FEN or, as a control, 2 μl of H$_2$O.

| | |
| --- | --- |
| 3 μl | template |
| 0.7 μl | 10x FEN buffer |
| 2.00 μl | enzyme or H$_2$O |
| 1.3 μl | H$_2$O |
| 7.00 μl | total volume |

Samples are incubated for one hour at 50° C. in a Robocyler 96 hot top thermal cycler. Following the addition of 2 μl of Sequencing Stop dye solution, samples are heated at 99° C. for five minutes. Samples are loaded on an eleven-inch long, hand-poured, 20% acrylamide/bis acrylamide, 7M urea gel. The gel is run at 20 watts until the bromophenol blue has migrated approximately ⅔ the total distance. The gel is removed from the glass plates and soaked for 10 minutes in fix (15% methanol, 5% acetic acid) and then for 10 minutes in water. The gel is placed on Whatmann 3 mm paper, covered with plastic wrap and dried for 2 hours in a heated vacuum gel dryer. The gel is exposed overnight to X-ray film.

2. FEN endonuclease activity can also be measured according to the method of Kaiser et al., supra). Briefly, reactions are carried out in a 10 μl volume containing 10 mM MOPS, pH 7.5, 0.05% Tween 20, 0.05% Nonidet P-40, 10 1 g/ml tRNA, and 200 mM KCl for TaqPol and TthPol or 50 mM KCl for all other enzymes. Reaction conditions can be varied depending on the cleavage structure being analyzed. Substrates (2 μM) and varying amounts of enzyme are mixed with the indicated (above) reaction buffer and overlaid with Chill-out (MJ Research) liquid wax. Substrates are heat denatured at 90° C. for 20 s and cooled to 50° C., then reactions are started by addition of MgCl$_2$ or MnCl$_2$ and incubated at 50° C. for the specified length of time. Reactions are stopped by the addition of 1011 of 95% formamide containing 10 mM EDTA and 0.02% methyl violet (Sigma). Samples are heated to 90° C. for 1 min immediately before electrophoresis on a 20% denaturing acrylamide gel (19:1 cross-linked), with 7M urea, and in a buffer of 45 mM Tris borate, pH 8.3, 1.4 mM EDTA. Unless otherwise indicated, 1 μl of each stopped reaction is loaded per lane. Gels are scanned on an FMBIO-100 fluorescent gel scanner (Hitachi) using a 505-nm filter. The fraction of cleaved product is determined from intensities of bands corresponding to uncut and cut substrate with FMBIO Analysis software (version 6.0, Hitachi). The fraction of cut product should not exceed 20% to ensure that measurements approximate initial cleavage rates. The cleavage rate is defined as the concentration of cut product divided by the enzyme concentration and the time of the reaction (in minutes). For each enzyme three data points are used to determine the rate and experimental error.

3. FEN endonuclease activity can also be measured according to the method of Hosfield et al., 1998a, supra. Briefly, in a final volume of 13 µl, varying amounts of FEN and 1.54 pmol of labeled cleavage substrate are incubated at different temperatures for 30 min before the reaction is quenched with an equal volume of stop solution (10 mM EDTA, 95% deionized formamide, and 0.008% bromophenol blue and xylene cyanol). Samples are electrophoresed through denaturing 15% polyacrylamide gels, and the relative amounts of starting material and product are quantitated using the IPLabGel system (Stratagene) running MacBAS image analysis software. Most reactions are performed in standard assay buffer (10 mM Tris-HCl (pH 8.0), 10 mM $MgCl_2$, and 50 µg/ml bovine serum albumin); however, in a series of experiments the effect of different divalent metals and pH levels are studied by varying the standard buffer. For divalent metals, $MgCl_2$ is omitted, and different metal ions are used at a final concentration of 10 mM. To study the influence of pH, buffers containing different amounts of Tris-HCl, glycine, and sodium acetate are used at a final concentration of 10 mM to obtain a wide range of pH levels at 25° C.

4. FEN endonuclease activity can also be measured according to the method of Matusi et al., 1999, supra. Briefly, the enzyme reactions are performed in a 15-µl reaction mixture containing 50 mM Tris-HCl (pH 7.4), 1.5 mM $MgCl_2$, 0.5 mM β-mercaptoethanol, 100 µg/ml bovine serum albumin, and 0.6 pmol of a labeled cleavage structure. After incubation for 30 min at 60° C., the reaction is terminated by adding 15 µl of 95% formamide containing 10 mM EDTA and 1 mg/ml bromphenol blue. The samples are heated at 95° C. for 10 min, loaded onto a 15% polyacrylamide gel (35 cm×42.5 cm) containing 7M urea and 10×TBE (89 mM Tris-HCl, 89 mM boric acid, 2 mM EDTA (pH 8.0)), and then electrophoresed for 2 h at 2000 V. Reaction products are visualized and quantified using a PhosphorImager (Bio-Rad). Size marker, oligonucleotides are 5' end-labeled with [γ-$^{32}$P]ATP and T4 polynucleotide kinase.

To determine the optimum pH, the reaction is performed in an assay mixture (15 µl) containing 1.5 mM $MgCl_2$, 0.5 mM β-mercaptoethanol, 100 µg/ml bovine serum albumin, and 0.6 pmol of 5' end-labeled cleavage structure in 50 mM of one of the following buffers at 60° C. for 30 min. Three different 50 mM buffers are used to obtain a wide pH range as follows: sodium acetate buffer (pH 4.0-5.5), phosphate buffer (pH 5.5-8.0), and borate buffer (pH 8.0-9.4).

B. FEN EXONUCLEASE ACTIVITY ASSAY

The exonuclease activity of a FEN nuclease according to the invention can be measured by the method of measuring FEN-1 endonuclease activity described in Matsui et al., 1999, supra and summarized above.

Alternatively, the exonuclease activity of a FEN enzyme can be analyzed by the method described in Hosfield et al., 1998b, supra. Briefly, exonuclease activities are assayed using a nicked substrate of FEN under conditions identical to those described for the endonuclease assays (described above).

The precise positions of DNA cleavage in both the exonuclease and endonuclease experiments can be obtained by partial digestion of a 5'$^{32}$P-labeled template strand using the 3'-5' exonuclease activity of Klenow fragment.

A cleavage structure according to the invention is described in the section entitled "Cleavage Structure".

VI. Determining the Stability of the Secondary Structure of a Probe

A. Melting Temperature Assay

A melting temperature assay, takes advantage of the different absorption properties of double stranded and single stranded DNA, that is, double stranded DNA (the double stranded DNA being that portion of a nucleic acid sequence that has folded back on itself to generate an antiparallel duplex structure wherein complementary sequences (base pairs) are associated via hydrogen bonding) absorbs less light than single stranded DNA at a wavelength of 260 nm, as determined by spectrophotometric measurement.

The denaturation of DNA occurs over a narrow temperature range and results in striking changes in many of the physical properties of DNA. A particularly useful change occurs in optical density. The heterocyclic rings of nucleotides adsorb light strongly in the ultraviolet range (with a maximum close to 260 nm that is characteristic for each base). However, the adsorption of DNA is approximately 40% less than would be displayed by a mixture of free nucleotides of the same composition. This effect is called hyperchromism and results from interactions between the electron systems of the bases, made possible by their stacking in the parallel array of the double helix. Any departure from the duplex state is immediately reflected by a decline in this effect (that is, by an increase in optical density toward the value characteristic of free bases (FIG. 13a). The denaturation of double stranded DNA can therefore be followed by this hyperchromicity (FIGS. 13b and 13c)

The midpoint of the temperature range over which the strands of DNA separate is called the melting temperature, denoted $T_m$. An example of a melting curve determined by change in optical absorbance is shown in FIG. 13c. The curve always takes the same form, but its absolute position on the temperature scale (that is, its $T_m$) is influenced by both the base composition of the DNA and the conditions employed for denaturation.

The melting temperature of a DNA molecule depends markedly on its base composition. DNA molecules rich in GC base pairs have a higher Tm than those having an abundance of AT base pairs (FIG. 13b). The Tm of DNA from many species varies linearly with GC content, rising from 77° to 100° C. as the fraction of GC pairs increases from 20% to 78%. That is, the dependence of $T_m$ on base composition is linear, increasing about 0.4° C. for every percent increase in G-C content. GC base pairs are more stable than AT pairs because their bases are held together by three hydrogen bonds rather than by two. In addition, adjacent GC base pairs interact more strongly with one another than do adjacent AT base pairs. Hence, the AT-rich regions of DNA are the first to melt.

A major effect on $T_m$ is exerted by the ionic strength of the solution. The $T_m$ increases 16.6° C. for every tenfold increase in monovalent cation concentration. The most commonly used condition is to perform manipulations of DNA in 0.12 M phosphate buffer, which provides a monovalent Na+ concentration of 0.18M, and a $T_m$ of the order of 90° C.

The $T_m$ can be greatly varied by performing the reaction in the presence of reagents, such as formamide, that destabilize hydrogen bonds. This allows the $T_m$ to be reduced to as low as 40° C. with the advantage that the DNA does not suffer damage (such as strand breakage) that can result from exposure to high temperatures. (Stryer, *Biochemistry*, 1998, 3$^{rd}$ Edition, W.H. Freeman and Co., pp. 81-82 and Lewin, Genes II, 1985, John Wiley & Sons, p. 63-64).

The stability of the secondary structure of the probe according to the invention is determined in a melting temperature assay as follows.

A standard curve for the probe (for example FIG. 13c), wherein absorbance is plotted versus temperature, is prepared by incubating a sample comprising from about 0.2 µg/ml to 100 µg/ml of the probe in a buffer which allows for denaturing and reannealing of the probe at various temperature and for a time sufficient to permit denaturing and reannealing of the probe, and measuring the absorbance of a sample in a quartz cuvette (with a pathlength appropriate for the spectrophotometer being used, e.g., 1-cm), in a spectrophotometer over a range of temperatures wherein the lower temperature limit of the range is at least 50° C. below, and the upper temperature limit of the range is at least 50° C. above the Tm or predicted Tm of the probe. The Tm of the probe is predicted based on the base pair composition according to methods well known in the art (see, Sambrook, supra; Ausubel, supra). Standard curves are generated and compared, using a variety of buffers (e.g., 1×TNE buffer (10×-0.1M Tris base, 10 mM EDTA, 2.0 M NaCl, pH 7.4), FEN nuclease buffer, described herein, 1× Cloned Pfu buffer, described herein, 1× Sentinel Molecular beacon buffer, described herein) including a buffer that is possible and preferentially optimal for the particular nuclease to be employed in the cleavage reaction. The pH of the buffer will be monitored as the temperature increases, and adjusted as is needed.

The assay is performed in a single-beam ultraviolet to visible range (UV-VIS) spectrophotometer. Preferably, the assay is performed in a double-beam spectrophotometer to simplify measurements by automatically comparing the cuvette holding the sample solution to a reference cuvette (matched cuvette) that contains the blank. The blank is an equal volume of sample buffer.

The temperature of the spectrophotometer can be controlled such that the absorbance of the sample is measured at specific temperatures. Spectrophotometers useful according to the invention include but are not limited to the Beckman Coulter DU® 600/7000 Spectrophotometers in combination with the MicroTm Analysis Accessory (Beckman Coulter, Inc., Columbia, Md.).

The stability of the secondary structure of a probe at a particular temperature and in a buffer that is possible and preferentially optimal for the nuclease to be employed in the cleavage reaction of the probe, is determined by measuring the absorbance of the probe at a particular temperature, as above, and determining if the value of the absorbance is less than the absorbance at the Tm, as determined from the standard curve, wherein the standard curve is generated using either the same buffer as used at the test temperature, or a buffer known to produce a comparable standard curve, as described above. The secondary structure of the probe is "stable" in a melting temperature assay, at a temperature that is at or below the temperature of the cleavage reaction (i.e., at which cleavage is performed) if the level of light absorbance at the temperature at or below the temperature of the cleavage reaction is less (i.e., at least 5%, preferably 20% and most preferably 25% or more) than the level of light absorbance at a temperature that is equal to the Tm of the probe (see FIGS. 13c and 13d).

B. FRET

A FRET assay is useful in the invention for two purposes. The first is to determine whether the secondary structure of a probe is "stable" as defined herein. The second is to determine whether the secondary structure of the probe has undergone a "change" upon binding of the probe to the target nucleic acid or whether the probe has been cleaved by a cleavage means.

"FRET" is a distance-dependent interaction between the electronic excited states of two dye molecules in which excitation is transferred from a donor molecule to an acceptor molecule. FRET is caused by a change in the distance separating a fluorescent donor group from an interacting resonance energy acceptor, either another fluorophore, a chromophore, or a quencher. Combinations of donor and acceptor moieties are known as "FRET pairs". Efficient FRET interactions require that the absorption and emission spectra of the dye pairs have a high degree of overlap.

In most embodiments, the donor and acceptor dyes for FRET are different, in which case FRET can be detected by the appearance of sensitized fluorescence of the acceptor and/or by quenching of donor fluorescence. When the donor and acceptor are the same, FRET is detected by the resulting fluorescence depolarization. FRET is dependent on the inverse sixth power of the intermolecular separation (Stryer et al., 1978, Ann. Rev. Biochem., 47:819; Selvin, 1995, Methods Enzymol., 246:300).

As used herein, the term "donor" refers to a fluorophore which absorbs at a first wavelength and emits at a second, longer wavelength. The term "acceptor" refers to a fluorophore, chromophore or quencher with an absorption spectrum which overlaps the donor's emission spectrum and is able to absorb some or most of the emitted energy from the donor when it is near the donor group (typically between 1-100 nm). If the acceptor is a fluorophore capable of exhibiting FRET, it then re-emits at a third, still longer wavelength; if it is a chromophore or quencher, then it releases the energy absorbed from the donor without emitting a photon. Although the acceptor's absorption spectrum overlaps the donor's emission spectrum when the two groups are in proximity, this need not be the case for the spectra of the molecules when free in solution. Acceptors thus include fluorophores, chromophores or quenchers which exhibit either FRET or quenching when placed in proximity, on a probe according to the invention, to the donor due to the presence of a probe secondary structure that changes upon binding of the probe to the target nucleic acid, as defined herein. Acceptors do not include fluorophores, chromophores or quenchers that exhibit FRET or quenching a) at temperatures equal to or greater than the Tm (e.g. more than 5° C. above the Tm, for example 6° C., 10° C., 25° C., 50° C. or more above the Tm) or b) in the presence of a target nucleic acid.

Reference herein to "fluorescence" or "fluorescent groups" or "fluorophores" include luminescence, luminescent groups and suitable chromophores, respectively. Suitable luminescent probes include, but are not limited to, the luminescent ions of europium and terbium introduced as lanthium chelates (Heyduk & Heyduk, 1997). The lanthanide ions are also good donors for energy transfer to fluorescent groups (Selvin 1995). Luminescent groups containing lanthanide ions can be incorporated into nucleic acids utilizing an 'open cage' chelator phosphoramidite.

As used herein, the term "quenching" refers to the transfer of energy from donor to acceptor which is associated with a reduction of the intensity of the fluorescence exhibited by the donor.

The donor and acceptor groups may independently be selected from suitable fluorescent groups, chromophores and quenching groups. Donors and acceptors useful according to the invention include but are not limited to: 5-FAM (also called 5-carboxyfluorescein; also called Spiro(isobenzofuran-1(3H), 9'-(9H)xanthene)-5-carboxylic acid,3',6'-dihydroxy-3-oxo-6-carboxyfluorescein); 5-Hexachloro-Fluorescein ([4,7,2',4',5',7'-hexachloro-(3',6'-dipivaloylfluorosceinyl)-6-carboxylic acid]); 6-Hexachloro-Fluorescein ([4,7,2',4',5',7'-hexachloro-(3',6'-dipivaloylfluorosceinyl)-5-carboxylic acid]); 5-Tetrachloro-Fluorescein ([4,7,2',7'-tetrachloro-(3',6'-dipivaloylfluorosceinyl)-5-carboxylic acid]); 6-Tetrachloro-Fluorescein ([4,7,2',7'-tetrachloro-(3',6'-dipivaloylfluorosceinyl)-6-carboxylic acid]); 5-TAMRA (5-carboxytetramethylrhodamine; Xanthylium, 9-(2,4-dicarboxyphenyl)-3,6-bis(dimethylamino); 6-TAMRA (6-carboxytetramethylrhodamine; Xanthylium, 9-(2,5-dicarboxyphenyl) -3,6-bis(dimethylamino); EDANS (5-((2-aminoethyl) amino)naphthalene-1-sulfonic acid); 1,5-IAEDANS (5-((((2-iodoacetyl)amino)ethyl) amino) naphthalene-1-sulfonic acid); DABCYL (4-((4-(dimethylamino)phenyl) azo)benzoic acid) Cy5 (Indodicarbocyanine-5) Cy3 (Indodicarbocyanine-3); and BODIPY FL (2,6-dibromo-4,4-difluoro-5,7-dimethyl-4-bora-3a,4a-diaza-s-indacene-3-proprionic acid), as well as suitable derivatives thereof.

In certain embodiments of the invention, a probe may also be labeled with two chromophores, and a change in the absorption spectra of the label pair is used as a detection signal, as an alternative to measuring a change in fluorescence.

In the method of the invention, fluorescence intensity of the probe is measured at one or more wavelengths with a fluorescence spectrophotometer or microtitre plate reader, according to methods known in the art.

C. Fluorescence Quenching Assay

A fluorescence quenching assay is useful in the invention for two purposes. The first is to determine whether the secondary structure of a probe is "stable" as defined herein. The second is to determine whether the secondary structure of the probe has undergone a "change" upon binding of the probe to the target nucleic acid.

A probe according to the invention is labeled with a pair of interactive labels (e.g., a FRET or non-FRET pair) wherein one member of the pair is a fluorophore and the other member of the pair is a quencher. For example, a probe according to the invention is labeled with a fluorophore and a quencher and fluorescence is measured in the absence of a target nucleic acid, over a range of temperatures, e.g., wherein the lower temperature limit of the range is at least 50° Celsius below, and the upper temperature limit of the range is at least 50° Celsius above the Tm or the predicted Tm of the probe.

D. Stability

The "stability" of the secondary structure of a probe according to the invention is determined as follows. A probe is labeled with a pair of interactive labels (either FRET or non-FRET pairs) described herein, according to methods well known in the art (for example, as described in Glazer and Mathies, 1997, *Curr. Opin. Biotechnol.*, 8:94; Ju et al., 1995, *Analytical Biochemistry,* 231: 131)). The location of the interactive labels on the probe is such that the labels are separated when the secondary structure of the probe changes following binding of the probe to the target nucleic acid.

A standard curve for the probe (for example FIG. 13*e*), wherein fluorescence is plotted versus temperature, is prepared by incubating a sample comprising typically 125 nM probe in 1× Melting Buffer (20 mM Tris-HCl, pH 8.0, 1 mM MgCl$_2$) or alternatively, in 5 mM Tris-HCl, pH 8.0, 0.1 mM EDTA, or other appropriate buffers for a time that is sufficient to permit denaturing and reannealing of the probe (typically the standard curve is generated using a fluorometer or spectrometer that undergoes a 1° C. per minute change, and measuring the fluorescence in a fluorometer or scanning fluorescence spectrophotometer over a range of temperatures wherein the lower temperature limit of the range is at least 50° C. below, and the upper temperature limit of the range is at least 50° C. above the Tm or predicted Tm of the probe. The Tm of the probe is predicted based on the base pair composition according to methods well known in the art (see, Sambrook, supra; Ausubel, supra).

Standard curves are generated and compared, using a variety of buffers (e.g., 1×TNE buffer (10×-0.1M Tris base, 10 mM EDTA, 2.0 M NaCl, pH 7.4), FEN nuclease buffer, described herein, 1× Cloned Pfu buffer, described herein, 1× Sentinel Molecular beacon buffer, described herein) including a buffer that is possible and preferentially optimal for the particular nuclease to be employed in the cleavage reaction. The pH of the buffer will be monitored as the temperature increases, and adjusted as is needed.

The temperature of the fluorometer or spectrophotometer can be controlled such that the fluorescence of the sample is measured at specific temperatures. Fluorescence can be measured for example with a Perkin-Elmer LS50B Luminescence Spectrometer in combination with a temperature regulatable water bath (e.g., for example available from Fisher Scientific).

Figure 13F:
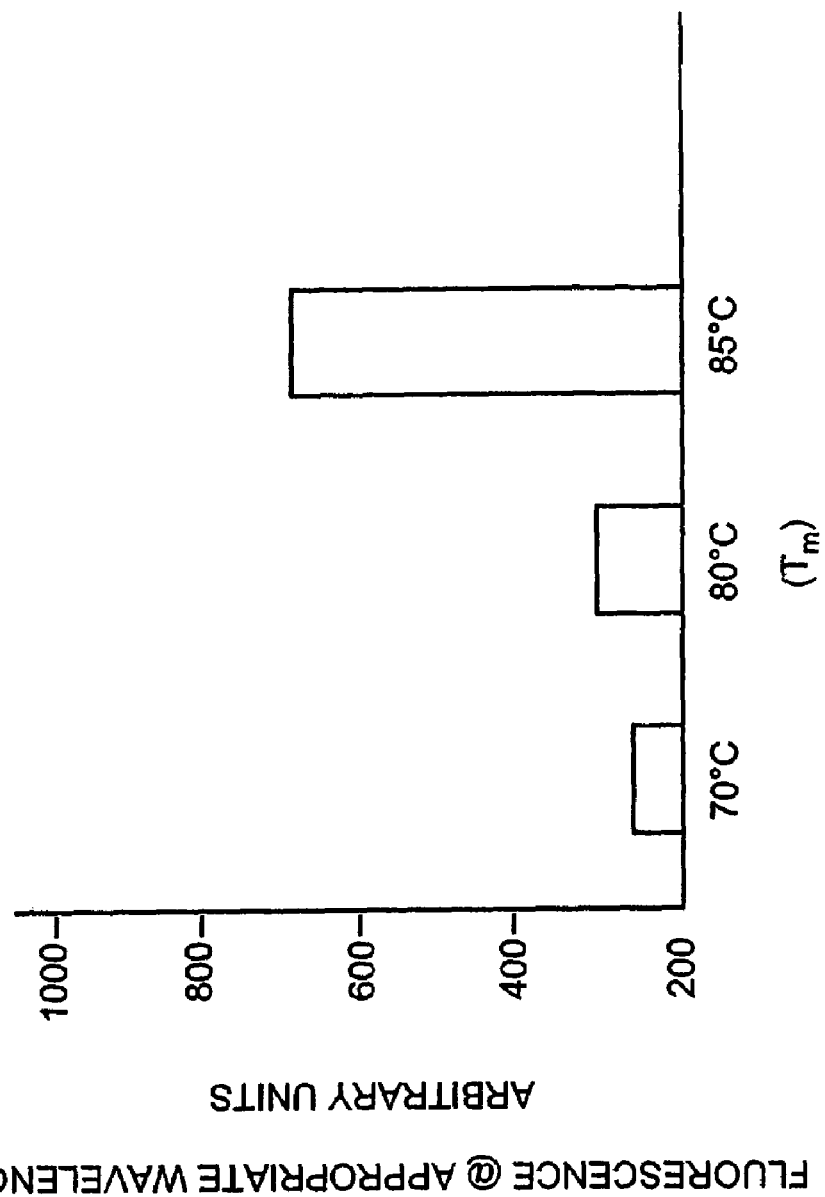
FIG. 13f is a graph demonstrating the effects of temperature on the fluorescence of DNA labeled with a pair of interactive labels.

The stability of the secondary structure of a probe at a particular temperature is determined by measuring the fluorescence of the probe at a particular temperature, as above, and determining if the value of the fluorescence is less than the fluorescence at the Tm, as determined from the standard curve. The secondary structure of the probe is "stable" in a FRET assay, at a temperature that is at or below the temperature of the cleavage reaction (i.e., at which cleavage is performed) if the level of fluorescence at the temperature at or below the temperature of the cleavage reaction is altered (i.e., at least 5%, preferably 20% and most preferably 25% more or less than) the level of fluorescence at a temperature that is equal to the Tm of the probe. The secondary structure of the probe is "stable" in a fluorescence quenching assay, at a temperature that is at or below the temperature of the cleavage reaction (i.e., at which cleavage is performed) if the level of fluorescence at the temperature at or below the temperature of the cleavage reaction is altered (i.e., at least 5%, preferably 20% and most preferably 25% more or less than) the level of fluorescence at a temperature that is equal to the Tm of the probe. (see FIGS. 13*f* and 9*g*).

Alternatively, the stability of the secondary structure of the probe is determined by modifying the method of Gelfand et al. (1999, *Proc. Natl. Acad. Sci.* USA, 96:6113), incorporated herein by reference, to determine the fluorescence of a probe labeled with a pair of interactive labels over a range of temperatures, as described hereinabove.

VII. Detecting a Secondary Structure

A secondary structure according to the invention is detected by generating a standard curve of fluorescence versus temperature for a probe comprising a pair of interactive labels in a FRET assay, as described above (see FIG. 13*e*). A probe that exhibits a change in fluorescence that correlates with a change in temperature (see FIG. 13*e*) (e.g., fluorescence increases as the temperature of the FRET reaction is increased) is capable of forming a secondary structure.

VIII. Measuring a Change in Secondary Structure

A "change" in secondary structure according to the invention is detected by analyzing a probe comprising a pair of interactive labels in a FRET or fluorescence quenching assay at a particular temperature below the Tm of the probe, (e.g., the cleaving temperature), as described above, in the presence of absence of 100 nM to 10 µM of a target nucleic acid sequence (typically the target nucleic acid sequence is in a 2-4 molar excess over the probe concentration, i.e., 250-500 nM target nucleic acid sequence is used).

Alternatively, a change in the secondary structure of the probe is determined by modifying the method of Gelfand et al. (1999, *Proc. Natl. Acad. Sci.* USA, 96:6113), incorporated herein by reference, to determine the fluorescence of a probe labeled with a pair of interactive labels in the presence or absence of a target nucleic acid as described hereinabove.

Figure 13G:
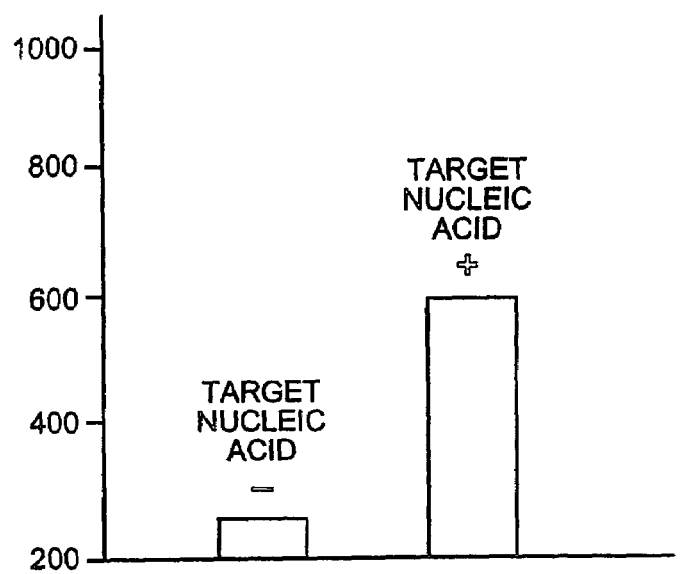
FIG. 13g is a graph demonstrating the effects of a target nucleic acid on the fluorescence of DNA labeled with a pair of interactive labels.

A "change" in secondary structure that occurs when a probe according to the invention binds to a target nucleic acid, is measured as an increase in fluorescence, such that the level of fluorescence after binding of the probe to the target nucleic acid at the temperature below the Tm of the probe, is greater than (e.g., at least 5%, preferably 5-20% and more preferably 25 or more) the level of fluorescence observed in the absence of a target nucleic acid sequence (see FIG. 13g).

IX. Methods of Use

The invention provides for a method of detecting a target nucleic acid by linear amplification.

The invention also provides for a method of detecting a target nucleic acid by exponential amplification.

Both methods of the invention can be performed isothermally or performed under conditions of thermal cycling, e.g., PCR, nucleic acid amplification.

X. Samples

The invention provides for a method of detecting or measuring a target nucleic acid sequence in a sample, as defined herein. As used herein, "sample" refers to any substance containing or presumed to contain a nucleic acid of interest (a target nucleic acid sequence) or which is itself a target nucleic acid sequence, containing or presumed to contain a target nucleic acid sequence of interest. The term "sample" thus includes a sample of target nucleic acid sequence (genomic DNA, cDNA or RNA), cell, organism, tissue, fluid or substance including but not limited to, for example, plasma, serum, spinal fluid, lymph fluid, synovial fluid, urine, tears, stool, external secretions of the skin, respiratory, intestinal and genitourinary tracts, saliva, blood cells, tumors, organs, tissue, samples of in vitro cell culture constituents, natural isolates (such as drinking water, seawater, solid materials,) microbial specimens, and objects or specimens that have been "marked" with nucleic acid tracer molecules.

EXAMPLES

The invention is illustrated by the following nonlimiting examples wherein the following materials and methods are employed. The entire disclosure of each of the literature references cited hereinafter are incorporated by reference herein.

Example 1

Linear Isothermal Amplification

A target nucleic acid sequence can be detected and/or measured by the following method of linear isothermal amplification.

Step 1:

A labeled first duplex is formed prior to the addition of a nuclease by incubating a sample containing a target nucleic acid (A'B'C', FIG. 2), a downstream, 5' radioactively, end labeled second oligonucleotide (FC, FIG. 2) comprising a 5' region that is not complementary to the target nucleic acid sequence, and an upstream first oligonucleotide (A, FIG. 2) under conditions that permit hybridization and formation of a first duplex wherein the 5' region of the second oligonucleotide is a flap and the extension region of the target nucleic acid is not hybridized to the flap. For example, the sample is heated at 95° C. for 5 minutes and then cooled to approximately 50-60° C. Alternatively, the target nucleic acid, the second oligonucleotide and the first oligonucleotide are hybridized at a temperature (for example, 72° C. or 69° C.), that is optimal for hybridization, and subsequent steps of polymerization and cleavage, and for a time sufficient to permit hybridization and formation of a first duplex, wherein the 5' region of the probe is a flap and the extension region of the target nucleic acid is single stranded, for example, 15 min-1 hour.

In certain embodiments of the invention, a first or second duplex is formed by incubating the components of a first or second duplex in the presence of a denaturing agent (e.g., DMSO or glycerol) at a concentration that is sufficient to permit hybridization and formation of a first or second duplex, according to the invention, as well as subsequent steps of polymerization and cleavage, described below. A concentration of a denaturing agent that is useful according to the invention will vary depending on the base pair compositions of the components of the duplex.

Step 2:

A labeled first cleavage structure is prepared as follows. A nucleic acid polymerization activity is added (for example Taq polymerase), and incubated under conditions that permit the polymerase to extend a first oligonucleotide (A, FIG. 2) such that it is adjacent to the flap of the downstream second oligonucleotide (FC, FIG. 2), for example 72° C. or 69° C. in 1×Pfu buffer (Stratagene) for 5 minutes to 1 hour, thereby forming a first cleavage structure.

Step 3:

The labeled first cleavage structure prepared in Step 2 is cleaved with a preparation of PfuFEN-1 (i.e. cloned *Pyrococcus furiosus* FEN-1 that is prepared as described below in Example 5). Cleaving is performed at the same temperature at which all polymerization and subsequent hybridization steps are performed, for example, 72° C. or 69° C.

For Example, cleavage is carried out by adding 2 µl of PfuFEN-1 to a 7 µl reaction mixture containing the following:

| | |
|---|---|
| 3 µl | cleavage structure (10 ng-10 µg) |
| 0.7 µl | 10x FEN nuclease buffer (10X FEN nuclease buffer contains 500 mM Tris-HCl pH 8.0, 100 mM MgCl$_2$) |
| 2.00 µl | PfuFEN-1 enzyme or H$_2$O |
| 1.3 µl | H$_2$O |
| 7.00 µl | total volume |

Samples are incubated for one hour at 72° C. or 69° C. in a Robocyler 96 hot top thermal cycler.

Step 4:

A labeled second duplex is formed as follows. A sample containing a template nucleic acid (F'G'H', FIG. 2) and an upstream, 5' radioactively, end labeled third oligonucleotide (FH, FIG. 2) comprising a 5' region that is not complementary to the template nucleic acid sequence, is incubated under conditions that permit hybridization of the template nucleic acid and the third oligonucleotide (as described in Step 1). The hybridized template nucleic acid/third oligonucleotide is combined with an amount of the sample containing the cleavage products of the first cleavage structure, that is the released flap of the second oligonucleotide (F, FIG. 2), prepared in Step 3, that is sufficient to form a second duplex wherein the 5' region of the third oligonucleotide is a flap and the extension region of the template nucleic acid is single stranded. The resulting mixture is incubated at 72° C. or 69° C. in the presence or absence of added denaturing agent (as above), for a time sufficient to permit hybridization, for example, 15 min-1 hour.

Step 5:

A labeled second cleavage structure is prepared as follows. A nucleic acid polymerization activity is added (for example Taq polymerase), and incubated under conditions that permit the polymerase to extend the flap of the second oligonucleotide (F, FIG. 2) such that it is adjacent to the flap of the downstream third oligonucleotide, for example 72° C. or 69° C. in 1×Pfu buffer (Stratagene) for 5 minutes to 1 hour, thereby forming a second cleavage structure.

Step 6:

The labeled second cleavage structure prepared in Step 5 is cleaved with a preparation of PfuFEN-1, as described in step 3.

Step 7:

Following the addition of 2 µl of Sequencing Stop dye solution (included in the Stratagene Cyclist DNA sequencing kit, catalog #200326), samples are heated at 99° C. for five minutes. Released, labeled, flaps are analyzed by gel electrophoresis as follows. Samples are loaded on an eleven inch long, hand-poured, 20% acrylamide/bis acrylamide, 7M urea gel. The gel is run at 20 watts until the bromophenol blue has migrated approximately ⅔ the total distance. The gel is removed from the glass plates and soaked for 10 minutes in fix solution (15% methanol, 5% acetic acid) and then for 10 minutes in water. The gel is placed on Whatmann 3 mm paper, covered with plastic wrap and dried for 2 hours in a heated vacuum gel dryer (~800 C). The gel is exposed overnight to X-ray film to detect the presence of a signal that is indicative of the presence of a target nucleic acid sequence.

Alternatively, extension and cleavage are performed with an enzyme that exhibits both activities. The polymerization activity employed in step 2 can be different from the polymerization activity employed in step 5. The cleavage means employed in step 3 can be different from the cleavage means of step 6.

Example 2

Linear Isothermal Amplification

A target nucleic acid sequence can be detected and/or measured by the following method of linear isothermal amplification.

Step 1:

A labeled first duplex is formed prior to the addition of a nuclease by incubating a sample containing a target nucleic acid (A'B'C', FIG. 2), a downstream, 5' radioactively, end labeled second oligonucleotide (FC, FIG. 2) comprising a 5' region that is complementary to the target nucleic acid sequence, and an upstream first oligonucleotide (A, FIG. 2) under conditions that permit hybridization and formation of a first duplex wherein the 5' region of the second oligonucleotide is hybridized to the target nucleic acid. For example, the sample is heated at 95° C. for 5 minutes and then cooled to approximately 50-60° C. The first and second oligonucleotide hybridize to non-overlapping regions of the target nucleic acid. Alternatively, the target nucleic acid, the second oligonucleotide and the first oligonucleotide are hybridized at a temperature (for example, 72° C. or 69° C. that is optimal for hybridization, and subsequent steps of polymerization and cleavage, and for a time sufficient to permit hybridization and formation of a first duplex, wherein the 5' region of the probe is hybridized to the target nucleic acid, for example, 15 min-1 hour.

In certain embodiments of the invention, a first or second duplex is formed by incubating the components of a first or second duplex in the presence of a denaturing agent (e.g., DMSO or glycerol) as described in step 1 of Example 1.

Step 2:

A labeled first cleavage structure is prepared as follows. A nucleic acid polymerization activity with strand displacement activity is added (for example Vent DNA polymerase), and incubated under conditions that permit the polymerase to extend a first oligonucleotide (A, FIG. 2) such that it partially displaces the 5' end of the second oligonucleotide FC (for example 72° C. or 69° C. in 1× ThermoPol Buffer (10 mM KCL, 20 mM Tris-HCl (pH 8.8 at 25° C.), 10 mM $(NH_4)_2SO_4$, 2 mM $MgSO_4$, 0.1% Triton X-100, New England Biolabs) for 5 minutes to 1 hour), thereby forming a first cleavage structure. The displaced region of oligonucleotide FC, that is F, forms a 5' flap that is cleaved upon the addition of a nuclease (e.g., a FEN nuclease).

Step 3:

The labeled first cleavage structure prepared in Step 2 is cleaved with a preparation of PfuFEN-1 (i.e. cloned *Pyrococcus furiosus* FEN-1 that is prepared as described below in Example 5). Cleaving is performed at the same temperature at which all polymerization and subsequent hybridization steps are performed, for example, 72° C. or 69° C.

For Example, cleavage is carried out by adding 2 µl of PfuFEN-1 to a 7 µl reaction mixture containing the following:

| | |
|---|---|
| 3 µl | cleavage structure (10 ng-10 µg) |
| 0.7 µl | 10x FEN nuclease buffer (10X FEN nuclease buffer contains 500 mM Tris-HCl pH 8.0, 100 mM $MgCl_2$) |
| 2.00 µl | PfuFEN-1 enzyme or $H_2O$ |
| 1.3 µl | $H_2O$ |
| 7.00 µl | total volume |

Samples are incubated for one hour at 72° C. or 69° C. in a Robocyler 96 hot top thermal cycler.

Step 4:

A labeled second duplex is formed as follows. A sample containing a template nucleic acid (F'G'H', FIG. 2) and an upstream, 5' radioactively, end labeled third oligonucleotide (FH, FIG. 2) comprising a 5' region that is complementary to the template nucleic acid sequence is incubated under conditions that permit hybridization of the template nucleic acid and the third oligonucleotide (as described in Step 1). The hybridized template nucleic acid/third oligonucleotide is combined with an amount of the sample containing the cleavage products of the first cleavage structure, that is the released flap of the second oligonucleotide (F, FIG. 2), prepared in Step 3, that is sufficient to form a second duplex wherein the 5' region of the third oligonucleotide is hybridized to the template nucleic acid. The resulting mixture is incubated at 72° C. or 69° C. in the presence or absence of added denaturing agent (as above), for a time sufficient to permit hybridization, for example, 15 min-1 hour. The flap of the second oligonucleotide and the third oligonucleotide hybridize to non-overlapping regions of the template nucleic acid.

Step 5:

A labeled second cleavage structure is prepared as follows. A nucleic acid polymerization activity is added (for example VENT DNA polymerase), and incubated under conditions that permit the polymerase to extend the flap of the second oligonucleotide (F, FIG. 2) such that it partially displaces the 5' end of the third oligonucleotide FH (as in step 2, above), thereby forming a second cleavage structure. The displaced region of oligonucleotide FH, that is F, forms a 5' flap that is cleaved upon the addition of a FEN nuclease.

Step 6:

The labeled second cleavage structure prepared in Step 5 is cleaved with a preparation of PfuFEN-1, as described in step 3.

Step 7:

Following the addition of 2 µl of Sequencing Stop dye solution (included in the Stratagene Cyclist DNA sequencing kit, catalog #200326), samples are heated at 99° C. for five minutes. Released, labeled, flaps are analyzed by gel electrophoresis as follows. Samples are loaded on an eleven inch long, hand-poured, 20% acrylamide/bis acrylamide, 7M urea gel. The gel is run at 20 watts until the bromophenol blue has migrated approximately ⅔ the total distance. The gel is removed from the glass plates and soaked for 10 minutes in fix solution (15% methanol, 5% acetic acid) and then for 10 minutes in water. The gel is placed on Whatmann 3 mm paper, covered with plastic wrap and dried for 2 hours in a heated vacuum gel dryer (~800 C). The gel is exposed overnight to X-ray film to detect the presence of a signal that is indicative of the presence of a target nucleic acid sequence.

Alternatively, extension and cleavage are performed with an enzyme that exhibits both activities. The polymerization activity employed in step 2 can be different from the polymerization activity employed in step 5. The cleavage means employed in step 3 can be different from the cleavage means of step 6.

Example 3

Exponential Isothermal Amplification

A target nucleic acid sequence can be detected and/or measured by the following method of exponential isothermal amplification.

Steps 1-3 of Example 1 are performed.

Step 4:

A labeled second duplex is formed as follows. A sample containing a template nucleic acid (F'G1'H1'G2'H2', FIG. 5), an upstream, 5' radioactively, end labeled third oligonucleotide (FH1, FIG. 5) comprising a 5' region that is not complementary to the template nucleic acid sequence, and an upstream, 5' radioactively, end labeled fourth oligonucleotide (FH2, FIG. 5) comprising a 5' region that is not complementary to the template nucleic acid sequence, is incubated under conditions that permit hybridization of the template nucleic acid and the third and fourth oligonucleotides (as described in Step 1 of Example 1). The hybridized template nucleic acid/third and fourth oligonucleotides is combined with an amount of the sample containing the cleavage products of the first cleavage structure, that is the released flap of the second oligonucleotide (F, FIG. 5), prepared in Step 3, that is sufficient to form a second duplex wherein the 5' regions of the third and fourth oligonucleotides are flaps and the extension regions of the template nucleic acid are single stranded. The resulting mixture is incubated at 72° C. or 69° C. in the presence or absence of added denaturing agent (as above), for a time sufficient to permit hybridization, for example, 15 min-1 hour.

Step 5:

A labeled second cleavage structure is prepared as follows. A nucleic acid polymerization activity is added (for example Taq polymerase), and incubated under conditions that permit the polymerase to extend the flap of the second oligonucleotide (F, FIG. 5) such that it is adjacent to the flap of the downstream third oligonucleotide (FH1, FIG. 5), for example 72° C. or 69° C. in 1×Pfu buffer (Stratagene) for 5 minutes to 1 hour, thereby forming a second cleavage structure.

Step 6:

The labeled second cleavage structure prepared in Step 5 is cleaved with a preparation of PfuFEN-1, as described in step 3 of Example 1 to release the flap of the third oligonucleotide (F, FIG. 5, step 2).

Step 7:

A labeled third cleavage structure is prepared as follows. A nucleic acid polymerization activity is added (for example Taq polymerase), and incubated under conditions that permit the polymerase to extend the flap of the second oligonucleotide (F, FIG. 5) such that it is adjacent to the flap of the downstream fourth oligonucleotide, for example 72° C. or 69° C. in 1×Pfu buffer (Stratagene) for 5 minutes to 1 hour, thereby forming a third cleavage structure.

Step 8:

The labeled second cleavage structure prepared in Step 5 is cleaved with a preparation of PfuFEN-1, as described in step 3 of Example 1 to release the flap of the fourth oligonucleotide (F, FIG. 5, step 4).

Step 9:

Following the addition of 2 µl of Sequencing Stop dye solution (included in the Stratagene Cyclist DNA sequencing kit, catalog #200326), samples are heated at 99° C. for five minutes. Released, labeled, flaps are analyzed by gel electrophoresis as follows. Samples are loaded on an eleven inch long, hand-poured, 20% acrylamide/bis acrylamide, 7M urea gel. The gel is run at 20 watts until the bromophenol blue has migrated approximately ⅔ the total distance. The gel is removed from the glass plates and soaked for 10 minutes in fix solution (15% methanol, 5% acetic acid) and then for 10 minutes in water. The gel is placed on Whatmann 3 mm paper, covered with plastic wrap and dried for 2 hours in a heated vacuum gel dryer (~800 C). The gel is exposed overnight to X-ray film to detect the presence of a signal that is indicative of the presence of a target nucleic acid sequence.

Alternatively, extension and cleavage are performed with an enzyme that exhibits both activities. The polymerization activity employed in step 2 can be different from the polymerization activity employed in step 5 and the polymerization activity of step 7. The cleavage means employed in step 3 can be different from the cleavage means of step 6 and the cleavage means of step 8.

Example 4

Exponential Isothermal Amplification

A target nucleic acid sequence can be detected and/or measured by the following method of exponential isothermal amplification.

Steps 1-3 of Example 2 are performed.

Step 4:

A labeled second duplex is formed as follows. A sample containing a template nucleic acid (F'G1'H1'G2'H2', FIG. 5), an upstream, 5' radioactively, end labeled third oligonucleotide (FH1, FIG. 5) comprising a 5' region that is at least partially complementary to the template nucleic acid sequence, and an upstream, 5' radioactively, end labeled fourth oligonucleotide (FH2, FIG. 5) comprising a 5' region that is complementary to the template nucleic acid sequence, is incubated under conditions that permit hybridization of the template nucleic acid and the third and fourth oligonucleotides (as described in Step 1 of Example 1). The hybridized template nucleic acid/third and fourth oligonucleotides is combined with an amount of the sample containing the cleavage products of the first cleavage structure, that is the released flap of the second oligonucleotide (F, FIG. 5), prepared in Step 3, that is sufficient to form a second duplex wherein the 5' regions of the third and fourth oligonucleotides are hybridized to the template nucleic acid. The resulting mixture is incubated at 72° C. or 69° C. in the presence or absence of added denaturing agent (as above), for a time sufficient to permit hybridization, for example, 15 min-1 hour. Each of the flap of the second oligonucleotide, the third oligonucleotide and the fourth oligonucleotide hybridize to non-overlapping regions of the template nucleic acid.

Step 5:

A labeled second cleavage structure is prepared as follows. A nucleic acid polymerization activity is added (for example VENT DNA polymerase), and incubated under conditions that permit the polymerase to extend the flap of the second oligonucleotide (F, FIG. 5) such that it partially displaces the 5' end of the third oligonucleotide FH1 (as in step 2, above), thereby forming a second cleavage structure. The displaced region of oligonucleotide FH1, that is F, forms a 5' flap that is cleaved upon the addition of a nuclease (e.g., a FEN nuclease).

Step 6:

The labeled second cleavage structure prepared in Step 5 is cleaved with a preparation of PfuFEN-1, as described in step 3 of Example 2 to release the flap of the third oligonucleotide (F, FIG. 5, step 2).

Step 7:

A labeled third cleavage structure is prepared as follows. A nucleic acid polymerization activity is added (for example VENT DNA polymerase), and incubated under conditions that permit the polymerase to extend the flap of the second oligonucleotide (F, FIG. 5) such that it partially displaces the 5' end of the fourth oligonucleotide FH2 (as in step 2, above), thereby forming a third cleavage structure. The displaced region of oligonucleotide FH2, that is F, forms a 5' flap that is cleaved upon the addition of a nuclease (e.g., a FEN nuclease).

Step 8:

The labeled third cleavage structure prepared in Step 7 is cleaved with a preparation of PfuFEN-1, as described in step 3 of Example 2 to release the flap of the fourth oligonucleotide (F, FIG. 5, step 4).

Step 9:

Following the addition of 2 μl of Sequencing Stop dye solution (included in the Stratagene Cyclist DNA sequencing kit, catalog #200326), samples are heated at 99° C. for five minutes. Released, labeled, flaps are analyzed by gel electrophoresis as follows. Samples are loaded on an eleven inch long, hand-poured, 20% acrylamide/bis acrylamide, 7M urea gel. The gel is run at 20 watts until the bromophenol blue has migrated approximately ⅔ the total distance. The gel is removed from the glass plates and soaked for 10 minutes in fix solution (15% methanol, 5% acetic acid) and then for 10 minutes in water. The gel is placed on Whatmann 3 mm paper, covered with plastic wrap and dried for 2 hours in a heated vacuum gel dryer (~800 C). The gel is exposed overnight to X-ray film to detect the presence of a signal that is indicative of the presence of a target nucleic acid sequence.

Alternatively, extension and cleavage are performed with an enzyme that exhibits both activities. The polymerization activity employed in step 2 can be different from the polymerization activity employed in step 5 and the polymerization activity of step 7. The cleavage means employed in step 3 can be different from the cleavage means of step 6 and the cleavage means of step 8.

Example 5

Cloning Pfu FEN-1

A thermostable FEN nuclease enzyme useful according to the invention can be prepared according to the following method.

The thermostable FEN nuclease gene can be isolated from genomic DNA derived from *P. furiosus* (ATCC#43587) according to methods of PCR cloning well known in the art. The cloned PfuFEN-1 can be overexpressed in bacterial cells according to methods well known in the art and described below.

The following pCAL-n-EK cloning oligonucleotides were synthesized and purified:

a.
5'GACGACGACAAGATGGGTGTCCCAATTGGTGAGATTATACCAAGAAAA G 3'
and b.
5'GGAACAAGACCCGTTTATCTCTTGAACCAACTTTCAAGGGTTGATTGT TTTCCACT 3'.

The Affinity® Protein Expression and Purification System was obtained from Stratagene and used according to the manufacturer's protocols.

Amplification

The insert DNA was prepared by PCR amplification with gene-specific primers (oligonucleotides a and b, described above) that include 12 and 13-nucleotide sequences at the 5' ends that are complementary to the pCAL-n-EK vector single-stranded tails, thus allowing for directional cloning. The FEN-1 sequence was amplified from genomic DNA derived from *P. furiosus* by preparing amplification reactions (five independent 100 μl reactions) containing:

| | |
|---|---|
| 50 μl | 10x cPfu Buffer (Stratagene) |
| 7.5 μl | Pfu Genomic DNA (approx. 100 ng/μl) |

-continued

| | | |
|---|---|---|
| 7.5 µl | PfuTurbo(2.5 u/µl), (Stratagene, Catalog # 600250) | |
| 15 µl | mixed primer pair (100 ng/µl each) (oligonucleotides a and b, described above) | |
| 4 µl | 100 mM dNTP | |
| 416 µl | H$_2$O | |
| 500 µl | total | | and carrying out the amplification under the following conditions using a Stratagene Robocycler 96 hot top thermal cycler:

| | | | |
|---|---|---|---|
| Window 1 | 95° C. | 1 minute | 1 cycle |
| Window 2 | 95° C. | 1 minute | |
| | 50° C. | 1 minute | 30 cycles |
| | 72° C. | 3 minutes | |

The PCR products from each of the five reactions were combined into one tube, purified using StrataPrep PCR and eluted in 50 µl 1 mM Tris-HCl pH 8.6. The FEN-1 PCR product was analyzed on a gel and was determined to be approximately 1000 bp.

The PCR product comprising the fen-1 gene was cloned into the pCALnEK LIC vector (Stratagene) by creating ligation independent cloning termini (LIC), annealing the PCR product comprising the fen-1 gene to the pCALnEK LIC vector (Stratagene), and transforming cells with the annealing mixture according to the following method. Briefly, following PCR amplification, the PCR product is purified and treated with Pfu DNA polymerase in the presence of dATP (according to the manual included with the Affinity® Protein Expression and Purification System, Stratagene, catalog #200326). In the absence of dTTP, dGTP and dCTP, the 3' to 5'-exonuclease activity of Pfu DNA polymerase removes at least 12 and 13 nucleotides at the respective 3' ends of the PCR product. This activity continues until the first adenine is encountered, producing a DNA fragment with 5'-extended single-stranded tails that are complementary to the single-stranded tails of the pCAL-n-EK vector.

Creating LIC Termini
LIC termini were created by preparing the following mixture:

45 µl purified PCR product (~0.5 µg/µl)

2.5 µl 10 mM dATP

5 µl 10× cPfu buffer

1 µl cPfu (2.5 u/µl)

0.5 µl H$_2$O cPfu and cPfu buffer can be obtained from Stratagene (cPfu, Stratagene Catalog #600153 and cPfu buffer, Stratagene Catalog #200532).

Samples were incubated at 72° C. for 20 minutes and products were cooled to room temperature. To each sample was added 40 ng prepared pCALnEK LIC vector (the prepared vector is available commercially from Stratagene in the Affinity LIC Cloning and Protein Purification Kit (214405)). The vector and insert DNA are combined, allowed to anneal at room temperature and transformed into highly competent bacterial host cells (Wyborski et al., 1997, Strategies, 10:1).

Preparing Cells for Production of FEN
Two liters of LB-AMP was inoculated with 20 ml of an overnight culture of a FEN-1 clone (clone 3). Growth was allowed to proceed for approximately 11 hours at which point cells had reached an OD$_{600}$=0.974. Cells were induced overnight (about 12 hours) with 1 mM IPTG. Cells were collected by centrifugation and the resulting cell paste was stored at −20° C.

Purification of tagged FEN-1
Cells were resuspended in 20 ml of Calcium binding buffer CaCl$_2$ binding Buffer 50 mM Tris-HCl (pH 8.0)

150 mM NaCl 1.0 mM MgOAc 2 mM CaCl$_2$

The samples were sonicated with a Branson Sonicator using a microtip. The output setting was 5 and the duty cycle was 90%. Samples were sonicated three times and allowed to rest on ice during the intervals. The sonicate was centrifuged at 26,890×g. Cleared supernatants were mixed with 1 ml of washed (in CaCl$_2$ binding buffer) calmodulin agarose (CAM agarose) in a 50 ml conical tube and incubated on a slowly rotating wheel in a cold room (40 C) for 5 hours. The CAM agarose was collected by light centrifugation (5000 rpm in a table top centrifuge).

Following removal of the supernatant, the CAM agarose was washed with 50 ml CaCl$_2$ binding buffer and transferred to a disposable drip column. The original container and pipet were rinsed thoroughly to remove residual agarose. The column was rinsed with approximately 200 ml of CaCl$_2$ binding buffer.

Elution was carried out with 10 ml of 50 mM NaCl elution buffer (50 mM NaCl, 50 mM Tris-HCl pH 8.0, 2 mM EGTA). 0.5 ml fractions were collected. A second elution step was carried out with 1M NaCl elution buffer wherein 0.5 ml fractions were collected.

Figure 15:
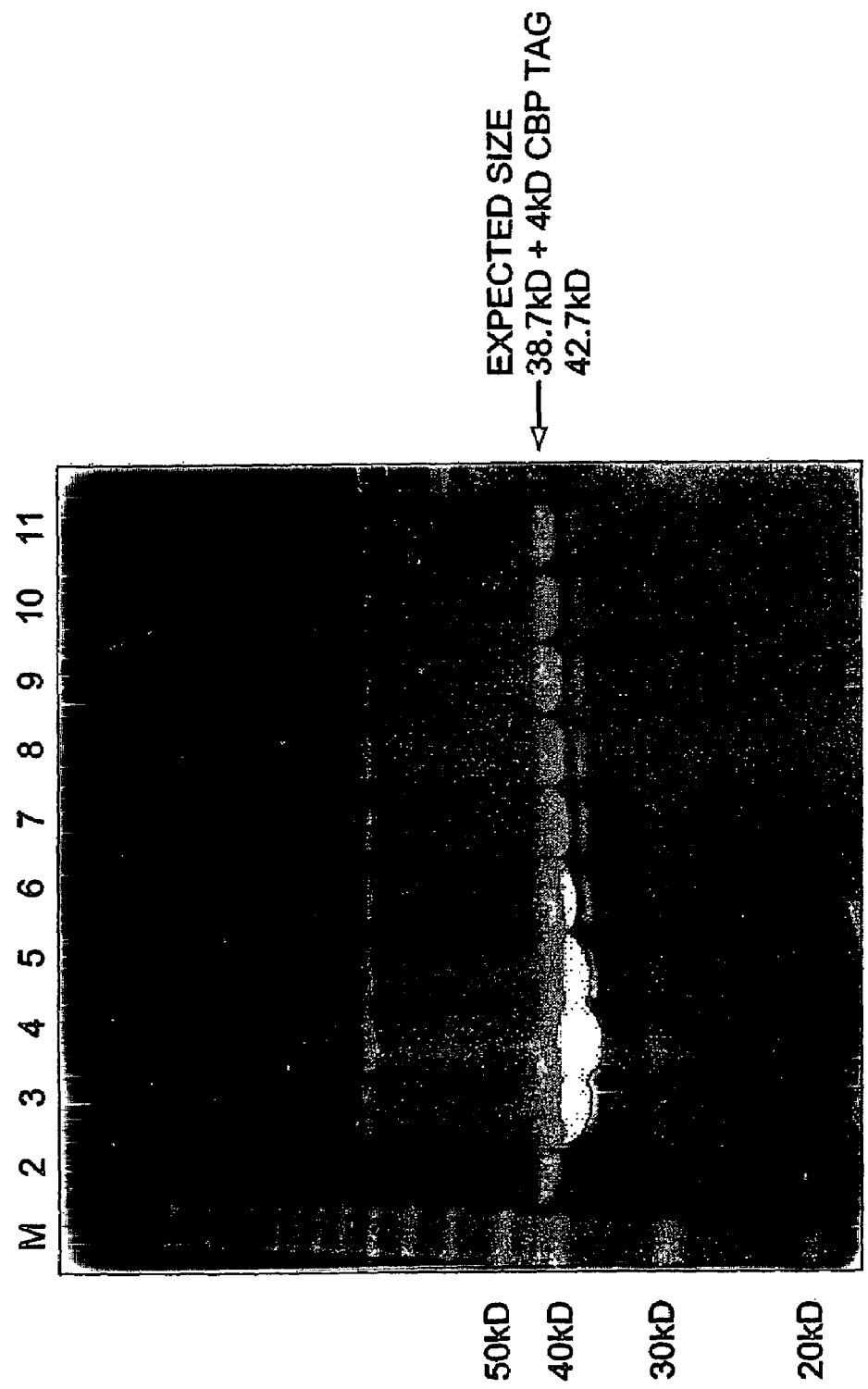
FIG. 15 is a Sypro Orange stained polyacrylamide gel demonstrating CBP-tagged PFU FEN-1 protein.

Evaluation of Purified Tagged FEN-1
Fractions containing CBP-tagged Pfu FEN-1 eluted in 1M NaCl were boiled in SDS and analyzed by SDS-PAGE on a 4-20% gel stained with Sypro Orange (FIG. 15).

The protein concentration of uncleaved FEN-1 was determined to be approximately 150 ng/microliter (below).

Enterokinase Protease (EK) Cleavage of the Purified FEN-1
Fractions 3-9 were dialyzed in 50 mM NaCl, 50 mM Tris-HCl pH 8.0 and 2 mM CaCl$_2$ overnight at 4° C.

An opaque, very fine precipitate appeared in the dialyzed FEN-1. When the sample was diluted ½0 the precipitate was removed. When the sample was diluted ⅓ insoluble material was still detectable. The ⅓ diluted material was heated at 37° C. for 2 minutes and mixed with Tween 20 to a final concentration of 0.1%. Upon the addition of the Tween 20, there was an almost immediate formation of "strings" and much coarser solids in the solution which could not be reversed even after the solution was adjusted to 1M NaCl.

EK cleavage was carried out using as a substrate the sample that was diluted ½0 as well as with a dilute sample prepared by rinsing the dialysis bag with 1×EK buffer. EK cleavage was carried out by the addition of 1 µl EK (1 u/µl) overnight at room temperature (about 16 hours).

100 µl of STI agarose combined with 100 µl of CAM agarose were rinsed twice with 10 ml of 1×STI buffer (50 mM Tris-HCl pH 8.0, 200 mM NaCl, 2 mM CaCl$_2$, 0.1%

Tween 20). NaCl was added to the two EK samples to bring the final concentration to 200 mM NaCl. The two samples were combined and added to the rinsed agarose. The samples were rotated slowly on a wheel at 4° C. for three hours and separated by light centrifugation in a table top centrifuge (as described). The supernatant was removed and the resin was rinsed twice with 500 µl 1×STI. The two rinses were combined and saved separately from the original supernatant. Samples were analyzed by SDS-PAGE on a 4-20% gel.

The concentration of digested product was approximately 23 ng/µl as determined by comparison to a Pfu standard at a concentration of approximately 50 ng/ml.

Example 6

FEN Nuclease Activity

The endonuclease activity of a FEN nuclease and the cleavage structure requirements of a FEN nuclease prepared as described in Example 5 can be determined according to the methods described either in the section entitled "FEN nucleases" or below.

Briefly, three templates (FIG. 14) are used to evaluate the activity of a FEN nuclease according to the invention. Template 1 is a 5' $^{33}$P labeled oligonucleotide (Heltest4) with the following sequence:

5' AAAATAAATAAAAAAAT ACTGTTGGGAAGGGCGATCGGTGCG3'.

The underlined section of Heltest4 represents the region complementary to M13mp 18+. The cleavage product is an 18 nucleotide fragment with the sequence AAAATAAATAAAAAAAT. Heltest4 binds to M13 to produce a complementary double stranded domain as well as a non-complementary 5' overhang. This duplex forms template 2 (FIG. 14). Template 3 (FIG. 14) has an additional primer (FENAS) bound to M13 which is directly adjacent to Heltest 4. The sequence of FENAS is: 5'CCATTCGCCAT-TCAGGCTGCGCA 3'. In the presence of template 3, a FEN nuclease binds the free 5' terminus of Heltest4, migrates to the junction and cleaves Heltest4 to produce an 18 nucleotide fragment. The resulting cleavage products are separated on a 6% acrylamide, 7M urea sequencing gel.

Templates are prepared as described below:

|  | Template 1 | Template 2 | Template 3 |
|---|---|---|---|
| Heltest4 | 14 µl | 14 µl | 14 µl |
| M13 | ** | 14 µl | 14 µl |
| FENAS | ** | ** | 14 µl |
| H$_2$O | 28 µl | 14 µl | ** |
| 10x Pfu Buff. | 4.6 µl | 4.6 µl | 4.6 µl |

Pfu buffer can be obtained from Stratagene (Catalog #200536).

The template mixture is heated at 95° C. for five minutes, cooled to room temperature for 45 minutes and stored at 4° C. overnight.

The enzyme samples are as follows:

A. H$_2$O (control)
B. 2 µl undiluted uncleaved FEN-1 (~445 ng/µl)
C. 2 µl ⅒ dilution of uncleaved FEN-1 (~44.5 ng/µl)
D. 2 µl enterokinase protease (EK) cleaved FEN-1 (~23 ng/µl)

The four reaction mixtures are mixed with the three templates as follows:

| 3 µl | template 1, template 2 or template 3 |
|---|---|
| 0.7 µl | 10x cloned Pfu buffer |
| 0.6 µl | 100 mM MgCl$_2$ |
| 2.00 µl | FEN-1 or H$_2$O |
| 0.7 µl | H$_2$O |
| 7.00 µl | total volume |

The reactions are allowed to proceed for 30 minutes at 50° C. and stopped by the addition of 2 µl formamide "Sequencing Stop" solution to each sample. Samples are heated at 95° C. for five minutes and loaded on a 6% acrylamide 7M urea CastAway gel (Stratagene).

Alternatively, FEN nuclease activity can be analyzed in the following buffer wherein a one hour incubation time is utilized.

10×FEN Nuclease Buffer 500 mM Tris-HCl pH 8.0

100 mM MgCl$_2$

The reaction mixture is as follows:

| 3 µl | template 1, template 2 or template 3 |
|---|---|
| 0.7 µl | 10x FEN nuclease buffer |
| 2.00 µl | FEN-1 or H$_2$O (A-D, above) |
| 1.3 µl | H$_2$O |
| 7.00 µl | total volume |

Samples are incubated for one hour at 50° C. in the Robocyler 96 hot top thermal cycler. Following the addition of 2 µl of Sequencing Stop (95% formamide, 20 mM EDTA, 0.05% bromophenol blue, 0.05% xylene cyanol, available from Stratagene) dye solution, samples are heated at 99° C. for five minutes. Samples are loaded on an eleven inch long, hand-poured, 20% acrylamide/bis acrylamide, 7M urea gel. The gel is run at 20 watts until the bromophenol blue has migrated approximately ⅔ the total distance. The gel is removed from the glass plates and soaked for 10 minutes in fix solution (15% methanol, 5% acetic acid) and then for 10 minutes in water. The gel is placed on Whatmann 3 mm paper, covered with plastic wrap and dried for 2 hours in a heated vacuum gel dryer (~800 C). The gel is exposed overnight to X-ray film.

An autoradiograph of a FEN-1 nuclease assay wherein templates 1, 2 and 3 (prepared as described above) are cleaved by the addition of:

A. H$_2$O
B. 2 µl of CBP-tagged Pfu FEN-1
C. 2 µl of CBP-tagged Pfu FEN-1 diluted (1:10)
D. 2 µl of EK cleaved Pfu FEN-1 is presented in FIG. 16.

The lanes are as follows. Lanes 1A, 1B, 1C and 1D represent template 1 cleaved with H$_2$O, undiluted CBP-tagged Pfu FEN-1, a 1:10 dilution of CBP-tagged Pfu FEN-1 and EK cleaved Pfu FEN-1, respectively. Lanes 2A, 2B, 2C and 2D represent template 2 cleaved with H$_2$O, undiluted CBP-tagged Pfu FEN-1, a 1:10 dilution of CBP-tagged Pfu FEN-1 and EK cleaved Pfu FEN-1, respectively. Lanes 3A, 3B, 3C and 3D represent template 3 cleaved with H$_2$O, undiluted CBP-tagged Pfu FEN-1, a 1:10 dilution of CBP-tagged Pfu FEN-1 and EK cleaved Pfu FEN-1, respectively.

Tagged Pfu FEN-1 contains the N-terminal CBP affinity purification tag. Any differences in activity between tagged and untagged versions of FEN-1 are due to differences in protein concentration (concentrations of enzyme samples are provided above) since the amounts of tagged versus untagged FEN-1 are not equivalent. Both tagged and untagged Pfu FEN-1 demonstrate cleavage activity.

FIG. 16 demonstrates the background level of cleavage in the absence of FEN-1 (lanes 1A, 2A and 3A). Further, this figure demonstrates that tagged Pfu FEN-1 cleaves more of template 2 as compared to template 1. In particular, the greatest amount of template 2 is cleaved in the presence of undiluted, tagged Pfu FEN-1 (lane 2B). Analysis of template 3 demonstrates that the greatest amount of template 3 is cleaved by undiluted, tagged Pfu FEN-1 and the least amount of template 3 is cleaved by diluted tagged FEN-1. Labeled probe migrates as a 40-43 nucleotide band. FEN-1 preferentially cleaves template 3 (which comprises an upstream primer) as compared to template 2. The cleavage product bands are the major bands migrating at 16-20 nucleotides. Heterogeneity in the labeled cleavage products is the result of heterogeneity in the labeled substrate, which was not gel-purified prior to use.

Example 7

Target Nucleic Acid Detection Using Nucleic Acid Amplification Reaction Conditions A target nuclei acid sequence can be detected and/or measured by the following method.

Step 1: Prepare reaction mixture

Figure 17B:
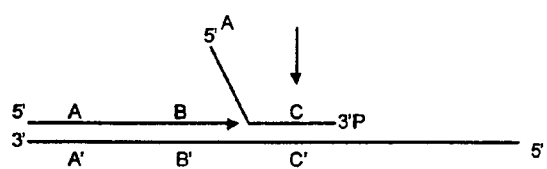
Figure 17C:
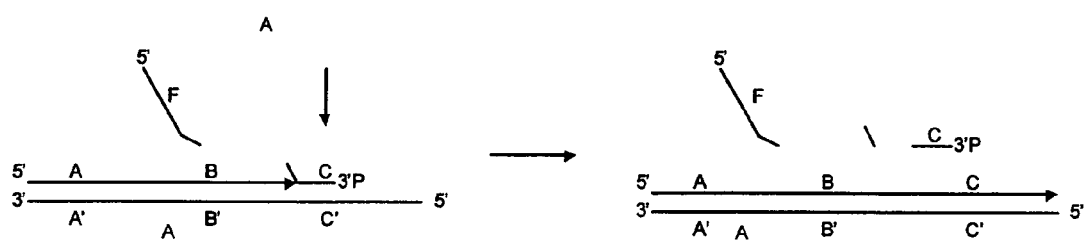

One or more reactions are prepared that contain the oligonucleotides of the invention. The oligonucleotides include a first oligonucleotide (A, FIG. 17), a second oligonucleotide (F-C, FIG. 17), a target nucleic acid (A'B'C', FIG. 17), a template nucleic acid (F'G'H', FIG. 17), and a third oligonucleotide (H, FIG. 17). The second oligonucleotide and template nucleic acid are blocked at the 3' nucleotide. The third oligonucleotide and the template nucleic acid are each coupled to one member of a pair of interactive labels. In the embodiment depicted in FIG. 17, the third oligonucleotide is coupled to a fluorescer on its 3' end and the template nucleic acid is coupled to a quencher on its 5' end. The oligonucleotides are added to a reaction mixture containing standard PCR reagents as well as a cleavage enzyme. The amplification and detection reaction can be performed with the FullVelocity™ QPCR Master Mix (Stratagene, Catalog No. 600561). This system is described further in U.S. Pat. Nos. 6,528,254 and 6,548,250 (each incorporated herein by reference in their entirety). Typical reaction conditions to which the oligonucleotides are added include:

| | |
|---|---|
| 1X | FullVelocity buffer (containing dNTPs) |
| 5 U | Pfu V93R exo(−) polymerase, |
| 200 ng | FEN-1 endonuclease |

The reaction mixture is placed in a thermal cycler. Thermal cyclers are known in the art and include the Mx3000p real-time PCR instrument (Stratagene. Calif.). Typical cycling parameters include: an initial 2 min at 95° C. for 1 cycle, followed by 50 cycles of 10 sec at 95° C., 30 sec at 60° C.

Step 2:

The oligonucleotides are denatured at 95° C. for either 2 minutes or 10 sec.

Step 3:

A first duplex is formed by incubating the reaction mixture under conditions that permit hybridization and formation of a first duplex wherein the 5' region of the second oligonucleotide is a flap and the extension region of the target nucleic acid is not hybridized to the flap. For example, the duplex is formed when the reaction mixture is cooled to approximately 50-60° C. for a time sufficient to permit hybridization and formation of the first duplex. The first duplex includes the target nucleic acid, the first oligonucleotide and the second oligonucleotide. See FIG. 17 A. The first oligonucleotide hybridizes to the first region of the target nucleic acid (A'; FIG. 17A). The 3' region of the second oligonucleotide hybridizes to the second region of the target nucleic acid (C'; FIG. 17A), while the 5' region of the second oligonucleotide forms a flap (F; FIG. 17A). The extension region of the target nucleic acid is single stranded (B'; FIG. 17A). The flap is complementary to a first region of the template nucleic acid (F'; FIG. 17D).

Step 4:

A first cleavage structure is prepared as follows. The reaction is incubated under conditions that permit the polymerase to extend the first oligonucleotide such that it is adjacent to the flap of the downstream second oligonucleotide. See FIG. 17B. The extension may be performed at the same temperature as that applied during the formation of the first duplex or at a distinct temperature which allows polymerization. The temperature is applied for a time sufficient to permit extension of the first oligonucleotide into the extension region of the target nucleic acid (B', FIG. 17B). The polymerase displaces the second oligonucleotide Step 5:

The first cleavage structure is cleaved with the PfuFEN-1 of the FullVelocity multi-enzyme formulation. See FIG. 17C. Preferably the cleavage reaction is performed at the same temperature at which all polymerization and/or hybridization steps are performed, e.g., 60 C. The cleavage reaction releases the 5' flap of the second oligonucleotide (F, FIG. 17C).

Step 6:

A second duplex is formed as follows. The second duplex is formed by incubating the reaction mixture under conditions that permit hybridization and formation of a second duplex. The conditions are preferably the same as those that result in the formation of the first duplex (Step 3). The second duplex may form simultaneously with the first duplex. The second duplex is formed when the cleaved flap from the second oligonucleotide (F'; FIG. 17D) hybridizes to the first region of the template nucleic acid (F'; FIG. 17D) and the third oligonucleotide (H; FIG. 17D) hybridizes to the second region (H'; FIG. 17D) of the template nucleic acid. Formation of the second duplex allows the reporter and quencher moieties operably coupled to the template nucleic acid and the third oligonucleotide to interact; substantially quenching the reporter.

Step 7:

A labeled second cleavage structure is prepared as follows. The reaction is incubated under conditions that permit the polymerase to extend the released flap of the second oligonucleotide (A, FIG. 17E). These conditions are preferably the same as described in Step 4 for the first cleavage structure. The flap is extended, by the polymerase activity, into the extension region of the template nucleic acid. The polymerase partially displaces the third oligonucleotide. (FIG. 17E).

Step 8:

The second cleavage structure is cleaved in a similar manner to that described in step 5 for the first cleavage reaction. However, during this cleavage reaction a detectable signal is produced, e.g., fluorescence. See FIG. 17F. The signal is produced when the third oligonucleotide is cleaved causing the third oligonucleotide and template nucleic acid to dissociate. Separation of the pair of interactive labels results in a detectable signal.

The reaction may be repeated for one or more additional cycles.

Example 8

Real-Time QPCR Detection Utilizing the Oligonucleotides of the Invention

The following experiment was performed to detect a target nucleic acid.

Primers:

HPRT-Fwd: 5'-AATTATGGACAGGACTGAACGTCTTGCT-3'

HPRT-Rev: 5'-TCCAGCAGGTCAGCAAAGAATTTATAGC-3'

Probes:
Second Oligonucleotide:

5'--BHQ2-
CAGTTCAGGGGCCTCATCTCGGTTTTTCCCAGATGAGCCCCCAGAACTC
-FAM-3'

The underlined portion of the second oligonucleotide corresponds to the 5' flap that that was released in the cleavage reaction. The flap was complementary to the first portion of the template nucleic acid and served as a primer in subsequent extension reactions.

Third Oligonucleotide:
5'-tGaAcGaTgcc-Hex-3'

The third oligonucleotide is complementary to the second portion of the template nucleic acid.

Template Nucleic Acid:

5'--BHQ2-GGCATCGTTCAAAAGGAAAAACCGAGATGAGGCC-PO3-3'

The template nucleic acid had a first region (bold), which was complementary to and hybridizes with the released flap, an extension region and a second region, which was complementary to and hybridized with the third oligonucleotide (underlined). The template nucleic acid was blocked at the 3' nucleotide and was coupled to a quencher at the 5' nucleotide.

The oligonucleotides described above were used in a FullVelocity Q-PCR reaction (Stratagene) according to the manufacturer's instructions. Briefly, the following reagents were combined in the reaction mixture: 1×FullVelocity buffer (containing dNTPs), Xul of the FullVelocity Multi-enzyme formulation, 400 nM the HPRT Fwd primer and 200 nM of the HPRT Rev primer, 400 nM of the second oligonucleotide, 300 nM of the third oligonucleotide 300 nM of the template nucleic acid and 10 pg of PCR template. A non-template control (NTC) was also tested. The reaction was carried out in a total volume of 50 µl The reaction was performed in a Mx3000P real-time PCR instrument under the following parameters: 1 cycle at 95° C. for 2 minutes, followed by 40 cycles of:
95° C. for 10 seconds
60° C. for 30 seconds Fluorescence data was collected at the end of the 60° C. step of each cycle.

Figure 18:
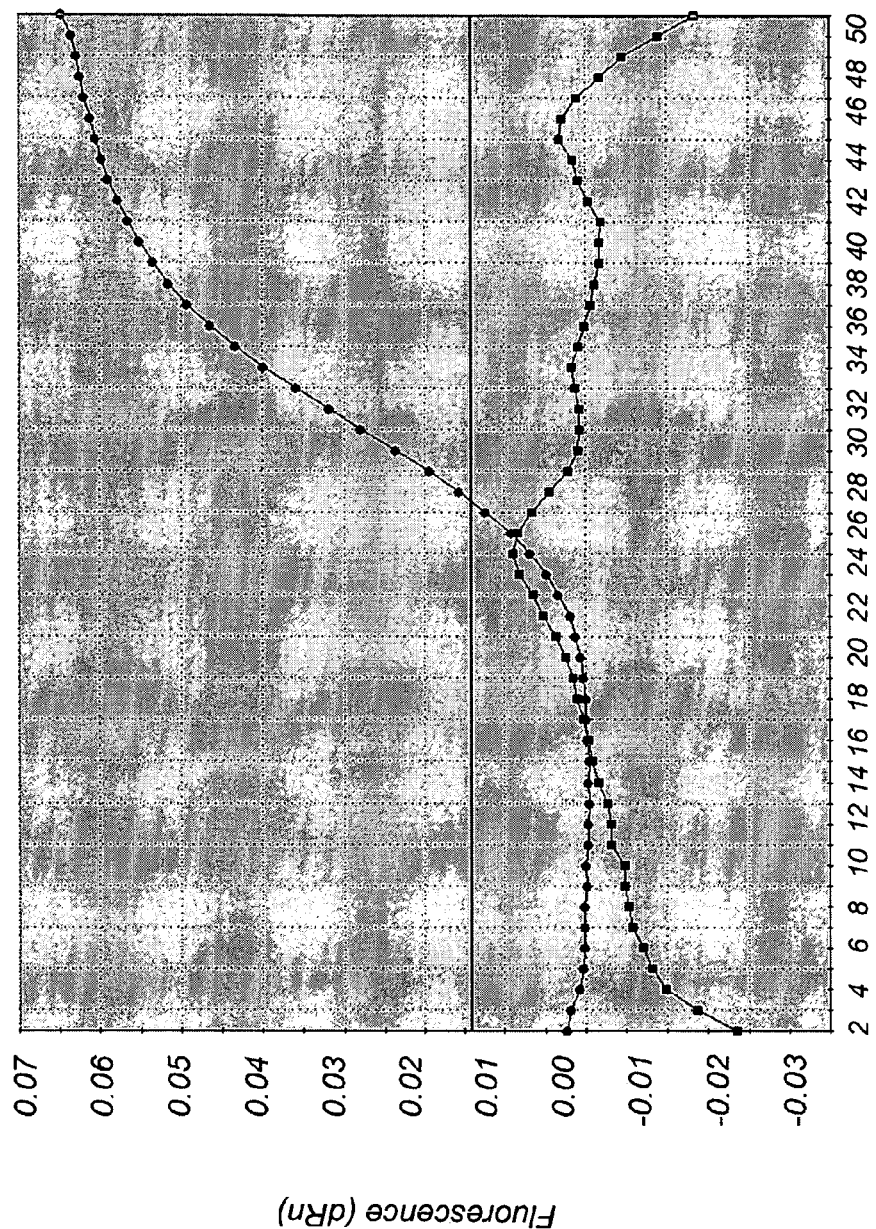
FIG. 18 is a graphical representation of the data generated using one embodiment of the invention in a real-time QPCR reaction.

The results are graphically represented in FIG. 18.

Example 9

Titration Curve of the Second Oligonucleotide

The following experiment was performed to determine the optimum concentration of the second oligonucleotide in a method of the invention.

Primers:

HPRT-Fwd: 5'-AATTATGGACAGGACTGAACGTCTTGCT-3'

HPRT-Rev: 5'-TCCAGCAGGTCAGCAAAGAATTTATAGC-3'

Probes:
Second Oligonucleotide:
5'-BHQ2
-CAGTTCAGGGGCCTCATCTCGGTTTTTCCCAGATG
AGCCCCCAGAACTC-FAM-3'

The underlined portion of the second oligonucleotide corresponds to the 5' flap that was cleaved in the cleavage reaction. The flap was complementary to the first portion of the template nucleic acid and served as a primer in subsequent extension reactions.

Third Oligonucleotide:
5'-tGaAcGaTgcc-Hex-3'

The third oligonucleotide was complementary to the second portion of the template nucleic acid.

Template Nucleic Acid:
BHQ2-
GGCATCGTTCAAAAGGAAAAACCGAGATGAGGCC-PO3

The template nucleic acid had a first region, which was complementary to and hybridizes with the cleaved flap (underlined), an extension region and a second region, which was complementary to and hybridizes with the third oligonucleotide (bolded). The template nucleic acid was blocked at the 3' nucleotide and was operably coupled to a quencher at the 5' nucleotide.

The oligonucleotides described above were used in a FullVelocity Q-PCR reaction (Stratagene, Calif.) according to the manufacturer's instructions. Briefly, the following reagents were combined in the reaction mixture: 1×FullVelocity buffer (containing dNTPs), Xul of the FullVelocity Multi-enzyme formulation, 400 nM the HPRT Fwd primer, 200 nM of the HPRT Rev primer, 300 nM of the third oligonucleotide, 300 nM of the template nucleic acid and 100 fg of PCR template. The second oligonucleotide was added to the reaction mixtures at various concentrations: 1000 nM, 200 n, 300 nM, 400 mM, 500 nM, 600 nM, 700 nM or 800 nM. A non-template control (NTC) was also tested. The reaction was performed in 50 µl total reaction volume.

The reaction was performed in a Mx3000P real-time PCR instrument (Stratagene, Calif.) under the following reaction conditions: 1 cycle at 95° C. for 2 minutes, followed by 50 cycles of:
95° C. for 30 seconds
60° C. for 60 seconds Fluorescence data was collected at the end of the 60° C. step of each cycle.

Figure 19A:
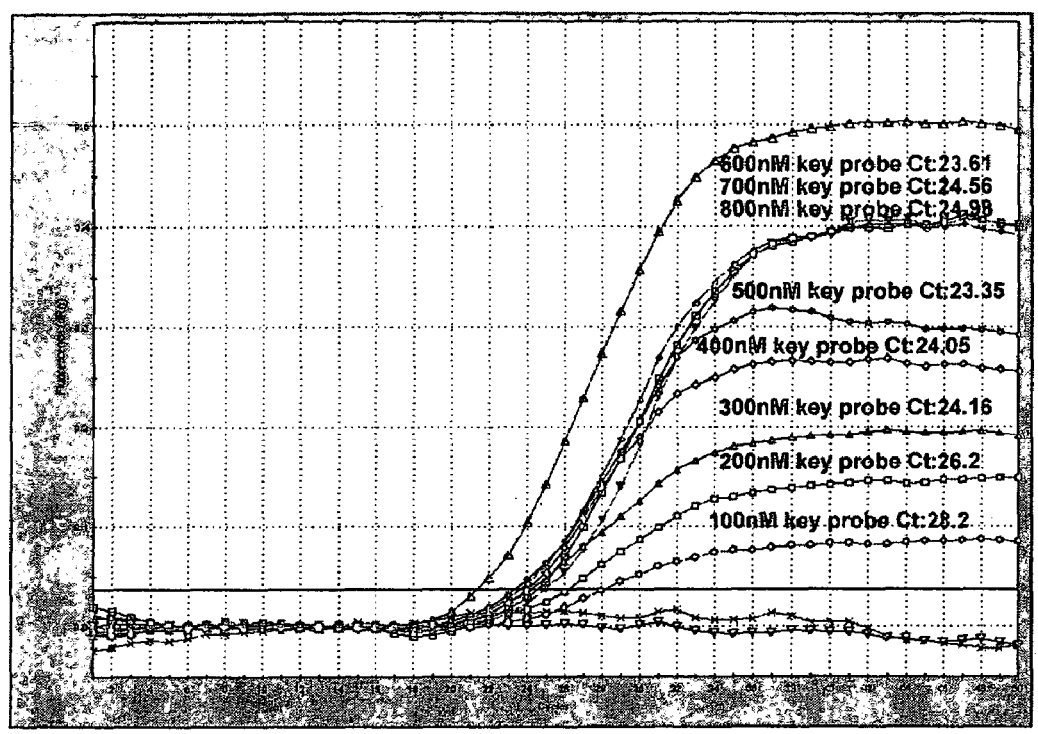
FIG. 19A is a titration curve of the second oligonucleotide of the invention in a Q-PCR reaction. The graph shows the fluorescent signal produced upon cleavage of the first cleavage structure.
Figure 19B:
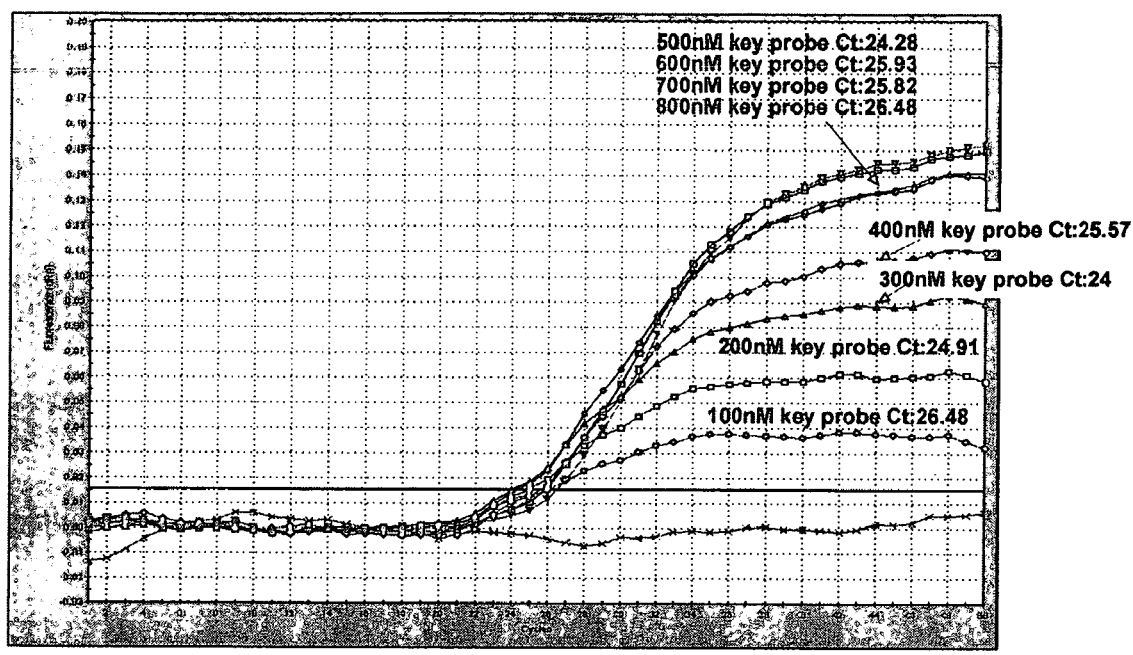
FIG. 19B is a titration curve of the second oligonucleotide of the invention in a Q-PCR reaction. The graph shows the fluorescent signal produced upon cleavage of the second cleavage structure.

Fluorescence was detected for both the first cleavage reaction, HEX, (FIG. 19A) and the second cleavage reaction, FAM (FIG. 19B) at each concentration of the second oligonucleotide.

Example 10

Titration Curve of the Third Oligonucleotide

The following experiment was performed to determine the optimum concentration of the third oligonucleotide in a method of the invention.
Primers:

HPRT-Fwd: 5'-AATTATGGACAGGACTGAACGTCTTGCT-3'

HPRT-Rev: 5'-TCCAGCAGGTCAGCAAAGAATTTATAGC-3'

Probes:
Second Oligonucleotide:

5'--BHQ2-
CAGTTCAGGGGCCTCATCTCGGTTTTTCCCAGATGAGCCCCAGAACTC
-FAM-3'

The underlined portion of the second oligonucleotide corresponds to the 5' flap that was cleaved in the cleavage reaction. The flap was complementary to the first portion of the template nucleic acid and served as a primer in subsequent extension reactions.
Third Oligonucleotide:
tGaAcGaTgcc-Hex
The third oligonucleotide was complementary to the second portion of the template nucleic acid.
Template Nucleic Acid:
5'-BHQ2-
GGCATCGTTCAAAAGGAAAAACCGAGATGAGGCC-PO3-3'

The template nucleic acid had a first region, which was complementary to and hybridize with the cleaved flap (bolded), an extension region and a second region, which was complementary to and hybridizes with the third oligonucleotide (underlined). The template nucleic acid was blocked at the 3' nucleotide and was attached to a quencher at the 5' nucleotide.

The oligonucleotides described above were used in a FullVelocity Q-PCR reaction (Stratagene, Calif.) according to the manufacturer's instructions. Briefly, the following reagents were combined in the reaction mixture: 1×FullVelocity buffer (containing dNTPs), Xul of the FullVelocity Multi-enzyme formulation, 400 nM the HPRT Fwd primer, 200 nM of the HPRT Rev primer, 500 nM of the second oligonucleotide, 300 nM of the template nucleic acid and 100 fg of PCR template. In order to determine the optimal concentration of the third oligonucleotide the third oligonucleotide was added to the reaction mixtures at varying concentrations: 100 nM, 200 n, 300 nM, 400 nM, 500 nM, 600 nM, 700 nM, 800 nM or 900 nM A non template control (NTC) was also tested. The reaction was carried out in 50 µl total reaction volume.

The reaction was performed in a Mx3000P real-time PCR instrument (Stratagene, California) under the following reaction conditions: 1 cycle at 95° C. for 2 minutes, followed by 50 cycles of:

95° C. for 10 seconds

60° C. for 30 seconds

Fluorescence data was collected at the end of the 60° C. step of each cycle.

Figure 20A:
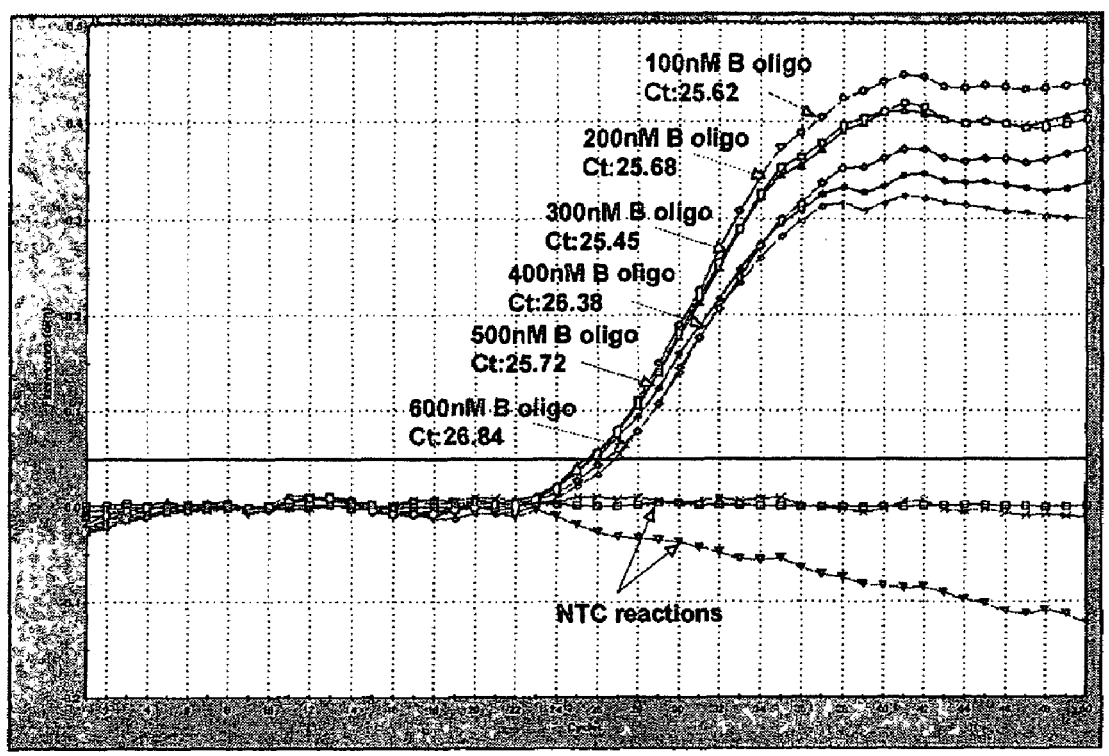
FIG. 20A is a titration curve (100 nM to 600 nM) of the second oligonucleotide of the invention in a Q-PCR reaction. The graph shows the fluorescent signal produced upon cleavage of the first cleavage structure.
Figure 20B:
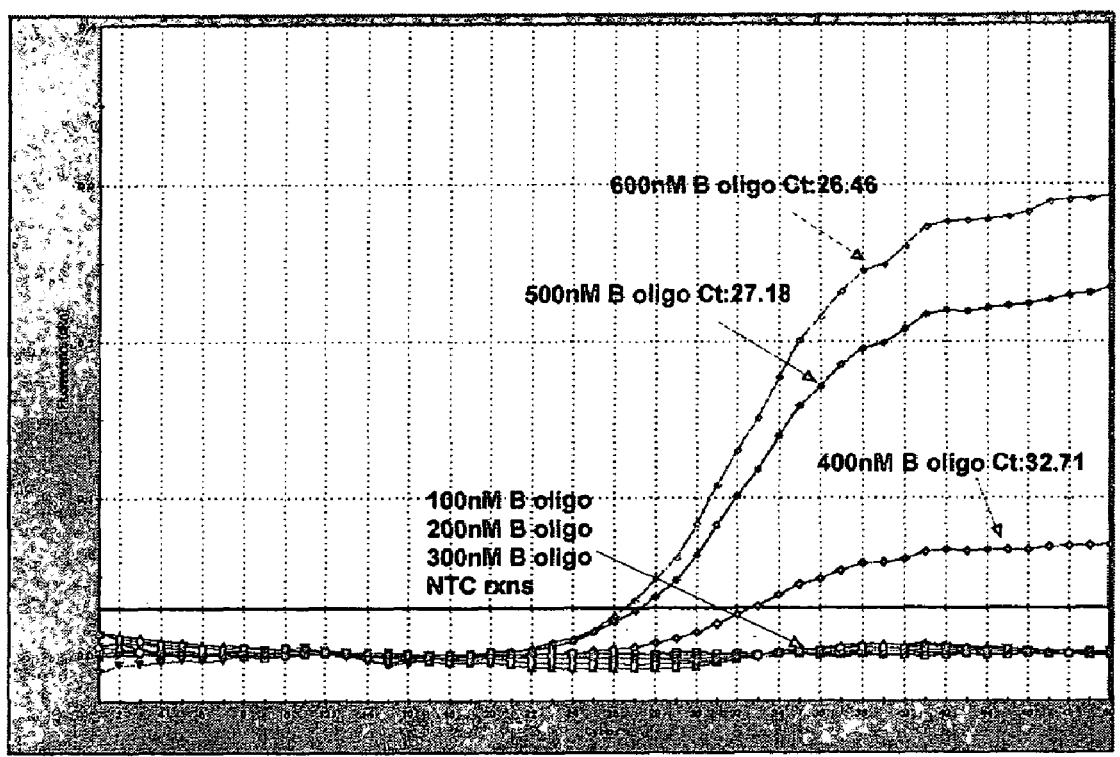
FIG. 20B is a titration curve (100 nM to 600 nM) of the second oligonucleotide of the invention in a Q-PCR reaction. The graph shows the fluorescent signal produced upon cleavage of the second cleavage structure.
Figure 20C:
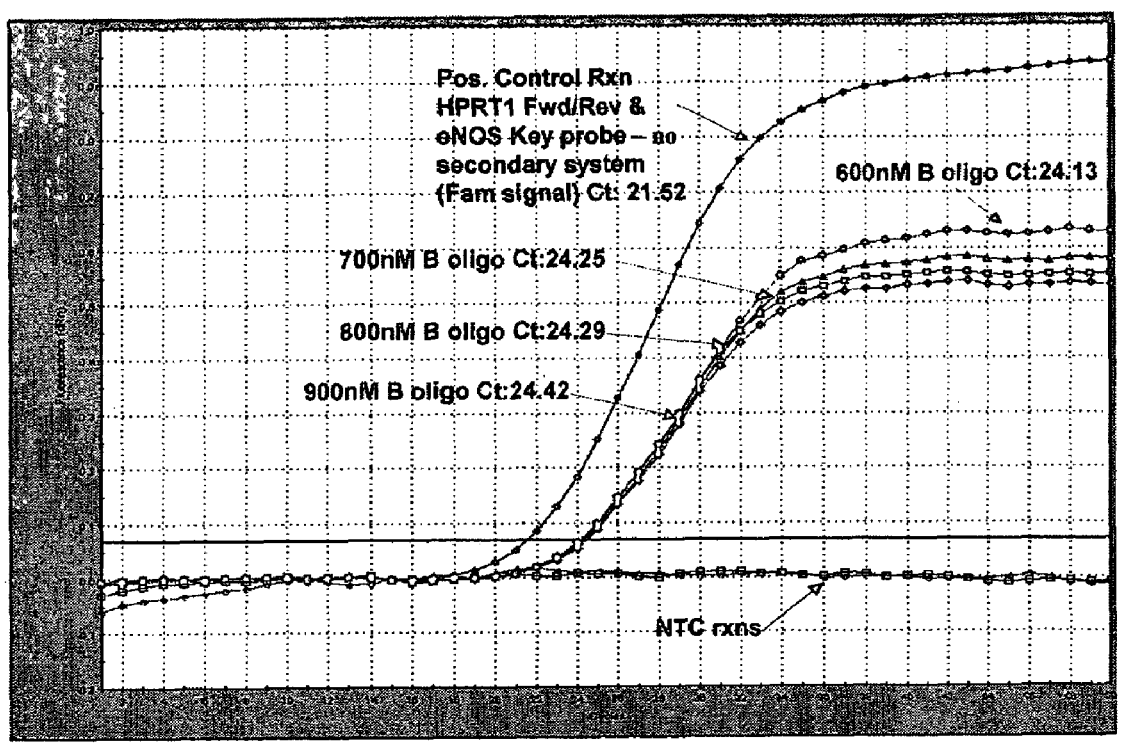
FIG. 20C is a titration curve (700 nM to 900 nM) of the third oligonucleotide of the invention in a Q-PCR reaction. The graph shows the fluorescent signal produced upon cleavage of the first cleavage structure.

Fluorescence was determined for the first cleavage reaction, FAM, (FIG. 20A) or the second cleavage reaction, HEX (FIG. 20B) for third oligonucleotide concentrations of 100 nM to 600 nM. Fluorescence was also determined for the first cleavage reaction, FAM, (FIG. 20C) or the second cleavage reaction, HEX for third oligonucleotide concentrations of 700 nM to 900 nM.

I claim:

1. A method of detecting a target nucleic acid, comprising
(a) providing:
said target nucleic acid, which comprises in 3' to 5' order a first region, an extension region, and a second region,
a template nucleic acid, which comprises in 3' to 5' order a first region, an extension region, and a second region,
a first oligonucleotide that is at least partially complementary to said first region of said target nucleic acid,
a second oligonucleotide comprising a 5' region and a 3' region, wherein said 3' region is at least partially complementary to said second region of said target nucleic acid and wherein said 5' region is not complementary to said target nucleic acid but is at least partially complementary to said first region of said template nucleic acid,
a third oligonucleotide comprising a 5' region and a 3' region, wherein said 3' region is at least partially complementary to said second region of said template nucleic acid and said 5' region is not complementary to said template nucleic acid,
a cleavage means, and
a polymerization activity;
(b) mixing said target nucleic acid, said template nucleic acid, said first oligonucleotide, said second oligonucleotide, said third oligonucleotide, said cleavage means and said polymerization activity under a series of reaction conditions, wherein said series of reaction conditions permit:
formation of a duplex between said target nucleic acid and each of said first oligonucleotide and said 3' region of said second oligonucleotide, wherein said 5' region of said second oligonucleotide is a flap,
extension of said first oligonucleotide by polymerization of a nucleic acid strand complementary to a length of said extension region of said target nucleic acid sufficient to form a first cleavage structure,
cleavage of said first cleavage structure within said second oligonucleotide by said cleavage means, thereby permitting release of said flap of said second oligonucleotide,
formation of a second duplex with said released flap of said second oligonucleotide, said template nucleic acid, and said third oligonucleotide, wherein said 5' region of said third oligonucleotide is a second flap,
extension of said released flap by polymerization of a nucleic acid strand complementary to a length of said extension region of said template nucleic acid sufficient to form a second cleavage structure, and
cleavage of said second cleavage structure within said third oligonucleotide by said cleavage means, thereby permitting cleavage and release of said third oligonucleotide; and
(c) detection of a signal generated by said release of said third oligonucleotide from said template nucleic acid.

2. A method of detecting a target nucleic acid, comprising
(a) providing:
said target nucleic acid, which comprises in 3' to 5' order a first region, an extension region, and a second region,
a template nucleic acid, which comprises in 3' to 5' order a first region, an extension region, and a second region,
a first oligonucleotide that is at least partially complementary to said first region of said target nucleic acid,
a second oligonucleotide comprising a 5' region and a 3' region, wherein said 3' region is at least partially complementary to said second region of said target nucleic acid and wherein said 5' region is not complementary to said target nucleic acid but is at least partially complementary to said first region of said template nucleic acid,
a third oligonucleotide comprising a 5' region and a 3' region, wherein said 3' region is at least partially complementary to said second region of said template nucleic acid and said 5' region is at least partially complementary to a region that is 3' of said second region,
a cleavage means, and
a polymerization activity;
(b) mixing said target nucleic acid, said template nucleic acid, said first oligonucleotide, said second oligonucleotide, said third oligonucleotide said cleavage means and said polymerization activity under a series of reaction conditions, wherein said series of reaction conditions permit:
formation of a duplex between said target nucleic acid and each of said first oligonucleotide and said 3' region of said second oligonucleotide, wherein said 5' region of said second oligonucleotide is a flap,
extension of said first oligonucleotide by polymerization of a nucleic acid strand complementary to a length of said extension region of said target nucleic acid sufficient to form a first cleavage structure,
cleavage of said first cleavage structure within said second oligonucleotide by said cleavage means, thereby permitting release of said flap of said second oligonucleotide,
formation of a second duplex with said released flap of said second oligonucleotide, said template nucleic acid, and said third oligonucleotide,
extension of said released flap by polymerization of a nucleic acid strand complementary to a length of said extension region of said template nucleic acid sufficient to form a second cleavage structure,
cleavage of said second cleavage structure within said third oligonucleotide by said cleavage means, thereby permitting cleavage and release of said third oligonucleotide; and
(c) detection of a signal generated by said release of said third oligonucleotide from said template nucleic acid.

3. The method of claim 1 or 2, wherein said polymerase lacks 5' to 3' exonuclease activity.

4. The method of claim 1 or 2, wherein said polymerase is a DNA polymerase.

5. The method of claim 1 or 2, wherein said polymerase is thermostable.

6. The method of claim 1 or 2, wherein said polymerization comprises strand displacement activity.

7. The method of claim 1 or 2, wherein a single enzyme comprises said polymerization activity and said cleavage means.

8. The method of claim 7, wherein said enzyme is *E. coli* DNA polymerase I, T7 DNA polymerase, Tth DNA polymerase, or Taq DNA polymerase.

9. The method of claim 1 or 2, wherein a first enzyme comprises a polymerization activity and a second enzyme comprises said cleavage means.

10. The method of claim 1 or 2, wherein said cleavage means comprises a 5' nuclease activity.

11. The method of claim 1 or 2, wherein said cleavage means comprises a FEN-1 nuclease.

12. The method of claim 11, wherein said FEN-1 nuclease is a flap specific nuclease.

13. The method of claim 1, wherein said FEN-1 nuclease is thermostable.

14. The method of claim 9, wherein said first and second enzymes are provided in a single formulation.

15. The method of claim 9, said first enzyme is a Pfu DNA Polymerase and said second enzyme is a FEN-1 nuclease.

16. The method of claim 1 or 2, wherein said series of reaction conditions are nucleic acid polymerization reaction conditions.

17. The method of claim 16, wherein said nucleic acid polymerization reaction conditions are polymerase chain reaction conditions.

18. The method of claim 1 or 2, wherein said extension reaction polymerizes nucleotides complementary to a length of the extension region sufficient to form a cleavage structure, the polymerized complementary nucleic acid is adjacent at its 3' end to the downstream oligonucleotide in the duplex.

19. The method of claim 1 or 2, wherein said extension reaction polymerizes nucleotides complementary to a length of the extension region sufficient to form a cleavage structure said length of said extension region is a length such that said extension region is a fully duplexed nucleic acid.

20. The method of claim 1 or 2, wherein said extension reaction polymerizes nucleotides complementary to a length of the extension region sufficient to form a cleavage structure, said length of said extension region is such that the template strand of said extension region comprises a 2 nucleotide gap between the 3' end of the complementary polymerized nucleic acid and the downstream oligonucleotide.

21. The method of claim 1 or 2, wherein said extension reaction polymerizes nucleotides complementary to a length of the extension region sufficient to form a cleavage structure, said length of said extension region is such that the template strand of said extension region comprises a 4 nucleotide gap between the 3' end of the complementary polymerized nucleic acid and the downstream oligonucleotide.

22. The method of claim 1 or 2, wherein said extension reaction polymerizes nucleotides complementary to a length of the extension region sufficient to form a cleavage structure, said length of said extension region is such that the template strand of said extension region comprises a 6 nucleotide gap between the 3' end of the complementary polymerized nucleic acid and the downstream oligonucleotide.

23. The method of claim 1 or 2, wherein said extension reaction polymerizes nucleotides complementary to a length of the extension region sufficient to form a cleavage structure, said length of said extension region is such that the template strand of said extension region comprises a 8 nucleotide gap between the 3' end of the complementary polymerized nucleic acid and the downstream oligonucleotide.

24. The method of claim 1 or 2, wherein said extension reaction polymerizes nucleotides complementary to a length of the extension region sufficient to form a cleavage structure, said length of said extension region is such that the template strand of said extension region comprises a 10 nucleotide gap between the 3' end of the complementary polymerized nucleic acid and the downstream oligonucleotide.

25. The method of claim 1 or 2, wherein said second oligonucleotide does not comprise a detectable label.

26. The method of claim 1 or 2, wherein said template nucleic acid further comprises a first member of a pair of interactive labels and said third oligonucleotide further comprises a second member of said pair of interactive labels.

27. The method of claim 26, wherein said first member of said pair of interactive labels is operatively coupled to the 5' nucleotide of said template nucleic acid.

28. The method of claim 26, wherein said second member of said pair of interactive labels is operatively coupled to the 3' nucleotide of said third oligonucleotide.

29. The method of claim 26, wherein said pair of interactive labels comprises a fluorophore and a quencher.

30. The method of claims 26, wherein said detection of a signal comprises detecting a change in fluorescent between said first and second members of said pair of interactive labels upon release of said third oligonucleotide.

31. The method of claim 1 or 2, wherein said 5' portion of said second oligonucleotide is at least partially complementary to said 3' portion of said second oligonucleotide.

32. The method of claim 1 or 2, wherein said 3' portion and said 5' portion of said second oligonucleotide form a stem structure when the second oligonucleotide is not hybridize to the target nucleic acid.

33. The method of claim 1 or 2, wherein said second oligonucleotide further comprise a linker sequence between said 5' portion and said 3' portion of said second oligonucleotide.

34. The method of claim 33, wherein said linker portion is not complementary to said target nucleic acid but is complementary to the first portion of said template nucleic acid.

35. The method of claim 1 or 2, wherein the 3' nucleotide of said second oligonucleotide is blocked.

36. The method of claim 1 or 2, wherein the 3' nucleotide of said template nucleic acid is blocked.

37. The method of claim 1 or 2, wherein said polymerization activity is provided by a polymerase.

38. The method of claim 1 or 2, wherein said first and said second cleavage structures are formed by the displacement of said second and said third oligonucleotides by said polymerase.

39. The method of claim 1 or 2, wherein said series of reaction conditions are performed on a solid substrate.

40. A composition comprising:
(i) a target nucleic acid, which comprises in 3' to 5' order a first region, an extension region, and a second region;
(ii) a template nucleic acid, which comprises in 3' to 5' order a first region, an extension region, and a second region and wherein said template nucleic acid has a first member of a pair of interactive labels;
(iii) a first oligonucleotide that is at least partially complementary to said first region of said target nucleic acid;
(iv) a second oligonucleotide comprising a 5' region and a 3' region, wherein said 3' region is at least partially complementary to said second region of said target nucleic acid and wherein said 5' region is not complementary to said target nucleic acid but is at least partially complementary to said first region of said template nucleic acid; and
(v) a third oligonucleotide comprising a 5' region and a 3' region, wherein said 3' region is at least partially complementary to said second region of said template nucleic acid and said 5' region is not complementary to said template nucleic acid and wherein said third oligonucleotide has a second member of said pair of interactive labels.

41. A composition comprising:
(i) a target nucleic acid, which comprises in 3' to 5' order a first region, an extension region, and a second region,
(ii) a template nucleic acid, which comprises in 3' to 5' order a first region, an extension region, and a second region and wherein said template nucleic acid has a first member of a pair of interactive labels
(iii) a first oligonucleotide that is at least partially complementary to said first region of said target nucleic acid, and
(iv) a second oligonucleotide comprising a 5' region and a 3' region, wherein said 3' region is at least partially complementary to said second region of said target nucleic acid and wherein said 5' region is not complementary to said target nucleic acid but is at least partially complementary to said first region of said template nucleic acid; and
(v) a third oligonucleotide comprising a 5' region and a 3' region, wherein said 3' region is at least partially complementary to the second region of the template nucleic acid and said 5' region is at least partially complementary to a region that is 3' of said second region of said template nucleic acid and wherein said third oligonucleotide has a second member of said pair of interactive labels.

42. The composition of claim 40 or 41, further comprising a cleavage means.

43. The composition of claim 40 or 41, further comprising a polymerase.

44. A kit comprising a composition of claim 40 or 41, and packaging materials therefore.

45. The kit of claim 44, further comprising a cleavage means.

46. The kit of claim 44, further comprising a nucleic acid polymerase.

* * * * *